(12) United States Patent
Duan et al.

(10) Patent No.: US 8,846,673 B2
(45) Date of Patent: Sep. 30, 2014

(54) AZAINDAZOLES AS KINASE INHIBITORS AND USE THEREOF

(75) Inventors: Jingwu Duan, Yardley, PA (US); Bin Jiang, Norristown, PA (US); Zhonghui Lu, King of Prussia, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 321 days.

(21) Appl. No.: 13/388,700

(22) PCT Filed: Aug. 11, 2010

(86) PCT No.: PCT/US2010/045109
§ 371 (c)(1),
(2), (4) Date: Feb. 3, 2012

(87) PCT Pub. No.: WO2011/019780
PCT Pub. Date: Feb. 17, 2011

(65) Prior Publication Data
US 2012/0129852 A1    May 24, 2012

Related U.S. Application Data

(60) Provisional application No. 61/232,860, filed on Aug. 11, 2009.

(51) Int. Cl.
*A61K 31/535*    (2006.01)
*C07D 471/04*    (2006.01)

(52) U.S. Cl.
CPC .................................. *C07D 471/04* (2013.01)
USPC ................... 514/234.2; 514/303; 514/253.04; 514/255.05; 514/262.1; 544/362; 544/118; 544/405; 544/262; 544/127

(58) Field of Classification Search
CPC .. C07D 487/04; C07D 471/04; C07D 495/04; C07D 473/06; C07D 513/04
USPC ......... 514/234.2, 303, 253.04, 255.05, 262.1; 544/362, 118, 405, 262, 127
See application file for complete search history.

(56) References Cited

U.S. PATENT DOCUMENTS

| | | | |
|---|---|---|---|
| 4,224,322 A | 9/1980 | Roch et al. | |
| 4,260,621 A | 4/1981 | Roch et al. | |
| 8,008,322 B2 | 8/2011 | Ronan et al. | |
| 2003/0139427 A1 | 7/2003 | Castelhano et al. | |

FOREIGN PATENT DOCUMENTS

| | | |
|---|---|---|
| DE | 2160780 | 6/1973 |
| DE | 2232038 | 1/1974 |
| DE | 2643753 | 4/1978 |
| DE | 156812 | 9/1982 |
| DE | 209459 | 5/1984 |
| EP | 1 683 796 | 7/2006 |
| EP | 1 867 647 | 12/2007 |
| EP | 1 867 648 | 12/2007 |
| FR | 2880891 | 7/2006 |
| WO | WO 00/43394 | 7/2000 |
| WO | WO 01/19828 | 3/2001 |
| WO | WO 02/24679 | 3/2002 |
| WO | WO 02/055082 | 7/2002 |
| WO | WO 02/088078 | 11/2002 |
| WO | WO 03/064397 | 8/2003 |
| WO | WO 03/080616 | 10/2003 |
| WO | WO 2004/076450 | 9/2004 |
| WO | WO 2004/096130 | 11/2004 |
| WO | WO 2004/113303 | 12/2004 |
| WO | WO 2005/110410 | 11/2005 |
| WO | WO 2005/117909 | 12/2005 |
| WO | WO 2006/013095 | 2/2006 |
| WO | WO 2006/044687 | 4/2006 |
| WO | WO 2006/046023 | 5/2006 |
| WO | WO 2006/050109 | 5/2006 |
| WO | WO 2006/063805 | 6/2006 |
| WO | WO 2006/077168 | 7/2006 |
| WO | WO 2006/077319 | 7/2006 |
| WO | WO 2006/101783 | 9/2006 |
| WO | WO 2007/017577 | 2/2007 |
| WO | WO 2007/023110 | 3/2007 |
| WO | WO 2007/103308 | 9/2007 |
| WO | WO 2007/125310 | 11/2007 |
| WO | WO 2007/125315 | 11/2007 |
| WO | WO 2007/137030 | 11/2007 |
| WO | WO 2007/144202 | 12/2007 |

(Continued)

OTHER PUBLICATIONS

Cheney, I.W., et al., "Identification and structure-activity relationships of substituted pyridones as inhibitors of Pim-1 kinase", Bioorganic & Medicinal Chemistry Letters, vol. 17, pp. 1679-1683 (2007).

Dai, Y. et al., "Identification of aminopyrazolopyridine ureas as potent VEGFR/PDGFR multitargeted kinase inhibitors", Bioorganic & Medicinal Chemistry Letters, vol. 18, pp. 386-390 (2008).

Elnagdi, M.H., et al, Pyrimidine Derivatives and Related Compounds. A Novel Synthesis of Pyrimidines, Pyrazolo[4,3-*d*]pyrimidines and Isoxazolo [4,3-*d*] pyrimidine, Journal of Heterocyclic Chemistry, vol. 16, pp. 1109-1111 (1979).

(Continued)

*Primary Examiner* — Jason Sims
*Assistant Examiner* — Ibrahim D Bori
(74) *Attorney, Agent, or Firm* — Gary D. Greenblatt; Hong Liu

(57) ABSTRACT

Compounds having the formula (I), and enantiomers, and diastereomers, pharmaceutically-acceptable salts, thereof, (I) are useful as kinase modulators, including Btk modulation, wherein $A_1, A_2, A_3, R_4$ are as defined herein.

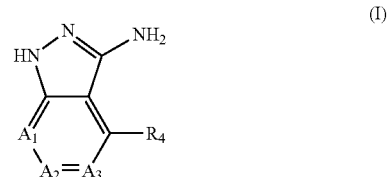

16 Claims, No Drawings

(56) References Cited

FOREIGN PATENT DOCUMENTS

| | | |
|---|---|---|
| WO | WO 2007/144203 | 12/2007 |
| WO | WO 2007/144204 | 12/2007 |
| WO | WO 2008/012635 | 1/2008 |
| WO | WO 2008/033858 | 3/2008 |
| WO | WO 2008/071456 | 6/2008 |
| WO | WO 2008/121742 | 10/2008 |

OTHER PUBLICATIONS

Elneairy, M.A.A., et al., "Reactions with Dimethylformamide-Dimethylacetal: Synthesis and Reactions of Several New Pyridine and Pyrazolo[3,4-*b*]pyridine Derivatives", Heteroatom Chemistry, vol. 18, No. 4, pp. 399-404 (2007).

Gad-Elkareem, M.A.M., et al., "Pyrazolo[3,4-*b*]pyridine in heterocyclic synthesis: synthesis of new pyrazolo[3,4-*b*]pyridines, imidazo[1',2':1,5]pyrazolo[3,4-*b*]pyridines, and pyrido[2',3':3,4]pyrazolo[1,5-*a*]pyrimidines," Canadian Journal of Chemistry, vol. 85, pp. 592-299 (2007).

Mohamed, O.S., et al., "Studies on the synthesis of some new cyanopyridine-thione and thieno[2,3-b]pyridine derivatives," Phosphorus, Sulfur and Silicon and the Related Elements, vol. 182, pp. 1061-1082 (2007).

Nagar, D.N., et al., "Facile Generation of Pyridopyrazoles: Synthesis of 3-Amino-4-aryl-6-(p-benzamidophenyl)-pyrido-[2,3-d]-1-H-pyrazoles", J. Inst. Chemists (India), vol. 74, Part 4, pp. 129-131 (2002).

Ram, V.J., "Synthesis of Pyrimidines and Fused Pyrimidines as Leishmanicides," Journal fuer Praktische Chemie (Leipzig), vol. 331, pp. 957-963 (1989).

Schmidt, R.R., "Novel Synthesis of Pyrimidine Derivatives," Chemische Berichte, vol. 98, pp. 346-351 (1965).

Seada, M., et al., "Synthesis and Biological Activities of Some New Pyrazolo [3,4-d] Pyrimidine Derivatives", Asian Journal of Chemistry, vol. 4, No. 3, pp. 588-596 (1992).

Stocks, M.J., et al., "Structure-driven HtL: Design and synthesis of novel aminoindazole inhibitors of c-Jun N-terminal kinase activity", Bioorganic & Medicinal Chemistry Letters, vol. 15, pp. 3459-3462 (2005).

Youssef, M.S.K., et al., "Synthesis of heterocycles derived from 4-amino-2-(3-methyl-5-oxo-1-phenyl-2-pyrazolin-4-yl)-6-phenylpyrimidine-5-carbonitrile with anticipated biological activity." Afinidat, vol. 63, pp. 315-320 (2006).

Compound RN 253132-99-9 Registry, Entered STN: Jan. 19, 2000.
Compound RN 438020-37-2 Registry, Entered STN: Jul. 10, 2002.
Compound RN 692775-16-9 Registry, Entered STN: Jun. 14, 2004.
Compound RN 775232-07-0 Registry, Entered STN: Nov. 4, 2004.
Compound RN 785723-68-4 Registry, Entered STN: Nov. 21, 2004.
Compound RN 791843-44-2 Registry, Entered STN: Dec. 3, 2004.
Compound RN 850781-30-5 Registry, Entered STN: May 19, 2005.
Compound RN 852453-68-0 Registry, Entered STN: Jun. 17, 2005.
Compound RN 852453-69-1 Registry, Entered STN: Jun. 17, 2005.
Compound RN 852453-83-9 Registry, Entered STN: Jun. 17, 2005.
Compound RN 852454-01-4 Registry, Entered STN: Jun. 17, 2005.
Compound RN 852454-02-5 Registry, Entered STN: Jun. 17, 2005.
Compound RN 852454-03-6 Registry, Entered STN: Jun. 17, 2005.
Compound RN 852454-45-6 Registry, Entered STN: Jun. 17, 2005.
Compound RN 892251-29-5 Registry, Entered STN: Jul. 12, 2006.
Compound RN 892251-36-4 Registry, Entered STN: Jul. 12, 2006.
Compound RN 892251-50-2 Registry, Entered STN: Jul. 12, 2006.
Compound RN 852453-66-8 Registry, Entered STN: Jun. 17, 2005.
Compound RN 852454-00-3 Registry, Entered STN: Jun. 17, 2005.
Compound RN 852454-44-5 Registry, Entered STN: Jun. 17, 2005.
Compound RN 892251-43-3 Registry, Entered STN: Jul. 12, 2006.
Compound RN 903296-80-0 Registry, Entered STN: Aug. 22, 2006.
Compound RN 904276-83-1 Registry, Entered STN: Aug. 24, 2006.
Compound RN 907957-85-1 Registry, Entered STN: Sep. 20, 2006.
Compound RN 927802-30-0 Registry, Entered STN: Mar. 21, 2007.
PCT International Search Report completed Nov. 2, 2010.

AZAINDAZOLES AS KINASE INHIBITORS AND USE THEREOF

CROSS-REFERENCE TO RELATED APPLICATIONS

The present application claims the priority benefit of U.S. Provisional Application No. 61/232,860, filed Aug. 11, 2009, which is expressly incorporated fully herein by reference.

FIELD OF THE INVENTION

This invention relates to fused heterocyclic compounds useful as kinase modulators, including the modulation of Bruton's tyrosine kinase (Btk). Provided herein are fused heterocyclic compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk, in a mammal.

BACKGROUND OF THE INVENTION

Protein kinases, the largest family of human enzymes, encompass well over 500 proteins. Btk is a member of the Tec family of tyrosine kinases, and is a regulator of early B-cell development, as well as mature B-cell activation, signaling and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signaling upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SU), Btk deficiency has been shown to result in a marked amelioration of disease progression. Moreover, Btk deficient mice are also resistant to developing collagen-induced arthritis and are less susceptible to Staphylococcus-induced arthritis.

A large body of evidence supports the role of B-cells and the humoral immune system in the pathogenesis of autoimmune and/or inflammatory diseases. Protein-based therapeutics (such as RITUXAN®) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNT-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

Inhibitors of protein kinases are widely sought and small molecule compounds capable of modulating protein kinases have been reported. Among them, substituted pyrazolopyridines are disclosed as useful protein kinase inhibitors in PCT Publication Nos. WO 2004/113303, WO 2005/110410, WO 2006/077319, WO 2006/440187, WO 2006/050109, WO 2006/077168, WO 2006/063805, WO 2007/144202 and WO 2007/144204. In addition, WO 2008/033858 discloses methods of inhibiting Btk activity with various Btk binding chemical compounds. The compounds described in the present invention are substituted azaindazoles distinguishable from those in the aforementioned references in that they do not contain a urea moiety.

Thus, the present invention relates to a new class of compounds useful as protein kinases inhibitors, especially Btk inhibitors. These novel compounds are provided to be useful as pharmaceuticals with desirable stability, bioavailability, therapeutic index and toxicity values that are important to their drugability.

SUMMARY OF THE INVENTION

The invention is directed to azaindazoles of Formulae (I)-(V) that inhibit protein kinase enzymes, especially Bruton's tyrosine kinase for the treatment of allergic disorders, autoimmune and/or inflammatory diseases, and cancers.

The present invention provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibiting the activity of Btk comprising administering to a host in need of such treatment a therapeutically effective amount of at least one of the compounds of the present invention or stereoisomers, tautomers, pharmaceutically acceptable salts, solvates, or prodrugs thereof.

The present invention also provides methods for inhibiting B-cell mediated pathogenic activity comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, in preparing a medicament for the treatment of cancer in a human patient, particularly a cancer receptive to treatment via inhibition of the Btk enzyme.

These and other features of the invention will be set forth in the expanded form as the disclosure continues.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine, chlorine, bromine and iodine.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluoroethoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle," "carbocyclic residue," or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As noted above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge converts a monocyclic ring into a tricyclic ring. When a ring is bridged, the substituents recited for the ring may also be present on the bridge. When the term "carbocycle," "carbocyclic residue," or "carbocyclyl" is used, it is intended to include "aryl". Preferred carbocycles, unless otherwise specified, are cyclopropyl, cyclobutyl, cyclopentyl, cyclohexyl, phenyl, and indanyl.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle," "heterocyclyl," or "heterocyclic group" is intended to mean a stable 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge converts a monocyclic ring into a tricyclic ring. When a ring is bridged, the substituents recited for the ring may also be present on the bridge. When the term "heterocycle," "heterocyclyl," or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined).

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R_{3a}$, then said group may optionally be substituted with up to three $R_{3a}$ groups and $R_{3a}$ at each occurrence is selected independently from the definition of $R_{1a}$. Also, combinations of substituents and/or variables are permissible only if such combinations result in stable compounds.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The present application provides at least one chemical entity chosen from the compounds of formula (I), including enantiomers, diastereomers, prodrugs, solvates, hydrates, or pharmaceutically-acceptable salts thereof:

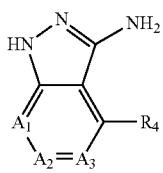

(I)

wherein $A_1$ is selected from N and $CR_1$;

$A_2$ is selected from N and $CR_2$;

$A_3$ is selected from N and $CR_3$; wherein at least one of $A_1$, $A_2$, and $A_3$ is N; and $A_1$ and $A_2$ are not simultaneously N;

$R_1$ is selected from H, F, Cl, Br, $NO_2$, CN, $NR_aR_a$, $C_{1-6}$alkyl substituted with 0-5 $R_{1a}$, $C_{2-6}$alkenyl substituted with 0-5 $R_{1a}$, $C_{2-6}$alkynyl substituted with 0-5 $R_{1a}$, —O—$C_{1-6}$alkyl, —O—(CHR)$_r$-carbocyclyl substituted with 0-5 $R_{1a}$, —(CHR)$_r$-carbocyclyl substituted with 0-5 $R_{1a}$, and —(CHR)$_r$-heterocyclyl substituted with 0-5 $R_{1a}$;

$R_{1a}$, at each occurrence, is independently selected from $C_{1-6}$alkyl substituted with 0-5 $R_e$, $C_{2-6}$alkenyl substituted with 0-5 $R_e$, $C_{2-6}$alkynyl substituted with 0-5 $R_e$, $C_{1-6}$haloalkyl, F, Cl, Br, $NO_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_1$), —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$NR$_a$P(O)$_p$R$_b$, —(CHR)$_r$-C$_{3-6}$-carbocyclyl substituted with 0-5 $R_e$ and/or —(CHR)$_r$-heterocyclyl substituted with 0-5 $R_e$;

$R_2$ is selected from H, F, Cl, Br, $NO_2$, CN, $NR_aR_a$, $C_{1-6}$alkyl substituted with 0-5 $R_{2a}$, $C_{2-6}$alkenyl substituted with 0-5 $R_{2a}$, $C_{2-6}$alkynyl substituted with 0-5 $R_{2a}$, —O—$C_{1-6}$alkyl substituted with 0-5 $R_{2a}$, —O—(CHR)$_r$-carbocyclyl substituted with 0-5 $R_{2a}$, —(CHR)$_r$-carbocyclyl substituted with 0-5 $R_{2a}$, and —(CHR)$_r$-heterocyclyl substituted with 0-5 $R_{2a}$;

$R_{2a}$, at each occurrence, is independently selected from $C_{1-6}$alkyl, $C_{2-6}$alkenyl, $C_{2-6}$alkynyl, $C_{1-6}$haloalkyl, —(CH$_2$)$_r$C$_{3-10}$cycloalkyl, F, Cl, Br, $NO_2$, CN, —(CHR)$_r$OH, —(CHR)$_r$SH, —(CHR)$_r$OR$_b$, —(CHR)$_r$S(O)$_p$R$_b$), —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$C(O)$_r$C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$(CHR)$_r$C(O)OR$_d$, —(CHR)$_r$-carbocyclyl substituted with 0-5 $R_e$ and/or —(CHR)$_r$-heterocyclyl substituted with 0-5 $R_e$;

$R_3$ is selected from H, F, Cl, Br, $NO_2$, CN, $C_{1-6}$alkyl substituted with 0-5 $R_{3a}$, $C_{2-6}$alkenyl substituted with 0-5 $R_{3a}$, $C_{2-6}$alkynyl substituted with 0-5 $R_{3a}$, —O—$C_{1-6}$alkyl substituted with 0-5 $R_{3a}$, —O-carbocyclyl substituted with 0-5 $R_{3a}$, —(CHR)$_r$-carbocyclyl substituted with 0-5 $R_3$, and —(CHR)$_r$-heterocyclyl substituted with 0-5 $R_{3a}$;

$R_{3a}$, at each occurrence, is independently selected from $C_{1-6}$alkyl, $C_{2-6}$alkenyl, $C_{2-6}$alkynyl, $C_{1-6}$haloalkyl, —(CH$_2$)$_r$C$_{3-10}$cycloalkyl, F, Cl, Br, $NO_2$, CN, —(CHR)$_r$OH, —(CHR)$_r$SH, —(CHR)$_r$O(CHR)$_r$R$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$), —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$-aryl substituted with 0-5 $R_e$, and/or —(CHR)$_r$-heterocyclyl substituted with 0-5 $R_e$;

alternatively, $R_1$ and $R_2$, or $R_2$ and $R_3$, are taken together with the ring atoms to which they are attached to form a fused carbocyclyl or heterocyclyl;

$R_4$ is selected from carbocyclyl substituted with 0-5 $R_{4a}$ and heterocyclyl substituted with 0-5 $R_{4a}$;

$R_{4a}$, at each occurrence, is independently selected from F, Cl, Br, $NO_2$, CN, $C_{1-6}$alkyl, $C_{2-6}$alkenyl, $C_{2-6}$alkynyl, $C_{1-6}$haloalkyl, —(CHR)$_r$OH, —(CHR)$_r$SH, —(CHR)$_r$O(CHR)$_r$R$_c$ (CHR)$_r$S(O)$_p$(CHR)$_r$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$C$_{3-6}$-carbocyclyl substituted with 0-5 $R_e$, and/or —(CHR)$_r$-heterocyclyl substituted with 0-5 $R_e$;

R, at each occurrence, is independently selected from H, $C_{1-6}$alkyl, $C_{1-6}$haloalkyl, and/or —(CH$_2$)$_r$-aryl;

$R_a$, at each occurrence, is independently selected from H, $NH_2$, $C_{1-6}$alkyl substituted with 0-3 $R_e$, $C_{2-6}$alkenyl substituted with 0-3 $R_e$, $C_{2-6}$alkynyl substituted with 0-3 $R_e$, $C_{1-6}$haloalkyl, —O—$C_{1-6}$alkyl substituted with 0-3 $R_e$, —(CH$_2$)$_r$OH, (CH$_2$)$_r$—C$_{3-10}$ carbocyclyl substituted with 0-3 $R_e$, and/or —(CH$_2$)$_r$-heterocyclyl substituted with 0-3 $R_e$, or $R_a$ and $R_a$ together with the nitrogen atom to which they are both attached form a heterocyclyl substituted with 0-3 $R_e$;

$R_b$, at each occurrence, is independently selected from $C_{1-6}$alkyl substituted with 0-3 $R_e$, $C_{1-6}$haloalkyl, $C_{2-6}$alkenyl substituted with 0-3 $R_e$, $C_{2-6}$alkynyl substituted with 0-3 $R_e$, —(CH$_2$)$_r$C$_{3-10}$-carbocyclyl substituted with 0-3 $R_e$, and/or —(CH$_2$)$_r$-heterocyclyl substituted with 0-3 $R_e$;

$R_c$, at each occurrence, is independently selected from $C_{1-6}$alkyl substituted with 0-3 $R_g$, $C_{2-6}$alkenyl substituted with 0-3 $R_g$, $C_{2-6}$alkynyl substituted with 0-3 $R_g$, $C_{1-6}$haloalkyl, —(CH$_2$)$_r$OH, —(CH$_2$)$_r$—C$_{3-10}$-carbocyclyl substituted with 0-3 R$_g$, and/or —(CH$_2$)$_r$-heterocyclyl substituted with 0-3 R$_g$;

R$_d$, at each occurrence, is independently selected from H, C$_{1-6}$alkyl substituted with 0-3 R$_e$, C$_{1-6}$haloalkyl, C$_{2-6}$alkenyl substituted with 0-3 R$_e$, C$_{2-6}$alkynyl substituted with 0-3 R$_e$, —(CH$_2$)$_r$—C$_{3-10}$-carbocyclyl substituted with 0-3 R$_e$, and/or —(CH$_2$)$_r$-heterocyclyl substituted with 0-3 R$_e$;

R$_e$, at each occurrence, is independently selected from C$_{1-6}$alkyl, C$_{2-6}$alkynyl, C$_{2-6}$alkynyl, —(CH$_2$)$_r$C$_{3-6}$cycloalkyl, F, Cl, Br, CN, NO$_2$, —(CH$_2$)$_r$CO$_2$H, —(CH$_2$)$_r$OC$_{1-5}$alkyl, OH, SH, —(CH$_2$)$_r$SC$_{1-5}$alkyl, —(CH$_2$)$_r$NR$_f$R$_f$, —C(O)NR$_f$R$_f$, —(CH$_2$)$_r$C(O)NR$_f$R$_f$, —(CH$_2$)$_r$heterocyclyl;

R$_f$, at each occurrence, is independently selected from H, C$_{1-5}$alkyl, and C$_{3-6}$cycloalkyl, and/or phenyl;

R$_g$, at each occurrence, is independently selected from C$_{1-6}$alkyl, (CH$_2$)$_r$C$_{3-6}$cycloalkyl, F, Cl, Br, CN, NO$_2$, —(CH$_2$)$_r$CO$_2$H, —(CH$_2$)$_r$OC$_{1-6}$alkyl, OH, —(CH$_2$)$_r$phenyl, and/or —(CH$_2$)$_r$heterocyclyl.

p, at each occurrence, is independently selected from 0, 1, and/or 2; r, at each occurrence, is independently selected from 0, 1, 2, 3, and/or 4;

provided that:

(1) if A$_1$ is N, A$_2$ is CR$_2$, and A$_3$ is N, then R$_4$ is phenyl substituted with 1-4 R$_{4a}$ wherein at least one R$_{4a}$ is —O—(CHR)$_r$-phenyl substituted with 0-5 R$_g$;

(2) if A$_1$ is N, A$_2$ is CR$_2$, and A$_3$ is CR$_3$, then R$_4$ is phenyl substituted with 1-4 R$_{4a}$ wherein at least one R$_{4a}$ is —O—(CHR)$_r$-phenyl substituted with 0-5 R$_g$ and R$_2$ is other than C$_{1-6}$alkyl, cyclohexyl, or 1,4-dioxaspiro[4,5]Declaration-8-yl, each substituted or unsubstituted; and (3) if A$_1$ is CR$_1$, A$_2$ is N, A$_3$ is CR$_3$, and R$_{4a}$ is NH$_2$ or phenyl, then R$_1$ is not hydrogen.

The above provisos were introduced in view of the structurally related compounds disclosed in the following scientific literature and publications.

PCT Publication Nos. WO 2006/077319, WO 2006/050109, WO 2006/050109, WO 2006/077168, WO 2007/144202 and WO 2007/144204 disclose urea-substituted pyrazolopyridines useful as kinase inhibitors.

In PCT Publication No. WO 2005/110410, a pyrazolopyridine intermediate is described (Preparation #168 on page 331).

Dai et al. (*Bioorganic & Medicinal Chemistry Letters*, 18(1):386-390 (2008)) disclose aminopyrazolopyridines ureas as kinase inhibitors and an aminopyrazolopyridine intermediate (Compounds 9 and 10 on page 387).

PCT Publication No. WO 2006/063805 discloses 3-aminopyrazolo[3,4b]pyridines as Eph receptor inhibitors.

U.S. Pat. No. 4,260,621 discloses substituted pyrazolopyridines as antithrombotic agents.

The present invention also provides at least one chemical entity chosen from compounds of formula (II) or (III), including enantiomers, diastereomers, prodrugs, solvates, hydrates, or pharmaceutically-acceptable salts thereof:

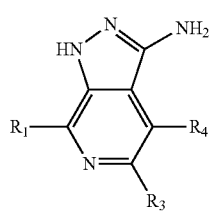

(II)

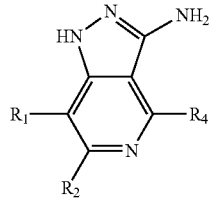

(III)

in which

R$_1$ is selected from H, F, Cl, Br, NR$_a$R$_a$, C$_{1-4}$alkyl substituted with 0-3 R$_{1a}$, —O—C$_{1-4}$alkyl, —O-aryl substituted with 0-3 R$_{1a}$, —(CHR)$_r$-aryl substituted with 0-3 R$_{1a}$, —(CHR)$_r$-heterocyclyl substituted with 0-3 R$_{1a}$;

R$_{1a}$, at each occurrence, is independently selected from C$_{1-4}$alkyl substituted with 0-3 R$_e$, C$_{1-4}$haloalkyl, F, Cl, Br, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$NR$_a$P(O)$_p$R$_b$, —(CHR)$_r$C$_{3-6}$-carbocyclyl substituted with 0-3 R$_e$, and/or —(CHR)$_r$heterocyclyl substituted with 0-3 R$_a$;

R$_2$ is selected from H, F, Cl, Br, NO$_2$, CN, NR$_a$R$_a$, C$_{1-4}$alkyl substituted with 0-3 R$_{2a}$, —O—C$_{1-4}$alkyl substituted with 0-3 R$_{2a}$, —O-carbocyclyl substituted with 0-3 R$_{2a}$, —(CHR)$_r$-carbocyclyl substituted with 0-3 R$_{2a}$, and heterocyclyl substituted with 0-3 R$_{2a}$;

R$_{2a}$, at each occurrence, is independently selected from C$_{1-4}$alkyl, C$_{2-4}$alkenyl, C$_{2-4}$alkynyl, C$_{1-4}$haloalkyl, —(CH$_2$)$_r$C$_{3-6}$cycloalkyl, F, Cl, Br, NO$_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$C(O)$_r$C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$(CHR)$_r$C(O)OR$_d$, —(CHR)$_r$carbocyclyl substituted with 0-3 R$_e$ and/or —(CHR)$_r$-heterocyclyl substituted with 0-3 R$_e$;

alternatively, R$_1$ and R$_2$ of Formula (III) are taken together with the ring atoms to which they are attached to form a fused carbocyclyl or heterocyclyl;

R$_3$ is selected from H, F, Cl, Br, NO$_2$, CN, C$_{1-4}$alkyl substituted with 0-3 R$_{3a}$, —O—C$_{1-4}$alkyl substituted with 0-3 R$_{3a}$, —O-aryl substituted with 0-3 R$_{3a}$, —(CHR)$_r$-aryl substituted with 0-3 R$_{3a}$, and —(CHR)$_r$-heterocyclyl substituted with 0-3 R$_{3a}$;

R$_{3a}$, at each occurrence, is independently selected from C$_{1-4}$alkyl, C$_{2-4}$alkenyl, C$_{2-4}$alkynyl, C$_{1-4}$haloalkyl, F, Cl, Br, NO$_2$, CN, —(CHR)$_r$OH, —(CHR)$_r$SH, —(CHR)$_r$O(CHR)$_r$R$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, (CHR)$_r$S(O)$_p$NR$_a$R$_a$, —(CHR)$_r$NR$_a$S(O)$_p$R$_b$, —(CHR)$_r$-aryl substituted with 0-3 R$_e$, and/or —(CHR)$_r$-heterocyclyl substituted with 0-3 R$_e$;

R$_4$ is selected from aryl substituted with 0-3 R$_{4a}$ and heterocyclyl substituted with 0-3 R$_{4a}$;

R$_{4a}$, at each occurrence, is independently selected from F, Cl, Br, C$_{1-4}$alkyl, —(CHR)$_r$OH, —(CHR)$_r$OR$_a$, —(CHR)$_r$SR$_b$, —(CHR)$_r$C(O)R$_d$, —(CHR)$_r$NR$_a$R$_a$, —(CHR)$_r$NHC (O)R$_d$—(CHR)$_r$C(O)NR$_a$R$_a$, —(CHR)$_r$—C$_{3-6}$-carbocyclyl substituted with 0-3 R$_e$, and/or —(CHR)$_r$-heterocyclyl substituted with 0-3 R$_e$.

R, at each occurrence, is independently selected from H, C$_{1-6}$alkyl, and/or C$_{1-6}$haloalkyl;

R$_a$, at each occurrence, is independently selected from H, NH$_2$, C$_{1-4}$alkyl substituted with 0-3 R$_e$, CF$_3$, —(CH$_2$)$_r$OH, —(CH$_2$)$_r$C$_{3-6}$cycloalkyl substituted with 0-3 R$_e$, —(CH$_2$)$_r$phenyl substituted with 0-3 R$_e$, and/or —(CH$_2$)$_r$heterocyclyl substituted with 0-3 R$_e$, or R$_a$, and R$_a$ together with the nitrogen atom to which they are both attached form a heterocyclyl substituted with 0-3 R$_e$;

R$_b$, at each occurrence, is independently selected from C$_{1-4}$alkyl substituted with 0-3 R$_e$, CF$_3$, phenyl substituted with 0-3 R$_e$, and/or heterocyclyl substituted with 0-3 R$_e$;

R$_c$, at each occurrence, is independently selected from C$_{1-4}$alkyl substituted with 0-3 R$_g$, C$_{2-4}$alkenyl substituted with 0-3 R$_g$, C$_{2-4}$alkynyl substituted with 0-3 R$_g$, C$_{1-4}$haloalkyl, —(CH$_2$)$_r$OH, —(CH$_2$)$_r$-aryl substituted with 0-3 R$_g$, —(CH$_2$)$_r$—C$_{3-10}$cycloalkyl substituted with 0-3 R$_g$ and/or —(CH$_2$)$_r$-heterocyclyl substituted with 0-3 R$_g$;

R$_d$, at each occurrence, is independently selected from H, C$_{1-4}$alkyl substituted with 0-3 R$_e$, C$_{2-4}$alkenyl substituted with 0-3 R$_e$, C$_{2-4}$alkynyl substituted with 0-3 R$_e$, CF$_3$, —(CH$_2$)$_r$phenyl substituted with 0-3 R$_e$, and/or heterocyclyl substituted with 0-3 R$_e$;

R$_e$, at each occurrence, is independently selected from C$_{1-4}$alkyl, C$_{3-6}$cycloalkyl, F, Cl, Br, CN, NO$_2$, —(CH$_2$)$_r$CO$_2$H, —(CH$_2$)$_r$C(O)NR$_f$R$_f$, —(CH$_2$)$_r$OC$_{1-4}$alkyl, OH, SH, —(CH$_2$)$_r$SC$_{1-5}$ alkyl, —(CH$_2$)$_r$phenyl and/or —(CH$_2$)$_r$heterocyclyl;

R$_f$, at each occurrence, is independently selected from H and/or C$_{1-5}$alkyl;

R$_g$, at each occurrence, is independently selected from C$_{1-4}$alkyl, —(CH$_2$)$_r$C$_{3-6}$cycloalkyl, F, Cl, Br, CN, NO$_2$, —(CH$_2$)$_r$OC$_{1-4}$alkyl, OH, and/or —(CH$_2$)$_r$phenyl; and r, at each occurrence, is independently selected from 0, 1, 2, and/or 3.

The present invention also provides at least one chemical entity chosen from compounds of formula (II) or (III), including enantiomers, diastereomers, prodrugs, solvates, hydrates, or pharmaceutically-acceptable salts thereof, wherein R$_1$ is —NH-aryl substituted with 0-3 R$_e$;

R$_4$ is selected from aryl substituted with 0-3 R$_{4a}$ and heterocyclyl substituted with 0-3 R$_{4a}$;

R$_{4a}$, at each occurrence, is independently selected from —(CH$_2$)$_r$OH, —OR$_c$, C$_{1-4}$alkyl, —NHC(O)R$_d$, —C(O)NHR$_a$, and/or NR$_a$R$_a$;

R$_a$, at each occurrence, is independently selected from H, NH$_2$, and/or C$_{1-4}$alkyl substituted with 0-3 R$_e$;

R$_c$, at each occurrence, is independently selected from C$_{1-4}$alkyl substituted with 0-3 R$_g$ and/or aryl substituted with 0-3 R$_g$;

R$_d$, at each occurrence, is independently selected from H, C$_{1-4}$alkyl substituted with 0-3 R$_e$ and/or phenyl substituted with 0-3 R$_e$;

R$_e$, at each occurrence, is independently selected from F, Cl, Br, and C$_{1-4}$alkyl; and R$_g$, at each occurrence, is independently selected from F, Cl, Br, OH, and/or C$_{1-4}$alkyl.

The present invention also provides at least one chemical entity chosen from compounds of formula (II) or (III), including enantiomers, diastereomers, prodrugs, solvates, hydrates, or pharmaceutically-acceptable salts thereof, wherein R$_4$ is substituted with 0-3 R$_{4a}$ and selected from pyrrolyl, pyrazolyl, imidazolyl, oxazolyl, isoxazolyl, thiazolyl, isothiazolyl, furyl, thienyl, piperidinyl, pyridyl, pyrazinyl, pyrimidinyl, triazolyl, indolyl, indazolyl, benzothiazolyl, benzoxazolyl, benzodioxolyl, benzothienyl, quinolinyl, isoquinolinyl, benzimidazolyl, benzofuryl, benzisothiazolyl, benzisoxazolyl, benzodiazinyl, and dibenzothienyl.

The present invention also provides at least one chemical entity chosen from compounds of formula (II) or (III), including enantiomers, diastereomers, prodrugs, solvates, hydrates, or pharmaceutically-acceptable salts thereof, wherein R$_4$ is selected from naphthyl and phenyl, each of which is substituted with 1-3 R$_{4a}$; and R$_{4a}$, at each occurrence, is independently selected from F, Cl, Br, C$_{1-4}$alkyl, —(CH$_2$)$_r$OH, —(CH$_2$)$_r$OR$_c$, and/or —(CH$_2$)$_r$SR$_b$).

The present application also provides at least one chemical entity chosen from the compounds of formula (IIa) and (IIa), including enantiomers, diastereomers, prodrugs, solvates, hydrates, or pharmaceutically-acceptable salts:

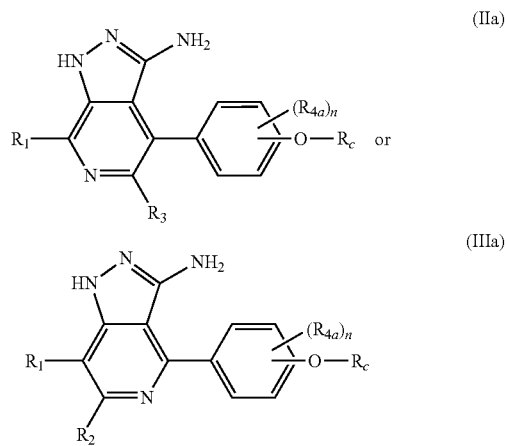

wherein

R$_1$ is selected from H, NHR$_a$, C$_{1-4}$alkyl substituted with 0-3 R$_{1a}$, —O—C$_{1-4}$alkyl, —O-aryl substituted with 0-3 R$_{1a}$, —(CH$_2$)$_r$aryl substituted with 0-3 R$_{1a}$, heterocyclyl substituted with 0-3 R$_{1a}$;

R$_{1a}$, at each occurrence, is independently selected from C$_{1-4}$alkyl substituted with 0-3 R$_e$, C$_{1-4}$haloalkyl, F, Cl, Br, —(CH$_2$)$_r$OH, —(CH$_2$)$_r$SH, —(CH$_2$)$_r$OR$_b$, —(CH$_2$)$_r$S(O)$_2$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$C(O)NHOR$_b$, —(CH$_2$)$_r$NHC(O)R$_d$, —(CH$_2$)$_r$NHC(O)OR$_b$, —(CH$_2$)$_r$OC(O)NR$_a$R$_a$, —(CH$_2$)$_r$C(O)OR$_d$, —(CH$_2$)$_r$S(O)$_2$NR$_a$R$_a$, —(CH$_2$)$_r$NHS(O)$_2$R$_b$, —(CH$_2$)$_r$NHP(O)$_p$R$_b$, —(CH$_2$)$_r$-phenyl substituted with 0-3 R$_e$ and/or —(CH$_2$)$_r$-heterocyclyl substituted with 0-3 R$_e$;

R$_2$ is selected from H, F, Cl, Br, NO$_2$, CN, NR$_a$R$_a$, C$_{1-4}$alkyl substituted with 0-3 R$_{2a}$, —O—C$_{1-4}$alkyl substituted with 0-3 R$_{2a}$, —O-aryl substituted with 0-3 R$_{2a}$, —(CH$_2$)$_r$-phenyl substituted with 0-3 R$_{2a}$, —(CH$_2$)$_r$—C$_{3-10}$ cycloalkyl substituted with 0-3 R$_{2a}$, and heterocyclyl substituted with 0-3 R$_{2a}$;

R$_{2a}$, at each occurrence, is independently selected from C$_{1-4}$alkyl, C$_{1-4}$haloalkyl, F, Cl, Br, NO$_2$, CN, —(CH$_2$)$_r$OH, —(CH$_2$)$_r$SH, —(CH$_2$)$_r$OR$_b$, —(CH$_2$)$_r$S(O)$_p$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$C(O)NR$_a$OR$_b$, —(CH$_2$)$_r$NHC(O)R$_d$, —(CH$_2$)$_r$NHC(O)NR$_a$R$_a$, —(CH$_2$)$_r$NHC(O)OR$_b$, —(CH$_2$)$_r$OC(O)NR$_a$R$_a$, —(CH$_2$)$_r$C(O)OR$_d$, —(CH$_2$)$_r$C(O)C(O)OR$_d$, —(CH$_2$)$_r$S(O)$_2$NR$_a$R$_a$, —(CH$_2$)$_r$NHS(O)$_2$R$_b$, —(CH$_2$)$_r$C(O)NHS(O)$_2$R$_d$, —(CH$_2$)$_r$C(O)NR$_a$(CH$_2$)$_r$C(O)OR$_d$, —(CH$_2$)$_r$C$_{3-6}$ cycloalkyl, —(CH$_2$)$_r$phenyl substituted with 0-3 R$_e$, and/or —(CH$_2$)$_r$-heterocyclyl substituted with 0-3 R$_e$;

R$_3$ is selected from H, C$_{1-4}$alkyl substituted with 0-3 R$_{3a}$, aryl substituted with 0-3 R$_{3a}$, and heterocyclyl substituted with 0-3 R$_{3a}$;

R$_{3a}$, at each occurrence, is independently selected from C$_{1-4}$alkyl, C$_{1-4}$haloalkyl, —(CH$_2$)$_r$OH, —(CH$_2$)$_r$OR$_b$, —(CH$_2$)$_r$S(O)$_2$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$NHC(O)R$_d$, —(CH$_2$)$_r$NHC(O)OR$_b$, —(CH$_2$)$_r$C(O)OR$_d$, —(CH$_2$)$_r$-phenyl substituted with 0-3 R$_e$ and/or —(CH$_2$)$_r$-heterocyclyl substituted with 0-3 R$_e$;

R$_a$, at each occurrence, is independently selected from H, NH$_2$, C$_{1-4}$alkyl substituted with 0-3 R$_e$, CF$_3$, —O—C$_{1-4}$alkyl, —(CH$_2$)$_r$OH, —(CH$_2$)$_r$C$_{3-6}$cycloalkyl substituted with 0-3 R$_e$, —(CH$_2$)$_r$phenyl substituted with 0-3 R$_e$, and/or —(CH$_2$)$_r$-heterocyclyl substituted with 0-3 R$_e$, or R$_a$ and R$_a$ together with the nitrogen atom to which they are both attached form a heterocyclyl substituted with 0-3 R$_e$;

R$_b$, at each occurrence, is independently selected from C$_{1-4}$alkyl substituted with 0-3 R$_e$, phenyl substituted with 0-3 R$_e$, and/or heterocyclyl substituted with 0-3 R$_e$;

R$_c$, at each occurrence, is independently selected from C$_{1-4}$alkyl substituted with 0-3 R$_g$, C$_{1-4}$haloalkyl, —(CH$_2$)$_r$—C$_{3-6}$cycloalkyl substituted with 0-3 R$_g$, —(CH$_2$)$_r$-aryl substituted with 0-3 R$_g$ and/or —(CH$_2$)$_r$-heterocyclyl substituted with 0-3 R$_g$;

R$_d$, at each occurrence, is independently selected from H, C$_{1-4}$alkyl substituted with 0-3 R$_e$, C$_{2-4}$alkenyl substituted with 0-3 R$_e$, —(CH$_2$)$_r$phenyl substituted with 0-3 R$_e$, and/or heterocyclyl substituted with 0-3 R$_e$;

R$_e$, at each occurrence, is independently selected from C$_{1-4}$alkyl, C$_{3-6}$cycloalkyl, F, Cl, Br, CN, NO$_2$, —(CH$_2$)$_r$CO$_2$H, —(CH$_2$)$_r$C(O)NR$_f$(C$_{1-4}$alkyl), —(CH$_2$)$_r$OC$_{1-5}$alkyl, OH, SH, —(CH$_2$)$_r$SC$_{1-4}$alkyl, (CH$_2$)$_r$phenyl and/or —(CH$_2$)$_r$heterocyclyl;

R$_g$, at each occurrence, is independently selected from C$_{1-4}$alkyl, F, Cl, Br, CN, NO$_2$, —(CH$_2$), OC$_{1-4}$alkyl, OH, and/or —(CH$_2$)$_r$phenyl;

r, at each occurrence, is independently selected from 0, 1, and/or 2; and n, at each occurrence, is independently selected from 0, 1, and/or 2.

The present invention further provides at least one chemical entity chosen from compounds of formula (IIb) or (IIIb), including enantiomers, diastereomers, prodrugs, solvates, hydrates, or pharmaceutically-acceptable salts thereof:

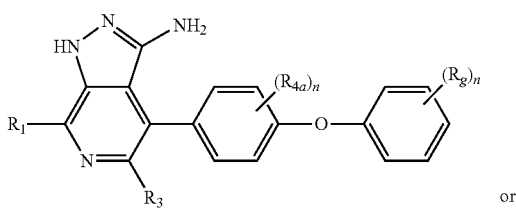

(IIb)

or

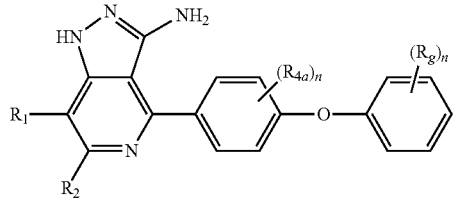

(IIIb)

in which

R$_1$ is selected from H, NHR$_a$, C$_{1-4}$alkyl substituted with 0-3 R$_{1a}$, —O—C$_{1-4}$alkyl, —(CH$_2$)$_r$aryl substituted with 0-3 R$_{1a}$, and heterocyclyl substituted with 0-3 R$_{1a}$;

R$_{1a}$, at each occurrence, is independently selected from C$_{1-4}$alkyl substituted with 0-3 R$_e$, CF$_3$, F, Cl, Br, —(CH$_2$)$_r$OH, —(CH$_2$)$_r$OR$_b$, —(CH$_2$)$_r$S(O)$_2$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$NHC(O)R$_d$, —(CH$_2$)$_r$NHC(O)OR$_b$, —(CH$_2$)$_r$C(O)OR$_d$, —(CH$_2$)$_r$S(O)$_2$NR$_a$R$_a$, —(CH$_2$)$_r$NHS(O)$_2$R$_b$, —(CH$_2$)$_r$-phenyl substituted with 0-3 R$_e$ and/or —(CH$_2$)$_r$-heterocyclyl substituted with 0-3 R$_e$;

R$_2$ is selected from H, F, Cl, Br, NHR$_a$, C$_{1-4}$alkyl substituted with 0-3 R$_{2a}$, —(CH$_2$)$_r$-aryl substituted with 0-3 R$_{2a}$, —(CH$_2$)$_r$—C$_{3-10}$ cycloalkyl substituted with 0-3 R$_{2a}$, and heterocyclyl substituted with 0-3 R$_{2a}$;

R$_{2a}$, at each occurrence, is independently selected from C$_{1-4}$alkyl, C$_{1-4}$haloalkyl, F, Cl, Br, NO$_2$, CN, —(CH$_2$)$_r$OH, —(CH$_2$)$_r$OR$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$NHC(O)R$_d$, —(CH$_2$)$_r$NHC(O)NR$_a$R$_a$, —(CH$_2$)$_r$C(O)OR$_d$, —(CH$_2$)$_r$C(O)C(O)OR$_d$, —(CH$_2$)$_r$C(O)NHS(O)$_2$R$_b$, —(CH$_2$)$_r$C(O)NR$_a$(CH$_2$)$_r$C(O)OR$_d$, —(CH$_2$)$_r$phenyl substituted with 0-3 R$_e$, and/or —(CH$_2$)$_r$-heterocyclyl substituted with 0-3 R$_e$;

R$_3$ is selected from H, C$_{1-4}$alkyl substituted with 0-3 R$_{3a}$, phenyl substituted with 0-3 R$_{3a}$, and heterocyclyl substituted with 0-3 R$_{3a}$;

R$_{3a}$, at each occurrence, is independently selected from —(CH$_2$)$_r$OR$_b$ and —(CH$_2$)$_r$C(O)NR$_a$R$_a$;

R$_a$, at each occurrence, is independently selected from H, NH$_2$, C$_{1-4}$alkyl substituted with 0-3 R$_e$, —(CH$_2$)$_r$OH, —(CH$_2$)$_r$C$_{3-6}$cycloalkyl substituted with 0-3 R$_e$, —(CH$_2$)$_r$phenyl substituted with 0-3 R$_e$, and/or —(CH$_2$)$_r$heterocyclyl substituted with 0-3 R$_e$, or R$_a$ and R$_a$ together with the nitrogen atom to which they are both attached form a heterocyclyl substituted with 0-3 R$_e$;

R$_b$, at each occurrence, is independently selected from C$_{1-4}$alkyl substituted with 0-3 R$_e$, phenyl substituted with 0-3 R$_e$, and/or heterocyclyl substituted with 0-3 R$_e$;

R$_d$, at each occurrence, is independently selected from H, C$_{1-4}$alkyl substituted with 0-3 R$_e$, C$_{2-4}$alkenyl substituted with 0-3 R$_e$, —(CH$_2$)$_r$phenyl substituted with 0-3 R$_e$, and/or heterocyclyl substituted with 0-3 R$_e$;

R$_e$, at each occurrence, is independently selected from F, Cl, C$_{1-4}$alkyl, —(CH$_2$)$_r$CO$_2$H, and/or —(CH$_2$)$_r$C(O)N(CH$_3$)$_2$;

R$_g$, at each occurrence, is independently selected from F, Cl, Br, OH, C$_{1-4}$alkyl, and/or —OC$_{1-4}$alkyl;

r, at each occurrence, is independently selected from 0, 1, and/or 2; and n, at each occurrence, is independently selected from 0, 1, and/or 2.

The present invention further provides at least one chemical entity chosen from compounds of formula (IV), including enantiomers, diastereomers, prodrugs, solvates, hydrates, or pharmaceutically-acceptable salts:

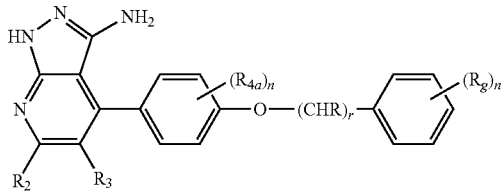

(IV)

wherein $R_2$ is selected from H, —O-aryl wherein said aryl is substituted with 0-3 $R_{2a}$, —O—$C_{1-4}$alkyl wherein said alkyl is substituted with 0-3 $R_{2a}$, $NR_aR_a$, $C_{3-6}$cycloalkyl substituted with 0-3 $R_{2a}$, aryl substituted with 0-3 $R_{2a}$, and heterocyclyl substituted with 0-3 $R_{2a}$;

$R_{2a}$, at each occurrence, is independently selected from $C_{1-6}$alkyl, $C_{2-6}$alkenyl, $C_{2-6}$alkynyl, $C_{1-6}$haloalkyl, —$(CH_2)_rC_{3-6}$cycloalkyl, F, Cl, Br, $NO_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$NR$_a$C(O)R$_a$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$C(O)OR$_d$, —(CHR)$_r$-aryl substituted with 0-5 R$_e$ and/or —(CHR)$_r$-heterocyclyl substituted with 0-5 R$_e$;

$R_3$ is selected from H, F, Cl, Br, $NO_2$, CN, —(CHR)$_r$-aryl substituted with 0-3 $R_{3a}$, —O—$C_{1-4}$alkyl, —O-aryl substituted with 0-3 $R_{3a}$, and —(CHR)$_r$heterocyclyl substituted with 0-3 $R_{3a}$;

$R_{3a}$, at each occurrence, is selected from $C_{1-4}$alkyl, $C_{2-4}$alkenyl, $C_{2-4}$alkynyl, $C_{1-4}$haloalkyl, —$(CH_2)_rC_{3-6}$cycloalkyl, F, Cl, Br, $NO_2$, CN, —(CHR)$_r$OH;

$R_a$, at each occurrence, is independently selected from H, $NH_2$, $C_{1-4}$alkyl substituted with 0-3 $R_e$, $CF_3$, —O—$C_{1-6}$alkyl, —$(CH_2)_r$OH, $C_{3-6}$cycloalkyl substituted with 0-3 $R_e$, phenyl substituted with 0-3 $R_e$, and/or heterocyclyl substituted with 0-3 $R_e$, or $R_a$ and $R_a$ together with the nitrogen atom to which they are both attached form a heterocyclyl substituted with 0-3 $R_e$;

$R_b$, at each occurrence, is independently selected from $C_{1-4}$alkyl, $CF_3$, phenyl substituted with 0-3 $R_e$, and/or heterocyclyl substituted with 0-3 $R_e$;

$R_d$, at each occurrence, is independently selected from H, $C_{1-4}$alkyl, $CF_3$, phenyl substituted with 0-3 $R_e$, and/or heterocyclyl substituted with 0-3 $R_e$;

$R_e$, at each occurrence, is independently selected from $C_{1-4}$alkyl, $C_{3-6}$cycloalkyl, F, Cl, Br, CN, $NO_2$, $NH_2$, $CO_2H$, —$(CH_2)_r$OC$_{1-5}$alkyl, OH, SH, (CH)$_r$SC$_{1-5}$alkyl, $(CH_2)_r$phenyl and/or $(CH_2)_r$heterocyclyl;

$R_g$, at each occurrence, is independently selected from $C_{1-4}$alkyl, F, Cl, Br, CN, $NO_2$, —$(CH_2)_r$OC$_{1-4}$alkyl, and/or OH;

r, at each occurrence, is independently selected from 0, 1, and/or 2; and n, at each occurrence, is independently selected from 0, 1, 2, and/or 3.

In one embodiment, $R_2$ is selected from $C_{3-6}$cycloalkyl, —NH—$C_{3-6}$cycloalkyl, —O-phenyl, phenyl, pyrrole, piperidine, piperazine, and pyridine, each ring substituted with 0-2 $R_{2a}$; and $R_{2a}$ at each occurrence, is independently selected from —O—$C_{1-4}$alkyl, OH, $NH_2$, —NHC(O)O—$C_{1-4}$alkyl, —NHC(O)—$C_{1-4}$alkyl, —NHC(O)NH-heteroaryl, —NHC(O)-phenyl unsubstituted or substituted with $C_{1-4}$alkyl, —C(O)—$C_{1-4}$alkyl, —C(O)-phenyl, —C(O)NH-phenyl, —C(O)NH—$C_{3-6}$cycloalkyl, —C(O)NH-heterocyclyl, —C(O)NH—$NH_2$, and/or —C(O)NR$_a$R$_a$ wherein $R_a$ and $R_a$ may be taken together with the nitrogen atom to which they are attached to form a 5- to 6-membered heterocyclyl.

The present invention further provides at least one chemical entity chosen from compounds of formula (V), including enantiomers, diastereomers, prodrugs, solvates, hydrates, or pharmaceutically-acceptable salts:

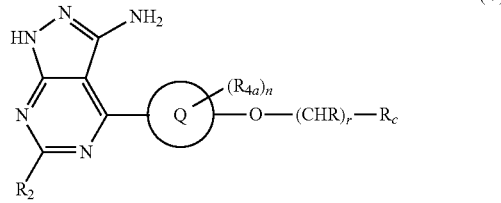

(V)

wherein $R_2$ is selected from H, F, Cl, Br, $NO_2$, CN, $NR_aR_a$, $C_{1-6}$alkyl, —(CHR)$_r$-carbocyclyl substituted with 0-5 $R_{2a}$, —O—$C_{1-6}$alkyl, —O—(CHR)$_r$-carbocyclyl substituted with 0-5 $R_{2a}$, heterocyclyl substituted with 0-5 $R_{2a}$;

$R_{2a}$, at each occurrence, is independently selected from $C_{1-4}$alkyl, $C_{2-4}$alkenyl, $C_{2-4}$alkynyl, $C_{1-4}$haloalkyl, F, Cl, Br, $NO_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$(CHR)$_r$C(O)OR$_d$, —(CHR)$_r$C$_{3-6}$-carbocyclyl substituted with 0-3 $R_e$ and/or —(CHR)$_r$C$_{3-6}$heterocyclyl substituted with 0-3 $R_e$;

Q is selected from aryl and heteroaryl;

$R_{4a}$ is selected from F, Cl, Br, OH, and $C_{1-6}$alkyl;

$R_a$, at each occurrence, is independently selected from H, $NH_2$, $C_{1-4}$alkyl substituted with 0-3 $R_e$, $CF_3$, —O—$C_{1-6}$alkyl, —$(CH_2)_r$OH, $C_{3-6}$cycloalkyl substituted with 0-3 $R_e$, phenyl substituted with 0-3 $R_e$, and/or heterocyclyl substituted with 0-3 $R_e$, or $R_a$ and $R_a$ together with the nitrogen atom to which they are both attached form a heterocyclyl substituted with 0-3 $R_e$;

$R_b$, at each occurrence, is independently selected from $C_{1-4}$alkyl, $CF_3$, phenyl substituted with 0-3 $R_e$, and/or heterocyclyl substituted with 0-3 $R_e$;

$R_c$ is selected from $C_{3-6}$cycloalkyl substituted with 0-3 $R_g$, aryl substituted with 0-3 $R_g$, and heterocyclyl substituted with 0-3 $R_g$;

$R_d$, at each occurrence, is independently selected from H, $C_{1-4}$alkyl, $CF_3$, phenyl substituted with 0-3 $R_e$, and/or heterocyclyl substituted with 0-3 $R_e$;

$R_e$, at each occurrence, is independently selected from $C_{1-4}$alkyl, $C_{3-6}$cycloalkyl, F, Cl, Br, CN, $NO_2$, $CO_2H$, —$(CH_2)_r$OC$_{1-5}$alkyl, OH, SH, —$(CH_2)_r$SC$_{1-5}$alkyl, —$(CH_2)_r$phenyl and/or —$(CH_2)_r$heterocyclyl;

$R_g$, at each occurrence, is independently selected from F, Cl, Br, OH, $C_{1-6}$alkyl, and/or —OC$_{1-5}$alkyl;

n, at each occurrence, is independently selected from 0, 1, and/or 2; and r, at each occurrence, is independently selected from 0, 1, and/or 2.

The present invention further provides at least one chemical entity chosen from compounds of formula (V), including enantiomers, diastereomers, prodrugs, solvates, hydrates, or pharmaceutically-acceptable salts, wherein Q is phenyl;

$R_2$ is selected from F, Cl, Br, $NO_2$, CN, $NR_aR_a$, —(CHR)$_r$—$C_{3-10}$cycloalkyl substituted with 0-3 $R_{2a}$, —(CHR)$_r$-aryl substituted with 0-3 $R_{2a}$, —O—$C_{1-4}$alkyl, —O—(CHR)$_r$-aryl substituted with 0-3 $R_{2a}$, and heterocyclyl substituted with 0-3 $R_{2a}$;

$R_{2a}$, at each occurrence, is independently selected from $C_{1-4}$alkyl, $C_{1-4}$haloalkyl, F, Cl, Br, $NO_2$, CN, —OH, —SH, —OR$_b$, —S(O)$_2$R$_b$, —C(O)R$_d$, —NR$_a$R$_a$, —C(O)NR$_a$R$_a$, —C(O)NR$_a$OR$_b$, —NHC(O)R$_d$, —NHC(O)NR$_a$R$_a$, —NHC(O)OR$_b$, —OC(O)NR$_a$R$_a$, —C(O)OR$_d$, —S(O)$_2$NR$_a$R$_a$, —NHS(O)$_2$R$_b$, —C(O)NHS(O)$_2$R$_b$, —C(O)NR$_a$(CH$_2$)$_r$C(O)OR$_d$, $C_{3-6}$cycloalkyl substituted with 0-3 $R_e$, phenyl substituted with 0-3 $R_e$ and/or heterocyclyl substituted with 0-3 $R_e$;

$R_c$ is phenyl substituted with 0-3 $R_g$; and r, at each occurrence, is independently selected from 0 and/or 1.

The present invention further provides at least one chemical entity chosen from compounds of formula (V), including enantiomers, diastereomers, prodrugs, solvates, hydrates, or pharmaceutically-acceptable salts, wherein $R_4$ is phenyl substituted with 0-2 $R_{4a}$;

$R_c$ is phenyl substituted with 0-3 $R_e$; $R_e$ is selected from methyl, ethyl, $C_{3-6}$cycloalkyl, F, Cl, Br, CN, $NO_2$, $CO_2H$, OH, SH, $C_{1-5}$alkyl, (CH$_2$)$_r$phenyl and (CH$_2$)$_r$heterocyclyl; and r is zero.

All aspects of the compounds described herein, including individual variable definitions, may be combined with other aspects to form other preferred compounds. For example, in one embodiment, $A_1$ is N, $A_2$ is $CR_2$, $A_3$ is $CR_3$, $R_4$ is phenyl substituted with —OR$_c$ wherein $R_c$ is substituted or unsubstituted phenyl. In another embodiment, $A_1$ is $CR_1$, $A_2$ is N, $A_3$ is $CR_3$, $R_4$ is phenyl substituted with —OR$_c$ wherein $R_c$ is substituted or unsubstituted phenyl. In still another embodiment, $A_1$ is $CR_1$, $A_2$ is $CR_2$, $A_3$ is N, $R_4$ is phenyl substituted with —OR$_c$ wherein $R_c$ is substituted or unsubstituted phenyl. In still another embodiment, $A_1$ and $A_3$ are both N, $A_2$ is $CR_2$, $R_4$ is phenyl substituted with —OK wherein $R_c$ is substituted or unsubstituted phenyl.

In one embodiment of the compounds of Formulae (I) and (IV), $R_4$ is phenyl substituted with —O—(CH$_2$)$_r$—R$_c$ wherein $R_c$ is phenyl substituted with one or more of any substituents defined or exemplified herein, r is zero, 1, or 2; $R_2$ is selected from H and $C_{3-6}$cycloalkyl substituted with 0-3 $R_{2a}$ Non-limiting examples of $C_{3-6}$cycloalkyl include cyclopropyl, cyclobutyl, cyclopentyl, cyclohexyl, and cycloheptyl.

In another embodiment of the compounds of Formulae (I) and (IV), $R_4$ is phenyl substituted with —O—(CH$_2$)$_r$—R$_c$ wherein $R_c$ is phenyl substituted with one or more of any substituents defined or exemplified herein, r is zero, 1, or 2; $R_2$ is aryl substituted with 0-3 $R_{2a}$. In a particular embodiment, $R_2$ is phenyl optionally substituted with one or more of $R_{2a}$ defined or exemplified herein. $R_{2a}$ may be —O—$C_{1-4}$alkyl. Non-limiting examples of $C_{1-4}$alkyl include methyl, ethyl, propyl, butyl, and t-butyl. $R_{2a}$ may also be —OH, —C(O)R$_d$, —C(O)OR$_d$, —NHC(O)R$_d$, wherein $R_d$ is H, $C_{1-4}$alkyl, aryl, and heterocyclo. $R_{2a}$ may also be —C(O)NR$_a$R$_a$, —NR$_a$R$_a$, or —NR$_a$C(O)NR$_a$R$_a$, wherein $R_a$ is H, $C_{1-4}$alkyl, $C_{3-6}$cycloalkyl, aryl, and heterocyclo, or $R_a$ and $R_a$ together with the nitrogen atom to which they are attached form a 5- or 6-membered heterocyclyl.

In another embodiment of the compounds of Formulae (I) and (IV), $R_4$ is phenyl substituted with —O—(CH$_2$)$_r$—R$_c$ wherein $R_c$ is phenyl substituted with one or more of any substituents defined or exemplified herein, r is zero, 1, or 2; $R_2$ is heterocyclyl optionally substituted with one or more of $R_{2a}$ defined or exemplified herein. Non-limiting examples of heterocyclyl include pyridinyl, furanyl, thienyl, pyrrolyl, pyrazolyl, pyrazinyl, pyrrolidinyl, imidazolinyl, oxazolidinyl, isoxazolinyl, thiazolidinyl, isothiazolidinyl, tetrahydrofuranyl, piperidyl, piperazinyl, piperidonyl, tetrahydropyranyl, and morpholinyl. $R_{2a}$ may be —O—$C_{1-4}$alkyl. Non-limiting examples of $C_{1-4}$alkyl include methyl, ethyl, propyl, butyl, and t-butyl. $R_{2a}$ may also be —OH, —C(O)R$_d$, —C(O)OR$_d$, —NHC(O)R$_d$, wherein $R_d$ is H, $C_{1-4}$alkyl, aryl, and heterocyclo. $R_{2a}$ may also be —C(O)NR$_a$R$_a$, —NR$_a$R$_a$, or —NR$_a$C(O)NR$_a$R$_a$, wherein $R_a$ is H, $C_{1-4}$alkyl, $C_{3-6}$cycloalkyl, aryl, and heterocyclo. Alternatively, $R_a$ and $R_a$ together with the nitrogen atom to which they are attached form a 5- or 6-membered heterocyclyl. Non-limiting examples of the heterocyclyl formed by $R_a$ and $R_a$ may include pyrrolidinyl, imidazolinyl, thiazolidinyl, isothiazolidinyl, piperidyl, piperazinyl, azepinyl, and morpholinyl.

In another embodiment of the compounds of Formulae (I) and (IV), $R_4$ is phenyl substituted with —O—(CH$_2$)$_r$—R$_c$ wherein $R_c$ is phenyl substituted with one or more of any substituents defined or exemplified herein, r is zero, 1, or 2; $R_2$ is —O-alkyl optionally substituted with $R_{2a}$, —O-aryl optionally substituted with $R_{2a}$ or $NR_aR_a$ wherein $R_{2a}$ may be OH or —O—$C_{1-4}$alkyl and $R_a$ is H, $C_{1-4}$alkyl, $C_{3-6}$cycloalkyl, aryl, and heterocyclo. Alternatively, $R_a$ and $R_a$ together with the nitrogen atom to which they are attached form a 5- or 6-membered heterocyclyl optionally substituted with $R_e$.

In another embodiment of the compounds of Formulae (I), (II), and (III), $R_4$ is aryl optionally substituted with $R_{4a}$. In a particular embodiment, $R_4$ is optionally substituted phenyl or naphthyl. $R_{4a}$ is selected from F, Cl, Br, $C_{1-4}$alkyl, —(CH$_2$)$_r$OH, —OR$_c$, $C_{1-4}$alkyl, —C(O)NR$_a$R$_a$, SR$_b$, $NR_aR_a$, and —(CH$_2$)$_r$-aryl. $R_a$ is selected from H, $C_{1-4}$alkyl, $C_{3-6}$cycloalkyl, aryl, and heterocyclo or $R_a$ and $R_a$ together with the nitrogen atom to which they are attached form an optionally substituted 5- or 6-membered heterocyclyl; $R_b$ is $C_{1-4}$alkyl; $R_a$ is selected from $C_{1-4}$alkyl, $C_{1-4}$haloalkyl, $C_{3-6}$cycloalkyl, and aryl, each group substituted with one or more of any substituents defined or exemplified herein.

In another embodiment of the compounds of Formulae (I), (IIa), (IIb) (IIIa), and (IIIb), $R_1$ is selected from H, F, Cl, Br, $NR_aR_a$, $C_{1-4}$alkyl substituted with 0-3 $R_{1a}$, —O—$C_{1-4}$alkyl, —O-aryl substituted with 0-3 $R_{1a}$, —(CHR)$_r$-aryl substituted with 0-3 $R_{1a}$, —(CHR)$_r$-heterocyclyl substituted with 0-3 $R_{1a}$.

In another embodiment of the compounds of Formulae (I), (IIa), (IIb) (IIIa), and (IIIb), $R_1$ is selected from H, $NHR_a$, $C_{1-4}$alkyl substituted with 0-3 $R_{1a}$, —O—$C_{1-4}$alkyl, —O-aryl substituted with 0-3 $R_{1a}$, —(CH$_2$)$_r$aryl substituted with 0-3 $R_{1a}$, heterocyclyl substituted with 0-3 $R_{1a}$, wherein aryl is any aryl defined or exemplified herein, and, when present, the substituents on said aryl include one or more of any substituents defined or exemplified herein.

In another embodiment of the compounds of Formulae (I), (IIa), (IIb) (IIIa), and (IIIb), $R_1$ is selected from phenyl or naphthyl substituted with 0-3 $R_{1a}$. $R_{1a}$ is selected from $C_{1-4}$alkyl substituted with 0-3 $R_e$, $CF_3$, F, Cl, Br, —(CH$_2$)$_r$OH, —(CH$_2$)$_r$OR$_b$, —(CH$_2$)$_r$S(O)$_2$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$NHC(O)R$_d$, —(CH$_2$)$_r$NHC(O)OR$_b$, —(CH$_2$)$_r$C(O)OR$_d$, —(CH$_2$)$_r$S(O)$_2$NR$_a$R$_a$, —(CH$_2$)$_r$NHS(O)$_2$R$_b$, —(CH$_2$)$_r$-phenyl substituted with 0-3 $R_e$ and/or —$(CH_2)_r$-heterocyclyl substituted with 0-3 $R_e$. $R_a$, $R_b$, $R_d$, and $R_e$ are as defined or exemplified herein.

In another embodiment of the compounds of Formulae (I), (IIa), (IIb) (IIIa), and (IIIb), $R_1$ is selected from heteroaryl substituted with 0-3 $R_{1a}$, wherein heteroaryl is any heteroaryl defined or exemplified herein. Non-limiting examples of heteroaryl include pyrrolyl, pyrazolyl, imidazolyl, oxazolyl, isoxazolyl, thiazolyl, isothiazolyl, furyl, thienyl, piperidinyl, pyridyl, pyrazinyl, pyrimidinyl, triazolyl, indolyl, indazolyl, benzothiazolyl, benzoxazolyl, benzodioxolyl, benzothienyl, quinolinyl, isoquinolinyl, benzimidazolyl, benzofuryl, benzisothiazolyl, benzisoxazolyl, benzodiazinyl, and dibenzothienyl. $R_{1a}$ is selected from $C_{1-4}$alkyl substituted with 0-3 $R_e$, $CF_3$, F, Cl, Br, —$(CH_2)_r$OH, —$(CH_2)_r$OR$_b$, —$(CH_2)_r$S(O)$_2$R$_b$, —$(CH_2)_r$C(O)R$_a$, —$(CH_2)_r$NR$_a$R$_a$, —$(CH_2)_r$C(O)NR$_a$R$_a$, —$(CH_2)_r$NHC(O)R$_d$, —$(CH_2)_r$NHC(O)OR$_b$, —$(CH_2)_r$C(O)OR$_d$, —$(CH_2)_r$S(O)$_2$NR$_a$R$_a$, —$(CH_2)_r$NHS(O)$_2$R$_b$, —$(CH_2)_r$-phenyl substituted with 0-3 $R_e$ and/or —$(CH_2)_r$-heterocyclyl substituted with 0-3 $R_e$. $R_a$, $R_b$, $R_d$, and $R_e$ are as defined or exemplified herein.

In another embodiment of the compounds of Formulae (I), (IIa), (IIb) (IIIa), and (IIIb), $R_1$ is $NHR_a$, wherein $R_a$ is selected from H, $NH_2$, $C_{1-4}$alkyl substituted with 0-3 $R_e$.

In another embodiment of the compounds of Formulae (I) and (V), $R_2$ is selected from H, F, Cl, Br, $NO_2$, CN, $NR_aR_a$, $C_{1-6}$alkyl, —(CHR)$_r$carbocyclyl substituted with 0-5 $R_{2a}$, —O—$C_{1-6}$alkyl, —O—(CHR)$_r$-carbocyclyl substituted with 0-5 $R_{2a}$, heterocyclyl substituted with 0-5 $R_{2a}$; $R_{2a}$ is selected from $C_{1-4}$alkyl, $C_{2-4}$alkenyl, $C_{2-4}$alkynyl, $C_{1-4}$haloalkyl, F, Cl, Br, $NO_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$(CHR)$_r$C(O)OR$_d$, —(CHR)$_r$C$_{3-6}$-carbocyclyl substituted with 0-3 $R_e$ and/or —(CHR)$_r$C$_{3-6}$heterocyclyl substituted with 0-3 $R_e$.

In another embodiment of the compounds of Formulae (I), (IIa), (IIb) (IIIa), and (IIIb), $R_1$ is —NH-aryl substituted with 0-3 $R_e$; $R_4$ is selected from aryl substituted with 0-3 $R_{4a}$; $R_{4a}$ is selected from —$(CH_2)_r$OH, —OR$_c$, $C_{1-4}$alkyl, —NHC(O)R$_d$, —C(O)NHR$_a$, $NR_aR_a$, and/or —$(CH_2)_r$—SR$_b$. In a particular embodiment, $R_4$ is phenyl or naphthyl.

In another embodiment of the compounds of Formulae (I), (II), and (III), $R_1$ is —NH-aryl substituted with 0-3 $R_e$; $R_4$ is selected from heterocyclyl substituted with 0-3 $R_{4a}$; $R_{4a}$ is selected from —$(CH_2)_r$OH, —OR$_a$, $C_{1-4}$alkyl, —NHC(O)R$_d$, —C(O)NHR$_a$NR$_a$R$_a$, and/or —$(CH_2)_r$SR$_b$. Non-limiting examples of heterocyclyl include pyrrolyl, pyrazolyl, imidazolyl, furyl, thienyl, piperidinyl, pyridyl, pyrazinyl, pyrimidinyl, triazolyl, indolyl, indazolyl, quinolinyl, isoquinolinyl, benzimidazolyl, benzofuryl, benzisothiazolyl, benzisoxazolyl, benzodiazinyl, and dibenzothienyl.

In another embodiment of the compounds of Formulae (I), (IIa), (IIb) (IIIa), and (IIIb), $R_2$ is selected from H, F, Cl, Br, $NO_2$, CN, $NR_aR_a$, $C_{3-4}$alkyl substituted with 0-3 $R_{2a}$, —O—$C_{1-4}$alkyl substituted with 0-3 $R_{2a}$, —O-aryl substituted with 0-3 $R_{2a}$, —$(CH_2)_r$-phenyl substituted with 0-3 $R_{2a}$, —$(CH_2)_r$—$C_{3-10}$ cycloalkyl substituted with 0-3 $R_{2a}$, and heterocyclyl substituted with 0-3 $R_{2a}$.

In another embodiment of the compounds of Formulae (I), (IIa), (IIb) (IIIa), and (IIIb), $R_2$ is selected from H, F, Cl, Br, $NHR_a$, $C_{1-4}$alkyl substituted with 0-3 $R_{2a}$, —$(CH_2)_r$-aryl substituted with 0-3 $R_{2a}$, —$(CH_2)_r$—$C_{3-10}$ cycloalkyl substituted with 0-3 $R_{2a}$, and heterocyclyl substituted with 0-3 $R_{2a}$.

In another embodiment of the compounds of Formulae (I), (IIa), (IIb) (IIIa), and (IIIb), $R_2$ is selected from phenyl or naphthyl, each substituted with 0-3 $R_{2a}$. $R_{2a}$, at each occurrence, is independently selected from $C_{1-4}$alkyl, $C_{1-4}$haloalkyl, F, Cl, Br, $NO_2$, CN, —$(CH_2)_r$OH, —$(CH_2)_r$SH, —$(CH_2)_r$OR$_b$, —$(CH_2)_r$S(O)$_p$R$_b$, —$(CH_2)_r$C(O)R$_d$, —$(CH_2)_r$NR$_a$R$_a$, —$(CH_2)_r$C(O)NR$_a$R$_a$, —$(CH_2)_r$C(O)NR$_a$OR$_b$, —$(CH_2)_r$NHC(O)R$_d$, —$(CH_2)_r$NHC(O)NR$_a$R$_a$, —$(CH_2)_r$NHC(O)OR$_b$, —$(CH_2)_r$OC(O)NR$_a$R$_a$, —$(CH_2)_r$C(O)OR$_d$, —$(CH_2)_r$C(O)C(O)OR$_d$, —$(CH_2)_r$S(O)$_2$NR$_a$R$_a$, —$(CH_2)_r$NHS(O)$_2$R$_b$, —$(CH_2)_r$C(O)NHS(O)$_2$R$_b$, —$(CH_2)_r$C(O)NR$_a$(CH$_2$)$_r$C(O)OR$_d$, —$(CH_2)_r$C$_{3-6}$cycloalkyl, —$(CH_2)_r$phenyl substituted with 0-3 $R_e$, and/or —$(CH_2)_r$-heterocyclyl substituted with 0-3 $R_e$; $R_a$, $R_b$, $R_d$, and $R_e$ are as defined or exemplified herein.

In another embodiment of the compounds of Formulae (I), (IIa), (IIb) (IIIa), and (IIIb), $R_2$ is selected from heteroaryl substituted with 0-3 $R_{2a}$, wherein heteroaryl is any heteroaryl defined or exemplified herein. Non-limiting examples of heteroaryl include pyrrolyl, pyrazolyl, imidazolyl, oxazolyl, isoxazolyl, thiazolyl, isothiazolyl, furyl, thienyl, piperidinyl, pyridyl, pyrazinyl, pyrimidinyl, triazolyl, indolyl, indazolyl, benzothiazolyl, benzoxazolyl, benzodioxolyl, benzothienyl, quinolinyl, isoquinolinyl, benzimidazolyl, benzofuryl, benzisothiazolyl, benzisoxazolyl, benzodiazinyl, and dibenzothienyl. $R_{2a}$ is selected from $C_{1-4}$alkyl, $C_{1-4}$haloalkyl, F, Cl, Br, $NO_2$, CN, —$(CH_2)_r$OH, —$(CH_2)_r$OR$_b$, —$(CH_2)_r$C(O)R$_d$, —$(CH_2)_r$NR$_a$R$_a$, —$(CH_2)_r$C(O)NR$_a$R$_a$, —$(CH_2)_r$NHC(O)R$_d$, —$(CH_2)_r$NHC(O)NR$_a$R$_a$, —$(CH_2)_r$C(O)OR$_d$, —$(CH_2)_r$C(O)C(O)OR$_d$, —$(CH_2)_r$C(O)NHS(O)$_2$R$_b$, —$(CH_2)_r$C(O)NR$_a$(CH$_2$)$_r$C(O)OR$_d$, —$(CH_2)_r$phenyl substituted with 0-3 $R_e$, and/or —$(CH_2)_r$-heterocyclyl substituted with 0-3 $R_e$. $R_a$, $R_b$, $R_d$, and $R_e$ are as defined or exemplified herein.

In another embodiment of the compounds of Formulae (I), (IIa), (IIb) (IIIa), and (IIIb), $R_3$ is selected from H, substituted with 0-3 $R_{3a}$, aryl substituted with 0-3 $R_{3a}$, and heterocyclyl substituted with 0-3 $R_{3a}$.

In another embodiment of the compounds of Formulae (I), (IIa), (IIb) (IIIa), and (IIIb), $R_3$ is selected from H, phenyl substituted with 0-3 $R_{3a}$, and heterocyclyl substituted with 0-3 $R_{3a}$;

In another embodiment, the present invention provides a process of preparing a compound of formula (I), comprising a step of reacting a compound of the formula:

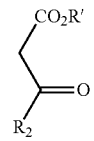

with a compound of the formula:

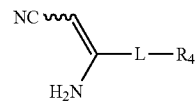

under microwave heating conditions to provide a compound of the formula:

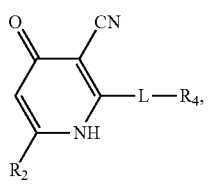

wherein R' may be without limitation an alkyl group, $R_2$, $R_4$ and L having meaning as defined above.

In another embodiment, the present invention provides a compound selected from the group consisting of Examples 1 to 263 and any subset list of the compounds within the group.

The compounds of formula (I), (II), (IIa), (IIb), (III), (IIIa), (IIIb), (IV), or (V) may exist in a free form (with no ionization) or can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I), (II), (IIa), (IIb), (III), (IIIa), (IIIb), (IV), or (V) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I), (II), (IIa), (IIb), (III), (IIIa), (IIIb), (IV), or (V) may be formed, for example, by reacting a compound of the formula (I), (II), (IIa), (IIb), (III), (IIIa), (IIIb), (IV), or (V) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Compounds of the formula (I), (II), (IIa), (IIb), (III), (IIIa), (IIIb), (IV), or (V) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

It should further be understood that solvates (e.g., hydrates) of the compounds of Formula (I), (II), (IIa), (IIb), (III), (IIIa), (IIIb), (IV), or (V) are also with the scope of the present invention. Methods of solvation are generally known in the art.

Prodrugs of the inventive compounds are also contemplated. The term "prodrug" denotes a compound which, upon administration to a subject, undergoes chemical conversion by metabolic or chemical processes to yield a compound of the formula (I), (II), (IIa), (IIb), (III), (IIIa), (IIIb), (IV), or (V), and/or a salt and/or solvate thereof. Any compound that will be converted in vivo to provide the bioactive agent (i.e., the compound for formula (I), (II), (IIa), (IIb), (III), (IIIa), (IIIb), (IV), or (V)) is a prodrug within the scope and spirit of the invention. For example, compounds containing a carboxy group can form physiologically hydrolyzable esters which serve as prodrugs by being hydrolyzed in the body to yield formula (I), (II), (IIa), (IIb), (III), (IIIa), (IIIb), (IV), or (V) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I), (II), (IIa), (IIb), (III), (IIIa), (IIIb), (IV), or (V) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, H. Bundgaard, ed., Elsevier (1985), and *Methods in Enzymology*, 112:309-396, K. Widder et al., eds., Academic Press (1985);

b) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and c) Bundgaard, H., *Adv. Drug Deliv. Rev.*, 8:1-38 (1992);

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The processes for preparation can use racemates, enantiomers, or diastereomers as starting materials. All processes used to prepare compounds of the present invention and intermediates made therein are considered to be part of the present invention.

When enantiomeric or diastereomeric products are prepared, they can be separated by conventional methods, for example, physical methods such as fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Utility

The compounds of the invention modulate kinase activity, including the modulation of Btk. Other types of kinase activity that may be modulated by the compounds of the instant invention include, but are not limited to, the Tec family of compounds, such as BMX, Btk, ITK, TXK and Tec, and mutants thereof.

Accordingly, compounds of formula (I), (II), (IIa), (IIb), (III), (IIIa), (IV), or (V) have utility in treating conditions associated with the modulation of kinase activity, and particularly the selective inhibition of Btk activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (I), (II), (IIa), (IIb), (III), (IIIa), (IIIb), (IV), or (V) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified, above as if repeated at length, as well as any other condition that is affected by Btk kinase activity.

The present invention thus provides methods for treating such conditions, comprising administering to a subject in need thereof a therapeutically-effective amount of at least one compound of Formula (I), (II), (IIa), (IIb), (III), (IIIa), (IIIb), (IV), or (V) or a salt thereof. Therapeutically effective amount" is intended to include an amount of a compound of the present invention that is effective when administered alone or in combination to inhibit Btk.

The methods of treating Btk kinase-associated conditions may comprise administering compounds of Formula (I), (II), (IIa), (IIb), (III), (IIIa), (IIIb), (IV), or (V) alone or in combination with each other and/or other suitable therapeutic agents useful in treating such conditions. Accordingly, "therapeutically effective amount" is also intended to include an amount of the combination of compounds claimed that is effective to inhibit Btk. The combination of compounds is preferably a synergistic combination. Synergy, as described, for example, by Chou et al., *Adv. Enzyme Regul.*, 22:27-55 (1984), occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-A] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathioprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I), (II), (IIa), (IIb), (III), (IIIa), (IIIb), (IV), or (V) and a pharmaceutically acceptable carrier or diluent.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula (I), (II), (IIIa), (IIb), (III), (IIIa), (IIIb), (IV), or (V) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of formula (I), (II), (IIa), (IIb), (III), (IIIa), (IIIb), (IV), or (V) as specified in the "Examples" section below, have been tested in one or more of the assays described below and have activity as inhibitors of Btk enzymes.

Biological Assays

Human Recombinant Btk Enzyme Assay

To V-bottom 384-well plates were added test compounds, human recombinant Btk (1 nM, Invitrogen Corporation), fluoresceinated peptide (1.5 µM), ATP (20 µM), and assay buffer (20 mM HEPES pH 7.4, 10 mM MgCl$_2$, 0.015% Brij35 and 4 mM DTT in 1.6% DMSO), with a final volume of 30 µL. After incubating at room temperature for 60 min, the reaction was terminated by adding 45 µl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis, and the preferred range is from 1 nM to 1 µM, and more preferably less than 0.1 µM.

The Table below lists IC$_{50}$ values for the following examples of the invention measured in the Human Recombinant Btk enzyme assay (LLE_Btk) described herein above.

| Example No. | LLE_Btk (IC$_{50}$, µM) |
|---|---|
| 5 | 0.29 |
| 17 | 8.64 |
| 20 | 27.91 |
| 31 | 9.41 |
| 43 | 9.31 |
| 44 | 9.49 |
| 47 | 40.57 |
| 61 | 14.86 |
| 62 | 0.27 |
| 82 | 9.18 |
| 92 | 0.28 |
| 95 | 0.25 |
| 96 | 0.28 |
| 102 | 14.00 |
| 107 | 12.68 |
| 108 | 16.09 |
| 113 | 13.84 |
| 120 | 0.24 |
| 128 | 0.29 |
| 130 | 0.23 |
| 132 | 0.26 |
| 137 | 0.24 |
| 155 | 0.26 |
| 193 | 0.001 |
| 216 | 0.002 |
| 217 | 0.0007 |
| 219 | 0.001 |
| 223 | 0.002 |
| 225 | 0.001 |
| 236 | 0.003 |
| 237 | 0.004 |
| 238 | 0.002 |
| 242 | 0.002 |
| 245 | 0.001 |
| 249 | 0.003 |
| 250 | 0.28 |
| 255 | 0.29 |
| 262 | 0.002 |

Mouse Splenic B Cell Proliferation Assay

Spleens from Balb/c mice (<12 weeks old) were mashed through screens and red blood cells were removed from splenocytes with RBC lysing buffer (Sigma-Aldrich Chemical Co, St. Louis, Mo.). T cells were depleted by incubation on nylon wool columns (Wako, Richmond, Va.). Resulting splenic B cells prepared this way were routinely >90% CD19$^+$ as measured by FACS analysis. B cells (1×10$^5$ cells per well) were added to serial dilutions of compounds in triplicate in 96-well flat-bottom plates in RPMI 1640 (Invitrogen, Grand Island, N.Y.), supplemented with 10% heat-inactivated fetal calf serum (FCS, Summit Biotechnology, Fort Collins, Colo.), containing 1% L-glutamine (Invitrogen), 50 µg/ml gentamicin (Invitrogen) and 5×10⁻⁵M β-mercaptoethanol (Sigma-Aldrich). Cells were stimulated with 10 μg/ml of AffiniPure F(ab')₂ fragment goat anti-mouse IgG IgM (Jackson ImmunoResearch, West Grove, Pa.). Cultures were incubated for 72 hours, and pulsed for the last 6 hours with one μCi/well of ³[H]-thymidine (PerkinElmer, Boston, Mass.) prior to harvest on a Packard cell harvester (PerkinElmer), and counted by liquid scintillation on a Packard TOPCOUNT® NXT (PerkinElmer). The most potent analogs were found to be below 1 μM.

Human Tonsillar B Cell Proliferation Assay

Tonsils were excised from patients undergoing routine tonsillectomy. Tonsil tissue was minced, mashed through screens and mononuclear cells were isolated on ficoll density gradients (Lymphocyte Separation Media; Mediatech Inc., Herndon, Va.). T cells were depleted from mononuclear cells by rosetting with sheep red blood cells (SRBC, Colorado Serum Company; Denver, Colo.). Tonsillar B cells prepared by this method were routinely>95% CD19⁺ as measured by FACS analysis. B cells (1×10⁵ cells per well) were added to serial dilutions of compounds in triplicate in 96-well flat-bottom plates in RPMI 1640, (Invitrogen, Grand Island, N.Y.), supplemented with 10% heat-inactivated fetal calf serum (FCS, Summit Biotechnology, Fort Collins, Colo.), and containing antibiotic/antimycotic (Invitrogen, 1:100 dilution) and gentamicin (Invitrogen, 5 μg/ml). Cells were stimulated with 40 μg/ml AffiniPure F(ab')2 Fragment Goat anti Human IgG IgM (Jackson ImmunoResearch, West Grove, Pa.) in a total volume of 0.2 ml. Cultures were incubated for 72 hours, and pulsed for the last 6 hours with one μCi/well of ³[H]-thymidine (PerkinElmer, Boston, Mass.) prior to harvest on a Packard cell harvester (PerkinElmer), and counted by liquid scintillation on a Packard TOPCOUNT® NXT (PerkinElmer).

Btk Phosphorylation Assay

Ramos cells (~6×10⁶ cells/10 were incubated in the presence of Btk inhibitors for 1 hr at 37° C. before being stimulated with anti-human IgM+IgG (F(ab')2 fragment, Jackson ImmunoResearch, Catalog No. 109-006-127) at 50 μg/mL for exactly 2 min at 37° C. Cells were immediately fixed by adding an equal volume of pre-warmed BD Phosflow Fix buffer I (BD Biosciences, catalog number 557870) to the cell suspension. After incubating at 37° C. for 10 minutes, the cells were washed once with 3 mL FACS washing buffer (1% FBS/PBS) and permeabilized by adding 0.5 mL of cold BD Phosflow Penn Buffer III (BD Biosciences, Catalog No. 558050) and incubating for 30 minutes on ice. The cells were washed an additional two times with 3 mL BD FACS washing buffer, re-suspended in 100 μL FACS washing buffer, stained with 20 μL, Alexa647 anti-Btk (pY551) (BD Biosciences, Catalog No. 558134), incubated at room temperature for 30 minutes in the dark, and washed once with 3 ml of FACS washing buffer. The cells were re-suspended in 400 μl FACS wash buffer and analyzed using FACSCalibur (BD Biosciences). Median fluorescent intensity (MFI) on Alexa 647 (FL-4) data were collected and used for calculations of inhibition. As an example, the $IC_{50}$ value of Example 6 was found to be 0.32 μM by this assay.

Ramos FLIPR Assay

Ramos RA1 B cells (ATCC® CRL-1596) at a density of 2×10⁶ cells/ml in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, RT, 5 minutes) and resuspended in RT RPMI minus phenol red with 50 mM HEPES and 10% FBS to a density of 1×10⁶ cells/ml. 150 μl aliquots (150,000/well) were plated into 96 well poly-D-lysine coated assay plates (BD 35 4640) and briefly centrifuged (Beckmann GS-CKR 800 rpm, 5 minutes, without brake). 50 μl compound dilutions in 0.4% DMSO/RPMI minus phenol red+50 mM HEPES+ 10% FBS were added to the wells and the plate was incubated at RT in the dark for 1 hour. Assay plate was briefly centrifuged as above prior to measuring calcium levels.

Using the FLIPR1 (Molecular Devices), cells were stimulated by adding 50 μl 200 μg/ml F(ab')2 anti-IgM/IgG (Jackson ImmunoResearch 109-006-127) diluted in 1×HBSS (Invitrogen 14025-076), 50 mM HEPES, 0.1% BSA. Changes in intracellular calcium concentrations were measured for 180 seconds and percent inhibition was determined relative to peak calcium levels seen in the presence of F(ab)2 anti-IgM/IgG only.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the preparations and examples section set out hereinafter. Example compounds are typically prepared as racemic mixtures. Preparation of Homochiral Examples May be Carried Out by Techniques Known to One skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates several end game strategies for the synthesis of azaindazole 3. In one such route, an appropriately functionalized nitrite (1) bearing a leaving group at ortho-position (e.g., a halogen or triflate) can be used as a key intermediate. Displacement of the leaving group with hydrazine can take place at room temperature or elevated temperature, typically with alcoholic solvents, such as methanol, ethanol, n-propanol, isopropanol or n-butanol, to give hydrazinyl intermediate 2. Subsequent cyclization to azaindazole 3 can be accomplished with an acid as catalyst (e.g., trifluoroacetic acid, hydrochloric acid or sulfuric acid) with or without heating depending on the reactivity, or at higher temperature when acid is not used. Alternatively, nitrile 1 can be directly converted to azaindazole 3 using hydrazine at higher temperature (typically, 80-150° C.) using ethanol, n-propanol, isopropanol or n-butanol as solvents.

The azaindazoles of the present invention can also be synthesized from ortho-amino-substituted nitrile 4 (Scheme 1). The heteroarylamine can be diazotized using well known conventional conditions such as sodium nitrite in strong acid (e.g., hydrochloric acid, sulfuric acid, tetrafluoroboric acid), typically at 0-5° C. The resulting diazonium salt can be reduced to the corresponding hydrazine in situ with tin(II) chloride in acid such as hydrochloric acid. Under the acidic reduction conditions, the resulting hydrazinyl product can cyclize to provide the desired aminoindaziole 3 in the same pot.

Another approach to the azaindazole scaffold starts from ortho-methyl-substituted heteroarylamine 5 (Scheme 1). Compound 5 can be first diazotized using conventional conditions such as sodium nitrite in hydrochloric acid, acetic acid or sulfuric at near 0° C. Upon warming to higher temperature, the resulting diazonium salt can cyclize with the vicinal methyl group to yield azaindazole 6. Alternatively, azaindazole 6 can be prepared from amine 5 by acetylation with acetic anhydride and subsequent diazotization and cyclization with isoamyl nitrite. Installation of amino group to compound 6 can be accomplished by nitration with nitric acid in sulfuric acid and subsequent reduction with Zn metal in an acidic media or tin(II) chloride.

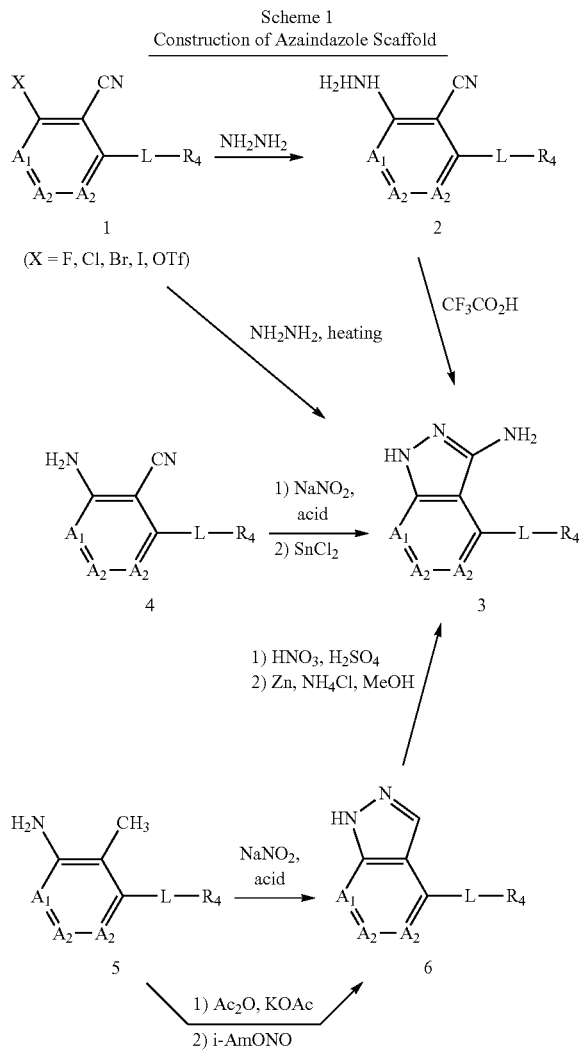

with appropriately functionalized malonate 9, under conventional or microwave heating, would produce pyridone product 10 (Rivkin, A. et al., *Tetrahedron Lett.*, 47:2395 (2006)), which can be converted to di-chloropyridine 11 upon heating with phosphoryl chloride. Palladium-catalyzed coupling of 11 with boronic acid $R_2B(OH)_2$ or organostanne $R_2$—$SnR'_3$ can provide intermediate 12. While palladium tetrakis(triphenylphosphine) is often used as a catalyst for the coupling reaction, many other palladium catalyst well known in the literature can also be used. Compound 11 can also be functionalized by direct displacement when $R_2$ group is attached via a nitrogen, oxygen or sulfur. Compound 12 can be converted to the final product 13 following conditions outlined in Scheme 1.

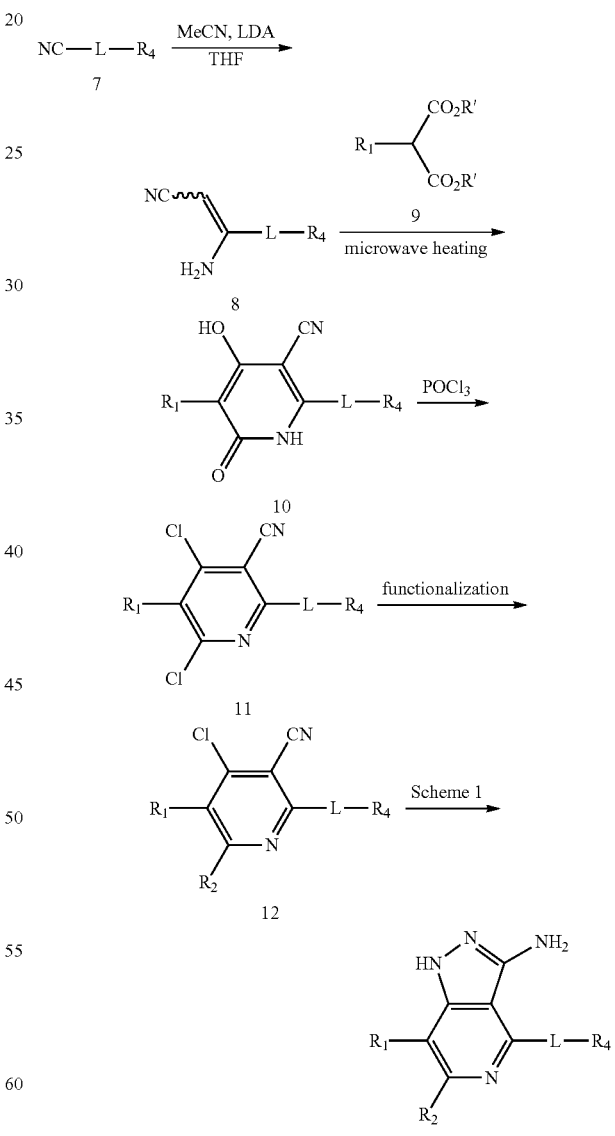

Scheme 2 illustrates one synthetic approach to 5-azaindazole isomers. Deprotonation of acetonitrile with lithium bistrimethylsilylamide (LDA) and addition to appropriately functionalized nitrile 7 can provide amino nitrile 8, often as a mixture of trans- and cis-isomers. Cyclocondensation of 8

Conversion of dichloride 11 to monochloride 12 sometimes can proceed with undesirable selectivity among the two chloro groups (Scheme 2). A modified synthesis is developed to overcome this issue (Scheme 3). In the new route, one of the partners for the cyclocondensation reaction is replaced with β-ketoester 14, which can be prepared from reaction of enolate of an acetate (AcOR') with appropriately functionalized ester or acid chloride ($R_2CO_2R$ or $R_2COCl$). Cyclocondensation of 14 with 8, under microwave or conventional heating, proceeds to yield 4-pyridone product 15, resulting in regioselective introduction of $R_2$ group to the pyridone. After treatment with phosphoryl chloride, the resulting chloropyridine 16 can be converted to the final compounds 17 following conditions shown in Scheme 1.

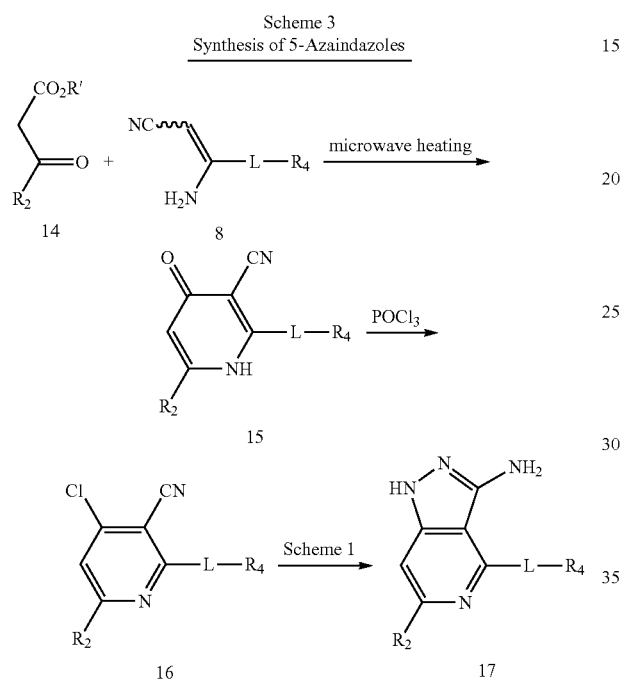

Scheme 4 illustrates a general synthesis of 6-azaindazoles. 3,5-Dichloroisonicotinonitrile (18) can react with boronic acid 19 (1 equivalent) using Suzuki conditions to give monochloride 20. Both palladium tetrakis(triphenylphosphine) and 1,1'-bis(di-t-butylphosphino)ferrocene/palladium acetate can be used as catalyst for the reaction. The chloro group in 20 can be replaced with a fluoro group using potassium fluoride in DMSO at elevated temperature. The resulting fluoro pyridine 21 can be oxidized with m-chloroperbenzoic acid to the corresponding pyridine-N-oxide 22, which upon treatment with phosphoryl chloride can give rise to chloropyridines 23 and 24. Each of the isomers can be taken forward via Suzuki coupling reaction to incorporate $R_1$ or $R_3$ group. Subsequent cyclization with hydrazine can yield the corresponding 6-azaindazoles 25 and 26.

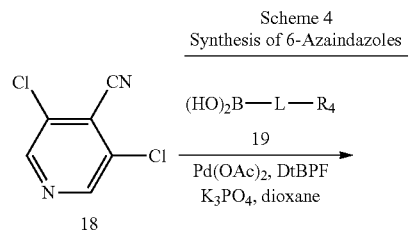

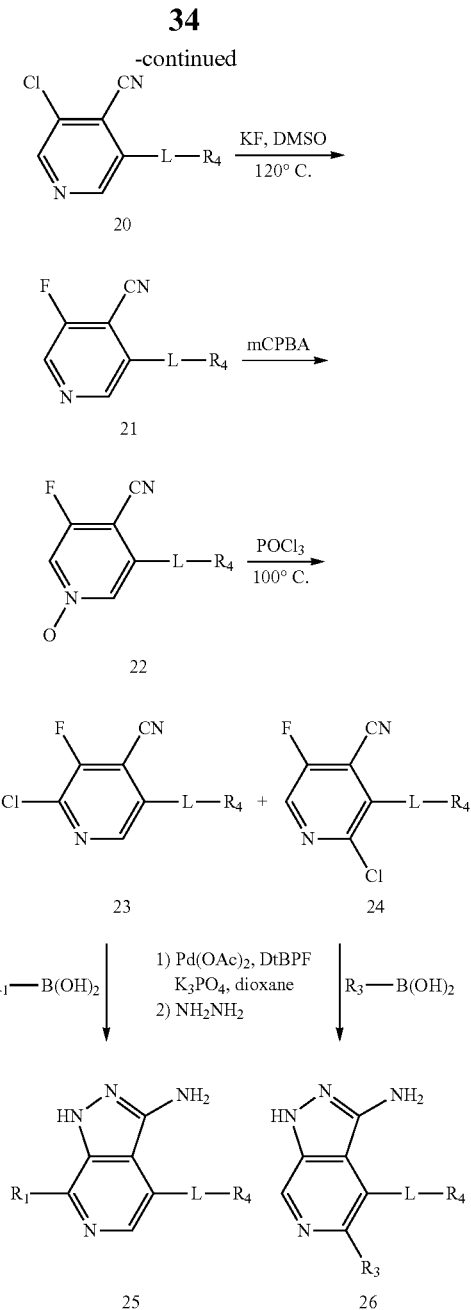

Scheme 5 illustrates two routes for the preparation of 7-azaindazoles. In the first route, condensation of 1,3-diketone 27 with cyanoacetamide (28) in the presence of piperidine and ethanol at reflux can provide pyridone 29 along with an isomer where $R_2$ and L-$R_4$ groups switch position. The ratio of the two isomers can vary depending on the nature of the two substituents. Alternatively, α,β-unsaturated ketone 30 can react with cyanoacetamide (28) using potassium tert-butoxide in DMSO in the presence of oxygen to give 29 (Jain, R. et al., *Tetrahedron Lett.*, 36:3307 (1995)). This route allows access to the desired product 29 in a regioselective fashion. Treatment of pyridone 29 with phosphoryl chloride at elevated temperature can provide the corresponding chloro-nitrile 31, which can be converted to 7-azaindazoles 32 using conditions shown in Scheme 1.

Scheme 5
Synthesis of 7-Azaindazoles

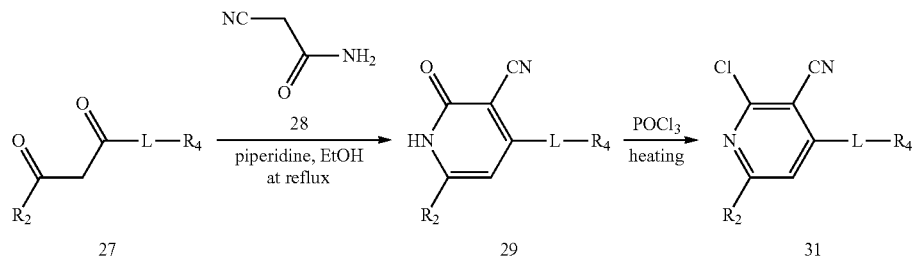

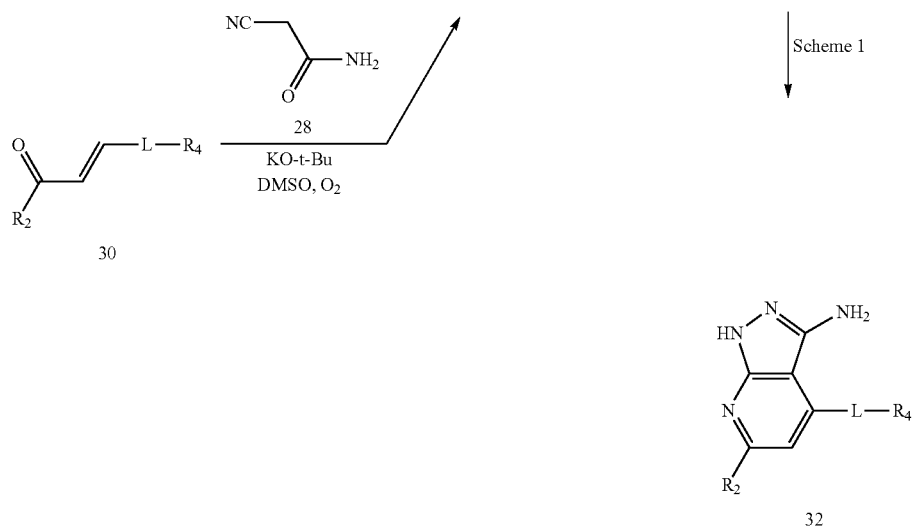

Scheme 6 illustrates an alternative route to 7-azaindazoles. Aldehyde 34, ethyl cyanoacetate (33) and pyridinium chloride 35 can be condensed in the presence of triethylamine to give inner salt 36 (Shestopalov, A. M. et al., *Synthesis*, 402 (1991)). Treatment with phosphoryl chloride at elevated temperature can result in elimination of pyridyl group and formation of di-chloride 37 (Harrington, P. et al., *Org. Process Res. Dev.*, 10:1157 (2006)). The chloro group at 6-position can be functionalized via Suzuki coupling with $R_2B(OH)_2$, Stille coupling with $R_2$—$SnR'_3$, or via direct displacement when $R_2$ is attached via a nitrogen, oxygen or sulfur, although the selectivity between the 2-chloro and 6-chloro may vary. The resulting compound 38 can be converted to the final product 32 following conditions shown in Scheme 1.

Scheme 6
Synthesis of 7-Azaindazoles

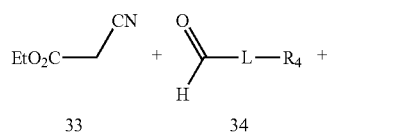

-continued

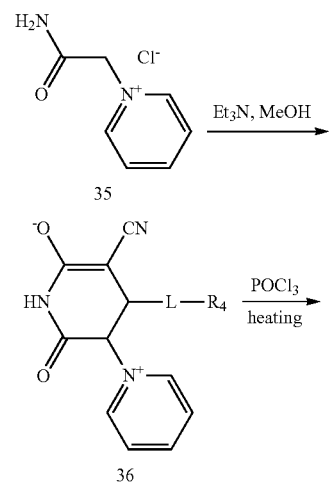

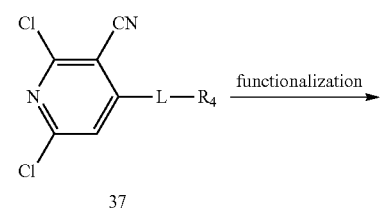

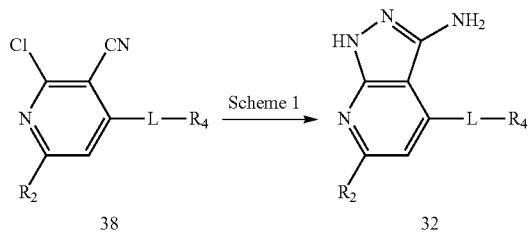

Scheme 7 illustrates a general synthesis of 5,7-diazaindazoles. Ethyl cyanoacetate (33) and aldehyde 34 can be condensed in the presence of potassium phosphate to give 39. Treatment of 39 with amidine or guanidine 40 while subject to air oxidation can result in formation pyrimidone 41. After treating with phosphoryl chloride at elevated temperature, the resulting chloropyrimidine 42 can be converted to 5,7-diazaindazole 43 using conditions shown in Scheme 1.

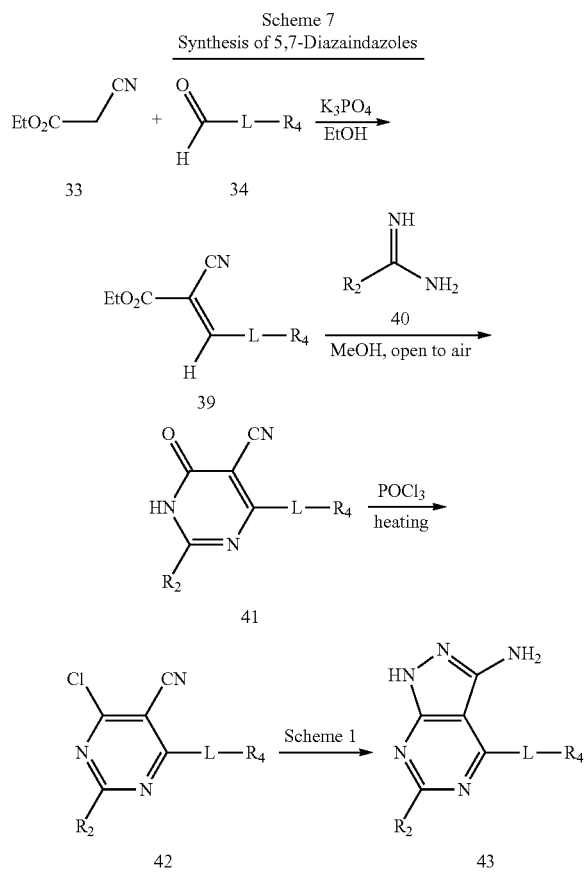

EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

For ease of reference, the following abbreviations are used herein:
BOC=tert-butoxycarbonyl
BOP=(benzotriazol-1-yloxy)tris(dimethylamino)phosphonium hexafluorophosphate
bp=boiling point
Bu=butyl
Cbz=carbonylbenzyloxy
DMAP=4-dimethylaminopyridine
DIPEA or DIEA=N,N-diisopropylethylamine
DME=1,2-dimethoxyethane
DMF=N,N'-dimethyl formamide
DppF–1,1'-bis(diphenylphosphino)ferrocene
EDCI=1-(3-dimethylaminopropyl)-3-ethylcarbodiimide
Et=ethyl
$Et_2O$=diethyl ether
HOBT=1-hydroxybenzotriazole
EtOAc=ethyl acetate
EtOH=ethanol
g=gram(s)
H=hydrogen
l=liter
mCPBA—meta chloro perbenzoic acid
Me=methyl
MeCN=acetonitrile
MeOH=methanol
nM=nanomole
NMP=1-methyl-2-pyrrolidinone
Pd2 $dba_3$=tris(dibenzylideneacetone)dipalladium (0)
Ph=phenyl
Pr=propyl
PS=polystyrene
TEA=triethylamine
TFA=trifluoroacetic acid
mg=milligram(s)
ml or mL=milliliter
µl=microliter
µmol mM millimole
µmol=µM=micromole
mol=mole
mp=melting point
RT or rt=room temperature
HPLC=high pressure liquid chromatography
LC/MS=liquid chromatography/mass spectrometry Analytical HPLC Methods Method A:
Linear gradient of 0 to 100% solvent B over 4 min, with 1 min hold at 100% B.
UV visualization at 220 nm
Column: YMC COMBISCREEN® ODS-A S5 4.6×50 mm
Flow rate: 4 mL/min
Solvent A: 0.2% phosphoric acid, 90% water, 10% methanol
Solvent B: 0.2% phosphoric acid, 90% methanol, 10% water
Method B:
Linear gradient of 0 to 100% solvent 13 over 4 min, with 1 min hold at 100% B.
UV visualization at 220 nm
Column: PHENOMENEX® Luna S5 C18 100A 4.6×50 mm
Flow rate: 4 mL/min
Solvent A: 0.2% phosphoric acid, 90% water, 10% methanol
Solvent B: 0.2% phosphoric acid, 90% methanol, 10% water

Example 1

6-Cyclopentyl-4-(4-phenoxyphenyl)-1H-pyrazolo[3,4-b]pyridin-3-amine

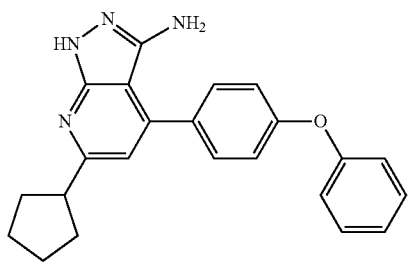 [SMILES: Nc1n[nH]c2nc(C3CCCC3)cc(-c3ccc(Oc4ccccc4)cc3)c12]

Step 1:

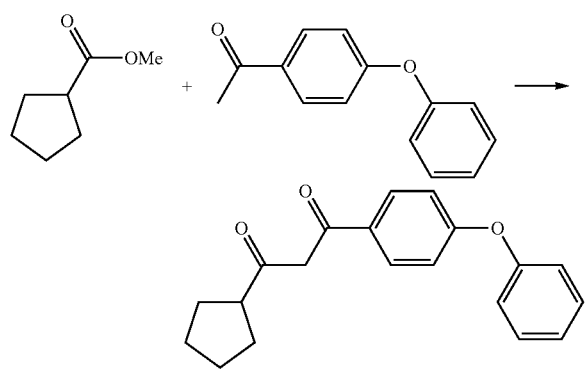

Sodium hydride (1.508 g, 37.7 mmol, 60% suspension in mineral oil) was added in small portions to a solution of methyl cyclopentanecarboxylate (1.449 g, 11.31 mmol) and 1-(4-phenoxyphenyl)ethanone (2.00 g, 9.42 mmol) in THF (100 mL). Ethanol (0.5 mL) was then added. The mixture was heated to reflux for 5.5 h, quenched with saturated NaCl (50 mL) and acidified to pH 2 with 1 N HCl. THF was evaporated in vacuo. The residue was extracted with ethyl acetate (3×50 mL). The combined extracts were washed with brine (10 mL), dried (MgSO$_4$) and concentrated. Silica gel chromatography, loading with 5% ethyl acetate in hexanes and eluting with 5-20% ethyl acetate in hexanes, gave 1-cycloperityl-3-(4-phenoxyphenyl)propane-1,3-dione as white solid (1.837 g, 63% yield). MS (ES+) m/z: 309 (M+H); LC retention time: 5.015 min (analytical HPLC Method A).

Step 2:

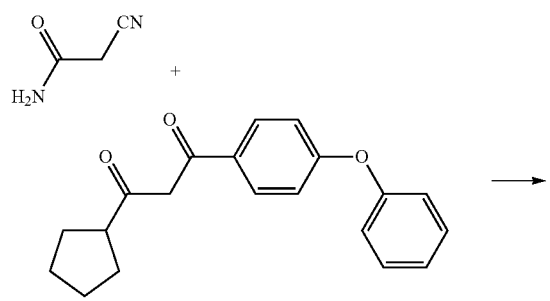

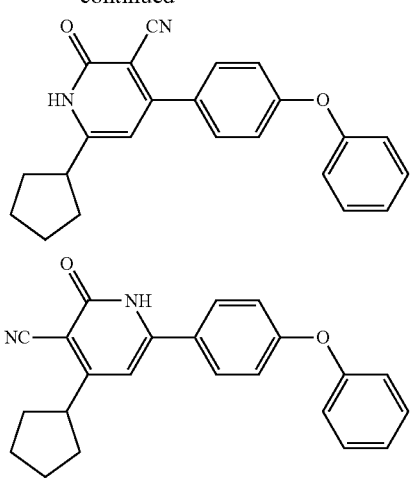

A mixture of 1-cyclopentyl-3-(4-phenoxyphenyl)propane-1,3-dione (1.837 g, 5.96 mmol), 2-cyanoacetamide (0.601 g, 7.15 mmol) and piperidine (0.118 mL, 1.191 mmol) in ethanol (20 mL) was heated at reflux for 22 h and then concentrated. The residue was diluted with ethyl acetate (150 mL), washed with brine (3×20 mL), dried and concentrated. The solid residue was treated with 20% ethyl acetate in hexanes (50 mL), stirred vigorously for 15 min, and filtered. The solid was washed with 20% ethyl acetate in hexanes (3×20 mL), dried under vacuum to give a 2:1 mixture of the two expected pyridones as a white powder (732 mg, 35% yield). MS (ES+) m/z: 257 (M+H); LC retention time: 4.350 and 4.413 min (analytical HPLC Method A).

Step 3:

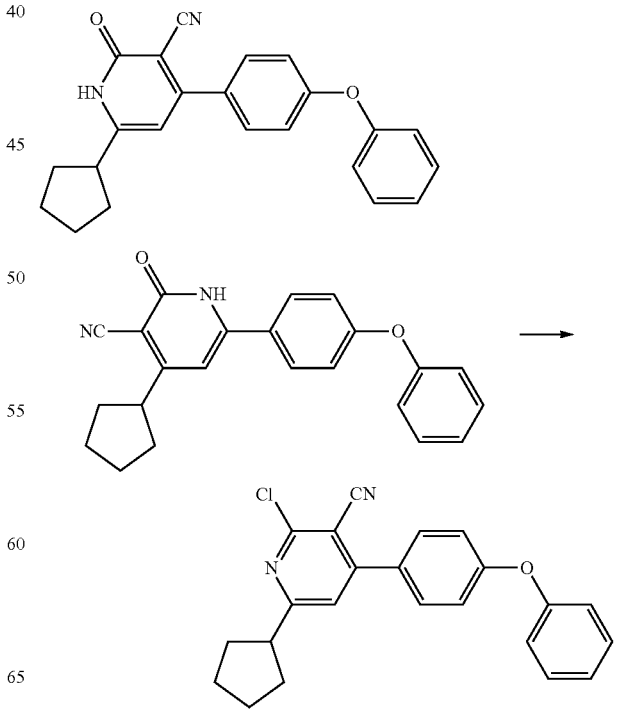

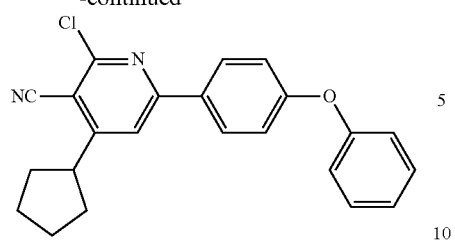

Phosphorus oxychloride (5 mL) was added to a mixture of the pyridones from Step 2 (732 mg). After 17 h at 110° C., the mixture was cooled to 0° C., diluted with ethyl acetate (50 mL), and carefully treated with saturated sodium bicarbonate ($CO_2$ evolution). The mixture was further neutralized to pH~7 with careful addition of solid potassium carbonate while stirring vigorously and extracted with ethyl acetate (3×50 mL). The combined extracts were washed with brine (10 mL), dried ($MgSO_4$), filtered through a silica gel plug and concentrated to give the two expected products (722.6 mg) in a ratio of 2:1. MS (ES+) m/z: 375 (M+H); LC retention time: 4.960 and 5.226 min (analytical HPLC Method A).

Step 4:

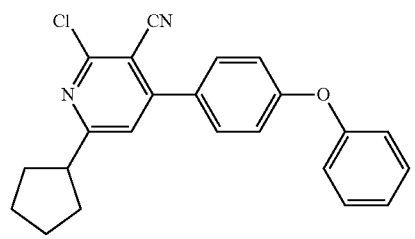

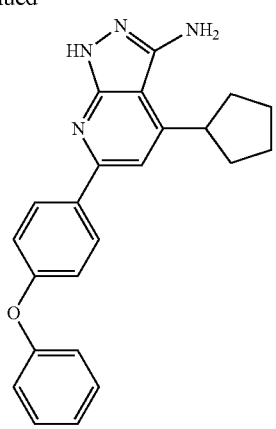

A 35% aqueous solution of hydrazine (0.139 mL, 1.547 mmol) was added to the product mixture from Step 3 (116 mg, 0.309 mmol) in ethanol (2 mL). After 18 h at 80° C., the mixture was diluted with ethyl acetate (40 mL), washed with water (10 mL), brine (2×10 mL), dried ($MgSO_4$) and concentrated. Purification with reverse phase HPLC (Sunfire S10 30×250 mm column), eluting with 70-100% solvent 13 (10% methanol-90% water-0.1% TFA) in solvent A (90% methanol-10% water-0.1% TFA), gave Example 1 as the faster eluting peak (66.0 mg, 36% yield), and the other isomer as the slower eluting peak (36.0 mg, 19% yield). Characterization of Example 1: $^1$H NMR (500 MHz, methanol-$d_4$) δ ppm 7.69 (2H, δ, J=8.80 Hz), 7.44 (2H, δ, J=7.97 Hz), 7.16-7.26 (3H, m), 7.13 (2H, δ, J=7.70 Hz), 7.00 (1H, s), 3.32-3.43 (1H, m), 2.18-2.31 (2H, m), 1.74-1.99 (6H, m); MS (ES+) m/z: 371 (M+H); LC retention time: 4.336 min (analytical HPLC Method A).

Example 2

4-(4-(Benzyloxy)phenyl)-6-cyclopentyl-1H-pyrazolo[3,4-b]pyridin-3-amine

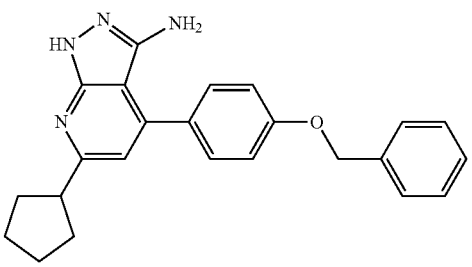 [SMILES: Nc1n[nH]c2nc(C3CCCC3)cc(-c3ccc(OCc4ccccc4)cc3)c12]

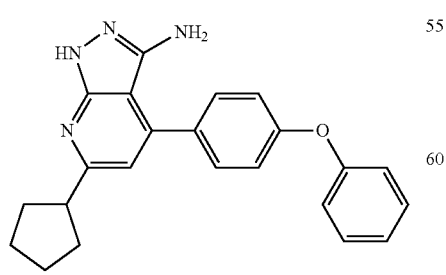

Example 1

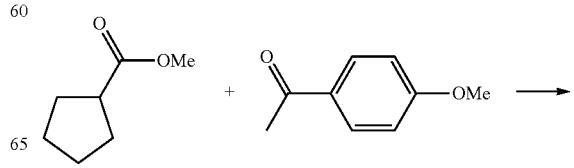

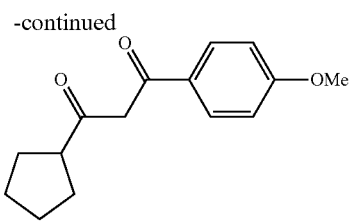

Step 1:

Sodium hydride (1.378 g, 59.9 mmol, 60% suspension in mineral oil) and ethanol (2.0 mL) were added to a solution of methyl cyclopentanecarboxylate (6.14 g, 47.9 mmol) and 1-(4-methoxyphenyl)ethanone (6.00 g, 40.0 mmol) in THF (200 mL). The mixture was heated to reflux for 11 h, quenched with water (100 mL) and acidified to pH~2 with 1 N HCl. The THF solvent was evaporated in vacuo. The residue was extracted with ethyl acetate (3×100 mL). The combined extracts were washed with brine (25 mL), dried (MgSO$_4$) and concentrated. Silica gel chromatography, loading with hexanes and small amount of toluene and eluting with 0-15% ethyl acetate in hexanes, gave 1-cyclopentyl-3-(4-methoxyphenyl)propane-1,3-dione as yellow liquid (5.494 g, 56% yield). MS (ES+) m/z: 247 (M+H); LC retention time: 4.510 and 3.578 min, likely a mixture of keto and enol forms (analytical HPLC Method A).

Step 2:

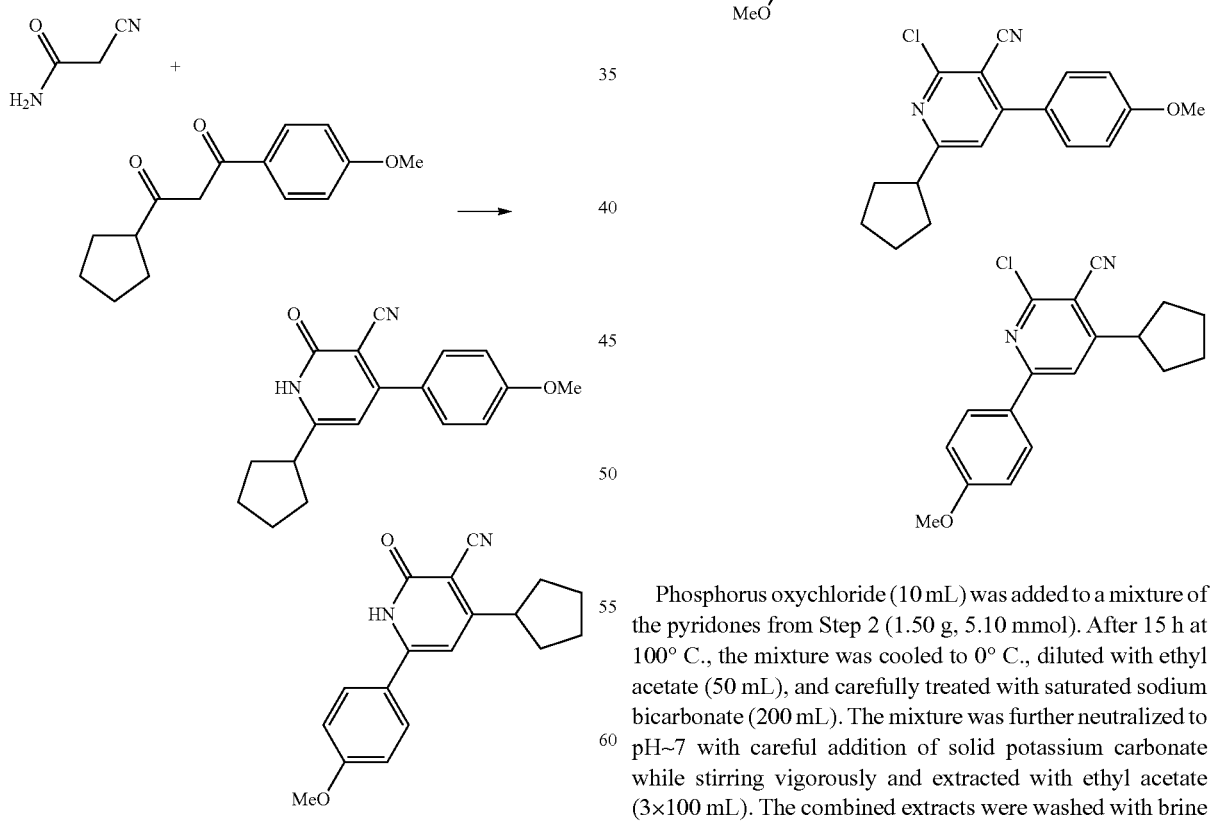

A mixture of 1-cyclopentyl-3-(4-methoxyphenyl)propane-1,3-dione (5.494 g, 22.31 mmol), 2-cyanoacetamide (2.81 g, 33.5 mmol) and piperidine (2.208 mL, 22.31 mmol) in n-butanol (100 mL) was heated to reflux for 3 days. The mixture was concentrated, diluted with ethyl acetate (400 mL), washed with water (50 mL), brine (50 mL), dried (MgSO$_4$) and concentrated. Silica gel chromatography, loading with dichloromethane and eluting with 0-7% methanol in dichloromethane, gave a 1:1 mixture of the two expected products (2.57 g) as tan solid. MS (ES+) m/z: 295 (M+H); LC retention time: 3.880 and 3.753 min (analytical HPLC Method A).

Step 3:

Phosphorus oxychloride (10 mL) was added to a mixture of the pyridones from Step 2 (1.50 g, 5.10 mmol). After 15 h at 100° C., the mixture was cooled to 0° C., diluted with ethyl acetate (50 mL), and carefully treated with saturated sodium bicarbonate (200 mL). The mixture was further neutralized to pH~7 with careful addition of solid potassium carbonate while stirring vigorously and extracted with ethyl acetate (3×100 mL). The combined extracts were washed with brine (40 mL), dried (MgSO$_4$) and concentrated. Silica gel chromatography, eluting with 0-10% ethyl acetate in hexanes, gave a 1:1 mixture of the expected products as a light yellow liquid (1.00 g, 63% yield). MS (ES+) m/z: 313 (M+H).

Step 4:

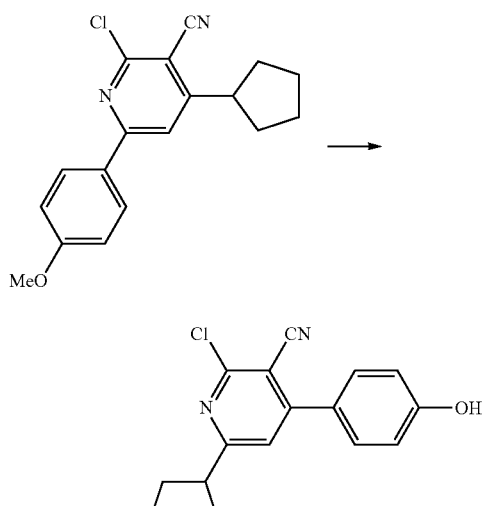

A 1.0 M dichloromethane solution of boron tribromide (15.35 mL, 15.35 mmol) was added to the product mixture from Step 3 (960 mg, 3.07 mmol) in dichloromethane (10 mL). After 2 h at room temperature, the mixture was diluted with ethyl acetate (50 mL), carefully quenched with saturated sodium bicarbonate (20 mL). The aqueous layer was separated and extracted with ethyl acetate (2×50 mL). The combined extracts were washed with water (30 mL), brine (30 mL), dried (MgSO$_4$) and concentrated. Silica gel chromatography, eluting with 5% to 30% ethyl acetate in hexanes, gave a 1:1 mixture of the expected products (650 mg, 71% yield). A portion (480 mg) of the mixture was purified by SFC chromatography (chiral OJ column, CO$_2$/methanol=70/30, 35° C.) to provide 2-chloro-6-cyclopentyl-4-(4-hydroxyphenyl)nicotinonitrile (Product A) as the faster eluting peak (180 mg). $^1$H NMR (500 MHz, methanol-d$_4$) δ ppm 7.50 (2H, δ, J=8.80 Hz), 7.33 (1H, s), 6.91 (2H, δ, J=8.80 Hz), 3.12-327 (1H, m), 1.93-2.16 (2H, m), 1.62-1.92 (4H, m); MS (ES+) m/z: 299 (M+H); LC retention time: 3.910 min (analytical HPLC Method A).

Step 5:

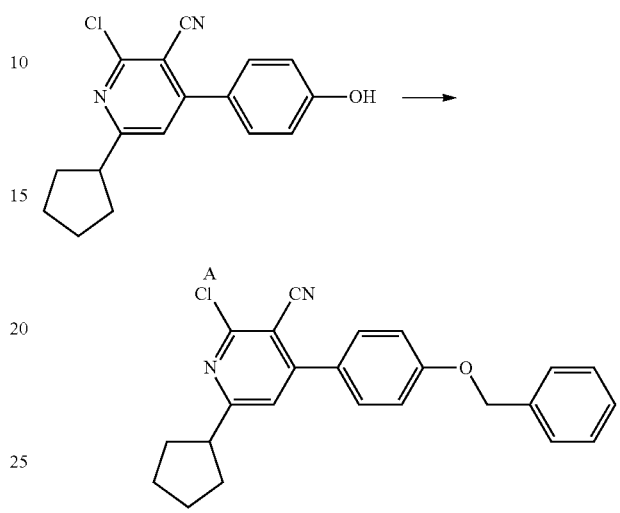

Cesium carbonate (39.3 mg, 0.120 mmol) was added to a solution of 2-chloro-6-cyclopentyl-4-(4-hydroxyphenyl)nicotinonitrile (18 mg, 0.060 mmol) and benzyl bromide (0.014 mL, 0.120 mmol) in DMSO (1 mL). After 16 h at room temperature, the mixture was diluted with ethyl acetate (80 mL), washed with saturated sodium bicarbonate (5 mL), brine (5 mL), dried (MgSO$_4$) and concentrated. Silica gel chromatography, eluting with 0-15% ethyl acetate in hexanes, gave 4-(4-(benzyloxy)phenyl)-2-chloro-6-cyclopentylnicotinonitrile as a white solid (20 mg, 85% yield). $^1$H NMR (400 MHz, CDCl$_3$) δ ppm 7.50-7.74 (2H, m), 7.30-7.48 (5H, m), 7.19 (1H, s), 7.00-7.15 (2H, m), 5.13 (2H, s), 3.10-3.34 (1H, m), 2.00-2.32 (2H, m), 1.64-1.95 (6H, m), MS (ES+) m/z: 389 (M+H); LC retention time: 4.431 min (analytical HPLC Method A).

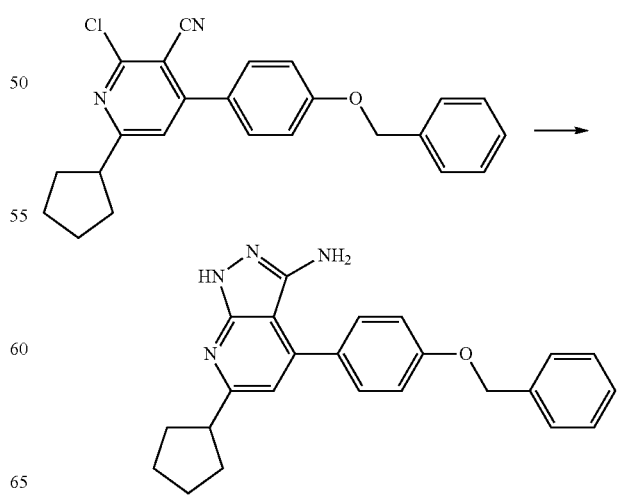

Step 6:

A 35% aqueous solution of hydrazine (0.046 mL, 0.514 mmol) was added to a mixture of 4-(4-(benzyloxy)phenyl)-2-chloro-6-cyclopentylnicotinonitrile (20 mg, 0.051 mmol) in ethanol (1.5 mL). After 15 h at 85° C., the mixture was diluted with ethyl acetate (60 mL) and washed with saturated sodium bicarbonate (5 mL), brine (5 mL), dried (MgSO$_4$) and concentrated. Purification with reverse phase HPLC (Sunfire S10 30×250 mm column), eluting with 40-90% solvent B (10% methanol-90% water-0.1% TFA) in solvent A (90% methanol-10% water-0.1% TFA), gave Example 2 as yellow solid, assumed as bis-TFA salt (13.0 mg, 41% yield). $^1$H NMR (500 MHz, CDCl$_3$) δ ppm 7.57 (2H, δ, J=8.80 Hz), 7.32-7.51 (5H, m), 7.19 (2H, δ, J=8.52 Hz), 6.89 (1H, s), 5.17 (2H, s), 3.35-3.58 (1H, m), 2.21-2.40 (2H, m), 1.72-1.99 (6H, m); MS (ES+) m/z: 385 (M+H); LC retention time: 3.823 min (analytical HPLC Method A).

Example 3

6-Cyclopentyl-4-(4-(2-methylphenoxy)phenyl)-1H-pyrazolo[3,4-b]pyridin-3-amine

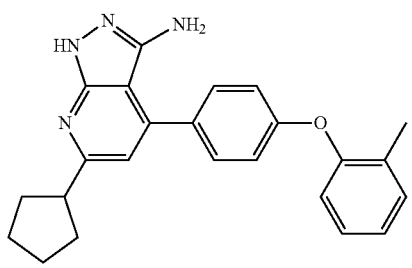 [SMILES: Cc1ccccc1Oc1ccc(-c2cc(C3CCCC3)nc3[nH]nc(N)c23)cc1]

Step 1:

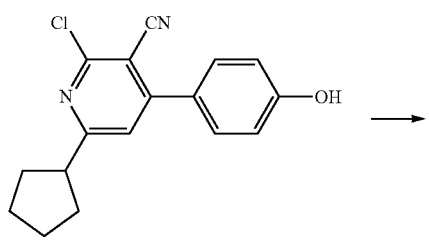

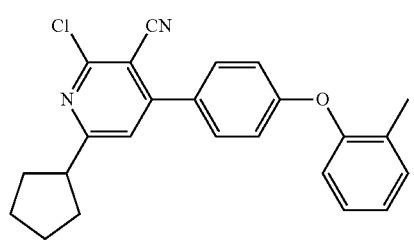

A mixture of 2-chloro-6-cyclopentyl-4-(4-hydroxyphenyl)nicotinonitrile (20 mg, 0.067 mmol, product A from Step 4 of Example 2), o-tolylboronic acid (36.4 mg, 0.268 mmol), copper(II) acetate (14.59 mg, 0.080 mmol) and 4 A molecular sieves (100 mg) in dichloromethane (3 mL) was stirred at room temperature while opening to the air for 40 h. The mixture was filtered through a CELITE® pad and the pad rinsed with ethyl acetate (50 mL). The filtrate was washed with saturated sodium bicarbonate (5 mL), water (5 mL), brine (5 mL), dried (MgSO$_4$) and concentrated. Silica gel chromatography, eluting with 0-15% ethyl acetate in hexanes, gave 2-chloro-6-cyclopentyl-4-(4-(o-tolyloxy)phenyl)nicotinonitrile as a colorless liquid (15 mg, 58% yield). $^1$H NMR (400 MHz, CDCl$_3$) δ ppm 7.50 (2H, δ, J=8.53 Hz), 7.07-7.32 (5H, m), 6.91-7.03 (2H, m), 3.05-3.28 (1H, m), 2.20 (3H, s), 1.98-2.13 (2H, m), 1.60-1.91 (6H, m); MS (ES+) m/z: 389 (M+H); LC retention time: 4.578 min (analytical HPLC Method A).

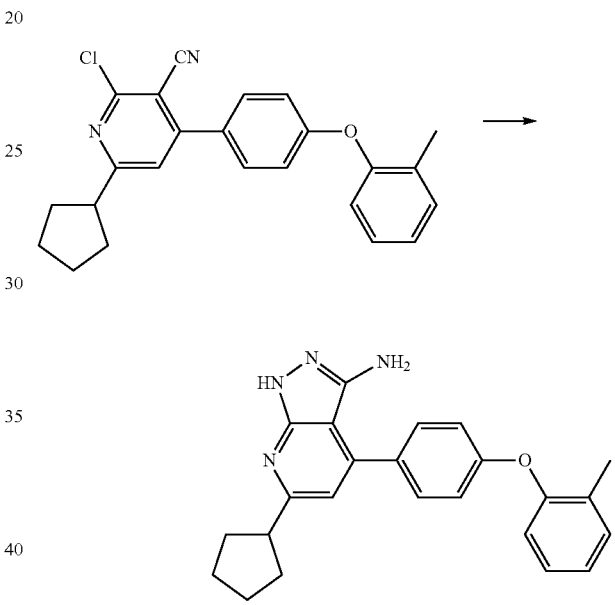

Step 2:

A 35% aqueous solution of hydrazine (0.032 mL, 0.360 mmol) was added to a mixture of 2-chloro-6-cyclopentyl-4-(4-(o-tolyloxy)phenyl)nicotinonitrile (14 mg, 0.036 mmol) in ethanol (1.5 mL). After 48 h at 85° C., the mixture was diluted with ethyl acetate (60 mL), washed with saturated sodium bicarbonate (5 mL), brine (5 mL), dried (MgSO$_4$) and concentrated. Silica gel chromatography, eluting with 20-80% ethyl acetate in hexanes, gave Example 3 as yellow solid (9.0 mg, 61% yield). $^1$H NMR (400 MHz, CDCl$_3$) δ ppm 7.44-7.55 (2H, m), 7.23 (1H, δ, J=7.53 Hz), 7.13-7.20 (1H, m), 7.04-7.13 (1H, m), 6.91-7.02 (3H, m), 6.79 (1H, s), 3.20-3.36 (1H, m), 2.19 (3H, s), 2.06-2.18 (2H, m), 1.75-1.93 (4H, m), 1.61-1.76 (2H, m); MS (ES+) m/z: 385 (M+H); LC retention time: 4.061 min (analytical HPLC Method A).

Examples 4 and 5

Examples 4 and 5 were prepared following conditions similar to Steps 1 and 2 of Example 3.

| Example No | Structure | Spectral data* |
|---|---|---|
| Example 4: 6-Cyclopentyl-4-(4-(4-methylphenoxy)phenyl)-1H-pyrazolo[3,4-b]pyridin-3-amine | 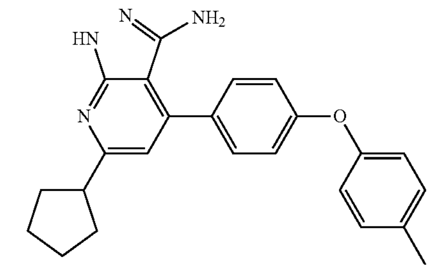 [SMILES: Cc1ccc(Oc2ccc(-c3cc(C4CCCC4)nc(N)c3C(=N)N)cc2)cc1] | ¹H NMR (500 MHz, CDCl₃) δ ppm 7.53-7.63 (2 H, m), 7.19-7.25 (2 H, m), 7.11-7.18 (2 H, m), 6.98-7.06 (2 H, m), 6.91 (1 H, s), 3.30-3.54 (1 H, m), 2.38 (3 H, s), 2.23-2.37 (2 H, m), 1.86-2.02 (2 H, m), 1.72-1.86 (4 H, m); MS (ES+) m/z: 3.85 (M + H); LC retention time: 4.040 min. |
| Example 5: 6-Cyclopentyl-4-(4-(3-methylphenoxy)phenyl)-1H-pyrazolo[3,4-b]pyridin-3-amine | 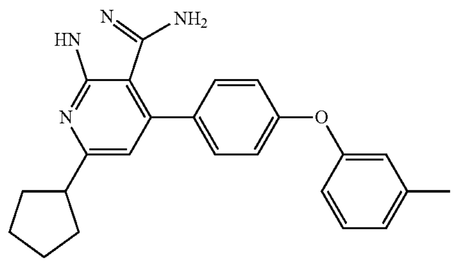 [SMILES: Cc1cccc(Oc2ccc(-c3cc(C4CCCC4)nc(N)c3C(=N)N)cc2)c1] | ¹H NMR (400 MHz, CDCl₃) δ ppm 7.53-7.64 (2 H, m), 7.25-7.35 (1 H, m), 7.09-7.20 (2 H, m), 7.02 (1 H, δ, J = 7.53 Hz), 6.82-6.98 (3 H, m), 3.20-3.46 (1 H, m) 2.39 (3 H, s), 2.14-2.30 (2 H, m), 1.82-2.01 (4 H, m), 1.69-1.83 (2 H, m); MS (ES+) m/z: 385 (M + H); LC retention time: 4.061 min. |

*Analytical HPLC Method A

Example 6

4-(4-Phenoxyphenyl)-1H-pyrazolo[3,4-b]pyridin-3-amine

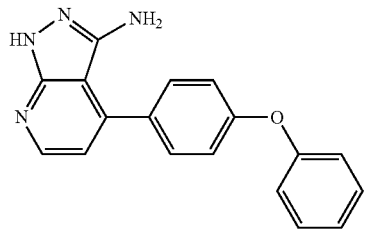 [SMILES: Nc1n[nH]c2nccc(-c3ccc(Oc4ccccc4)cc3)c12]

Step 1:

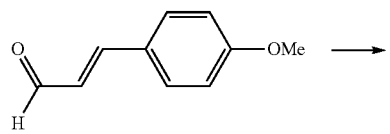

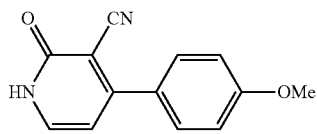

A mixture of potassium tert-butoxide (5.54 g, 49.3 mmol) in DMSO (20 mL) was added to a mixture of (E)-3-(4-methoxyphenyl)acrylaldehyde (2.0 g, 12.33 mmol) and 2-cyanoacetamide (1.140 g, 13.56 mmol) in DMSO (30 mL) dropwise under an oxygen balloon with a water bath cooling outside. After completion of addition, the mixture was stirred under oxygen for 1 h at room temperature, quenched with water (100 mL) and adjusted to pH 5-6 with careful addition of 1 N HCl. A brown precipitate was formed, collected by filtration, washed with water (2×50 mL), dried under vacuum to give 4-(4-methoxyphenyl)-2-oxo-1,2-dihydropyridine-3-carbonitrile (1.0 g, 36% yield). ¹H NMR (500 MHz, DMSO-d₆) δ ppm 7.69 (1H, δ, J=6.60 Hz), 7.62 (2H, δ, J=8.80 Hz), 7.11 (2H, δ, J=8.80 Hz), 639 (1H, δ, J=6.60 Hz), 3.87 (3H, s); MS (ES+) m/z: 227 (M+H); LC retention time: 2.532 min (analytical HPLC Method A).

Step 2:

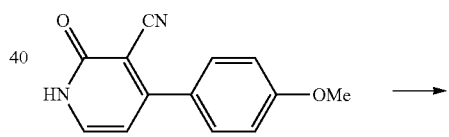

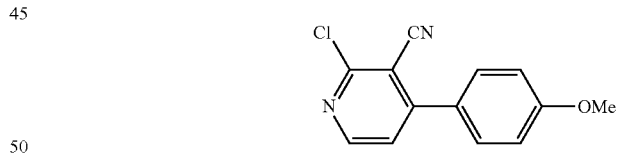

A mixture of 4-(4-methoxyphenyl)-2-oxo-1,2-dihydropyridine-3-carbonitrile (1.00 g, 4.42 mmol) and phosphoryl trichloride (8 mL, 87 mmol) was heated to 110° C. for 15 h. The mixture was diluted with ethyl acetate (100 mL), carefully treated with saturated sodium bicarbonate (100 mL), neutralized to pH~7 with careful addition of solid potassium carbonate while stirring vigorously, and extracted with ethyl acetate (3×100 mL). The combined extracts were washed with brine (40 mL), dried (MgSO₄) and concentrated to give 2-chloro-4-(4-methoxyphenyl)nicotinonitrile as a brown solid (960 mg, 89% yield). ¹H NMR (400 MHz, CDCl₃) δ ppm 8.54 (1H, δ, J=5.27 Hz), 7.48-7.82 (2H, m), 7.38 (1H, δ, J=5.27 Hz), 6.94-7.18 (2H, m), 3.90 (3H, s); MS (ES+) m/z: 245 (M+H); LC retention time: 3.303 min (analytical HPLC Method A).

Step 3:

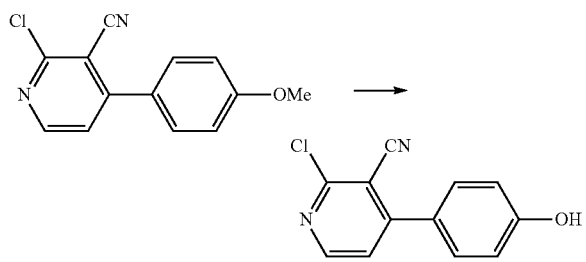

A 1.0 M dichloromethane solution of boron tribromide (12.26 mL, 12.26 mmol) was added to a solution of 2-chloro-4-(4-methoxyphenyl)nicotinonitrile (300 mg, 1.226 mmol) in dichloromethane (10 mL). The mixture was stirred at room temperature for 2 h, diluted with ethyl acetate (50 mL), and carefully quenched with saturated sodium bicarbonate (20 mL). The aqueous layer was separated and extracted with ethyl acetate (2×50 mL). The combined extracts were washed with water (30 mL), brine (30 mL), dried (MgSO$_4$) and concentrated. Silica gel chromatography, eluting with 10-50% ethyl acetate in hexanes, gave 2-chloro-4-(4-hydroxyphenyl)nicotinonitrile as a brown solid (50 mg, 18% yield). $^1$H NMR (500 MHz, CDCl$_3$) δ ppm 8.55 (1H, δ, J=5.22 Hz), 7.49-7.62 (2H, m), 7.38 (1H, δ, J=5.22 Hz), 6.94-7.05 (2H, m); MS (ES+) m/z: 231 (M+H); LC retention time: 2.841 min (analytical HPLC Method A).

Step 4:

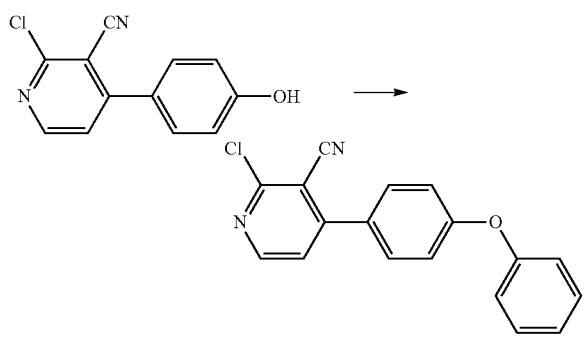

Following conditions described in Step 1 of Example 3, 2-chloro-4-(4-hydroxyphenyl)nicotinonitrile was reacted with phenylboronic acid to give 2-chloro-4-(4-phenoxyphenyl)nicotinonitrile (60 mg, 90% yield). $^1$H NMR (500 MHz, CDCl$_3$) δ ppm 8.56 (1H, δ, J=5.22 Hz), 7.53-7.67 (2H, m), 7.37-7.49 (3H, m), 7.22 (1H, t, J=7.42 Hz), 7.09-7.16 (4H, m); MS (ES+) m/z: 307 (M+H); LC retention time: 3.863 min (analytical HPLC Method A).

Step 5:

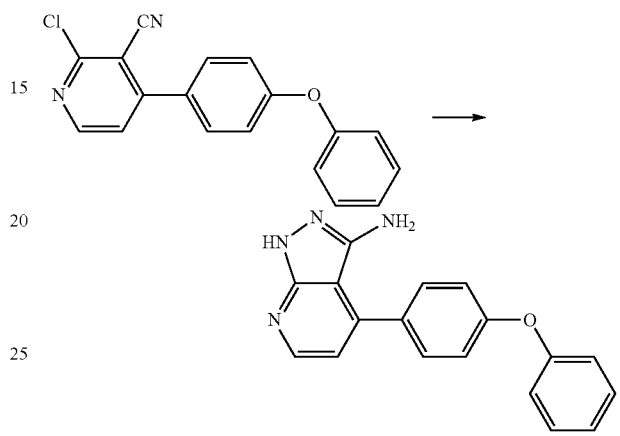

A mixture of 2-chloro-4-(4-phenoxyphenyl)nicotinonitrile (30 mg, 0.098 mmol), 35% aqueous hydrazine (0.088 mL, 0.978 mmol) and isopropanol (1.5 mL) was heated to 150° C. under microwave for 1 h. Purification with reverse phase HPLC (Sunfire S10 30×250 mm column), eluting with 40-100% solvent B (10% methanol-90% water-0.1% TFA) in solvent A (90% methanol-10% water-0.1% TFA), gave Example 6 as yellow solid, assumed as bis-TFA salt (30 mg, 58% yield). $^1$H NMR (500 MHz, methanol-d$_4$) δ ppm 8.46 (1H, δ, J=5.22 Hz), 7.63-7.83 (2H, m), 7.36-7.52 (2H, m), 7.16-7.27 (3H, m), 7.13 (2H, δ, J=7.42 Hz), 7.07 (1H, δ, J=5.50 Hz); MS (ES+) m/z: 303 (M+H); LC retention time: 3.366 min (analytical HPLC Method A).

Example 7

Example 7 was prepared from 2-chloro-6-cyclohexyl-4-(4-methoxyphenyl)nicotinonitrile following conditions similar to Steps 3 to 5 of Example 6.

| Example No. | Structure | Spectral data* |
|---|---|---|
| Example 7: 6-Cyclohexyl-4-(4-phenoxyphenyl)-1H-pyrazolo[3,4-b]pyridin-3-amine | 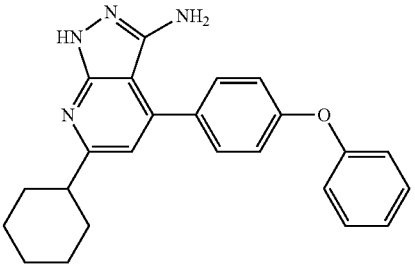 | $^1$H NMR (500 MHz, methanol-d$_4$) δ ppm 7.54-7.85 (2 H, m), 7.37-7.57 (2 H, m), 7.07-7.30 (5 H, m), 6.97 (1 H, s), 2.91 (1 H, t, J = 3.30 Hz), 1.97-2.14 (2 H, m), 1.89-1.97 (2 H, m), 1.77-1.86 (1 H, m), 1.60-1.75 (2 H, m), 1.42-1.56 (2 H, m), 1.29-1.41 (1 H, m); MS (ES+) m/z: 385 (M + H); LC retention time: 4.020 min. |

*Analytical HPLC Method A

Example 8

6-(4-Methoxyphenyl)-4-(4-phenoxyphenyl)-1H-1-pyrazolo[3,4-b]pyridin-3-amine

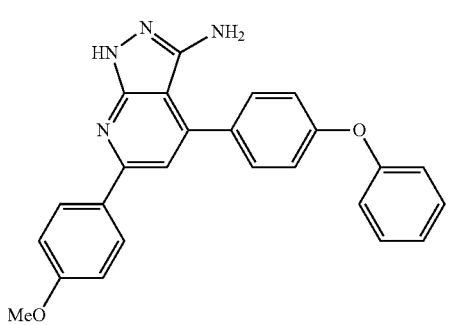

Step 1:

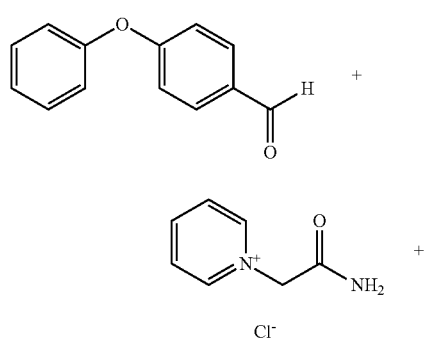

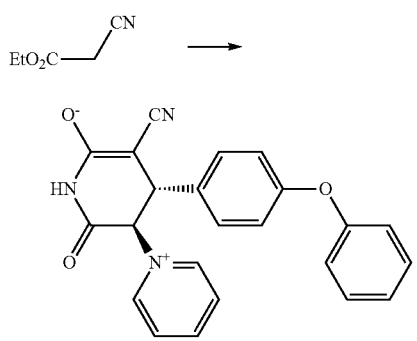

Triethylamine (3.06 mL, 21.98 mmol) was added to a mixture of 4-phenoxybenzaldehyde (3.96 g, 19.98 mmol), 1-(2-amino-2-oxoethyl)pyridinium chloride (3.45 g, 19.98 mmol) and ethyl 2-cyanoacetate (2.260 g, 19.98 mmol) in methanol (80 mL) at room temperature. The resultant yellow solution was stirred at room temperature for 15 h to give a suspension. The yellow solid was collected by filtration, washed with methanol (2×20 mL), toluene (2×20 mL), hexanes (2×20 mL) and dried under vacuum to give trans-3-cyano-6-oxo-4-(4-phenoxyphenyl)-5-(pyridinium-1-yl)-1,4,5,6-tetrahydropyridin-2-olate (7.00 g, 91% yield). MS (ES+) m/z: 384 (M+H); LC retention time: 2.472 min (analytical HPLC Method A).

Step 2:

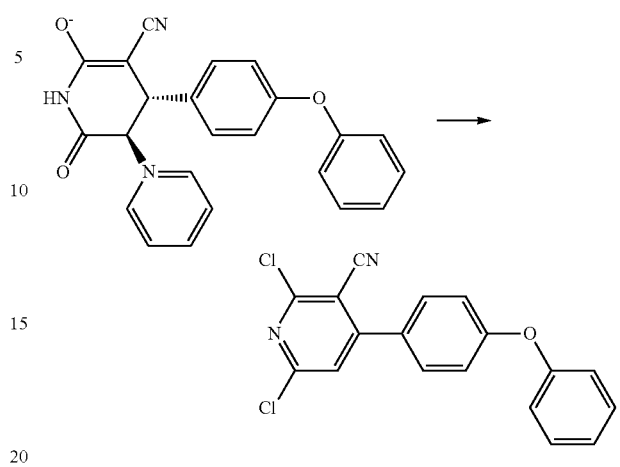

A mixture of phosphorus oxychloride (20 mL, 215 mmol) and trans-3-cyano-6-oxo-4-(4-phenoxyphenyl)-5-(pyridinium-1-yl)-1,4,5,6-tetrahydropyridin-2-olate (3.3 g, 8.61 mmol) was heated to 135° C. for 24 h. After cooling to room temperature, the mixture was diluted with ethyl acetate (200 mL), carefully treated with saturated sodium bicarbonate (200 mL), neutralized to pH~7 with careful addition of solid potassium carbonate while stirring vigorously, and extracted with ethyl acetate (3×200 mL). The combined extracts were washed with brine (100 mL), dried (MgSO$_4$) and concentrated. Silica gel chromatography, loading with toluene and eluting with 10% to 30% ethyl acetate in hexanes, gave 2,6-dichloro-4-(4-phenoxyphenyl)nicotinonitrile as a brown solid (1.20 g, 40% yield). MS (ES+) m/z: 341 (M+H); LC retention time: 4.046 min (analytical HPLC Method A).

Step 3:

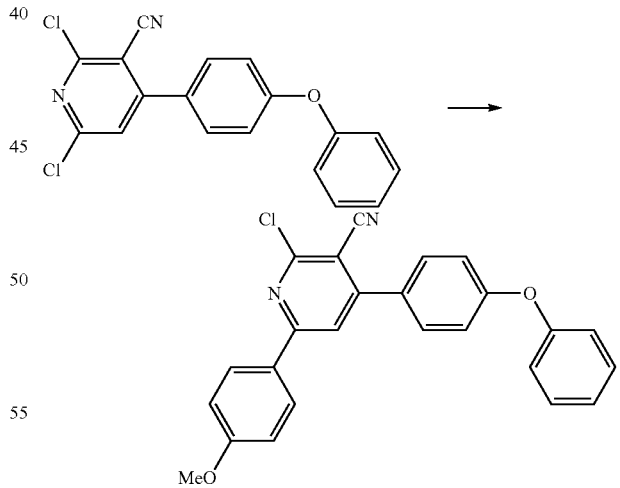

A mixture of 2,6-dichloro-4-(4-phenoxyphenyl)nicotinonitrile (110 mg, 0.322 mmol), 4-methoxyphenylboronic acid (53.9 mg, 0.355 mmol), palladium tetrakis(triphenylphosphine) (16.30 mg, 0.016 mmol) and potassium phosphate tribasic monohydrate (0.484 mL, 0.967 mmol) in N,N-dimethylformamide (3 mL) was heated under nitrogen to 100° C. for 15 h. After cooling to room temperature, the mixture was diluted with ethyl acetate (80 mL), washed with water (15 mL), brine (15 mL), dried (MgSO₄), and concentrated. Silica gel chromatography, loading with toluene and eluting with 5-30% ethyl acetate in hexanes, gave 2-chloro-6-(4-methoxyphenyl)-4-(4-phenoxyphenyl)nicotinonitrile as white solid (90 mg, 68% yield). ¹H NMR (500 MHz, CDCl₃) δ ppm 7.94-8.22 (2H, m), 7.69 (1H, s), 7.56-7.65 (2H, m), 7.42 (2H, t, J=7.97 Hz), 7.18-7.26 (1H, m), 7.06-7.19 (4H, m), 7.02 (2H, δ, J=8.80 Hz), 3.90 (3H, s); MS (ES+) m/z: 413 (M+H); LC retention time: 4.423 min (analytical HPLC Method A).

Step 4:

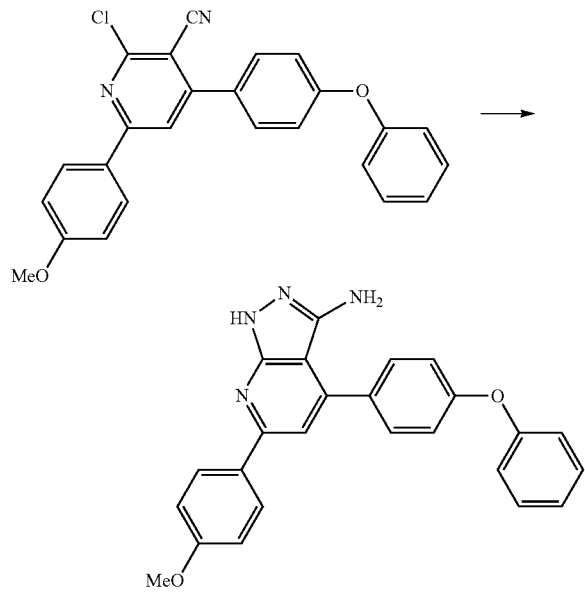

A mixture of 2-chloro-6-(4-methoxyphenyl)-4-(4-phenoxyphenyl)nicotinonitrile (90 mg, 0.218 mmol) and 35% aqueous hydrazine (0.195 mL, 2.180 mmol) in 2-propanol (2 mL) was heated to 160° C. under microwave for 1 h then cooled to room temperature to form yellow crystals. The crystals were collected by filtration, washed with cold methanol (2×2 mL), and dried under vacuum to give Example 8 (56 mg, 63% yield). ¹H NMR (400 MHz, CDCl₃) δ ppm 8.07 (2H, δ, J=8.78 Hz), 7.62 (2H, δ, J=8.53 Hz), 7.42 (3H, t, J=7.65 Hz), 7.36 (1H, s), 7.09-7.21 (4H, m), 7.03 (2H, δ, J=8.78 Hz), 3.89 (3H, s); MS (ES+) m/z: 409 (M+H); LC retention time: 4.035 min (analytical HPLC Method A).

Example 9

4-(4-Phenoxyphenyl)-6-(1-piperidinyl)-1H-pyrazolo [3,4-b]pyridin-3-amine

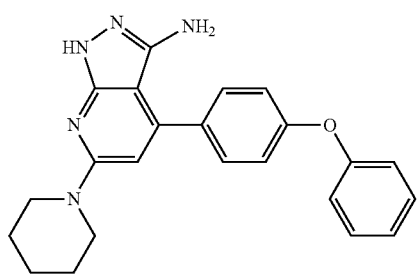 [SMILES: Nc1n[nH]c2nc(C3CCCCC3)cc(-c3ccc(Oc4ccccc4)cc3)c12]

Step 1:

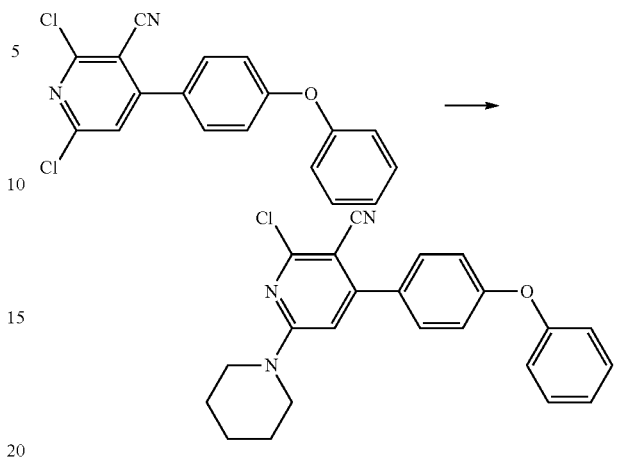

A mixture of 2,6-dichloro-4-(4-phenoxyphenyl)nicotinonitrile (34 mg, 0.100 mmol, from Step 2 of Example 8), triethylamine (0.028 mL, 0.199 mmol), 0.5 M acetonitrile solution of piperidine (0.199 mL, 0.100 mmol) in acetonitrile (1 mL) was stirred at room temperature for 36 h to give a suspension. The white solid was collected by filtration, washed with cold methanol (1 mL), dried under vacuum to give 2-chloro-4-(4-phenoxyphenyl)-6-(piperidin-1-yl)nicotinonitrile (15 mg, 39% yield). ¹H NMR (400 MHz, CDCl₃) δ ppm 7.51 (2H, δ, J=8.53 Hz), 7.39 (2H, t, J=8.03 Hz), 7.18 (1H, t, J=7.40 Hz), 6.98-7.12 (4H, 6.45 (1H, s), 3.63-3.81 (4H, m), 1.62-1.90 (7H, m), 1.52-1.80 (6H, s), 1.58 (9H, s); MS (ES+) m/z: 390 (M+H); LC retention time: 4.293 min (analytical HPLC Method A).

Step 2:

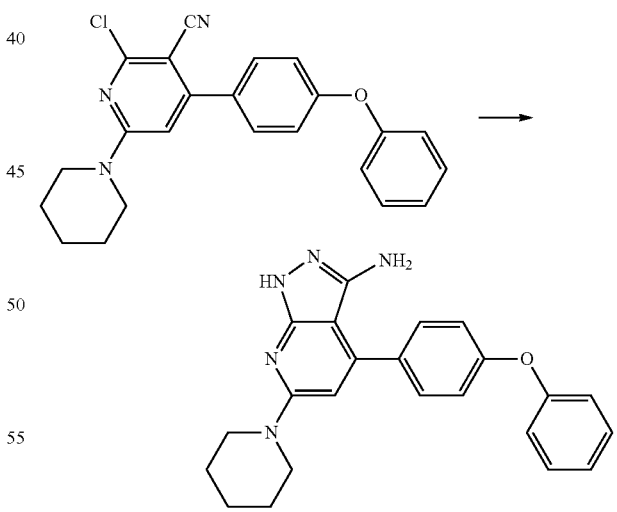

Following conditions described in Step 4 of Example 8, 2-chloro-4-(4-phenoxyphenyl)-6-(piperidin-1-yl)nicotinonitrile was reacted with hydrazine to give Example 9. ¹H NMR (400 MHz, methanol-d₄) δ ppm 7.47-7.65 (2H, m), 7.32-7.48 (2H, 7.15 (1H, t, J=7.40 Hz), 6.97-7.08 (2H, m), 6.96-7.13 (4H, m), 6.41 (1H, s), 3.52-3.73 (4H, m), 1.50-1.76 (6H, m). MS (ES+) m/z: 386 (M+H); LC retention time: 3.501 min (analytical HPLC Method A).

Example 10

6-Phenoxy-4-(4-phenoxyphenyl)-1H-pyrazolo[3,4-b]pyridin-3-amine

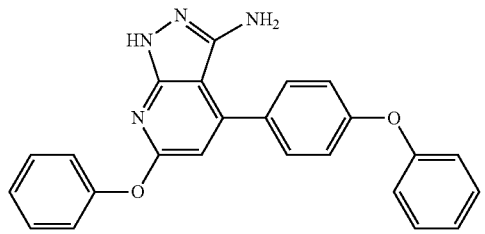 [SMILES: Nc1n[nH]c2nc(Oc3ccccc3)cc(-c3ccc(Oc4ccccc4)cc3)c12]

Step 1:

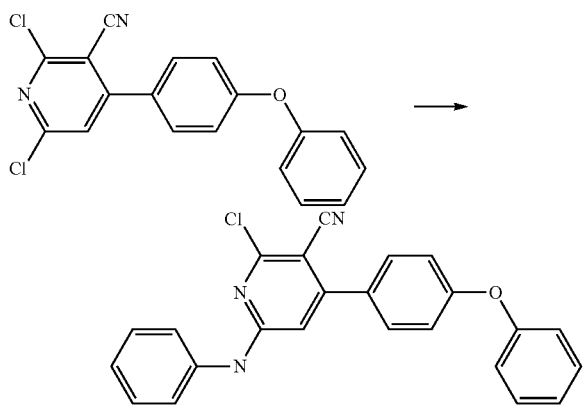

A mixture of 2,6-dichloro-4-(4-phenoxyphenyl)nicotinonitrile (51 mg, 0.149 mmol, from Step 2 of Example 8), phenol (15.47 mg, 0.164 mmol) and cesium carbonate (97 mg, 0.299 mmol) in DMSO (1.5 mL) was stirred at room temperature for 15 h. The mixture was diluted with ethyl acetate (60 mL), washed with water (2×5 mL), brine (5 mL), dried (MgSO₄) and concentrated. Silica gel chromatography, eluting with 0% to 20% ethyl acetate in hexanes, gave 2-chloro-6-phenoxy-4-(4-phenoxyphenyl)nicotinonitrile as a white solid (60 mg, 75% yield). $^1$H NMR (500 MHz, CDCl₃) δ ppm 7.52-7.73 (2H, m), 7.37-7.52 (4H, m), 7.25-7.36 (1H, m), 7.20-7.24 (1H, m), 7.08-7.18 (4H, m), 6.87 (1H, s); MS (ES+) m/z: 399 (M+H); LC retention time: 4.283 min (analytical HPLC Method A).

Step 2:

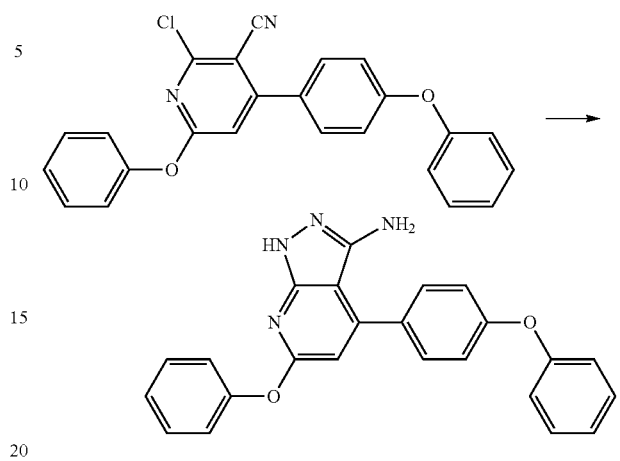

A mixture of 2-chloro-6-phenoxy-4-(4-phenoxyphenyl)nicotinonitrile (50 mg, 0.125 mmol) and 35% aqueous hydrazine (0.112 mL, 1.254 mmol) in 2-propanol (1.5 mL) was heated to 160° C. under microwave for 1 h. Purification with reverse phase HPLC (Sunfire S10 30×250 mm column), eluting with 70-100% solvent B (10% methanol-90% water-0.1% TFA) in solvent A (90% methanol-10% water-0.1% TFA), gave Example 10, as bis-TFA salt (9 mg, 12% yield). $^1$H NMR (400 MHz, methanol-d₄) δ ppm 7.54-7.67 (2H, m), 7.37-7.51 (4H, m), 7.22-7.31 (1H, m), 7.15-7.23 (5H, m), 7.12 (2H, δ), 6.73 (1H, s); MS (ES+) m/z: 395 (M+H); LC retention time: 4.053 min (analytical HPLC Method A).

Examples 11 to 23

Examples 11 to 14 were prepared from 2,6-dichloro-4-(4-phenoxyphenyl)nicotinonitrile following conditions similar to Steps 3 and 4 of Example 8. Examples 15 to 19 were prepared from 2,6-dichloro-4-(4-phenoxyphenyl)nicotinonitrile following conditions similar to Steps 1 and 2 of Example 9. Example 20 was prepared from 2,6-dichloro-4-(4-phenoxyphenyl)nicotinonitrile following conditions similar to Steps 1 and 2 of Example 10. Example 21 was prepared from 2,6-dichloro-4-(4-phenoxyphenyl)nicotinonitrile in the manner described above for the preparation of Example 10 except sodium methoxide was used as a base in the first step. Examples 22 and 23 were prepared following conditions similar to Step 3 of Example 6.

| Example No. | Structure | Spectral data* |
|---|---|---|
| Example 11: 4-(4-Phenoxyphenyl)-6-(4-pyridinyl)-1H-pyrazolo[3,4-b]pyridin-3-amine | 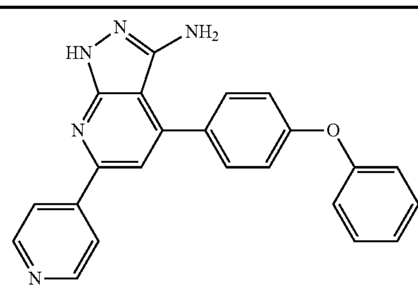 | $^1$H NMR (500 MHz, methanol-d₄) δ ppm 8.66 (2 H, δ, J = 5.77 Hz), 8.16 (2 H, δ, J = 6.05 Hz), 7.68 (2 H, δ, J = 8.52 Hz), 7.58 (1 H, s), 7.41 (2H, t, J = 7.97 Hz), 7.15-7.25 (3 H, m), 7.11 (2 H, δ, J = 7.70 Hz); MS (ES+) m/z: 380 (M + H); LC retention time: 3.200 min. |

-continued

| Example No. | Structure | Spectral data* |
|---|---|---|
| Example 12: 6-(3-Methoxyphenyl)-4-(4-phenoxyphenyl)-1H-pyrazolo[3,4-b]pyridin-3-amine | 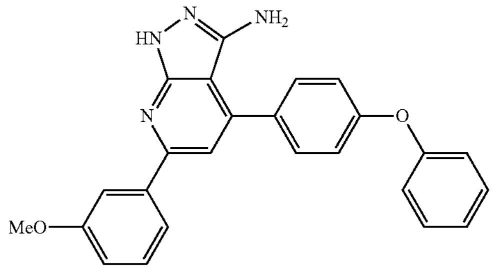 [SMILES: COc1cccc(-c2cc(-c3ccc(Oc4ccccc4)cc3)c3c(N)n[nH]c3n2)c1] | ¹H NMR (400 MHz, methanol-d₄) δ ppm 7.59-7.77 (4 H, m), 7.38-7.52 (4 H, m), 7.17-7.31 (3 H, m), 7.09-7.15 (2 H, m), 6.94-7.05 (1 H, m), 3.89 (3 H, s); MS (ES+) m/z: 409 (M + H); LC retention time: 4.098 min. |
| Example 13: 3-(3-Amino-4-(4-phenoxyphenyl)-1H-pyrazolo[3,4-b]pyridin-6-yl)benzoic acid | 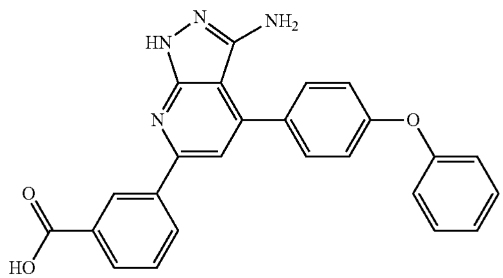 [SMILES: Nc1n[nH]c2nc(-c3cccc(C(=O)O)c3)cc(-c3ccc(Oc4ccccc4)cc3)c12] | ¹H NMR (500 MHz, methanol-d₄) δ ppm 8.73-8.87 (1 H, m), 8.37 (1 H, δ, J = 8.25 Hz), 8.14 (1 H, δ, J = 7.97 Hz), 7.67-7.77 (2 H, m), 7.64 (1 H, t, J = 7.70 Hz), 7.56 (1 H, s), 7.32-7.50 (2 H, m), 7.16-7.24 (3 H, m), 7.13 (2 H, δ, J = 7.70 Hz); MS (ES+) m/z: 423 (M + H); LC retention time: 3.936 min. |
| Example 14: 1-(3-(3-Amino-4-(4-phenoxyphenyl)-1H-pyrazolo[3,4-b]pyridin-6-yl)phenyl)ethanone | 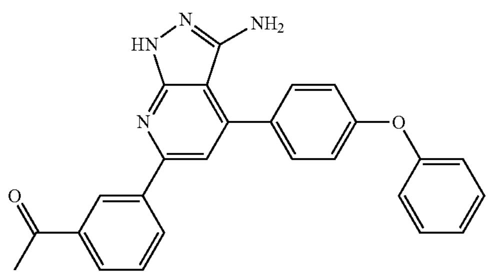 [SMILES: CC(=O)c1cccc(-c2cc(-c3ccc(Oc4ccccc4)cc3)c3c(N)n[nH]c3n2)c1] | ¹H NMR (400 MHz, methanol-d₄) δ ppm 8.65 (1 H, s), 8.22-8.35 (1 H, m), 7.91-8.06 (1 H, m), 7.78 (1 H, s), 7.49-7.65 (3 H, m), 7.46 (1 H, s), 7.24-7.41 (2 H, m), 6.98-7.14 (4 H, m), 2.61 (3 H, s); MS (ES+) m/z: 421 (M + H); LC retention time: 3.970 min. |
| Example 15: 4-(4-Phenoxyphenyl)-6-(1-pyrrolidinyl)-1H-pyrazolo[3,4-b]pyridin-3-amine | 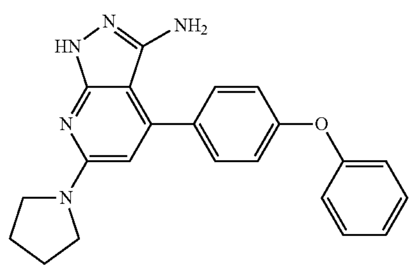 [SMILES: Nc1n[nH]c2nc(N3CCCC3)cc(-c3ccc(Oc4ccccc4)cc3)c12] | ¹H NMR (400 MHz, methanol-d₄) δ ppm 7.58 (2 H, δ, J = 8.78 Hz), 7.30-7.51 (2 H, m), 7.02-7.25 (5 H, m), 6.20 (1 H, s), 3.50-3.68 (4 H, m), 2.01-2.19 (4 H, m); MS (ES+) m/z: 372 (M + H); LC retention time: 3.196 min. |
| Example 16: N⁶-Cyclopentyl-4-(4-phenoxyphenyl)-1H-pyrazolo[3,4-b]pyridine-3,6-diamine | | ¹H NMR (400 MHz, methanol-d₄) δ ppm 7.45-7.73 (2 H, m), 7.31-7.45 (2 H, m), 7.12-7.25 (1 H, m), 6.96-7.13 (4 H, m), 6.14 (1 H, s), 4.16-4.35 (1 H, m), 1.98-2.18 (2 H, m), 1.69-1.84 (2 H, m), 1.63 (1 H, δ, J = 4.52 Hz), 1.43-1.69 (4 H, m); MS (ES+) m/z: 386 (M + H); LC retention time: 3.491 min. |
| Example 17: tert-Butyl(1-(3-amino-4-(4-phenoxyphenyl)-1H-pyrazolo[3,4-b]pyridin-6-yl)-3-pyrrolidinyl)carbamate | 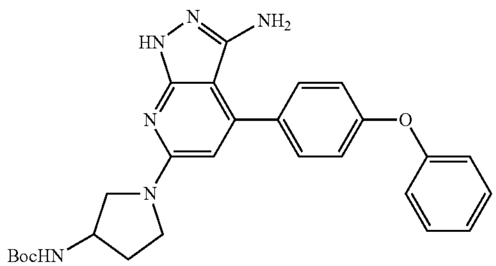 [SMILES: CC(C)(C)OC(=O)NC1CCN(c2cc(-c3ccc(Oc4ccccc4)cc3)c3c(N)n[nH]c3n2)C1] | ¹H NMR (400 MHz, methanol-d₄) δ ppm 7.55-7.72 (2 H, m), 7.34-7.48 (2 H, m), 7.06-7.31 (5 H, m), 6.27 (1 H, s), 4.21-4.39 (1 H, m), 3.82-4.00 (1 H, m), 3.62-3.81 (2 H, m), 3.42-3.61 (1 H, m), 2.20-2.42 (1 H, m), 1.95-2.15 (1 H, m), 1.45 (9 H, s); MS (ES+) m/z: 487 (M + H); LC retention time: 3.541 min. |

-continued

| Example No. | Structure | Spectral data* |
|---|---|---|
| Example 18: tert-Butyl(1-(3-amino-4-(4-phenoxyphenyl)-1H-pyrazolo[3,4-b]pyridin-6-yl)-4-piperidinyl)carbamate | 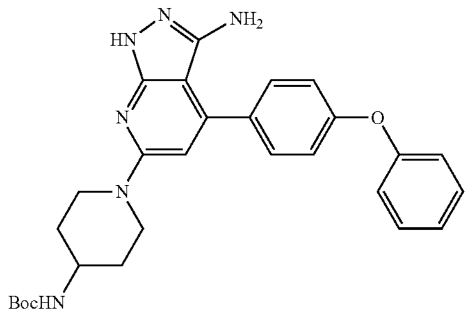 [SMILES: CC(C)(C)OC(=O)NC1CCN(c2cc(-c3ccc(Oc4ccccc4)cc3)c3c(N)n[nH]c3n2)CC1] | $^1$H NMR (500 MHz, methanol-$d_4$) δ ppm 7.48-7.70 (2 H, m), 7.33-7.53 (2 H, m), 7.00-7.28 (5 H, m), 6.62 (1 H, s), 4.30-4.56 (2 H, m), 3.50-3.79 (1 H, m), 3.10-3.24 (2 H, m), 1.75-2.05 (2 H, m), 1.44-1.59 (2 H, m), 1.43 (9 H, s); MS (ES+) m/z: 501 (M + H); LC retention time: 3.616 min. |
| Example 19: 6-(4-Benzoyl-1-piperazinyl)-4-(4-phenoxyphenyl)-1H-pyrazolo[3,4-b]pyridin-3-amine | 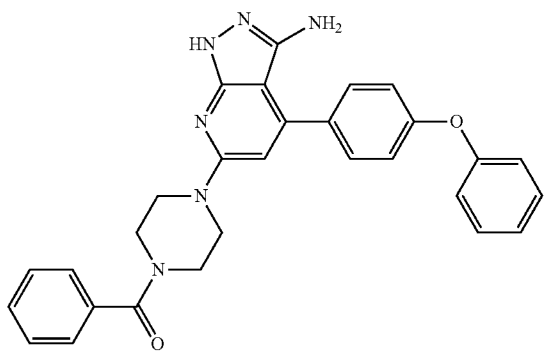 [SMILES: Nc1n[nH]c2nc(N3CCN(C(=O)c4ccccc4)CC3)cc(-c3ccc(Oc4ccccc4)cc3)c12] | $^1$H NMR (400 MHz, methanol-$d_4$) δ ppm 7.55-7.70 (2 H, m), 7.46-7.58 (5 H, m), 7.37-7.45 (2 H, m), 7.15-7.27 (3 H, m), 7.02-7.16 (2 H, m), 6.71 (1 H, s), 3.55-4.07 (8 H, m); MS (ES+) m/z: 491 (M + H); LC retention time: 3.315 min. |
| Example 20: 6-(4-Methoxyphenoxy)-4-(4-phenoxyphenyl)-1H-pyrazolo[3,4-b]pyridin-3-amine | 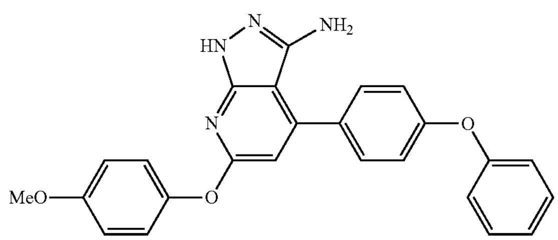 [SMILES: COc1ccc(Oc2cc(-c3ccc(Oc4ccccc4)cc3)c3c(N)n[nH]c3n2)cc1] | $^1$H NMR (400 MHz, methanol-$d_4$) δ ppm 7.60 (2 H, δ, J = 8.78 Hz), 7.35-7.50 (2 H, m), 7.06-7.29 (7 H, m), 6.97 (2 H, δ, J = 9.04 Hz), 6.69 (1 H, s), 3.81 (3 H, s); MS (ES+) m/z: 426 (M + H); LC retention time: 4.078 min. |
| Example 21: 6-Methoxy-4-(4-phenoxyphenyl)-1H-pyrazolo[3,4-b]pyridin-3-amine | 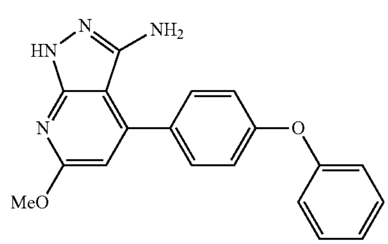 [SMILES: COc1cc(-c2ccc(Oc3ccccc3)cc2)c2c(N)n[nH]c2n1] | $^1$H NMR (500 MHz, methanol-$d_4$) δ ppm 7.50-7.70 (2 H, m), 7.34-7.48 (2 H, m), 7.17-7.24 (1 H, m), 7.06-7.18 (4 H, m), 6.57 (1 H, s), 4.03 (3 H, s); MS (ES+) m/z: 333 (M + H); LC retention time: 3.718 min. |
| Example 22: 4-(3-Amino-4-(4-phenoxyphenyl)-1H-pyrazolo[3,4-b]pyridin-6-yl)phenol | 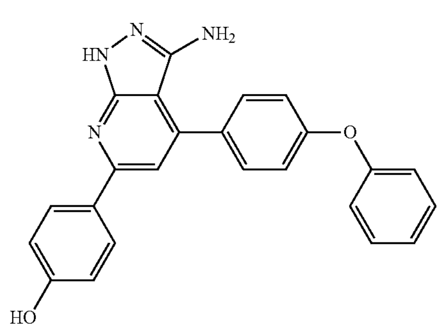 [SMILES: Nc1n[nH]c2nc(-c3ccc(O)cc3)cc(-c3ccc(Oc4ccccc4)cc3)c12] | $^1$H NMR (400 MHz, methanol-$d_4$) δ ppm 7.91-8.06 (2 H, m), 7.59-7.72 (2 H, m), 7.42 (2 H, t, J = 8.03 Hz), 7.37 (1 H, s), 7.14-7.24 (3 H, m), 7.03-7.16 (2 H, m), 6.84-7.00 (2 H, m); MS (ES+) m/z: 395 (M + H); LC retention time: 3.723 min. |

| Example No. | Structure | Spectral data* |
|---|---|---|
| Example 23: 3-(3-Amino-4-(4-phenoxyphenyl)-1H-pyrazolo[3,4-b]pyridin-6-yl)phenol | 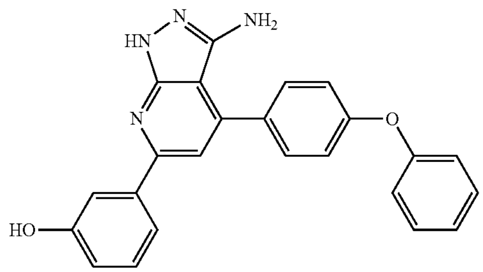 [SMILES: Nc1n[nH]c2nc(-c3cccc(O)c3)cc(-c3ccc(Oc4ccccc4)cc3)c12] | $^{1}$H NMR (400 MHz, methanol-$d_4$) δ ppm 7.63-7.81 (2 H, m), 7.49-7.59 (2 H, m), 7.40-7.48 (3 H, m), 7.33-7.40 (1 H, m), 7.18-7.25 (3 H, m), 7.07-7.16 (2 H, m), 6.90-7.03 (1 H, m); MS (ES+) m/z: 395 (M + H); LC retention time: 3.835 min. |

*Analytical HPLC Method A

Examples 24 and 25

N-(3-(3-Amino-4-(4-phenoxyphenyl)-1H-pyrazolo[3,4-b]pyridin-6-yl)phenyl)acetamide, and 6-(3-Aminophenyl)-4-(4-phenoxyphenyl)-1H-pyrazolo[3,4-b]pyridin-3-amine, respectively

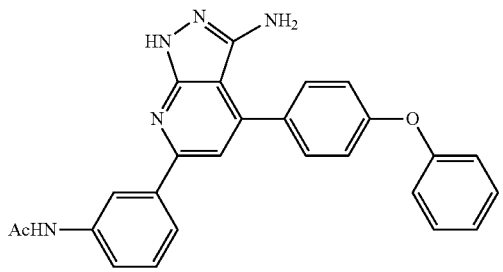

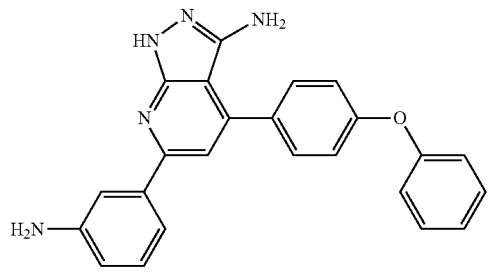

Step 1:

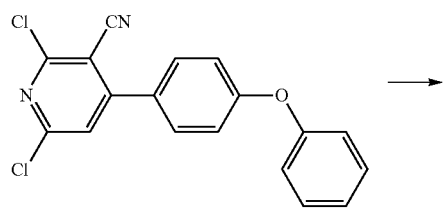

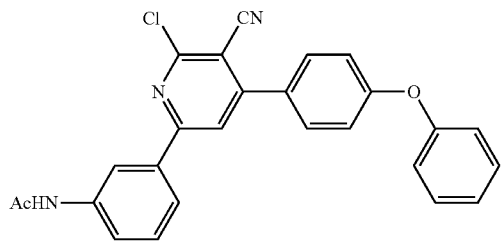

A mixture of 2,6-dichloro-4-(4-phenoxyphenyl)nicotinonitrile (51 mg, 0.149 mmol, from Step 2 of Example 8), 3-acetamidophenylboronic acid (29.4 mg, 0.164 mmol), palladium tetrakis(triphenylphosphine) (15.12 mg, 0.015 mmol) and potassium phosphate tribasic monohydrate (0.299 mL, 0.598 mmol) in N,N-dimethylformamide (1.5 mL) was heated to 90° C. under nitrogen for 2 h. After cooling to room temperature, the mixture was diluted with ethyl acetate (80 mL), washed with water (10 mL), brine (10 mL), dried (MgSO$_4$) and concentrated. Silica gel chromatography, eluting with 5-40% ethyl acetate in hexanes, gave N-(3-(6-chloro-5-cyano-4-(4-phenoxyphenyl)pyridin-2-yl)phenyl)acetamide as white solid (28 mg, 42% yield). $^{1}$H NMR (400 MHz, CDCl$_3$) δ ppm 8.26 (1H, s), 7.79-7.89 (1H, m), 7.77 (1H, s), 7.67-7.73 (1H, m), 7.58-7.66 (2H, m), 7.50-7.57 (1H, m), 7.37-7.47 (3H, m), 7.17-7.24 (1H, m), 7.05-7.16 (4H, m), 2.22 (3H, s); MS (ES+) m/z: 440 (M±H); LC retention time: 4.165 min (analytical HPLC Method A).

Step 2:

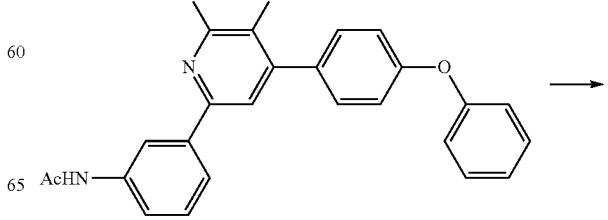

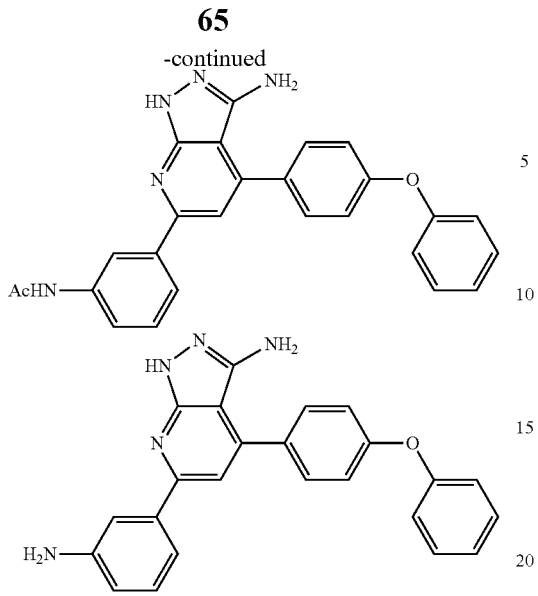

A mixture of N-(3-(6-chloro-5-cyano-4-(4-phenoxyphenyl)pyridin-2-yl)phenyl)acetamide (25 mg, 0.057 mmol) and 35% aqueous hydrazine (0.051 mL, 0.568 mmol) in 2-propanol (1.5 mL) was heated to 160° C. under microwave for 1 h then cooled to room temperature. Purification with reverse phase HPLC (Sunfire S10 30×250 mm column), eluting with 60-90% solvent B (10% methanol-90% water-0.1% TFA) in solvent A (90% methanol-10% water-0.1% TFA), gave Example 25 as the faster eluting peak (18 mg, 41% yield, yellow solid) and Example 24 as the slower eluting peak (3 mg, 8% yield, yellow solid).

Characterization of Example 24: $^1$H NMR (400 MHz, methanol-d$_4$) δ ppm 8.31 (1H, s), 7.67-7.82 (1H, m), 7.62 (2H, δ, J=8.53 Hz), 7.48-7.60 (1H, m), 7.28-7.46 (4H, m), 7.09-7.21 (3H, m), 6.96-7.09 (2H, m), 2.08 (3H, s); MS (ES+) m/z: 436 (M+H); LC retention time: 3.836 min (analytical HPLC Method A).

Characterization of Example 25: $^1$H NMR (400 MHz, methanol-d$_4$) δ ppm 8.17-8.29 (2H, m), 7.63-7.73 (3H, m), 7.59 (1H, s), 7.47-7.53 (1H, m), 7.38-7.45 (2H, m), 7.17-7.24 (3H, m), 7.08-7.16 (2H, m); MS (ES+) m/z: 394 (M+H); LC retention time: 3.380 min (analytical HPLC Method A).

Example 26

6-(3-Amino-1-pyrrolidinyl)-4-(4-phenoxyphenyl)-1H-pyrazolo[3,4-b]pyridin-3-amine

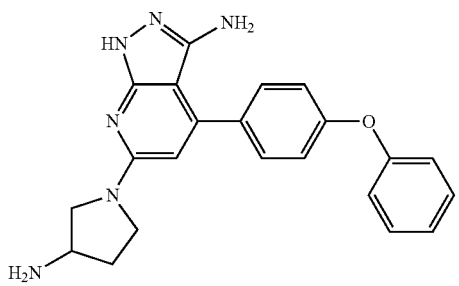 [SMILES: Nc1n[nH]c2nc(N3CCC(N)C3)cc(-c3ccc(Oc4ccccc4)cc3)c12]

Trifluoroacetic acid (0.5 mL, 6.49 mmol) was added to a mixture of tert-butyl 1-(3-amino-4-(4-phenoxyphenyl)-1H-pyrazolo[3,4-b]pyridin-6-yl)pyrrolidin-3-ylcarbarnate bis-TFA salt (120 mg, 0.168 mmol, from Example 17) in dichloromethane (1 mL). The mixture was stirred at room temperature for 2 h and concentrated under vacuum to give Example 26 as tris-TFA salt (123 mg, 100% yield). $^1$H NMR (400 MHz, methanol-d$_4$) δ ppm 7.59 (2H, δ, J=8.78 Hz), 7.34-7.49 (2H, m), 7.02-7.28 (5H, m), 6.38 (1H, s), 4.04-4.15 (1H, m), 3.91-4.03 (1H, m), 3.70-3.91 (3H, m), 2.42-2.67 (1H, m), 2.15-2.35 (1H, m); MS (ES+) m/z: 387 (M+H); LC retention time: 2.611 min (analytical HPLC Method A).

Example 27

1-(3-(3-Amino-4-(4-phenoxyphenyl)-1H-pyrazolo[3,4-b]pyridin-6-yl)phenyl)-3-(4-methyl-1,3-thiazol-2-yl)urea

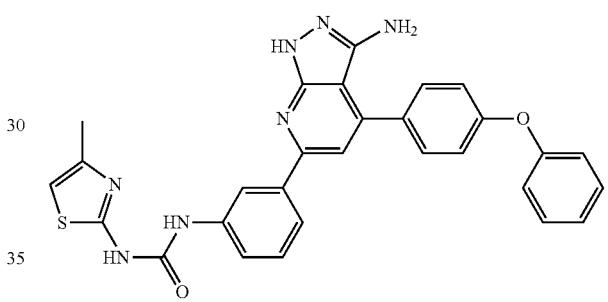

A mixture of Example 26 (9.4 mg, 0.013 mmol), triethylamine (10.69 μL, 0.077 mmol) and phenyl 4-methylthiazol-2-ylcarbamate (3.29 mg, 0.014 mmol) in dichloromethane (1 mL) was stirred at room temperature for 40 h and then concentrated. Purification with reverse phase HPLC (Sunfire S10 30×250 mm column), eluting with 60-90% solvent 13 (10% methanol-90% water-0.1% TFA) in solvent A (90% methanol-10% water-0.1% TFA), gave Example 27 as bis-TFA salt (4 mg, 38% yield, yellow solid). $^1$H NMR (400 MHz, methanol-d$_4$) δ ppm 8.39 (1H, s), 7.80-7.89 (1H, m), 7.68-7.80 (2H, m), 7.37-7.66 (5H, m), 7.18-7.27 (3H, m), 7.07-7.18 (2H, m), 6.74 (1H, s), 2.35 (3H, s); MS (ES+) m/z: 534 (M+H); LC retention time: 4.05 min (analytical HPLC Method A).

Examples 28 to 54

Examples 28 and 29 were prepared in a manner similar to the preparation of Examples 24 and 25. Example 30 was prepared from Example 18 in a similar manner to Example 26. Example 31 was prepared from Example 26 in a manner similar to preparation of Example 27. Example 32 was prepared from Example 30. Examples 33 to 37 were prepared from Example 13.

| Example No. | Structure | Spectral data* |
|---|---|---|
| Example 28:<br>6-(4-Aminophenyl)-4-(4-phenoxyphenyl)-1H-pyrazolo[3,4-b]pyridin-3-amine | | $^1$H NMR (500 MHz, methanol-d$_4$) δ ppm 7.95 (2 H, δ, J = 8.80 Hz), 7.63-7.75 (2 H, m), 7.38-7.50 (2 H, m), 7.35 (1 H, s), 7.15-7.24 (3 H, m), 7.12 (2 H, δ, J = 7.42 Hz), 6.99 (2 H, δ, J = 8.52 Hz); MS (ES+) m/z: 394 (M + H); LC retention time: 3.145 min. |
| Example 29:<br>N-(4-(3-Amino-4-(4-phenoxyphenyl)-1H-pyrazolo[3,4-b]pyridin-6-yl)phenyl)acetamide | | $^1$H NMR (500 MHz, methanol-d$_4$) δ ppm 8.08 (2 H, δ, J = 8.80 Hz), 7.75 (2 H, δ, J = 8.80 Hz), 7.70 (2 H, δ, J = 8.80 Hz), 7.47 (1 H, s), 7.34-7.45 (2 H, m), 7.16-7.25 (3 H, m), 7.13 (2 H, δ, J = 7.70 Hz), 2.17 (3 H, s); MS (ES+) m/z: 436 (M + H); LC retention time: 3.550 min. |
| Example 30:<br>6-(4-Amino-1-piperidinyl)-4-(4-phenoxyphenyl)-1H-pyrazolo[3,4-b]pyridin-3-amine | | $^1$H NMR (400 MHz, methanol-d$_4$) δ ppm 7.51-7.70 (2 H, m), 7.36-7.54 (2 H, m), 7.02-7.29 (5 H, m), 6.73 (1 H, s), 4.60-4.83 (2 H, m), 3.41-3.58 (1 H, m), 3.04-3.25 (2 H, m), 2.04-2.18 (2 H, m), 1.57-1.71 (2 H, m); MS (ES+) m/z: 401 (M + H); LC retention time: 2.700 min. |
| Example 31:<br>1-(1-(3-Amino-4-(4-phenoxyphenyl)-1H-pyrazolo[3,4-b]pyridin-6-yl)-3-pyrrolidinyl)-3-(4-methyl-1,3-thiazol-2-yl)urea | | $^1$H NMR (400 MHz, methanol-d$_4$) δ ppm 7.52-7.68 (2 H, m), 7.33-7.55 (2 H, m), 7.00-7.31 (5 H, m), 6.69 (1 H, s), 6.32 (1 H, s), 4.40-4.63 (1 H, m), 3.89-4.07 (1 H, m), 3.73-3.87 (2 H, m), 3.60-3.68 (1 H, m), 2.36-2.52 (1 H, m), 2.30 (3 H, s), 2.01-2.25 (1 H, m); MS (ES+) m/z: 527 (M + H); LC retention time: 3.466 min. |
| Example 32:<br>N-(1-(3-Amino-4-(4-phenoxyphenyl)-1H-pyrazolo[3,4-b]pyridin-6-yl)-4-piperidinyl)benzamide | | $^1$H NMR (400 MHz, methanol-d$_4$) δ ppm 7.74-7.92 (2 H, m), 7.50-7.65 (3 H, m), 7.37-7.48 (4 H, m), 7.04-7.29 (5 H, m), 6.70 (1 H, s), 4.49-4.77 (2 H, m), 4.15-4.40 (1 H, m), 3.13-3.29 (2 H, m), 1.92-2.20 (2 H, m), 1.53-1.82 (2 H, m); MS (ES+) m/z: 505 (M + H); LC retention time: 3.548 min. |

| Example No. | Structure | Spectral data* |
|---|---|---|
| Example 33: 3-(3-Amino-4-(4-phenoxyphenyl)-1H-pyrazolo[3,4-b]pyridin-6-yl)benzohydrazide | 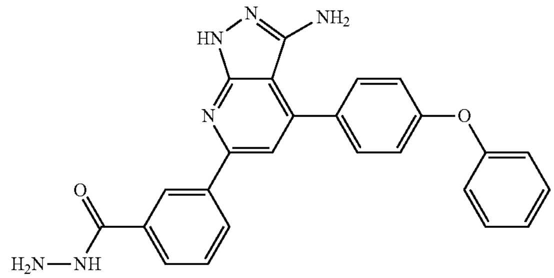 [SMILES: NNC(=O)c1cccc(-c2cc(-c3ccc(Oc4ccccc4)cc3)c3c(N)n[nH]c3n2)c1] | ¹H NMR (400 MHz, methanol-d₄) δ ppm 8.60 (1 H, s), 8.33 (1 H, δ, J = 8.78 Hz), 7.94 (1 H, δ, J = 7.53 Hz), 7.71 (2 H, s), 7.61-7.69 (4 H, m), 7.50 (1 H, s), 7.36-7.44 (2 H, m), 7.14-7.21 (2 H, m), 7.04-7.14 (2 H, m); MS (ES+) m/z: 437 (M + H); LC retention time: 3.418 min. |
| Example 34: 3-(3-Amino-4-(4-phenoxyphenyl)-1H-pyrazolo[3,4-b]pyridin-6-yl)-N-phenylbenzamide | 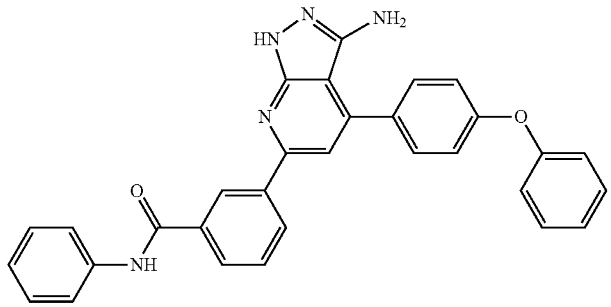 [SMILES: Nc1n[nH]c2nc(-c3cccc(C(=O)Nc4ccccc4)c3)cc(-c3ccc(Oc4ccccc4)cc3)c12] | ¹H NMR (400 MHz, methanol-d₄) δ ppm 8.72 (1 H, s), 8.38 (1 H, δ, J = 8.28 Hz), 8.07 (1 H, δ, J = 8.28 Hz), 7.65-7.78 (6 H, m), 7.30-7.50 (4 H, m), 7.06-7.26 (5 H, m); MS (ES+) m/z: 498 (M + H); LC retention time: 4.033 min. |
| Example 35: 6-(3-(4-Morpholinylcarbonyl)phenyl)-4-(4-phenoxyphenyl)-1H-pyrazolo[3,4-b]pyridin-3-amine | 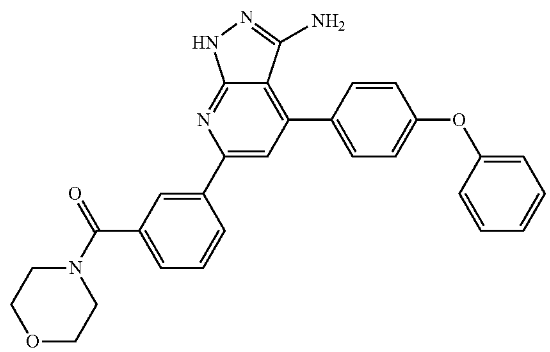 [SMILES: Nc1n[nH]c2nc(-c3cccc(C(=O)N4CCOCC4)c3)cc(-c3ccc(Oc4ccccc4)cc3)c12] | ¹H NMR (500 MHz, methanol-d₄) δ ppm 8.10-8.39 (2 H, m), 7.67-7.76 (2 H, m), 7.50-7.65 (3H, m), 7.36-7.52 (2 H, m), 7.19-7.29 (2 H, m), 7.04-7.18 (3 H, m), 3.71-3.92 (4 H, m), 3.60-3.71 (2 H, m), 3.45-3.58 (2 H, m); MS (ES+) m/z: 492 (M + H); LC retention time: 3.755 min. |
| Example 36: 3-(3-Amino-4-(4-phenoxyphenyl)-1H-pyrazolo[3,4-b]pyridin-6-yl)-N-cyclopropylbenzamide | 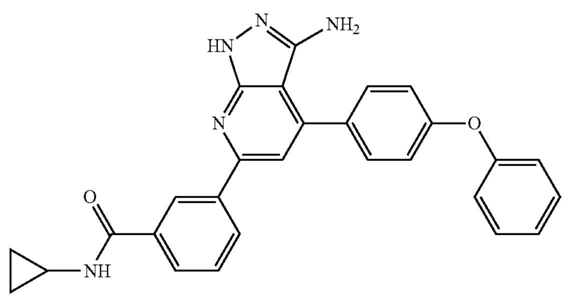 [SMILES: Nc1n[nH]c2nc(-c3cccc(C(=O)NC4CC4)c3)cc(-c3ccc(Oc4ccccc4)cc3)c12] | ¹H NMR (500 MHz, methanol-d₄) δ ppm 8.53 (1 H, s), 8.27 (1 H, δ, J = 7.70 Hz), 7.90 (1 H, δ, J = 7.97 Hz), 7.67 (2 H, δ, J = 8.80 Hz), 7.52-7.63 (2 H, m), 7.39 (2 H, t, J = 7.97 Hz), 7.12-7.25 (3 H, m), 7.09 (2 H, δ, J = 8.52 Hz), 2.74-2.93 (1 H, m), 0.69-0.90 (2 H, m), 0.49-0.68 (2 H, m); MS (ES+) m/z: 462 (M + H); LC retention time: 3.823 min. |
| Example 37: 3-(3-Amino-4-(4-phenoxyphenyl)-1H-pyrazolo[3,4-b]pyridin-6-yl)-N-1H-indol-2-ylbenzamide | 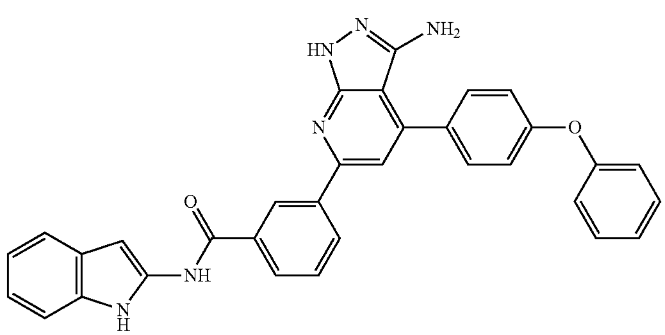 [SMILES: Nc1n[nH]c2nc(-c3cccc(C(=O)Nc4cc5ccccc5[nH]4)c3)cc(-c3ccc(Oc4ccccc4)cc3)c12] | ¹H NMR (500 MHz, methanol-d₄) δ ppm 8.76 (1 H, s), 8.38 (1 H, δ, J = 7.97 Hz), 8.08 (1 H, δ, J = 7.97 Hz), 7.64-7.76 (4 H, m), 7.62 (1 H, s), 7.33-7.46 (4 H, m), 7.14-7.25 (3 H, m), 7.11 (2 H, δ, J = 7.70 Hz), 6.94-7.07 (2 H, m); MS (ES+) m/z: 537 (M + H); LC retention time: 4.141 min. |

*Analytical HPLC Method A

Example 38

4-(2-Naphthyl)-1H-1-pyrazolo[3,4-c]pyridin-3-amine

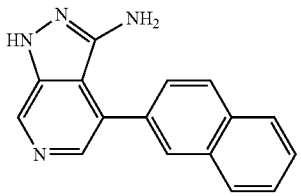 [SMILES: Nc1n[nH]c2cncc(-c3ccc4ccccc4c3)c12]

Step 1:

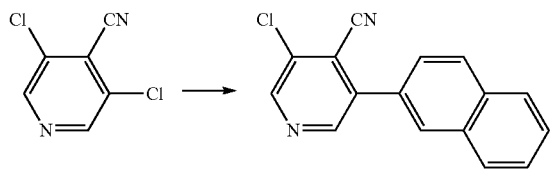

A mixture of 3,5-dichloroisonicotinonitrile (0.300 g, 1.734 mmol), naphthalen-2-ylboronic acid (0.328 g, 1.908 mmol), potassium phosphate (0.736 g, 3.47 mmol) and palladium tetrakis(triphenylphosphine) (0.100 g, 0.087 mmol) was pumped and backfilled with nitrogen 3 times. N,N-Dimethylacetamide (6 mL) was added. The mixture was again pumped and backfilled with nitrogen 3 times. The reaction tube was sealed and heated to 150° C. under microwave for 30 min. The mixture was diluted with ethyl acetate (80 mL), washed with 1:1 mixture of brine and water (30 mL), brine (30 mL), dried (MgSO$_4$) and concentrated. Silica gel chromatography, loading with toluene and eluting with 10-35% ethyl acetate in hexanes, gave 3-chloro-5-(naphthalen-2-yl)isonicotinonitrile as a white solid (240.5 mg, 46% yield). $^1$H NMR (400 MHz, CDCl$_3$) δ ppm 8.83 (1H, s), 8.81 (1H, s), 8.00-8.15 (2H, m), 7.87-8.00 (2H, m), 7.67 (1H, dd, J=8.53, 2.01 Hz), 7.53-7.64 (2H, m); MS (ES+) m/z: 265 (M+H); LC retention time: 4.066 min (analytical HPLC Method A).

Step 2:

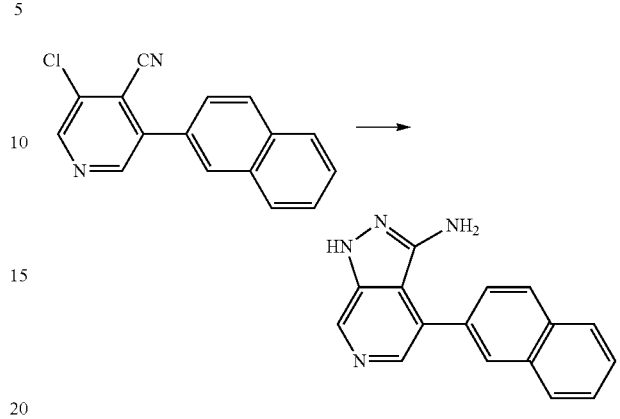

A suspension of 3-chloro-5-(naphthalen-2-yl)isonicotinonitrile (47.6 mg, 0.180 mmol) and 35% aqueous hydrazine (0.323 mL, 3.60 mmol) in 1-propanol (2 mL) in a microwave tube was sealed and heated to 160° C. under microwave for 1 h. Reverse phase HPLC (PHENOMENEX® Luna 5 u C18 100×21.2 mm column), eluting with 20-60% solvent B (10% methanol-90% water-0.1% TFA) in solvent A (90% methanol-10% water-0.1% TFA), gave Example 38 as yellow solid, assumed as bis-TFA salt (49.1 mg, 45% yield). $^1$H NMR (400 MHz, methanol-d$_6$) δ ppm 9.15 (1H, s), 8.16-8.29 (2H, m), 8.14 (1H, δ, J=8.53 Hz), 7.96-8.08 (2H, m), 7.75 (1H, dd, J=8.41, 1.88 Hz), 7.57-7.68 (2H, m); MS (ES+) m/z: 261 (M+H); LC retention time: 2.533 min (analytical HPLC Method A).

Examples 39 to 49

Examples 39 to 49 were Prepared Following Conditions Similar to Steps 1 and 2 of Example 38

| Example No. | Structure | Spectral data* |
|---|---|---|
| Example 39: 4-(4-Methoxyphenyl)-1H-pyrazolo[3,4-c]pyridin-3-amine | 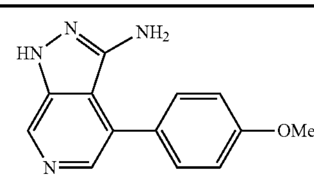 | $^1$H NMR (400 MHz, methanol-d$_4$) δ ppm 9.11 (1 H, s), 8.07 (1 H, s), 7.48-7.70 (2 H, m), 7.06-7.30 (2 H, m), 3.91 (3 H, s); MS (ES+) m/z: 241 (M + H); LC retention time: 1.840 min. |
| Example 40: 4-(3-Methoxyphenyl)-1H-pyrazolo[3,4-c]pyridin-3-amine | 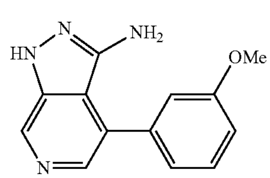 [SMILES: COc1cccc(-c2cncc3[nH]nc(N)c23)c1] | $^1$H NMR (400 MHz, methanol-d$_4$) δ ppm 9.17 (1 H, s), 8.11 (1 H, s), 7.54 (1 H, t, J = 8.03 Hz), 7.01-7.30 (3 H, m), 3.89 (3 H, s); MS (ES+) m/z: 241 (M + H); LC retention time: 1.775 min. |
| Example 41: 4-(4-Phenoxyphenyl)-1H-pyrazolo[3,4-c]pyridin-3-amine | 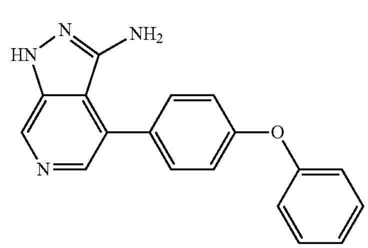 [SMILES: Nc1n[nH]c2cncc(-c3ccc(Oc4ccccc4)cc3)c12] | $^1$H NMR (400 MHz, methanol-d$_4$) δ ppm 9.07 (1 H, s), 8.07 (1 H, s), 7.53-7.74 (2 H, m), 7.33-7.52 (2 H, m), 7.15-7.29 (3 H, m), 7.01-7.15 (2 H, m), 5.48 (1 H, s); MS (ES+) m/z: 303 (M + H); LC retention time: 2.973 min. |

-continued

| Example No. | Structure | Spectral data* |
|---|---|---|
| Example 42: 4-(1,3-Benzodioxol-5-yl)-1H-pyrazolo[3,4-c]pyridin-3-amine | 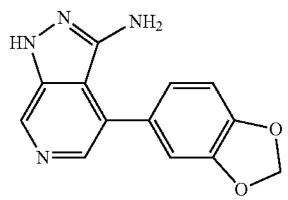 [SMILES: Nc1n[nH]c2cncc(-c3ccc4c(c3)OCO4)c12] | $^1$H NMR (400 MHz, methanol-d$_4$) δ ppm 9.14 (1 H, s), 8.07 (1 H, s), 6.72-7.33 (3 H, m), 6.10 (2 H, s); MS (ES+) m/z: 255 (M + H); LC retention time: 1.662 min. |
| Example 43: 4-(4-Isopropoxyphenyl)-1H-pyrazolo[3,4-c]pyridin-3-amine | 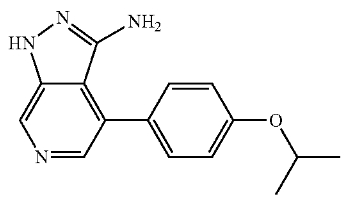 [SMILES: CC(C)Oc1ccc(-c2cncc3[nH]nc(N)c23)cc1] | $^1$H NMR (400 MHz, methanol-d$_4$) δ ppm 9.09 (1 H, s), 8.06 (1 H, s), 7.57 (2 H, δ, J = 8.53 Hz), 7.15 (2 H, δ, J = 8.78 Hz), 4.74 (1 H, dt, J = 12.05, 6.02 Hz), 1.38 (6 H, δ, J = 6.02 Hz); MS (ES+) m/z,: 269 (M + H); LC retention time: 2.457 min. |
| Example 44: 4-(4-(Cyclopentyloxy)phenyl)-1H-pyrazolo[3,4-c]pyridin-3-amine | 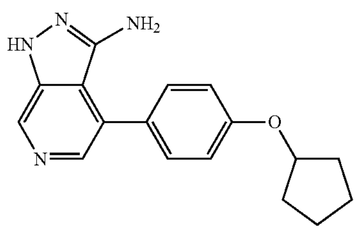 [SMILES: Nc1n[nH]c2cncc(-c3ccc(OC4CCCC4)cc3)c12] | $^1$H NMR (400 MHz, methanol-d$_4$) δ ppm 9.08 (1 H, s), 8.05 (1 H, s), 7.57 (2 H, δ, J = 8.53 Hz), 7.14 (2 H, δ, J = 8.78 Hz), 4.78-5.19 (1 H, m), 1.34-2.28 (8 H, m); MS (ES+) m/z: 295 (M + H); LC retention time: 2.958 min. |
| Example 45: 4-(4-(Methylsulfanyl)phenyl)-1H-pyrazolo[3,4-c]pyridin-3-amine | 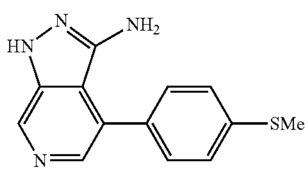 | $^1$H NMR (400 MHz, methanol-d$_4$) δ ppm 9.10 (1 H, s), 8.09 (1 H, s), 7.54-7.76 (2 H, m), 7.37-7.54 (2 H, m), 2.57 (3 H, s); MS (ES+) m/z: 257 (M + H); LC retention time: 2.233 min. |
| Example 46: 4-(4-(Trifluoromethoxy)phenyl)-1H-pyrazolo[3,4-c]pyridin-3-amine | 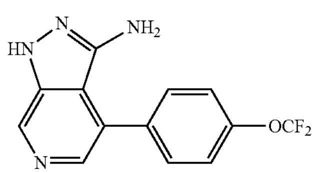 | $^1$H NMR (400 MHz, methanol-d$_4$) δ ppm 9.15 (1 H, s), 8.13 (1 H, s), 7.69-7.88 (2 H, m), 7.54 (2 H, δ, J = 8.03 Hz); MS (ES+) m/z: 295 (M + H); LC retention time: 2.565 min. |
| Example 47: 4-(4-(1-Pyrrolidinylcarbonyl)phenyl)-1H-pyrazolo[3,4-c]pyridin-3-amine | 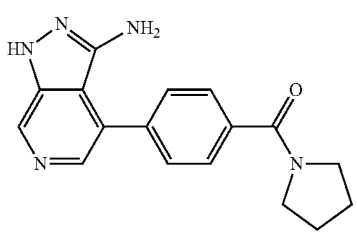 [SMILES: Nc1n[nH]c2cncc(-c3ccc(C(=O)N4CCCC4)cc3)c12] | $^1$H NMR (400 MHz, methanol-d$_4$) δ ppm 9.22 (1 H, s), 8.17 (1 H, s), 7.61-7.93 (4 H, m), 3.65 (2 H, t, J = 7.03 Hz), 3.56 (2 H, t, J = 6.53 Hz), 1.87-2.15 (4 H, m); MS (ES+) m/z: 308 (M + H); LC retention time: 1.857 min. |
| Example 48: 4-Dibenzo[b,δ]thiophen-2-yl-1H-pyrazolo[3,4-c]pyridin-3-amine | 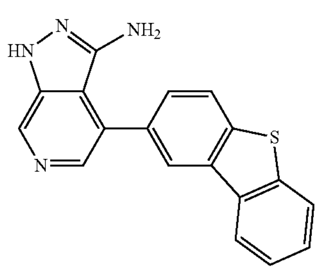 [SMILES: Nc1n[nH]c2cncc(-c3ccc4sc5ccccc5c4c3)c12] | $^1$H NMR (400 MHz, methanol-d$_4$) δ ppm 9.19 (1 H, s), 8.57 (1 H, δ, J = 1.26 Hz), 8.25 (1 H, s), 8.18 (1 H, δ, J = 8.28 Hz), 7.98 (1 H, dd, J = 6.65, 1.88 Hz), 7.77 (1 H, dd, J = 8.28, 1.76 Hz), 7.46-7.62 (3 H, m); MS (ES+) m/z: 317 (M + H); LC retention time: 3.161 min. |

| Example No. | Structure | Spectral data* |
|---|---|---|
| Example 49:<br>4-(6-Methoxy-2-naphthyl)-<br>1H-pyrazolo[3,4-c]pyridin-<br>3-amine | 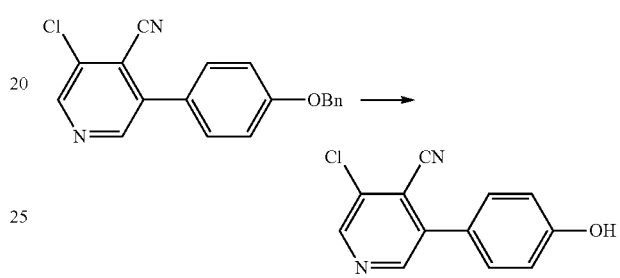 | $^1$H NMR (500 MHz, methanol-$d_4$) δ ppm 9.14 (1 H, s), 8.18 (1H, s), 8.09 (1H, δ, J = 1.37 Hz), 8.04 (1 H, δ, J = 8.52 Hz), 7.92 (1 H, δ, J = 8.80 Hz), 7.70 (1 H, dd, J = 8.25, 1.92 Hz), 7.39 (1 H, δ, J = 2.47 Hz), 3.97 (3 H, s); MS (ES+) m/z: 291 (M + H); LC retention time: 2.655 min. |

*Analytical HPLC Method A

Example 50

4-(4-(4-Methoxyphenoxy)phenyl)-1H-1-pyrazolo[3,4-c]pyridin-3-amine

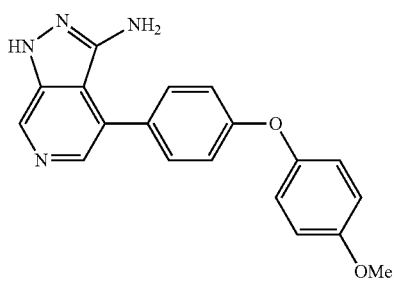 [SMILES: COc1ccc(Oc2ccc(-c3cncc4[nH]nc(N)c34)cc2)cc1]

Step 1:

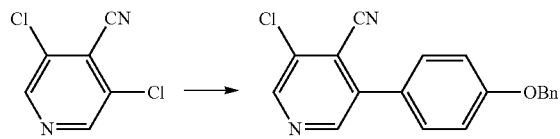 [SMILES: N#Cc1c(Cl)cncc1Cl ; N#Cc1c(Cl)cncc1-c1ccc(OCc2ccccc2)cc1]

A mixture of 3,5-dichloroisonicotinonitrile (2.50 g, 14.45 mmol), 4-(benzyloxy)phenylboronic acid (3.63 g, 15.90 mmol), potassium phosphate (6.13 g, 28.9 mmol) and palladium tetrakis(triphenylphosphine) (0.835 g, 0.723 mmol) was pumped and backfilled with nitrogen 3 times. N,N-Dimethylacetamide (40 mL) was added. The mixture was again pumped and backfilled with nitrogen 3 times and heated with a 150° C. oil bath for 1 h. The mixture was diluted with ethyl acetate (400 mL), washed twice with 1:1 mixture of brine and water (100 mL), brine (100 mL), dried (MgSO$_4$) and concentrated. Silica gel chromatography, loading with toluene and eluting with 10-35% ethyl acetate in hexanes, gave 3-(4-(benzyloxy)phenyl)-5-chloroisonicotinonitrile as a white solid (2.387 g, 52% yield). $^1$H NMR (500 MHz, CDCl$_3$) δ ppm 8.72 (1H, s), 8.69 (1H, s), 7.51-7.60 (2H, m), 7.40-7.50 (4H, m), 7.33-7.40 (1H, m), 7.10-7.19 (2H, m), 5.15 (2H, s); MS (ES+) m/z: 321 (M+H); LC retention time: 4.323 min (analytical HPLC Method A).

Step 2:

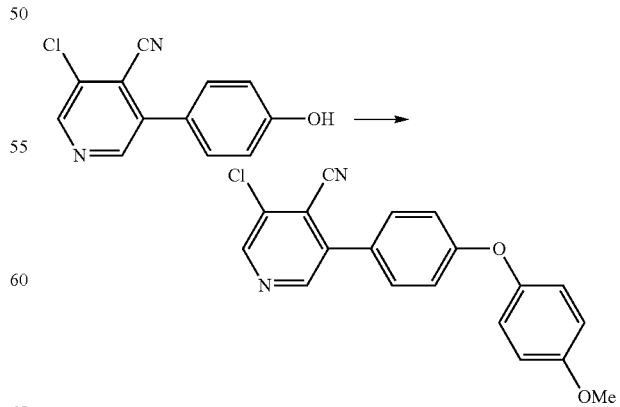

A 1 M dichloromethane solution of boron tribromide (13.39 mL, 13.39 mmol) was added to a solution of 3-(4-(benzyloxy)phenyl)-5-chloroisonicotinonitrile (2.147 g, 6.69 mmol) in dichloromethane (20 mL) in a room temperature water bath. The orange suspension was stirred at room temperature for 40 min, poured to a stirred solution of saturated sodium bicarbonate (300 mL), diluted with dichloromethane (150 mL) and the mixture stirred overnight. The two phases were separated. The aqueous phase was extracted with dichloromethane (2×100 mL). The combined extracts were washed with saturated sodium bicarbonate (50 mL), water (2×50 mL), brine (50 mL), dried (MgSO$_4$) and concentrated. The residue was diluted with methanol (10 mL), toluene (10 mL) and hexanes (30 mL), stirred for 1 h and filtered. The solid was rinsed with 1:3 mixture of toluene/hexanes to give 3-chloro-5-(4-hydroxyphenyl)isonicotinonitrile as tan solid (1.03 g, 65% yield). $^1$H NMR (400 MHz, methanol-$d_4$) δ ppm 8.75 (1H, s), 8.71 (1H, s), 7.42-7.61 (2H, m), 6.87-7.05 (2H, m); MS (ES+) m/z: 231 (M+H); LC retention time: 3.223 min (analytical HPLC Method A).

Step 3:

A mixture of 3-chloro-5-(4-hydroxyphenyl)isonicotinonitrile (50 mg, 0.217 mmol), 4-methoxyphenylboronic acid (132 mg, 0.867 mmol), copper(II) acetate (47.2 mg, 0.260 mmol), pyridine (0.140 mL, 1.734 mmol) and 4 A molecular sieves (300 mg) in dichloromethane (6 mL) was stirred under air at room temperature for 4 days. The mixture was filtered through a CELITE® pad to remove molecular sieves (rinsed with dichloromethane), quenched with saturated ammonium chloride (20 mL) and ammonium hydroxide (2 mL) and extracted with dichloromethane (3×10 mL). The combined extracts were dried (MgSO$_4$) and concentrated. Silica gel chromatography, loading with toluene and eluting with 5-30% ethyl acetate in hexanes, gave 3-chloro-5-(4-(4-methoxyphenoxy)phenyl)isonicotinonitrile as a white solid (49.7 mg, 67% yield). $^1$H NMR (400 MHz, CDCl$_3$) δ ppm 8.72 (1H, s), 8.68 (1H, s), 7.45-7.59 (2H, m), 6.99-7.14 (4H, m), 6.88-6.99 (2H, m), 3.83 (3H, s); MS (ES+) m/z: 337 (M+H); LC retention time: 4.321 min (analytical HPLC Method A).

Step 4:

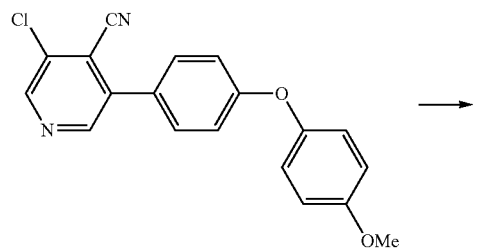

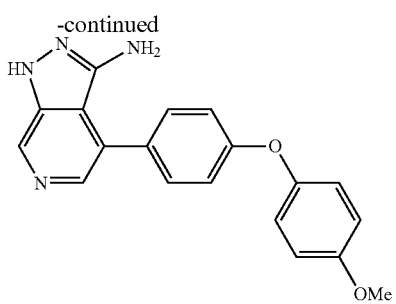

Following conditions similar to Step 2 of Example 38, 3-chloro-5-(4-(4-methoxyphenoxy)phenyl)isonicotinonitrile was reacted with hydrazine to give Example 50. $^1$H NMR (400 MHz, methanol-d$_4$) δ ppm 9.02 (1H, s), 8.05 (1H, s), 7.51-7.66 (2H, m), 7.10-7.19 (2H, m), 7.03-7.11 (2H, m), 6.93-7.03 (2H, m), 3.82 (3H, s); MS (ES+) m/z: 333 (M+H); LC retention time: 3.011 min (analytical HPLC Method A).

Examples 51 to 57

Examples 51 to 53 were prepared from 3-chloro-5-(4-hydroxyphenyl)isonicotinonitrile (from Step 3 of Example 50) following conditions described for Steps 3 and 4 of Example 50. Examples 54 to 56 were prepared from 4-(benzyloxy)-3-methylphenylboronic acid or 4-(benzyloxy)-3-fluorophenylboronic acid in a manner similar to conditions described for Example 50. Example 57 was prepared from Example 50 following conditions similar to Step 2 of Example 50.

| Example No. | Structure | Spectral data* |
|---|---|---|
| Example 51: 4-(4-(3-Methoxyphenoxy)phenyl)-1H-pyrazolo[3,4-c]pyridin-3-amine | 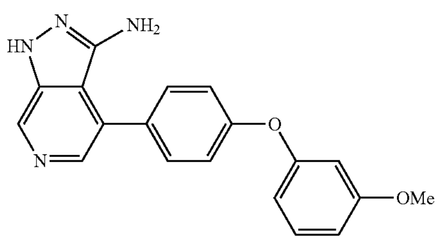 [SMILES: COc1cccc(Oc2ccc(-c3cncc4[nH]nc(N)c34)cc2)c1] | $^1$H NMR (400 MHz, methanol-d$_4$) δ ppm 9.07 (1 H, s), 8.08 (1 H, s), 7.64 (2 H, δ, J = 8.53 Hz), 7.26-7.38 (1 H, m), 7.22 (2 H, δ, J = 8.28 Hz), 6.78 (1 H, dd, J = 7.91, 1.88 Hz), 6.60-6.73 (2 H, m), 3.80 (3 H, s); MS (ES+) m/z: 333 (M + H); LC retention time: 3.068 min. |
| Example 52: 4-(4-(3-Ethoxyphenoxy)phenyl)-1H-pyrazolo[3,4-c]pyridin-3-amine | 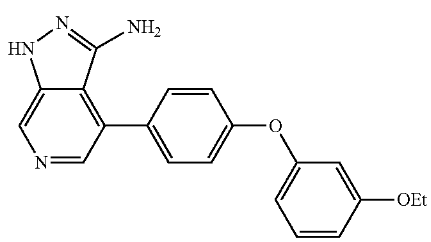 [SMILES: CCOc1cccc(Oc2ccc(-c3cncc4[nH]nc(N)c34)cc2)c1] | $^1$H NMR (400 MHz, methanol-d$_4$) δ ppm 9.08 (1 H, br. s), 8.09 (1 H, s), 7.58-7.72 (2 H, m), 7.26-7.37 (1 H, m), 7.15-7.25 (2 H, m), 6.72-6.83 (1 H, m), 6.59-6.72 (2 H, m), 4.03 (2 H, q, J = 7.03 Hz), 1.39 (3 H, t, J = 6.90 Hz); MS (ES+) m/z: 347 (M + H); LC retention time: 3.283 min. |
| Example 53: 4-(4-(3,5-Dimethylphenoxy)phenyl)-1H-pyrazolo[3,4-c]pyridin-3-amine | 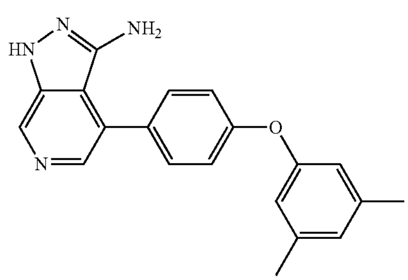 [SMILES: Cc1cc(C)cc(Oc2ccc(-c3cncc4[nH]nc(N)c34)cc2)c1] | $^1$H NMR (400 MHz, methanol-d$_4$) δ ppm 9.09 (1 H, s), 8.09 (1 H, s), 7.57-7.67 (2 H, m), 7.12-7.23 (2 H, m), 6.87 (1 H, s), 6.73 (2 H, s), 2.31 (6 H, s); MS (ES+) m/z: 331 (M + H); LC retention time: 3.471 min. |

-continued

| Example No. | Structure | Spectral data* |
|---|---|---|
| Example 54: 4-(3-Amino-1H-pyrazolo[3,4-c]pyridin-4-yl)-2-methylphenol | 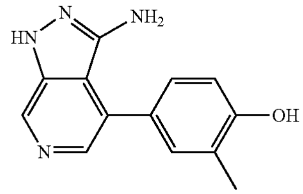 [SMILES: Cc1cc(-c2cncc3[nH]nc(N)c23)ccc1O] | $^1$H NMR (400 MHz, methanol-$d_4$) δ ppm 9.09 (1 H, s), 8.03 (1 H, s), 7.38 (1 H, δ, J = 1.51 Hz), 7.31 (1 H, dd, J = 8.28, 2.01 Hz), 6.98 (1 H, δ, J = 8.03 Hz), 2.30 (3 H, s); MS (ES+) m/z: 241 (M + H); LC retention time: 1.653 min. |
| Example 55: 4-(3-Methyl-4-phenoxyphenyl)-1H-pyrazolo[3,4-c]pyridin-3-amine | 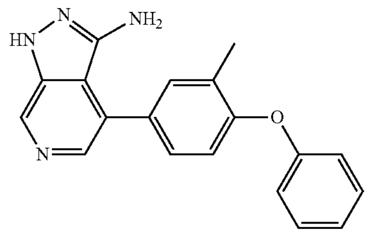 | $^1$H NMR (400 MHz, methanol-$d_4$) δ ppm 9.12 (1 H, s), 8.11 (1 H, s), 7.59 (1 H, δ, J = 1.51 Hz), 7.45 (1 H, dd, J = 8.28, 2.01 Hz), 7.32-7.43 (2 H, m), 7.15 (1 H, t, J = 7.40 Hz), 7.03 (3 H, δ, J = 8.78 Hz), 2.39 (3 H, s); MS (ES+) m/z: 317 (M + H); LC retention time: 3.190 min. |
| Example 56: 4-(3-Fluoro-4-phenoxyphenyl)-1H-pyrazolo[3,4-c]pyridin-3-amine | 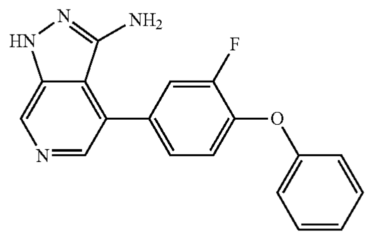 | $^1$H NMR (400 MHz, methanol-$d_4$) δ ppm 9.16 (1 H, s), 8.15 (1 H, s), 7.61 (1 H, dd, J = 11.17, 2.13 Hz), 7.34-7.51 (3 H, m), 7.25 (1 H, t, J = 8.28 Hz), 7.18 (1 H, t, J = 7.40 Hz), 7.10 2 H, δ, J = 7.78 Hz); MS (ES+) m/z: 321 (M + H); LC retention time: 3.013 min. |
| Example 57: 4-(4-(3-Amino-1H-pyrazolo[3,4-c]pyridin-4-yl)phenoxy)phenol | 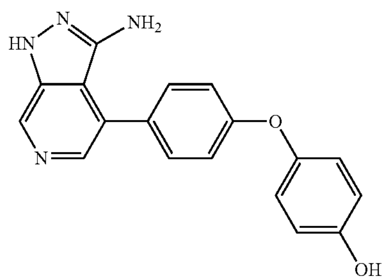 [SMILES: Nc1n[nH]c2cncc(-c3ccc(Oc4ccc(O)cc4)cc3)c12] | $^1$H NMR (400 MHz, methanol-$d_4$) δ ppm 9.14 (1 H, s), 8.09 (1 H, s), 7.50-7.71 (2 H, m), 7.05-7.19 (2 H, m), 6.91-7.03 (2 H, m), 6.77-6.90 (2 H, m); MS (ES+) m/z: 319 (M + H); LC retention time: 2.582 min. |

*Analytical HPLC Method A

Example 58

4-(4-Benzylphenyl)-1H-pyrazolo[3,4-e]pyridin-3-amine

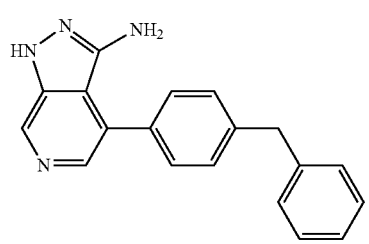 [SMILES: Nc1n[nH]c2cncc(-c3ccc(Cc4ccccc4)cc3)c12]

Step 1:

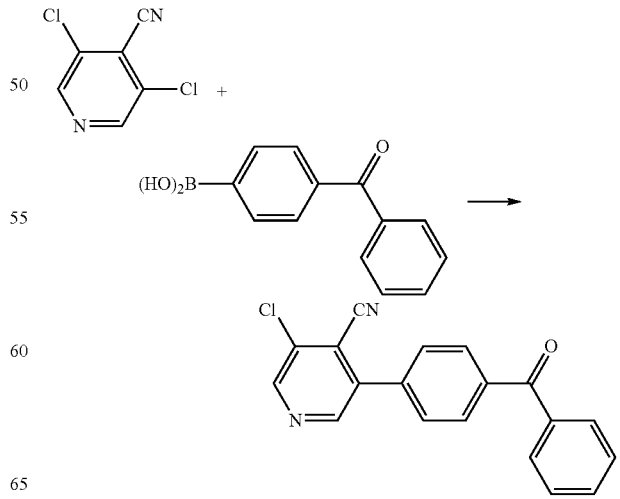

Following conditions described in Step 1 of Example 50, 3,5-dichloroisonicotinonitrile was reacted with 4-benzoylphenylboronic acid to give 3-(4-benzoylphenyl)-5-chloroisonicotinonitrile (~80% pure). MS (ES+) m/z: 351 (M+H); LC retention time: 3.980 min (analytical HPLC Method A).

Step 2:

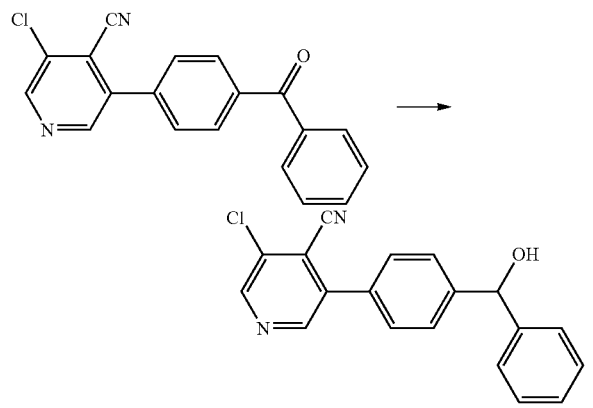

Granular sodium borohydride (225 mg, 5.94 mmol) was added to a solution of 3-(4-benzoylphenyl)-5-chloroisonicotinonitrile (473 mg, 1.187 mmol, 80% pure) in dichloromethane (10 mL) and methanol (10 mL). After 30 min at room temperature, the mixture was quenched with saturated ammonium chloride (30 mL). The organic solvents were evaporated in vacuo. The aqueous residue was extracted with ethyl acetate (2×40 mL). The combined extracts were washed with brine (5 mL), dried ($MgSO_4$) and concentrated. Silica gel chromatography, loading with dichloromethane and eluting with 20-60% ethyl acetate in hexanes, gave 3-chloro-5-(4-(hydroxy(phenyl)methyl)phenyl)isonicotinonitrile as white solid (327 mg, 69% yield), which was approximately 80% pure. MS (ES+) m/z: 303 (M-water+H); LC retention time: 3.798 min (analytical HPLC Method A).

Step 3:

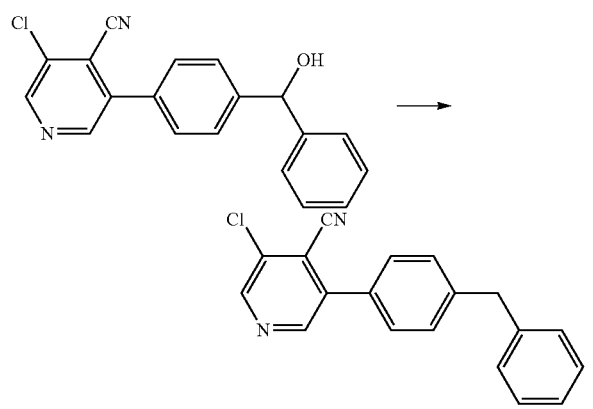

Trifluoroacetic acid (5 mL, 64.9 mmol) was added to a solution of 3-chloro-5-(4-(hydroxy(phenyl)methyl)phenyl) isonicotinonitrile (327 mg, 0.816 mmol, 80% pure) and triethylsilane (5 mL, 31.3 mmol) in dichloromethane (10 mL). After 1 h at room temperature, the mixture was concentrated, quenched with saturated sodium bicarbonate (30 mL) and extracted with dichloromethane (3×15 mL). The combined extracts were dried ($MgSO_4$) and concentrated. Silica gel chromatography, loading with toluene and eluting with 10-30% ethyl acetate in hexanes, gave 3-(4-benzylphenyl)-5-chloroisonicotinonitrile as colorless liquid (195.2 mg, 79% yield). $^1$H NMR (400 MHz, $CDCl_3$) δ ppm 8.74 (1H, s), 8.68 (1H, s), 7.45-7.58 (2H, m), 7.28-7.43 (4H, m), 7.15-7.28 (3H, m), 4.07 (2H, s). MS (ES+) m/z: 305 (M–$H_2O$+H); LC retention time: 4.391 min (analytical HPLC Method A).

Step 4:

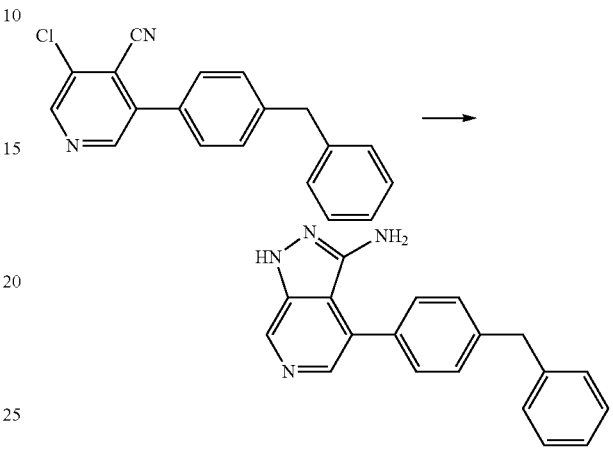

A suspension of 3-(4-benzylphenyl)-5-chloroisonicotinonitrile (76.8 mg, 0.252 mmol) and 35% aqueous hydrazine (0.226 mL, 2.52 mmol) in n-butanol (3 mL) in a microwave tube was sealed and heated to 150° C. for 15 h. The mixture was concentrated and purified by reverse phase HPLC(YMC ODS S5 30×100 mm column), eluting with 50-80% solvent B (10% methanol-90% water-0.1% TFA) in solvent A (90% methanol-10% water-0.1% TFA), to give Example 58 as yellow solid, assumed as bis-TFA salt (61.8 mg, 45% yield). $^1$H NMR (400 MHz, methanol-$d_4$) δ ppm 9.10 (1H, s), 8.07 (1H, s), 7.53-7.67 (2H, m), 7.42-7.52 (2H, m), 7.25-7.35 (4H, m), 7.12-7.25 (1H, m), 4.11 (2H, s); MS (ES+) m/z: 301 (M+H); LC retention time: 3.023 min (analytical HPLC Method A).

Example 59

4-(4-Phenoxyphenyl)-7-phenyl-1H-pyrazolo[3,4-c]pyridin-3-amine

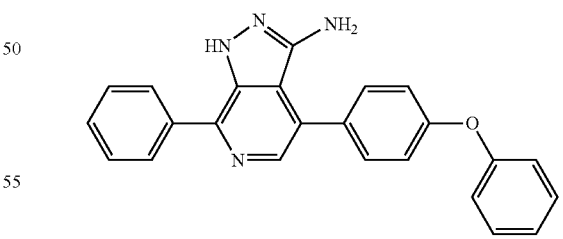

Step 1:

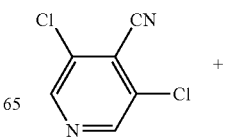

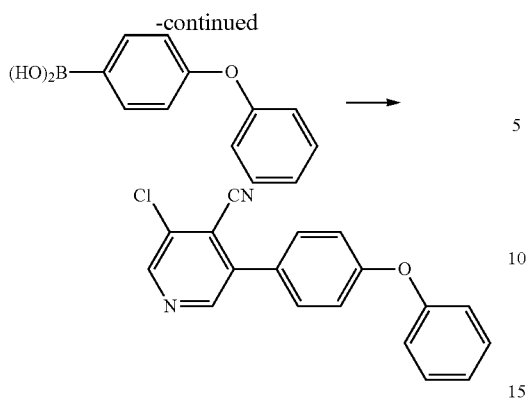

A mixture of 3,5-dichloroisonicotinonitrile (10.00 g, 57.8 mmol), 4-phenoxyphenylboronic acid (12.37 g, 57.8 mmol), palladium(II) acetate (0.389 g, 1.734 mmol), potassium phosphate (30.7 g, 145 mmol) and 1,1'-bis(di-t-butylphosphino)ferrocene (0.833 g, 1.734 mmol) was pumped and backfilled with nitrogen 3 times. Dioxane (200 mL) was added. The reaction vial was again pumped and backfilled with nitrogen 3 times, sealed and heated to gentle reflux for 20 h. The dioxane solvent was evaporated in vacuo. The residue was diluted with water (150 mL) and brine (150 mL) and extracted with ethyl acetate (3×100 mL). The combined extracts were washed with brine (25 mL), dried (MgSO$_4$) and concentrated. Silica gel chromatography, eluting with 0-15% ethyl acetate in dichloromethane-hexanes (1:2), gave 3-chloro-5-(4-phenoxyphenyl)isonicotinonitrile as tan liquid (9.71 g, 55% yield). $^1$H NMR (500 CDCl$_3$) δ ppm 8.74 (1H, s), 8.70 (1H, s), 7.50-7.59 (2H, m), 7.35-7.46 (2H, m), 7.20 (1H, t, J=7.42 Hz), 7.06-7.16 (4H, m); MS (ES+) m/z: 307 (M+H); LC retention time: 4.298 min (analytical HPLC Method A).

Step 2:

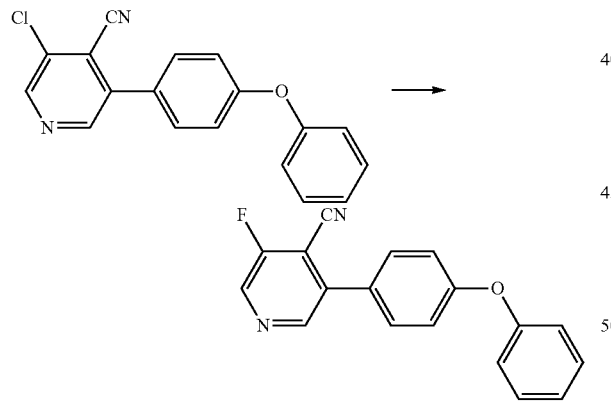

A mixture of 3-chloro-5-(4-phenoxyphenyl)isonicotinonitrile (11.8 g, 38.5 mmol) and potassium fluoride (11.17 g, 192 mmol) in DMSO (500 mL) was heated to 120° C. for 10 days. The mixture was diluted with water (1 L) and extracted with ethyl acetate (3×400 mL). The combined extracts were washed with brine (100 mL), dried (MgSO$_4$) and concentrated. Silica gel chromatography, eluting with 0-15% ethyl acetate in dichloromethane-hexanes (1:2), gave 3-fluoro-5-(4-phenoxyphenyl)isonicotinonitrile as tan solid (7.66 g, 69% yield). $^1$H NMR (500 MHz, CDCl$_3$) δ ppm 8.67 (1H, s), 8.64 (1H, s), 7.52-7.62 (2H, m), 7.36-7.46 (2H, m), 7.20 (1H, t, J=7.42 Hz), 7.05-7.17 (4H, m); MS (ES+) m/z: 291 (M+H); LC retention time: 4.118 min (analytical HPLC Method A).

Step 3:

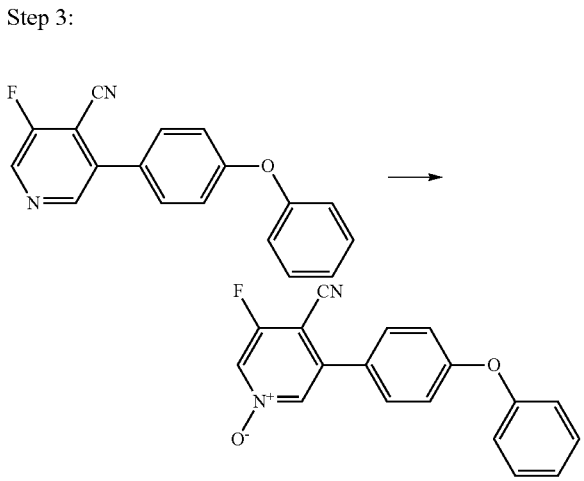

A solution of 3-fluoro-5-(4-phenoxyphenyl)isonicotinonitrile (7.66 g, 26.4 mmol) and 77% 3-chloroperbenzoic acid (29.6 g, 132 mmol) in dichloromethane (200 mL) was stirred at room temperature for 18 h, diluted with dichloromethane (500 mL), washed with 10% aqueous sodium sulfite (2×200 mL), 1 N NaOH (2×200 mL), brine (200 mL), dried (MgSO$_4$) and filtered through a CELITE® pad. The filter pad was rinsed with ethyl acetate. The filtrate was concentrated to give the expected product as white solid. The crude material (8.49 g, 5% overweight) was taken to next step without purification.

Step 4:

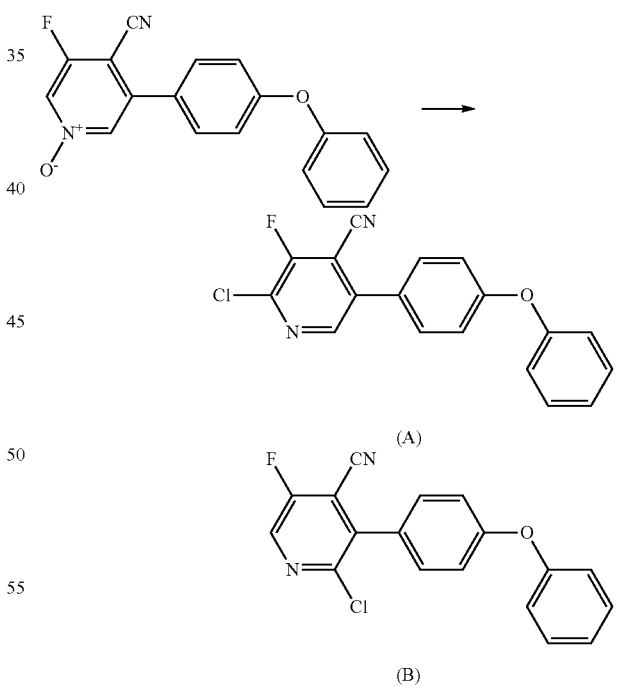

A suspension of 4-cyano-3-fluoro-5-(4-phenoxyphenyl)pyridine 1-oxide (8.09 g, 26.4 mmol) in phosphorus oxychloride (50 mL, 536 mmol) was heated to 100° C. for 1.5 h and concentrated. The residue was diluted with ethyl acetate (100 mL), cooled to 0° C. and quenched with careful addition of saturated sodium bicarbonate (300 mL). The mixture was further neutralized to pH~7 with careful addition of solid potassium carbonate, then extracted with ethyl acetate (3×100 mL). The combined extracts were washed with brine (50 mL), dried (MgSO₄) and concentrated. The solid residue was dissolved in toluene (30 mL) with heating, diluted with 5% dichloromethane in hexanes (30 mL), cooled to room temperature, and filtered to collect the solid. The solid was washed with 5% dichloromethane in hexanes to give product (A) as white solid (2.57 g). The combined filtrate was concentrated and purified by silica gel chromatography, loading with toluene and 5% ethyl acetate in hexanes and eluting with 5-15% ethyl acetate in hexanes, to give first peak as product (A) and second peak as product (B). The overlapping fractions were combined and purified again using same conditions. The total yield of product (A), 2-chloro-3-fluoro-5-(4-phenoxyphenyl)isonicotinonitrile, was 6.19 g (72% yield). The total yield of product (B), 2-chloro-5-fluoro-3-(4-phenoxyphenyl)isonicotinonitrile, was 1.71 g (20% yield). Characterization of product (A): $^1$H NMR (400 MHz, CDCl₃) δ ppm 8.43 (1H, s), 7.47-7.61 (2H, m), 7.35-7.46 (2H, m), 7.20 (1H, t, J=7.40 Hz), 7.04-7.16 (4H, m); MS (ES+) m/z: 325 (M+H); LC retention time: 3.550 min (analytical HPLC Method A except 50% to 100% solvent B gradient was used). Characterization of product (B): NMR (400 MHz, CDCl₃) δ ppm 8.47 (1H, s), 7.34-7.48 (4H, m), 7.17-7.24 (1H, m), 7.06-7.16 (4H, m); MS (ES+) m/z: 325 (M+H); LC retention time: 3.170 min (analytical HPLC Method A except 50% to 100% solvent B gradient was used).
Step 5:

A mixture of 2-chloro-3-fluoro-5-(4-phenoxyphenyl)isonicotinonitrile (20.2 mg, 0.062 mmol), phenylboronic acid (11.38 mg, 0.093 mmol), palladium(II) acetate (2.79 mg, 0.012 mmol), potassium phosphate (33.0 mg, 0.156 mmol) and 1,1'-bis(di-t-butylphosphino)ferrocene (5.98 mg, 0.012 mmol) was pumped and backfilled with nitrogen 3 times. Dioxane (2 mL) was added. The reaction vial was again pumped and backfilled with nitrogen 3 times, sealed and heated to 100° C. for 4 h. HPLC and LCMS analysis showed that the Suzuki coupling product was formed cleanly. A 35% aqueous solution of hydrazine (0.279 mL, 3.11 mmol) was added. The reaction vial was sealed and stirred at 120° C. for 20 h. The mixture was diluted with ethyl acetate (30 mL), washed with 1:1 mixture of water-brine (2×5 mL), dried (MgSO₄) and concentrated. Purification by reverse phase HPLC (Sunfire S10 30×250 mm column), eluting with 60-90% solvent B (10% methanol-90% water-0.1% TFA) in solvent A (90% methanol-10% water-0.1% TFA), gave Example 59, assumed as bis-TFA salt (20.4 mg, 53% yield). $^1$H NMR (400 MHz, methanol-d₄) δ ppm 7.99-8.11 (3H, m), 7.72-7.84 (3H, m), 7.64-7.71 (2H, m), 7.38-7.49 (2H, m), 7.17-7.26 (3H, m), 7.10-7.17 (2H, m); MS (ES+) m/z: 379 (M+H); LC retention time: 3.545 min (analytical HPLC Method A).

Examples 60 to 70

Example 60 was prepared from 2-chloro-3-fluoro-5-(4-phenoxyphenyl)isonicotinonitrile (product A from Step 4 of Example 59) following conditions described for Step 5 of Example 59. Examples 61 to 67 were prepared from 2-chloro-3-fluoro-5-(4-phenoxyphenyl)isonicotinonitrile (product A from Step 4 of Example 59) following conditions described for Step 5 of Example 59, except in a step-wise fashion where the Suzuki coupling product was purified by silica gel chromatography. Example 68 was prepared from 2-chloro-3-fluoro-5-(4-phenoxyphenyl)isonicotinonitrile (product A from Step 4 of Example 59) following conditions described for Step 5 of Example 59, except a Stille coupling with 2-1.0 (tributylstannyl)pyrazine was used instead of the Suzuki coupling. Examples 69 and 70 were prepared from 2-chloro-5-fluoro-3-(4-phenoxyphenyl)isonicotinonitrile (product B from Step 4 of Example 59) following conditions described for Step 5 of Example 59, except in a step-wise fashion where the Suzuki coupling product was purified by silica gel chromatography.

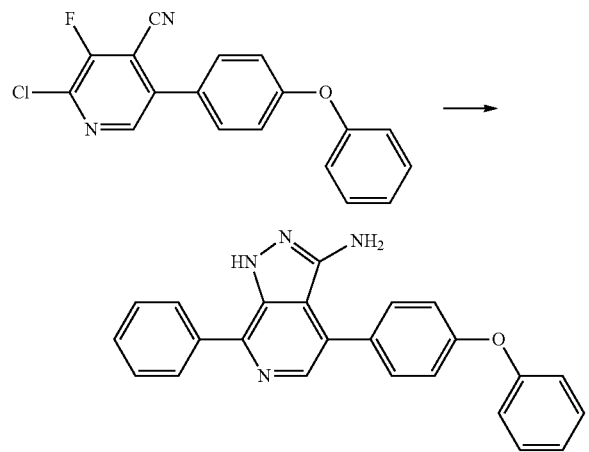

| Example No. | Structure | Spectral data* |
|---|---|---|
| Example 60: 7-(4-(4-Morpholinylcarbonyl)phenyl)-4-(4-phenoxyphenyl)-1H-pyrazolo[3,4-c]pyridin-3-amine | 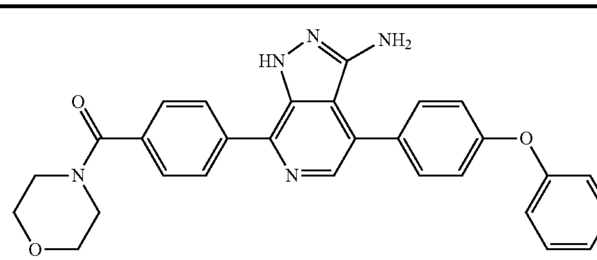 | $^1$H NMR (400 MHz, methanol-d₄) δ ppm 8.15 (2 H, δ, J = 8.53 Hz), 8.08 (1 H, s), 7.78 (2 H, δ, J = 8.28 Hz), 7.64-7.71 (2 H, m), 7.40-7.48 (2 H, m), 7.18-7.26 (3 H, m), 7.13 (2 H, δ, J = 7.78 Hz), 3.81 (4 H, br. s), 3.68 (2 H, br. s), 3.52 (2 H, br. s); MS (ES+) m/z: 492 (M + H); LC retention time: 3.655 min. |

-continued

| Example No. | Structure | Spectral data* |
|---|---|---|
| Example 61: N-(4-(3-Amino-4-(4-phenoxyphenyl)-1H-pyrazolo[3,4-c]pyridin-7-yl)phenyl)benzamide | 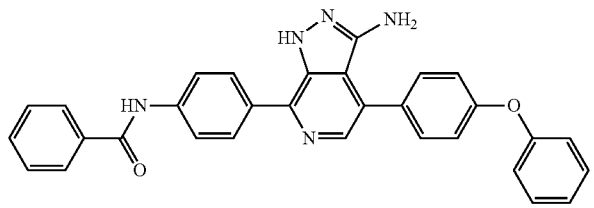 [SMILES: Nc1n[nH]c2c(-c3ccc(NC(=O)c4ccccc4)cc3)ncc(-c3ccc(Oc4ccccc4)cc3)c12] | $^1$H NMR (500 MHz, methanol-$d_4$) δ ppm 8.14-8.20 (2 H, m), 8.07-8.13 (2 H, m), 7.94-8.03 (3 H, m), 7.65-7.71 (2 H, m), 7.60-7.66 (1 H, m), 7.56 (2 H, t, J = 7.56 Hz), 7.40-7.48 (2 H, m), 7.18-7.26 (3 H, m), 7.14 (2 H, δ, J = 7.70 Hz); MS (ES+) m/z: 498 (M + H); LC retention time: 3.790 min. |
| Example 62: N-(3-(3-Amino-4-(4-phenoxyphenyl)-1H-pyrazolo[3,4-c]pyridin-7-yl)phenyl) methanesulfonamide | 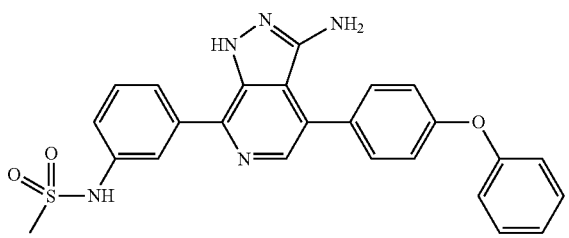 [SMILES: CS(=O)(=O)Nc1cccc(-c2ncc(-c3ccc(Oc4ccccc4)cc3)c3c(N)n[nH]c23)c1] | $^1$H NMR (500 MHz, methanol-$d_4$) δ ppm 8.04 (1 H, s), 7.92 (1 H, s), 7.74-7.81 (1 H, m), 7.63-7.73 (3 H, m), 7.54-7.61 (1 H, m), 7.38-7.48 (2 H, m), 7.18-7.26 (3 H, m), 7.13 (2 H, δ, J = 7.42 Hz), 3.11 (3 H, s); MS (ES+) m/z: 472 (M + H); LC retention time: 3.536 min. |
| Example 63: 4-(4-Phenoxyphenyl)-7-(4-(1-pyrrolidinylcarbonyl)phenyl)-1H-pyrazolo[3,4-c]pyridin-3-amine | 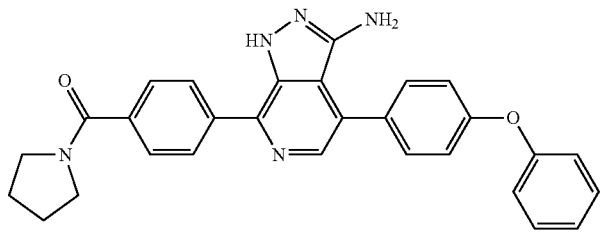 [SMILES: Nc1n[nH]c2c(-c3ccc(C(=O)N4CCCC4)cc3)ncc(-c3ccc(Oc4ccccc4)cc3)c12] | $^1$H NMR (500 MHz, methanol-$d_4$) δ ppm 8.13 (2 H, δ, J = 8.25 Hz), 8.07 (1 H, s), 7.86 (2 H, δ, J = 8.52 Hz), 7.62-7.72 (2 H, m), 7.39-7.48 (2 H, m), 7.18-7.27 (3 H, m), 7.14 (2 H, δ, J = 7.70 Hz), 3.66 (2 H, t, J = 7.01 Hz), 3.54 (2 H, t, J = 6.60 Hz), 2.01-2.10 (2 H, m), 1.91-2.00 (2 H, m); MS (ES+) m/z: 476 (M + H); LC retention time: 3.808 min. |
| Example 64: 7-(3-(Methylsulfonyl)phenyl)-4-(4-phenoxyphenyl)-1H-pyrazolo[3,4-c]pyridin-3-amine | 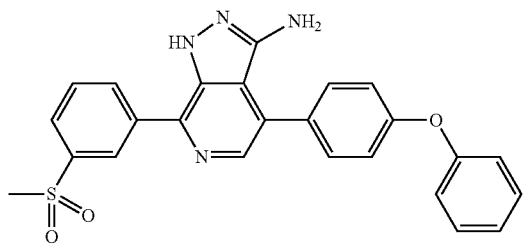 [SMILES: CS(=O)(=O)c1cccc(-c2ncc(-c3ccc(Oc4ccccc4)cc3)c3c(N)n[nH]c23)c1] | $^1$H NMR (400 MHz, methanol-$d_4$) δ ppm 10.34 (1 H, br. s), 8.62 (1 H, s), 8.34 (1 H, δ, J = 7.97 Hz), 8.22-8.30 (1 H, m), 8.07 (1 H, δ, J = 7.70 Hz), 7.82 (1 H, t, J = 7.70 Hz), 7.52-7.60 (2 H, m), 7.37-7.46 (2 H, m), 7.08-7.23 (5 H, m), 4.23 (2 H, br. s), 3.15 (3 H, s); MS (ES+) m/z: 457 (M + H); LC retention time: 3.821 min. |
| Example 65: 7-(3-(Methoxymethyl)phenyl)-4-(4-phenoxyphenyl)-1H-pyrazolo[3,4-c]pyridin-3-amine | 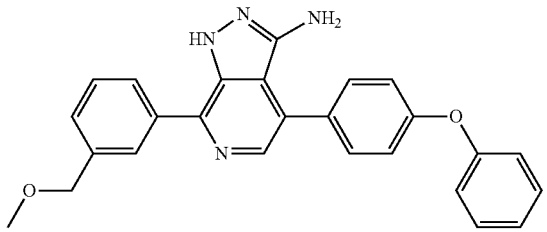 [SMILES: COCc1cccc(-c2ncc(-c3ccc(Oc4ccccc4)cc3)c3c(N)n[nH]c23)c1] | $^1$H NMR (500 MHz, methanol-$d_4$) δ ppm 8.01-8.06 (2 H, m), 7.93-8.00 (1 H, m), 7.72-7.77 (2 H, m), 7.64-7.71 (2 H, m), 7.40-7.49 (2 H, m), 7.19-7.27 (3 H, m), 7.10-7.16 (2 H, m), 4.65 (2 H, s), 3.49 (3 H, s); MS (ES+) m/z: 423 (M + H); LC retention time: 3.670 min. |
| Example 66: tert-Butyl (3-(3-amino-4-(4-phenoxyphenyl)-1H-pyrazolo[3,4-c]pyridin-7-yl)benzyl) carbamate | 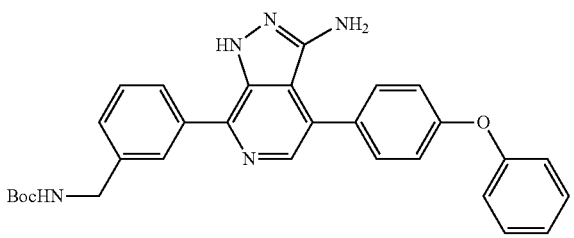 [SMILES: CC(C)(C)OC(=O)NCc1cccc(-c2ncc(-c3ccc(Oc4ccccc4)cc3)c3c(N)n[nH]c23)c1] | $^1$H NMR (500 MHz, methanol-$d_4$) δ ppm 8.04 (1 H, s), 7.87-7.97 (2 H, m), 7.64-7.77 (4 H, m), 7.40-7.48 (2 H, m), 7.18-7.26 (3 H, m), 7.14 (2 H, δ, J = 7.42 Hz), 4.40 (2 H, s), 1.46 (9 H, s); MS (ES+) m/z: 508 (M + H); LC retention time: 3.936 min. |

| Example No. | Structure | Spectral data* |
|---|---|---|
| Example 67: 4-(4-Phenoxyphenyl)-7-(2-pyridinyl)-1H-pyrazolo[3,4-c]pyridin-3-amine | 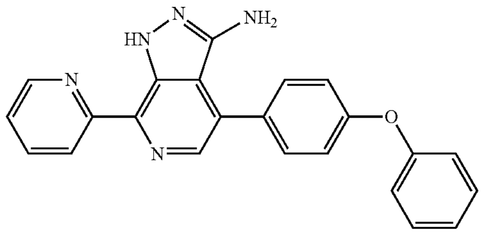 | $^1$H NMR (400 MHz, methanol-d$_4$) δ ppm 8.92 (1 H, d, J = 4.52 Hz), 8.71 (1 H, d, J = 7.78 Hz), 8.14 (1 H, td, J = 7.84, 1.63 Hz), 8.08 (1 H, s), 7.57-7.71 (3 H, m), 7.43 (2 H, t, J = 8.03 Hz), 7.17-7.27 (3 H, m), 7.13 (2 H, d, J = 7.78 Hz); MS (ES+) m/z: 380 (M + H); LC retention time: 4.330 min. |
| Example 68: 4-(4-Phenoxyphenyl)-7-(2-pyrazinyl)-1H-pyrazolo[3,4-c]pyridin-3-amine | 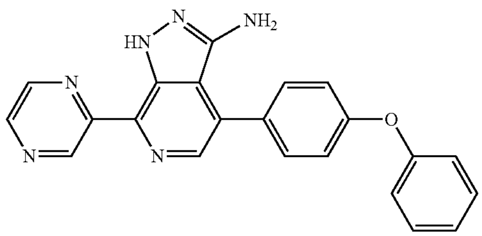 [SMILES: Nc1n[nH]c2c(-c3cnccn3)ncc(-c3ccc(Oc4ccccc4)cc3)c12] | $^1$H NMR (400 MHz, chloroform-d) δ ppm 9.89 (1 H, s), 8.77 (1 H, s), 8.69 (1 H, d, J = 2.51 Hz), 8.34 (1 H, s), 7.56 (2 H, d, J = 8.53 Hz), 7.43 (2 H, t, J = 7.91 Hz), 7.16-7.24 (3 H, m), 7.14 (2 H, d, J = 7.78 Hz); MS (ES+) m/z: 381 (M + H); LC retention time: 4.333 min. |
| Example 69: 4-(4-Phenoxyphenyl)-5-(4-(1-pyrrolidinylcarbonyl)phenyl)-1H-pyrazolo[3,4-c]pyridin-3-amine | 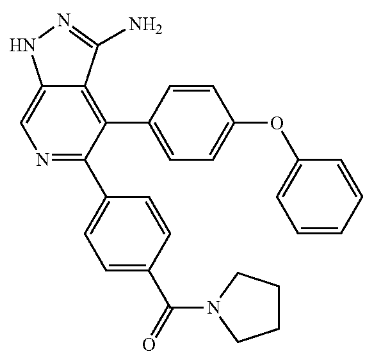 [SMILES: Nc1n[nH]c2cnc(-c3ccc(C(=O)N4CCCC4)cc3)c(-c3ccc(Oc4ccccc4)cc3)c12] | $^1$H NMR (500 MHz, methanol-d$_4$) δ ppm 9.17 (1 H, s), 7.50-7.61 (2 H, m), 7.46 (2 H, δ, J = 8.52 Hz), 7.36-7.43 (2 H, m), 7.29-7.35 (2 H, m), 7.18 (1 H, t, J = 7.42 Hz), 6.97-7.07 (4 H, m), 3.60 (2 H, t, J = 7.01 Hz), 3.38 (2 H, t, J = 6.74 Hz), 1.95-2.06 (2 H, m), 1.82-1.95 (2 H, m); MS (ES+) m/z: 476 (M + H); LC retention time: 3.466 min. |
| Example 70: 4,5-Bis(4-phenoxyphenyl)-1H-pyrazolo[3,4-c]pyridin-3-amine | 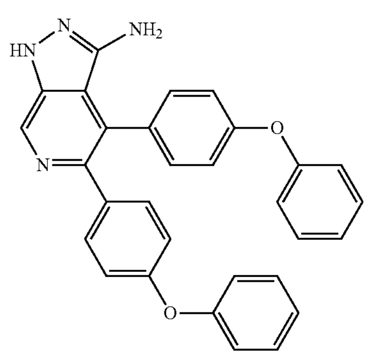 [SMILES: Nc1n[nH]c2cnc(-c3ccc(Oc4ccccc4)cc3)c(-c3ccc(Oc4ccccc4)cc3)c12] | $^1$H NMR (500 MHz, methanol-d$_4$) δ ppm 9.13 (1 H, s), 7.36-7.47 (4 H, m), 7.28-7.35 (4 H, m), 7.13-7.24 (2 H, m), 6.92-7.10 (8 H, m); MS (ES+) m/z: 471 (M + H); LC retention time: 4.105 min. |

*Analytical HPLC Method A

Example 71

7-(4-Methoxyphenyl)-4-(4-phenoxyphenyl)-1H-pyrazol[3,4-c]pyridin-3-amine

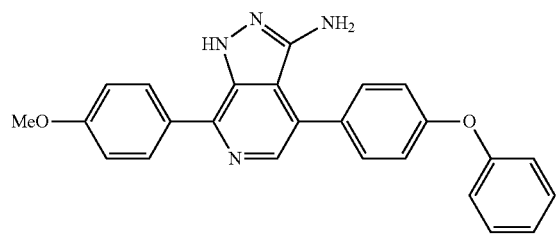

Step 1:

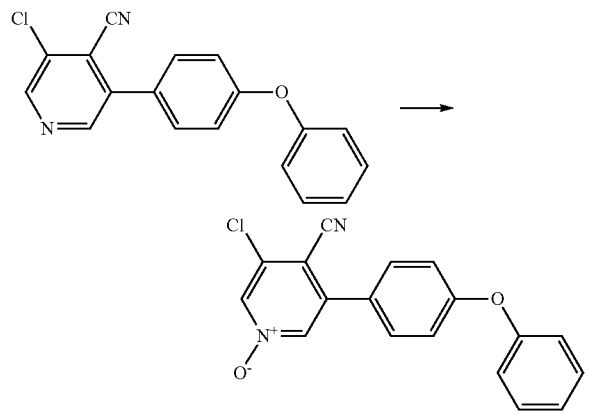

A solution of 3-chloro-5-(4-phenoxyphenyl)isonicotinonitrile (0.495 g, 1.614 mmol) and 77% 3-chloroperbenzoic acid (1.808 g, 8.07 mmol) in dichloromethane (20 mL) was stirred at room temperature. After 22 h at room temperature, the mixture was diluted with dichloromethane (100 mL), washed with 1 M sodium sulfite (25 mL), 1 N NaOH (2×25 mL), brined (25 mL), dried (MgSO$_4$) and concentrated. Silica gel chromatography, loading with dichloromethane and eluting with 20-50% ethyl acetate in hexanes, gave 3-chloro-4-cyano-5-(4-phenoxyphenyl)pyridine 1-oxide as white solid (328.8 mg, 63% yield). $^1$H NMR (400 MHz, CDCl$_3$) δ ppm 8.25 (1H, δ, J=1.51 Hz), 8.16 (1H, δ, J=1.51 Hz), 7.46-7.58 (2H, m), 7.36-7.45 (2H, m), 7.21 (1H, t, J=7.40 Hz), 7.03-7.16 (4H, m); MS (ES+) m/z: 323 (M+H); LC retention time: 3.863 min (analytical HPLC Method A).

Step 27

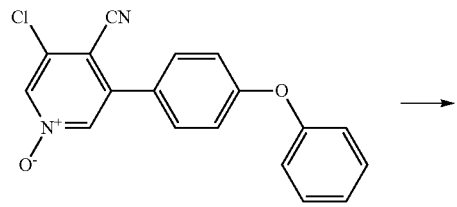

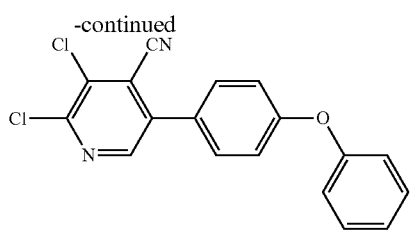

(A)

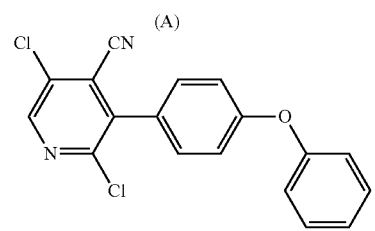

(B)

A suspension of 3-chloro-4-cyano-5-(4-phenoxyphenyl)pyridine 1-oxide (0.3068 g, 0.951 mmol) in phosphorus oxychloride (5 mL, 53.6 mmol) was heated to 100° C. for 1 h. The mixture was concentrated, diluted with ethyl acetate (100 mL), washed with saturated sodium bicarbonate (30 mL) and brine (30 mL), dried (MgSO$_4$) and concentrated. Silica gel chromatography, loading with toluene and eluting with 5-15% ethyl acetate in hexanes, gave 2,3-dichloro-5-(4-phenoxyphenyl)isonicotinonitrile (156.6 mg), 2,5-dichloro-3-(4-phenoxyphenyl)isonicotinonitrile (89.4 mg) and a 2:3 mixture of the two isomers (65.4 mg). Characterization of 2,3-dichloro-5-(4-pherioxyphenyl)isonicotinonitrile: $^1$H NMR (400 MHz, CDCl$_3$) δ ppm 8.49 (1H, s), 7.48-7.59 (2H, m), 7.35-7.46 (2H, m), 7.21 (1H, t, J=7.40 Hz), 7.05-7.18 (4H, m); MS (ES+) m/z: 341 (M+H); LC retention time: 4.601 min (analytical HPLC Method A). Characterization of 2,5-dichloro-3-(4-phenoxyphenyl)isonicotinonitrile: $^1$H NMR (400 MHz, CDCl$_3$) δ ppm 8.56 (1H, s), 7.33-7.48 (4H, m), 7.21 (1H, t, J=7.40 Hz), 7.07-7.18 (4H, m); MS (ES+) m/z: 341 (M+H); LC retention time: 4.438 min (analytical HPLC Method A).

Step 3:

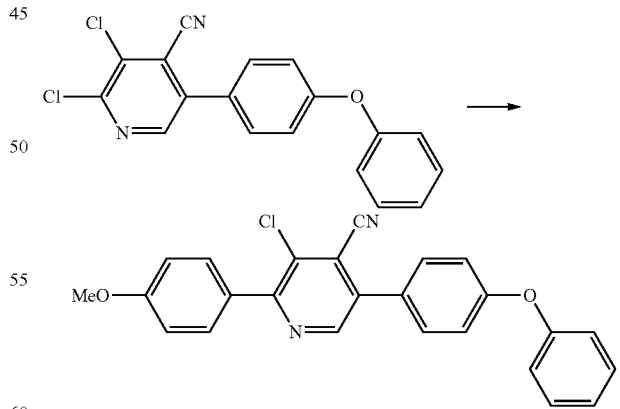

A mixture of 2,3-dichloro-5-(4-phenoxyphenyl)isonicotinonitrile (109 mg, 0.319 mmol), 4-methoxyphenylboronic acid (58.3 mg, 0.383 mmol), potassium phosphate (136 mg, 0.639 mmol) and palladium tetrakis(triphenylphosphine) (18.46 mg, 0.016 mmol) was pumped and backfilled with nitrogen 3 times. N,N-Dimethylacetamide (2 mL) was added.

The mixture was again pumped and backfilled with nitrogen 3 times. The reaction tube was sealed and heated to 150° C. under microwave for 30 min. The mixture was diluted with ethyl acetate (30 mL), washed with 1:1 mixture of brine and water (15 mL), brine (15 mL), dried (MgSO₄) and concentrated. Silica gel chromatography, loading with toluene and eluting with 5-30% ethyl acetate in hexanes, gave 3-chloro-2-(4-methoxyphenyl)-5-(4-phenoxyphenyl)isonicotinonitrile (72.7 mg, 52% yield). $^1$H NMR (500 MHz, CDCl₃) δ ppm 8.75 (1H, s), 7.74-7.83 (2H, m), 7.56-7.64 (2H, m), 7.37-7.47 (2H, m), 7.21 (1H, t, J=7.42 Hz), 7.09-7.18 (4H, m), 7.00-7.09 (2H, m), 3.90 (3H, s); MS (ES+) m/z: 413 (M+H); LC retention time: 4.810 min (analytical HPLC Method A).

Step 4:

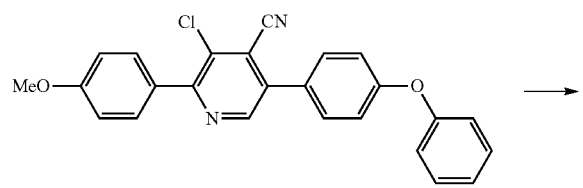

A mixture of 3-chloro-2-(4-methoxyphenyl)-5-(4-phenoxyphenyl)isonicotinonitrile (72.7 mg, 0.176 mmol), 35% aqueous hydrazine (0.790 mL, 8.80 mmol) and 1-propanol (3 mL) in a microwave tube was sealed and heated under microwave to 160° C. for 1 h. HPLC and LCMS analysis showed that most of the starting material remained unchanged. The reaction tube was re-sealed and placed in a 150° C. oil bath for 24 h. The mixture was concentrated and purified by reverse phase HPLC (YMC ODS S5 30×100 mm column), loading with methanol and eluting with 50-90% solvent B (90% methanol-10% water-0.1% TFA) in solvent A (10% methanol-90% water-0.1% TFA), to give Example 71 as yellow solid, assumed as bis-TFA salt (16.4 mg, 13% yield). $^1$H NMR (400 MHz, methanol-d₄) δ ppm 8.06 (2H, δ, J=8.78 Hz), 7.93 (1H, s), 7.66 (2H, δ, J=8.53 Hz), 7.44 (2H, t, J=8.03 Hz), 7.29 (2H, δ, J=9.03 Hz), 7.17-7.25 (3H, m), 7.13 (2H, δ, J=8.53 Hz), 3.97 (3H, s); MS (ES+) m/z: 409 (M+H); LC retention time: 3.518 min (analytical HPLC Method A).

Example 72

5-(4-Methoxyphenyl)-4-(4-phenoxyphenyl)-1H-pyrazolo[3,4-c]pyridin-3-amine

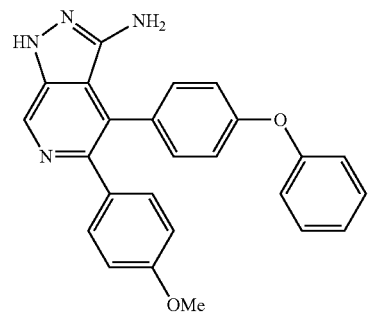 [SMILES: COc1ccc(-c2ncc3[nH]nc(N)c3c2-c2ccc(Oc3ccccc3)cc2)cc1]

Following conditions described in Steps 3 and 4 of Example 71, Example 72 was prepared from 2,5-dichloro-3-(4-phenoxyphenyl)isonicotinonitrile (product B from Step 2 of Example 71). $^1$H NMR (400 MHz, methanol-d₄) δ ppm 9.09 (1H, s), 7.36-7.46 (2H, m), 7.29 (4H, dd, J=15.94, 8.41 Hz), 7.18 (1H, t, J=7.28 Hz), 6.99-7.11 (4H, m), 6.95 (2H, δ, J=8.53 Hz), 3.82 (3H, s); MS (ES+) m/z: 409 (M+H); LC retention time: 3.501 min (analytical HPLC Method A).

Example 73

N-(3-(3-Amino-4-(4-phenoxyphenyl)-1H-pyrazolo[3,4-c]pyridin-7-yl)benzyl)acetamide

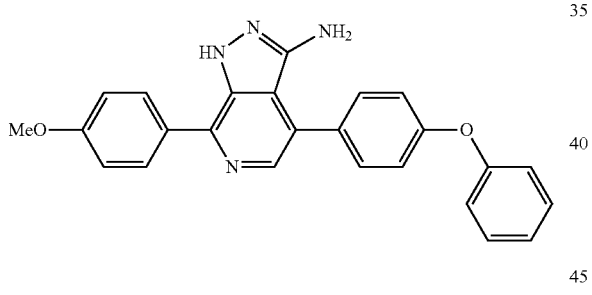

Step 1:

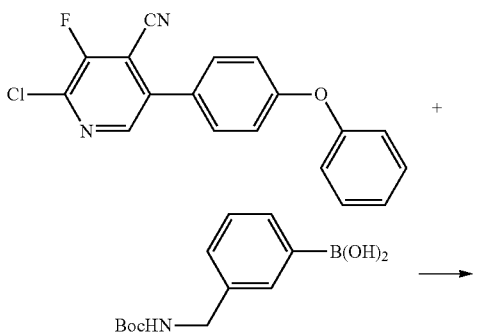

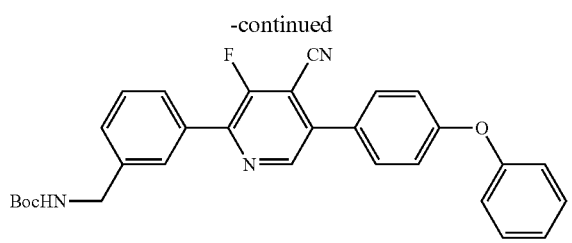

A mixture of 2-chloro-3-fluoro-5-(4-phenoxyphenyl) isonicotinonitrile (51.7 mg, 0.159 mmol, from Step 3 of Example 59), 3-((tert-butoxycarbonylamino)methyl)phenylboronic acid (60.0 mg, 0.239 mmol), palladium(II) acetate (7.15 mg, 0.032 mmol), potassium phosphate (84 mg, 0.398 mmol) and 1,1'-bis(di-t-butylphosphino)ferrocene (15.30 mg, 0.032 mmol) was pumped and backfilled with nitrogen 3 times. Dioxane (2 mL) was added. The reaction vial was again pumped and backfilled with nitrogen 3 times, sealed and heated to 100° C. for 2.5 h. The mixture was filtered through a CELITE® pad and the pad rinsed with ethyl acetate (30 mL). The filtrate was concentrated. Silica gel chromatography, loading with toluene and eluting with 5-30% ethyl acetate in hexanes, gave text-butyl 3-(4-cyano-3-fluoro-5-(4-phenoxyphenyl)pyridin-2-yl)benzylcarbamate as tan solid (70.1 mg, 83% yield). $^1$H NMR (500 MHz, CDCl$_3$) δ ppm 8.73 (1H, s), 7.94 (1H, s), 7.91 (1H, δ, J=7.70 Hz), 7.58-7.65 (2H, m), 7.36-7.54 (4H, m), 7.20 (1H, t, J=7.42 Hz), 7.13-7.18 (2H, m), 7.12 (2H, δ, J=7.42 Hz), 4.96 (1H, br. s), 4.34-4.48 (2H, m), 1.48 (9H, s); MS (ES+) m/z: 440 (M+H); LC retention time: 4.718 min (analytical HPLC Method A).

Step 2:

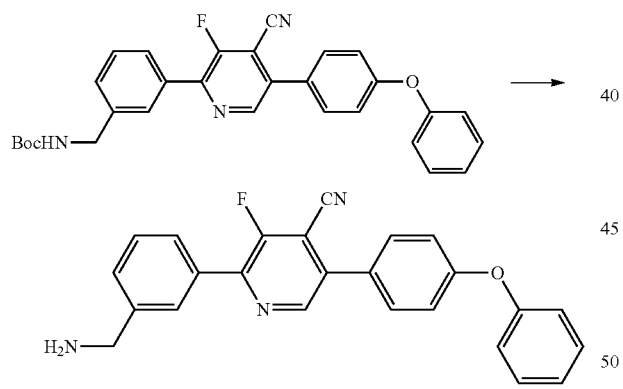

A 1 M dioxane solution of HCl (3 mL, 3.00 mmol) was added to a solution of tert-butyl 3-(4-cyano-3-fluoro-5-(4-phenoxyphenyl)pyridin-2-yl)benzylcarbamate (54.6 mg, 0.110 mmol) in dichloromethane (3 mL). After 3 h at room temperature, the mixture was concentrated and pumped under vacuum to give 2-(3-(aminomethyl)phenyl)-3-fluoro-5-(4-phenoxyphenyl)isonicotinonitrile as brown solid, assumed as bis-HCl salt (48 mg, 93% yield). $^1$H NMR (500 MHz, methanol-d$_4$) δ ppm 8.80 (1H, s), 8.16 (1H, s), 8.08 (1H, br. s), 7.72 (2H, δ, J=8.25 Hz), 7.65 (2H, δ, J=3.85 Hz), 7.42 (2H, t, J=7.70 Hz), 7.20 (1H, t, J=7.29 Hz), 7.16 (2H, δ, J=7.97 Hz), 7.10 (2H, δ, J=7.97 Hz), 4.25 (2H, s); MS (ES+) m/z: 396 (M+H); LC retention time: 3.768 min (analytical HPLC Method A).

Step 3:

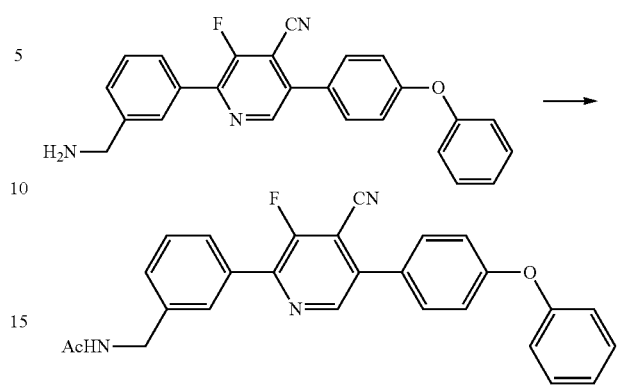

Hunig's base (0.045 mL, 0.256 mmol) was added to a mixture of 2-(3-(aminomethyl)phenyl)-3-fluoro-5-(4-phenoxyphenyl)isonicotinonitrile bis-HCl salt (12 mg, 0.026 mmol) and acetic anhydride (0.012 mL, 0.128 mmol) in dichloromethane (3 mL). After 1 h at room temperature, the mixture was diluted with brine (10 mL), water (10 mL) and extracted with dichloromethane (3×10 mL). The combined extracts were dried (MgSO$_4$) and concentrated. Silica gel chromatography, loading with dichloromethane and eluting with 50-100% ethyl acetate in hexanes, gave N-(3-(4-cyano-3-fluoro-5-(4-phenoxyphenyl)pyridin-2-yl)benzyl)acetamide as off-white solid (10.2 mg, 91% yield), $^1$H NMR (500 MHz, CDCl$_3$) δ ppm 8.73 (1H, s), 7.89-7.98 (2H, m), 7.57-7.66 (2H, m), 7.47-7.55 (1H, m), 7.37-7.47 (3H, m), 7.18-7.25 (1H, m), 7.14-7.18 (2H, m), 7.12 (2H, δ, J=7.70 Hz), 5.87 (1H, br. s), 4.55 (2H, δ, J=5.77 Hz), 2.07 (3H, s); MS (ES+) m/z: 438 (M+H); LC retention time: 4.388 min (analytical HPLC Method A).

Step 4:

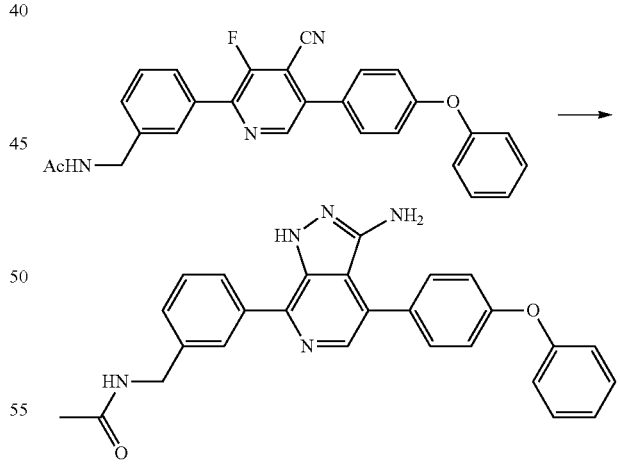

A mixture of N-(3-(4-cyano-3-fluoro-5-(4-phenoxyphenyl)pyridin-2-yl)benzyl)acetamide (10.2 mg, 0.023 mmol) and 35% aqueous hydrazine (0.209 mL, 2.332 mmol) in n-butanol (2 mL) in a reaction vial was sealed and placed in a 120° C. oil bath. After 15 h at 120° C., the mixture was treated with ethyl acetate (30 mL), washed with brine (2×5 mL), dried (MgSO$_4$) and concentrated. Purification by reverse phase HPLC (Surefire 510 30×250 mm column), eluting with 50-80% solvent B (10% methanol-90% water-0.1% TFA) in solvent A (90% methanol-10% water-0.1% TFA), gave Example 73 as yellow solid, assumed as bis-TFA salt (6.7 mg, 41% yield). ¹H NMR (500 MHz, methanol-d₄) δ ppm 8.04 (1H, s), 7.97 (1H, s), 7.93 (1H, δ, J=7.42 Hz), 7.62-7.78 (4H, m), 7.39-7.48 (2H, m), 7.19-7.27 (3H, m), 7.11-7.17 (2H, m), 4.53 (2H, s), 2.03 (3H, s); MS (ES+) m/z: 450 (M+H); LC retention time: 3.420 min (analytical HPLC Method A).

Examples 74 to 77

Example 74 was prepared from Example 66 by treating with HCl. Examples 75 to 77 were prepared from 2-(3-(aminomethyl)phenyl)-3-fluoro-5-(4-phenoxyphenyl)isonicotinonitrile (from Step 2 of Example 73) following conditions similar to Steps 3 and 4 of Example 73.

| Example No. | Structure | Spectral data* |
|---|---|---|
| Example 74: 7-(3-(Aminomethyl)phenyl)-4-(4-phenoxyphenyl)-1H-pyrazolo[3,4-c]pyridin-3-amine | 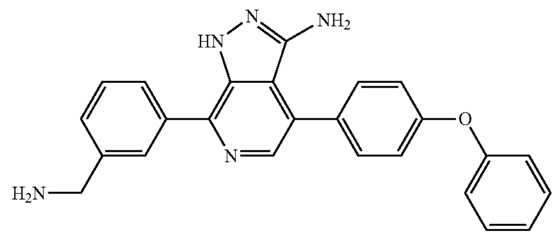 [SMILES: NCc1cccc(-c2ncc(-c3ccc(Oc4ccccc4)cc3)c3c(N)n[nH]c23)c1] | ¹H NMR (500 MHz, methanol-d₄) δ ppm 8.27 (1 H, s), 8.13 (1 H, δ, J = 7.42 Hz), 8.08 (1 H, s), 7.82-7.95 (2 H, m), 7.70 (2 H, δ, J = 8.52 Hz), 7.39-7.50 (2 H, m), 7.19-7.28 (3 H, m), 7.15 (2 H, δ, J = 7.70 Hz), 4.36 (2 H, s); MS (ES+) m/z: 408 (M + H); LC retention time: 3.141 min. |
| Example 75: N-(3-(3-Amino-4-(4-phenoxyphenyl)-1H-pyrazolo[3,4-c]pyridin-7-yl)benzyl)benzamide | 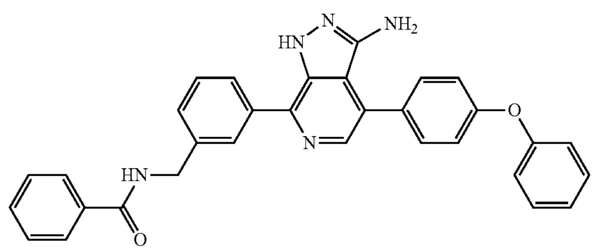 [SMILES: Nc1n[nH]c2c(-c3cccc(CNC(=O)c4ccccc4)c3)ncc(-c3ccc(Oc4ccccc4)cc3)c12] | ¹H NMR (500 MHz, methanol-d₄) δ ppm 8.05 (1 H, s), 8.03 (1 H, s), 7.94 (1 H, δ, J = 7.42 Hz), 7.86-7.91 (2 H, m), 7.71-7.81 (2 H, m), 7.63-7.70 (2 H, m), 7.53-7.60 (1 H, m), 7.39-7.52 (4 H, m), 7.19-7.26 (3 H, m), 7.14 (2 H, δ, J = 7.42 Hz), 4.75 (2 H, s); MS (ES+) m/z: 512 (M + H); LC retention time: 3.788 min. |
| Example 76: N-(3-(3-Amino-4-(4-phenoxyphenyl)-1H-pyrazolo[3,4-c]pyridin-7-yl)benzyl)methanesulfonamide | 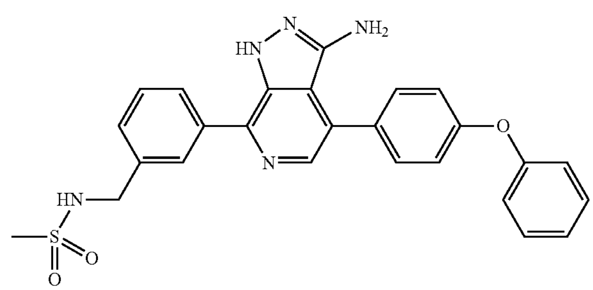 [SMILES: CS(=O)(=O)NCc1cccc(-c2ncc(-c3ccc(Oc4ccccc4)cc3)c3c(N)n[nH]c23)c1] | ¹H NMR (500 MHz, methanol-d₄) δ ppm 8.06 (1 H, s), 8.04 (1 H, s), 7.97 (1 H, δ, J = 7.70 Hz), 7.77-7.83 (1 H, m), 7.72-7.77 (1 H, m), 7.63-7.71 (2 H, m), 7.38-7.49 (2 H, m), 7.18-7.27 (3 H, m), 7.14 (2 H, δ, J = 7.70 Hz), 4.45 (2 H, s), 2.99 (3 H, s); MS (ES+) m/z: 486 (M + H); LC retention time: 3.428 min. |
| Example 77: N-(3-(3-Amino-4-(4-phenoxyphenyl)-1H-pyrazolo[3,4-c]pyridin-7-yl)benzyl)benzenesulfonamide | 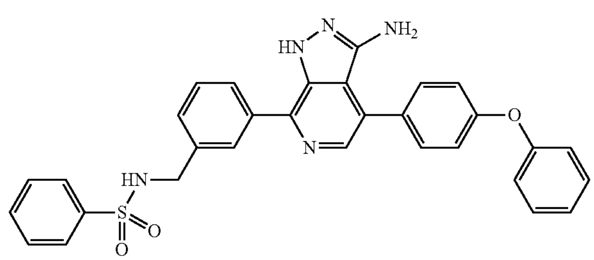 [SMILES: Nc1n[nH]c2c(-c3cccc(CNS(=O)(=O)c4ccccc4)c3)ncc(-c3ccc(Oc4ccccc4)cc3)c12] | ¹H NMR (500 MHz, methanol-d₄) δ ppm 8.03 (1 H, s), 7.90-7.95 (2 H, m), 7.85-7.89 (2 H, m), 7.63-7.71 (4 H, m), 7.49-7.61 (3 H, m), 7.40-7.47 (2 H, m), 7.19-7.27 (3 H, m), 7.14 (2 H, δ, J = 7.70 Hz), 4.26 (2 H, s); MS (ES+) m/z: 548 (M + H); LC retention time: 3.781 min. |

*Analytical HPLC Method A

Example 78

7-Hydrazino-4-(4-phenoxyphenyl)-1H-pyrazolo[3,4-c]pyridin-3-amine

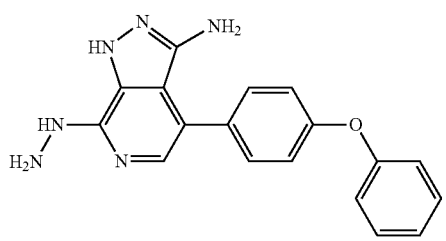 [SMILES: NNc1ncc(-c2ccc(Oc3ccccc3)cc2)c2c(N)n[nH]c12]

A mixture of 2-chloro-3-fluoro-5-(4-phenoxyphenyl) isonicotinonitrile (323 mg, 0.995 mmol, from Step 4 of Example 59) and 35% aqueous hydrazine (0.892 mL, 9.95 mmol) in n-propanol (5 mL) in a reaction vial was sealed and placed in a 100° C. oil bath for 20 h. Upon cooling, a precipitate was formed. The solid was collected by filtration, washed with 1:1 mixture of water-propanol (2×3 mL) to give Example 78 as gray solid (143.1 mg, 42% yield). $^1$H NMR (500 MHz, DMSO-$d_6$) δ ppm 11.56 (1H, br. s), 7.53-7.65 (1H, m), 7.34-7.50 (5H, m), 7.16 (1H, t, J=7.42 Hz), 7.05-7.13 (4H, m), 4.46 (2H, br. s), 4.41 (2H, br. s); MS (ES+) m/z: 333 (M+H); LC retention time: 3.070 min (analytical HPLC Method A).

Example 79

4-(4-Phenoxyphenyl)-7-(4-phenyl-1H-pyrazol-1-yl)-1H-pyrazolo[3,4-c]pyridin-3-amine

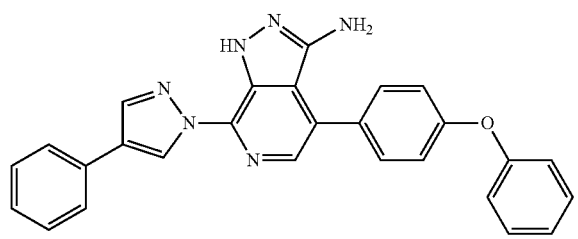 [SMILES: Nc1n[nH]c2c(-n3cc(-c4ccccc4)cn3)ncc(-c3ccc(Oc4ccccc4)cc3)c12]

A mixture of 7-hydrazinyl-4-(4-phenoxyphenyl)-1H-pyrazolo[3,4-c]pyridin-3-amine (15.4 mg, 0.046 mmol), 2-phenylmalonaldehyde (7.5 mg, 0.051 mmol, from Example 78) and ethanol (1 mL) in a sealed tube was stirred at 80° C. for 16 h and cooled to room temperature. The solid was collected by filtration to give Example 79 as tan solid (14.8 mg, 68% yield). $^1$H NMR (400 MHz, chloroform-d) d ppm 10.97 (1H, s), 8.96 (1H, s), 8.14 (1H, s), 7.88 (1H, s), 7.64 (2H, d, J=7.53 Hz), 7.55 (2H, d, J=8.78 Hz), 7.42 (4H, ddd, J=12.55, 7.78, 7.53 Hz), 7.31 (1H, t, J=7.53 Hz), 7.05-7.22 (5H, m), 4.02 (2H, s); MS (ES+) m/z: 445 (WE); LC retention time: 5.015 min (analytical HPLC Method A).

Example 80

4-(4-Phenoxyphenyl)-7-(1H-1,2,4-triazol-1-yl)-1H-pyrazolo[3,4-c]pyridin-3-amine

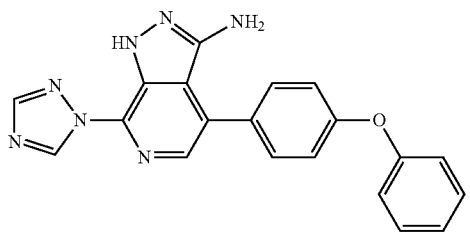 [SMILES: Nc1n[nH]c2c(-n3cncn3)ncc(-c3ccc(Oc4ccccc4)cc3)c12]

A mixture of 7-hydrazinyl-4-(4-phenoxyphenyl)-1H-pyrazolo[3,4-c]pyridin-3-amine (14.2 mg, 0.043 mmol, from Example 78), 1,3,5-triazine (4.16 mg, 0.051 mmol) and ethanol (1 mL) in a sealed tube was stirred at 80° C. for 16 h and at 100° C. for 5 h. Additional 1,3,5-triazine (2.1 mg, 0.025 mmol) was added. After another 15 h at 80° C., EtOH was evaporated. The residue was dissolved in TFA (0.1 mL) and MeOH and purified with reverse phase HPLC(YMC ODS S5 30×100 mm column), eluting with 60-95% solvent B (10% MeOH-90% H$_2$O-0.1% TFA) in solvent A (90% MeOH-10% H$_2$O-0.1% TFA), to give Example 80 (2.5 mg, 9% yield, assumed as bis-TFA salt. $^1$H NMR (400 MHz, MeOD) d ppm 9.49 (1H, s), 8.36 (1H, s), 7.90 (1H, d, J=1.51 Hz), 7.59 (2H, d, J=8.53 Hz), 7.42 (2H, t, J=8.03 Hz), 7.14-7.23 (3H, m), 7.11 (2H, d, J=8.53 Hz); MS (ES+) m/z: 370 (M+H); LC retention time: 4.203 min (analytical HPLC Method A).

Example 81

4-(4-Phenoxyphenyl)-7-(1H-pyrazol-1-yl)-1H-pyrazolo[3,4-c]pyridin-3-amine

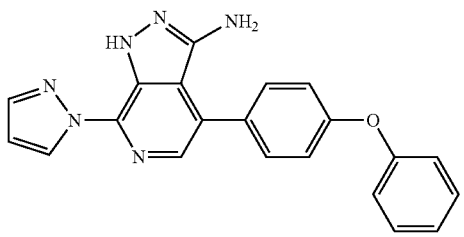 [SMILES: Nc1n[nH]c2c(-n3cccn3)ncc(-c3ccc(Oc4ccccc4)cc3)c12]

A mixture of 7-hydrazinyl-4-(4-phenoxyphenyl)-1H-pyrazolo[3,4-c]pyridin-3-amine (20 mg, 0.060 mmol, from Example 78), 1,1,3,3-tetramethoxypropane (9.88 mg, 0.060 mmol), concentrated hydrochloric acid (7.31 μL, 0.241 mmol) and ethanol (1 mL) in a sealed tube was stirred at 80° C. for 22 h. The resulting suspension was filtered. The filtrate was concentrated and purified with reverse phase HPLC (YMC ODS S5 30×100 mm column), eluting with 80-100% solvent B (10% MeOH-90% H$_2$O-0.1% TEA) in solvent A (90% MeOH-10% H$_2$O-0.1% TEA), to give Example 81 as tan solid, assumed as bis-TFA salt. $^1$H NMR (400 MHz, MeOD) d ppm 8.72 (1H, d, J=2.51 Hz), 7.94 (1H, s), 7.83 (1H, s), 7.52-7.65 (2H, m), 7.32-7.46 (2H, m), 7.14-7.21 (3H, m), 7.07-7.13 (2H, m), 6.50-6.70 (1H, m); MS (ES+) m/z: 369 (M+H); LC retention time: 4.490 min (analytical HPLC Method A).

Examples 82 to 113

Using a parallel synthesis approach, Examples 82 to 113 were synthesized from 2-chloro-3-fluoro-5-(4-phenoxyphenyl)isonicotinonitrile (product A from Step 4 of Example 59) using conditions similar to Step 5 of Example 59.

| Example No. | Structure | Spectral data* |
|---|---|---|
| Example 82: 7-(3,4-Dichlorophenyl)-4-(4-phenoxyphenyl)-1H-pyrazolo[3,4-c]pyridin-3-amine | 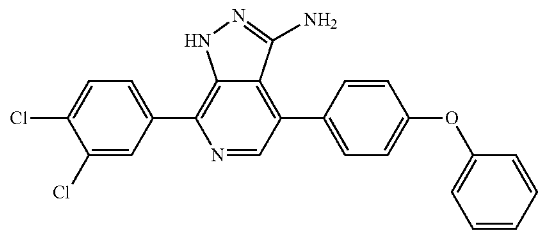 [SMILES: Nc1n[nH]c2c(-c3ccc(Cl)c(Cl)c3)ncc(-c3ccc(Oc4ccccc4)cc3)c12] | MS (ES+) m/z: 447 (M + H); LC retention time: 3.18 min. |
| Example 83: 3-(3-Amino-4-(4-phenoxyphenyl)-1H-pyrazolo[3,4-c]pyridin-7-yl)benzoic acid | 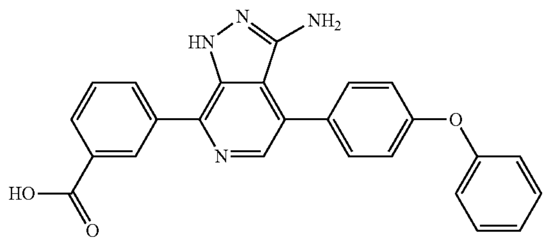 [SMILES: Nc1n[nH]c2c(-c3cccc(C(=O)O)c3)ncc(-c3ccc(Oc4ccccc4)cc3)c12] | MS (ES+) m/z: 423 (M + H); LC retention time: 1.73 min. |
| Example 84: 4-(3-Amino-4-(4-phenoxyphenyl)-1H-pyrazolo[3,4-c]pyridin-7-yl)benzoic acid | 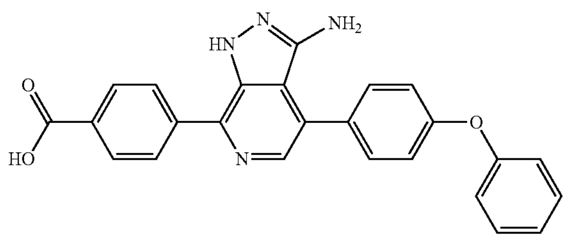 [SMILES: Nc1n[nH]c2c(-c3ccc(C(=O)O)cc3)ncc(-c3ccc(Oc4ccccc4)cc3)c12] | MS (ES+) m/z: 423 (M + H); LC retention time: 1.65 min. |
| Example 85: 7-(3-Methoxyphenyl)-4-(4-phenoxyphenyl)-1H-pyrazolo[3,4-c]pyridin-3-amine | 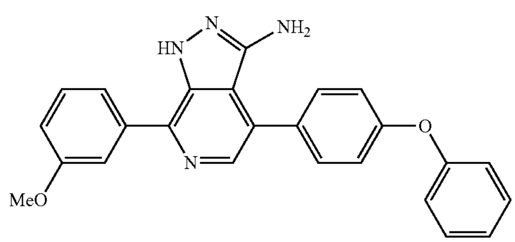 [SMILES: COc1cccc(-c2ncc(-c3ccc(Oc4ccccc4)cc3)c3c(N)n[nH]c23)c1] | MS (ES+) m/z: 409 (M + H); LC retention time: 2.57 min. |
| Example 86: 7-Dibenzo[b,δ]furan-1-yl-4-(4-phenoxyphenyl)-1H-pyrazolo[3,4-c]pyridin-3-amine | 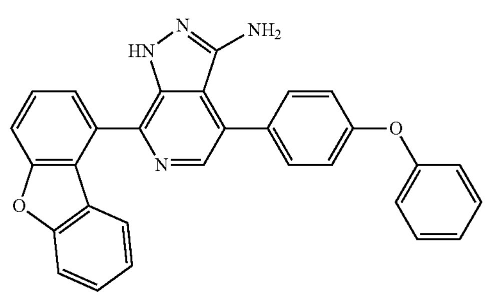 [SMILES: Nc1n[nH]c2c(-c3cccc4oc5ccccc5c34)ncc(-c3ccc(Oc4ccccc4)cc3)c12] | MS (ES+) m/z: 469 (M + H); LC retention time: 3.00 min. |

-continued

| Example No. | Structure | Spectral data* |
|---|---|---|
| Example 87: 4-(4-Phenoxyphenyl)-7-(6-quinolinyl)-1H-pyrazolo[3,4-c]pyridin-3-amine | 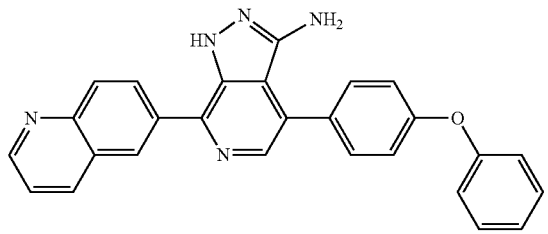 [SMILES: Nc1n[nH]c2c(-c3ccc4ncccc4c3)ncc(-c3ccc(Oc4ccccc4)cc3)c12] | MS (ES+) m/z: 430 (M + H); LC retention time: 2.41 min. |
| Example 88: 3-(3-Amino-4-(4-phenoxyphenyl)-1H-pyrazolo[3,4-c]pyridin-7-yl)-N,N-dimethylbenzamide | 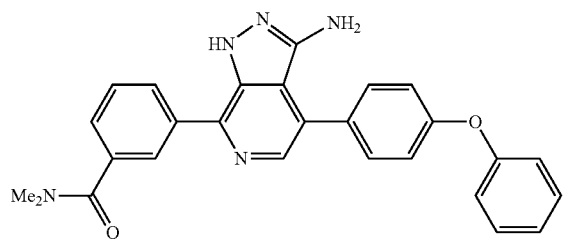 [SMILES: CN(C)C(=O)c1cccc(-c2ncc(-c3ccc(Oc4ccccc4)cc3)c3c(N)n[nH]c23)c1] | MS (ES+) m/z: 450 (M + H); LC retention time: 3.29 min. |
| Example 89: 3-(3-Amino-4-(4-phenoxyphenyl)-1H-pyrazolo[3,4-c]pyridin-7-yl)-N-(2-furylmethyl)benzamide | 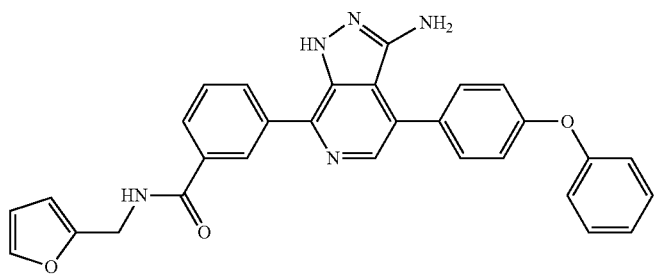 [SMILES: Nc1n[nH]c2c(-c3cccc(C(=O)NCc4ccco4)c3)ncc(-c3ccc(Oc4ccccc4)cc3)c12] | MS (ES+) m/z: 502 (M + H); LC retention time: 2.48 min. |
| Example 90: 7-(1,3-Benzodioxol-5-yl)-4-(4-phenoxyphenyl)-1H-pyrazolo[3,4-c]pyridin-3-amine | 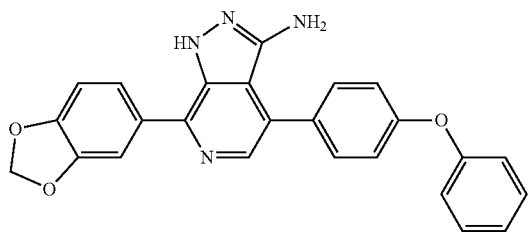 [SMILES: Nc1n[nH]c2c(-c3ccc4c(c3)OCO4)ncc(-c3ccc(Oc4ccccc4)cc3)c12] | MS (ES+) m/z: 423 (M + H); LC retention time: 2.53 min. |
| Example 91: 3-(3-Amino-4-(4-phenoxyphenyl)-1H-pyrazolo[3,4-c]pyridin-7-yl)phenol | 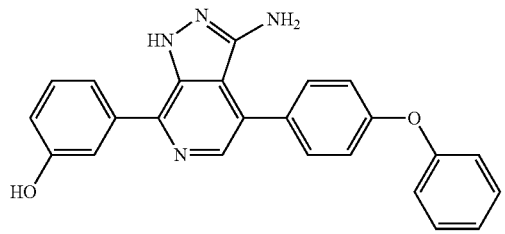 [SMILES: Nc1n[nH]c2c(-c3cccc(O)c3)ncc(-c3ccc(Oc4ccccc4)cc3)c12] | MS (ES+) m/z: 395 (M + H); LC retention time: 2.19 min. |
| Example 92: 3-(3-Amino-4-(4-phenoxyphenyl)-1H-pyrazolo[3,4-c]pyridin-7-yl)phenol | 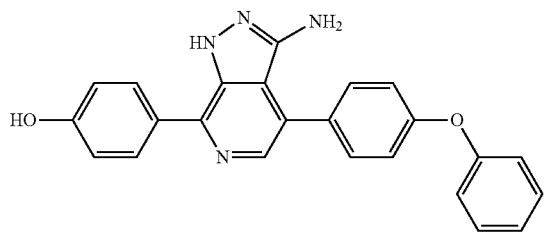 [SMILES: Nc1n[nH]c2c(-c3ccc(O)cc3)ncc(-c3ccc(Oc4ccccc4)cc3)c12] | MS (ES+) m/z: 395 (M + H); LC retention time: 2.16 min. |

-continued

| Example No. | Structure | Spectral data* |
|---|---|---|
| Example 93: (3-(3-Amino-4-(4-phenoxyphenyl)-1H-pyrazolo[3,4-c]pyridin-7-yl)phenyl)methanol | 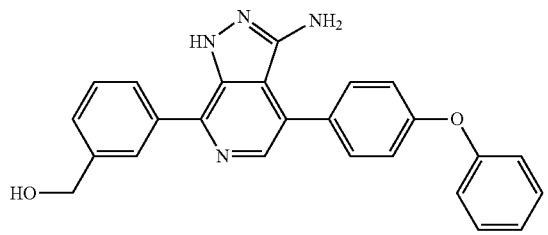 [SMILES: Nc1n[nH]c2c(-c3cccc(CO)c3)ncc(-c3ccc(Oc4ccccc4)cc3)c12] | MS (ES+) m/z: 409 (M + H); LC retention time: 2.17 min. |
| Example 94: 7-(3-(Dimethylamino)phenyl)-4-(4-phenoxyphenyl)-1H-pyrazolo[3,4-c]pyridin-3-amine | 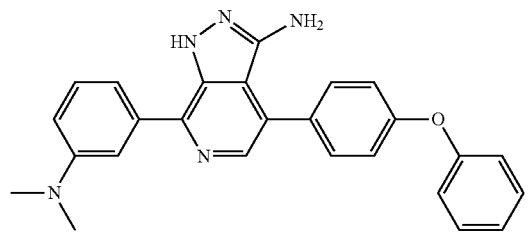 [SMILES: CN(C)c1cccc(-c2ncc(-c3ccc(Oc4ccccc4)cc3)c3c(N)n[nH]c23)c1] | MS (ES+) m/z: 422 (M + H); LC retention time: 2.66 min. |
| Example 95: 7-(1H-Indol-5-yl)-4-(4-phenoxyphenyl)-1H-pyrazolo[3,4-c]pyridin-3-amine | 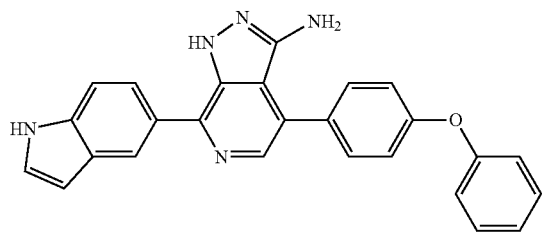 [SMILES: Nc1n[nH]c2c(-c3ccc4[nH]ccc4c3)ncc(-c3ccc(Oc4ccccc4)cc3)c12] | MS (ES+) m/z: 418 (M + H); LC retention time: 2.39 min. |
| Example 96: N-(4-(3-Amino-4-(4-phenoxyphenyl)-1H-pyrazolo[3,4-c]pyridin-7-yl)phenyl)methanesulfonamide | 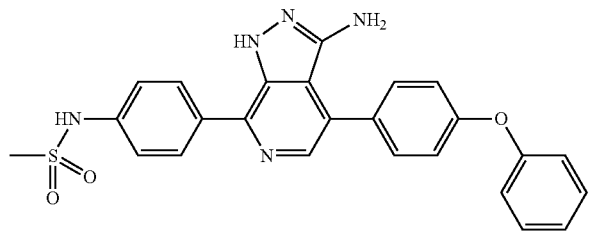 [SMILES: CS(=O)(=O)Nc1ccc(-c2ncc(-c3ccc(Oc4ccccc4)cc3)c3c(N)n[nH]c23)cc1] | MS (ES+) m/z: 472 (M + H); LC retention time: 2.22 min. |
| Example 97: 4-(3-Amino-4-(4-phenoxyphenyl)-1H-pyrazolo[3,4-c]pyridin-7-yl)benzamide | 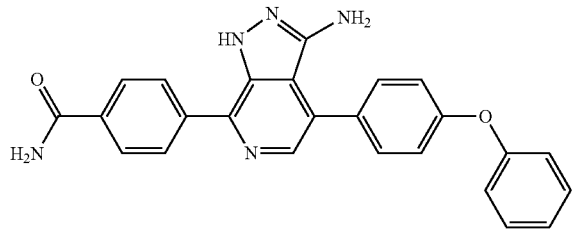 [SMILES: NC(=O)c1ccc(-c2ncc(-c3ccc(Oc4ccccc4)cc3)c3c(N)n[nH]c23)cc1] | MS (ES+) m/z: 422 (M + H); LC retention time: 2.00 min. |
| Example 98: 3-(3-Amino-4-(4-phenoxyphenyl)-1H-pyrazolo[3,4-c]pyridin-7-yl)benzamide | 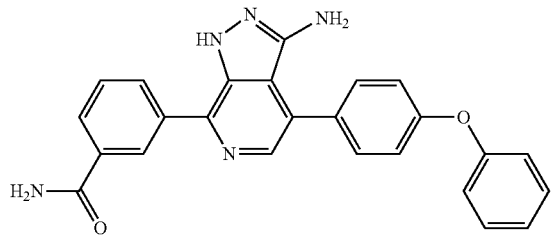 [SMILES: NC(=O)c1cccc(-c2ncc(-c3ccc(Oc4ccccc4)cc3)c3c(N)n[nH]c23)c1] | MS (ES+) m/z: 422 (M + H); LC retention time: 2.06 min. |

-continued

| Example No. | Structure | Spectral data* |
|---|---|---|
| Example 99:<br>N-(4-(3-Amino-4-(4-phenoxyphenyl)-1H-pyrazolo[3,4-c]pyridin-7-yl)benzyl)acetamide | | MS (ES+) m/z: 450 (M + H); LC retention time: 2.07 min. |
| Example 100:<br>4,7-Bis(4-phenoxyphenyl)-1H-pyrazolo[3,4-c]pyridin-3-amine | | MS (ES+) m/z: 471 (M + H); LC retention time: 3.10 min. |
| Example 101:<br>7-(3,5-Dimethylphenyl)-4-(4-phenoxyphenyl)-1H-pyrazolo[3,4-c]pyridin-3-amine | | MS (ES+) m/z: 407 (M + H); LC retention time: 2.89 min. |
| Example 102:<br>7-(3-Isobutoxyphenyl)-4-(4-phenoxyphenyl)-1H-pyrazolo[3,4-c]pyridin-3-amine | | MS (ES+) m/z: 451 (M + H); LC retention time: 3.16 min. |
| Example 103:<br>3-(3-(3-Amino-4-(4-phenoxyphenyl)-1H-pyrazolo[3,4-c]pyridin-7-yl)phenyl)propanoic acid | | MS (ES+) m/z: 451 (M + H); LC retention time: 1.79 min. |
| Example 104:<br>7-(3,4-Dimethoxyphenyl)-4-(4-phenoxyphenyl)-1H-pyrazolo[3,4-c]pyridin-3-amine | | MS (ES+) m/z: 439 (M + H); LC retention time: 2.39 min. |

-continued

| Example No. | Structure | Spectral data* |
|---|---|---|
| Example 105:<br>N-(4-(3-Amino-4-(4-phenoxyphenyl)-1H-pyrazolo[3,4-c]pyridin-7-yl)benzyl)methanesulfonamide | 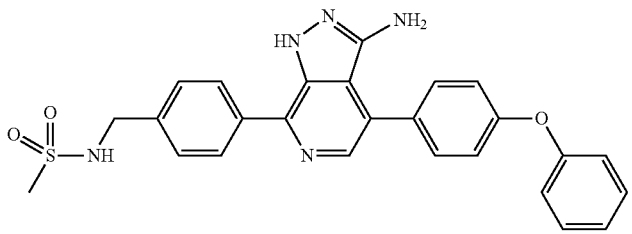 [SMILES: CS(=O)(=O)NCc1ccc(-c2ncc(-c3ccc(Oc4ccccc4)cc3)c3c(N)n[nH]c23)cc1] | MS (ES+) m/z: 486 (M + H); LC retention time: 2.21 min. |
| Example 106:<br>3-(3-Amino-4-(4-phenoxyphenyl)-1H-pyrazolo[3,4-c]pyridin-7-yl)benzenesulfonamide | 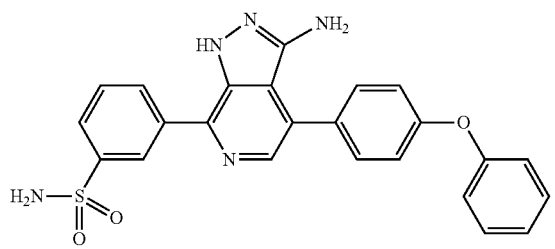 [SMILES: Nc1n[nH]c2c(-c3cccc(S(N)(=O)=O)c3)ncc(-c3ccc(Oc4ccccc4)cc3)c12] | MS (ES+) m/z: 458 (M + H); LC retention time: 2.13 min. |
| Example 107:<br>7-(2-Methylphenyl)-4-(4-phenoxyphenyl)-1H-pyrazolo[3,4-c]pyridin-3-amine | 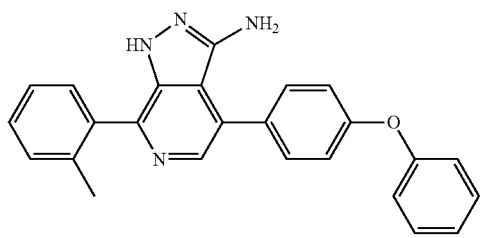 | MS (ES+) m/z: 393 (M + H); LC retention time: 2.53 min. |
| Example 108:<br>4-(4-Phenoxyphenyl)-7-(3-(trifluoromethyl)phenyl)-1H-pyrazolo[3,4-c]pyridin-3-amine | 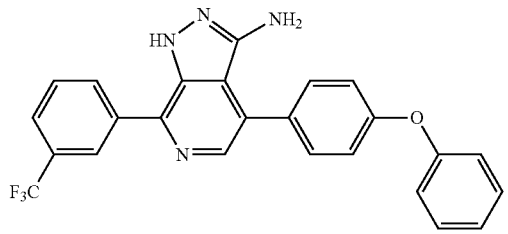 | MS (ES+) m/z: 447 (M + H); LC retention time: 2.99 min. |
| Example 109:<br>7-(2-Naphthyl)-4-(4-phenoxyphenyl)-1H-pyrazolo[3,4-c]pyridin-3-amine | 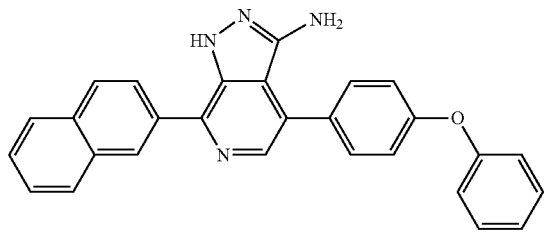 | MS (ES+) m/z: 429 (M + H); LC retention time: 2.95 min. |
| Example 110:<br>7-(2,3-Dihydro-1-benzofuran-5-yl)-4-(4-phenoxyphenyl)-1H-pyrazolo[3,4-c]pyridin-3-amine | 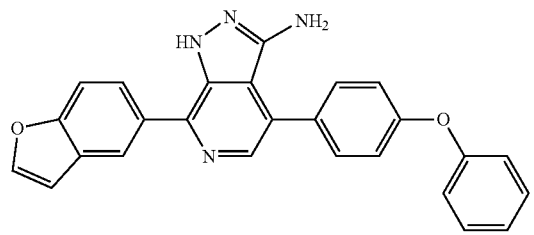 | MS (ES+) m/z: 421 (M + H); LC retention time: 2.52 min. |

| Example No. | Structure | Spectral data* |
|---|---|---|
| Example 111:<br>7-(4-Isobutoxyphenyl)-4-(4-phenoxyphenyl)-1H-pyrazolo[3,4-c]pyridin-3-amine | | MS (ES+) m/z: 451 (M + H); LC retention time: 3.13 min. |
| Example 112:<br>4-(4-Phenoxyphenyl)-7-(4-(trifluoromethoxy)phenyl)-1H-pyrazolo[3,4-c]pyridin-3-amine | | MS (ES+) m/z: 463 (M + H); LC retention time: 3.02 min. |
| Example 113:<br>4-(4-Phenoxyphenyl)-7-(3-(trifluoromethoxy)phenyl)-1H-pyrazolo[3,4-c]pyridin-3-amine | | MS (ES+) m/z: 463 (M + H); LC retention time: 3.05 min. |

*Analytical HPLC Method A

Example 114

6-Chloro-4-(4-phenoxyphenyl)-1H-pyrazolo[3,4-δ]pyrimidin-3-amine

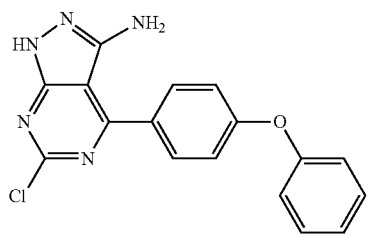

Step 1:

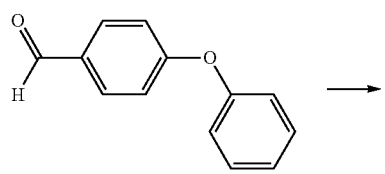

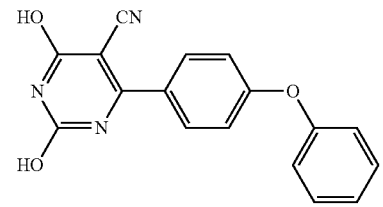

A mixture of 4-phenoxybenzaldehyde (1.98 g, 9.99 mmol), ethyl 2-1.0 cyanoacetate (1.13 g, 9.99 mmol), urea (0.600 g, 9.99 mmol) and potassium carbonate (1.381 g, 9.99 mmol) in ethanol (30 mL) was heated to reflux for 4 h and cooled to room temperature to give a suspension. The solid was collected by filtration, washed with cold ethanol (2×2 mL) and dried under vacuum. The white solid was re-dissolved in warm water, cooled to room temperature and acidified with acetic acid (4 mL). The yellow precipitate was filtered and washed with water (2×10 mL) and dried under vacuum. Recrystallization from acetic acid (8 mL) gave 2,4-dihydroxy-6-(4-phenoxyphenyl)pyrimidine-5-carbonitrile as yellow solid (450 mg, 15% yield). MS (ES+) m/z: 306 (M+H); LC retention time: 3.243 min (analytical HPLC Method A).

Step 2:

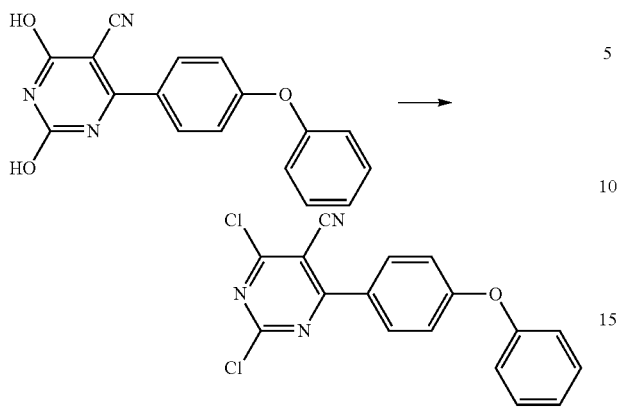

N,N-Diethylaniline (0.420 mL, 2.62 mmol) was added to the suspension of 2,4-dihydroxy-6-(4-phenoxyphenyl)pyrimidine-5-carbonitrile (400 mg, 1.310 mmol) in phosphorus oxychloride (3 mL, 32.2 mmol) at room temperature. The mixture was heated to 125° C. for 3 h, cooled to room temperature and carefully poured into ice water with stirring. The mixture was extracted with ether (3×40 mL). The combined extracts were washed with saturated sodium bicarbonate (10 mL), brine (10 mL), dried (MgSO$_4$) and concentrated. Silica gel chromatography, eluting with 5-40% ethyl acetate in hexanes, gave 2,4-dichloro-6-(4-phenoxyphenyl)pyrimidine-5-carbonitrile as white solid (400 mg, 89% yield). MS (ES+) m/z: 342 (M+H); LC retention time: 4.138 min (analytical HPLC Method. A).

Step 3:

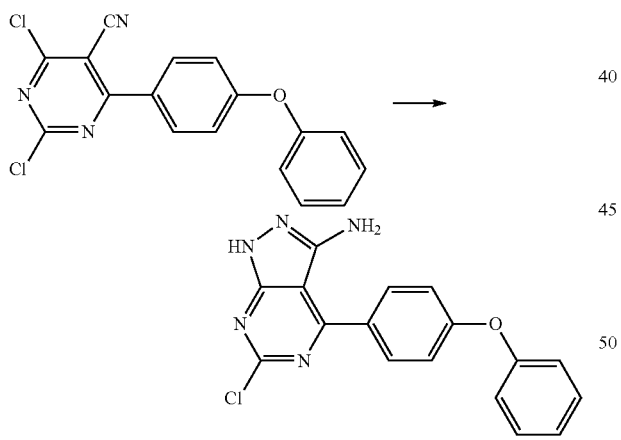

A 35% aqueous solution of hydrazine (53.5 mg, 0.584 mmol) was added to a solution of 2,4-dichloro-6-(4-phenoxyphenyl)pyrimidine-5-carbonitrile (100 mg, 0.292 mmol) in acetonitrile (2 mL) at 0° C. dropwise. After 30 min at 0° C., the mixture was diluted with ethyl acetate (100 mL) and washed with water (5 mL), brine (5 mL), dried (MgSO$_4$) and concentrated. Purification by reverse phase HPLC (Sunfire S10 30×250 mm column), eluting with 70-100% solvent B (10% methanol-90% water-0.1% TFA) in solvent A (90% methanol-10% water-0.1% TFA), gave Example 114 as yellow solid, assumed as bis-TFA salt (5 mg, 4% yield). $^1$H NMR (400 MHz, methanol-d$_4$) δ ppm 7.88 (2H, δ, J=8.53 Hz), 7.30-7.47 (2H, m), 7.00-7.25 (5H, m); MS (ES+) m/z: 338 (M+H); LC retention time: 3.448 min (analytical HPLC Method A).

Example 115

4-(4-Phenoxyphenyl)-6-phenyl-1H-pyrazolo[3,4-δ]pyrimidin-3-amine

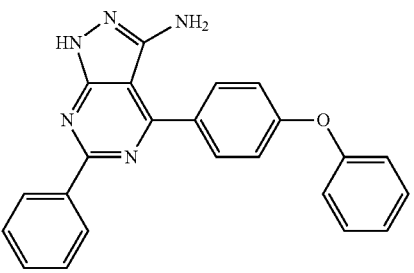

Step 1:

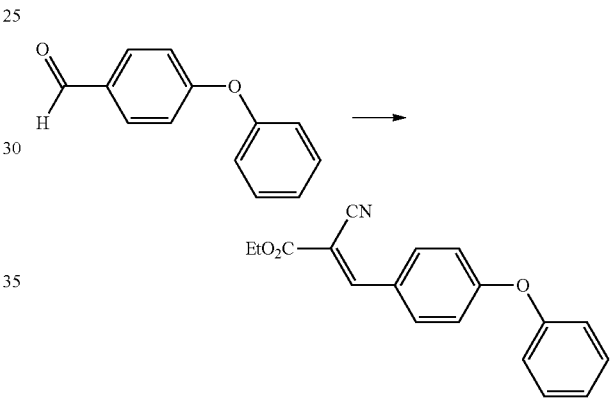

Potassium phosphate (0.751 g, 3.54 mmol) was added to a solution of ethyl 2-cyanoacetate (2.00 g, 17.68 mmol) and 4-phenoxybenzaldehyde (3.50 g, 17.68 mmol) in ethanol (50 mL). After 1 h at room temperature, the mixture was quenched with water (20 mL). The ethanol solvent was evaporated in vacuo. The residue was taken up in ethyl acetate (150 mL), washed with brine (2×10 mL), dried (MgSO$_4$) and concentrated. Silica gel chromatography, loading with toluene and eluting with 5 to 20% ethyl acetate in hexanes, gave (E)-ethyl 2-cyano-3-(4-phenoxyphenyl)acrylate as tan liquid. $^1$H NMR (500 MHz, CDCl$_3$) δ ppm 8.19 (1H, s), 7.92-8.05 (2H, m), 7.37-7.48 (2H, m), 7.24 (1H, t, J=7.42 Hz), 7.10 (2H, δ, J=7.70 Hz), 6.98-7.07 (2H, m), 4.38 (2H, q, J=7.15 Hz), 1.40 (3H, δ, J=7.15 Hz); MS (ES+) m/z: 294 (M+H); LC retention time: 4.405 min (analytical HPLC Method B).

Step 2:

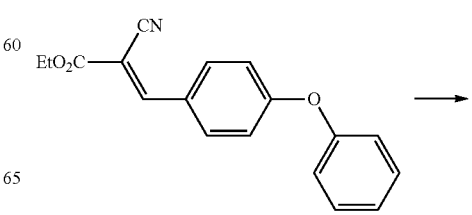

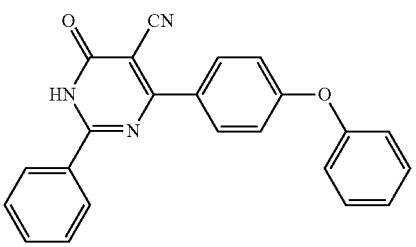

A mixture of (E)-ethyl 2-cyano-3-(4-phenoxyphenyl)acrylate (100 mg, 0.341 mmol) and benzamidine (45.1 mg, 0.375 mmol) in methanol (1 mL) was stirred at room temperature for 15 h while opening to the air. The mixture was treated with ethyl acetate (30 mL), washed with water (5 mL), brine (5 mL), dried (MgSO$_4$) and concentrated to give crude 6-oxo-4-(4-phenoxyphenyl)-2-phenyl-1,6-dihydropyrimidine-5-carbonitrile as tan solid. The crude material was taken to next reaction without purification. MS (ES+) m/z: 366 (M+H); LC retention time: 4.525 min (analytical HPLC Method B).

Step 3:

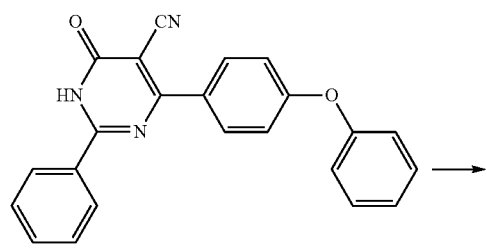

A mixture of crude 6-oxo-4-(4-phenoxyphenyl)-2-phenyl-1,6-dihydropyrimidine-5-carbonitrile and phosphorus oxychloride (4 mL) was stirred at 90° C. for 1 h, concentrated, dissolved in dichloromethane (10 mL) and water (20 mL) and carefully neutralized with solid potassium carbonate until CO$_2$ bubbling stopped. The mixture was extracted with dichloromethane (3×5 mL). The combined extracts were dried (MgSO$_4$) and concentrated to give crude 4-chloro-6-(4-phenoxyphenyl)-2-phenylpyrimidine-5-carbonitrile as tan solid. The crude material was taken to next reaction without purification. MS (ES+) m/z: 384 (M+H); LC retention time: 5.190 min (analytical HPLC Method 13 except with 2 min hold at 100% B).

Step 4:

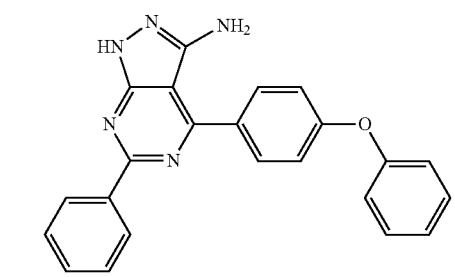 [SMILES: Nc1n[nH]c2nc(-c3ccccc3)nc(-c3ccc(Oc4ccccc4)cc3)c12]

A mixture of crude 4-chloro-6-(4-phenoxyphenyl)-2-phenylpyrimidine-5-carbonitrile and 35% aqueous hydrazine (0.50 mL, 5.58 mmol) in n-butanol (3 mL) in a reaction tube was sealed and placed in a 130° C. oil bath. After 14 h at 130° C., the mixture was diluted with water (3 mL), stirred at 0° C. for 15 min and filtered to collect the precipitate. The solid was washed with water (3 mL), 20% ethyl acetate in hexanes (2×3 mL) and pumped under vacuum to give Example 115 as tan solid. $^1$H NMR (400 MHz, DMSO-d$_6$) δ ppm 12.77 (1H, br. s), 8.50 (2H, dd, J=7.03, 2.76 Hz), 8.08 (2H, δ, J=8.78 Hz), 7.39-7.64 (5H, m), 7.10-7.30 (5H, m), 5.19 (2H, s); MS (ES+) m/z: 380 (M+H); LC retention time: 4.613 min (analytical HPLC Method B).

Examples 116 to 127

Examples 116 to 123 were prepared following conditions similar to the synthesis of Example 115 using (E)-ethyl 2-cyano-3-(4-phenoxyphenyl)acrylate (from Step 1 of Example 115) and appropriate amidines. Examples 124 to 127 were prepared following conditions similar to the synthesis of Example 115 using (E)-ethyl 2-cyano-3-(4-phenoxyphenyl)acrylate (from Step 1 of Example 115) and appropriate guanidines. The final products were obtained by filtration of precipitate in the product mixture if feasible, or by reverse phase HPLC on Sunfire S10 30×250 mm column.

| Example No. | Structure | Spectral data* |
|---|---|---|
| Example 116: 6-(4-Ethoxyphenyl)-4-(4-phenoxyphenyl)-1H-pyrazolo[3,4-δ]pyrimidin-3-amine | 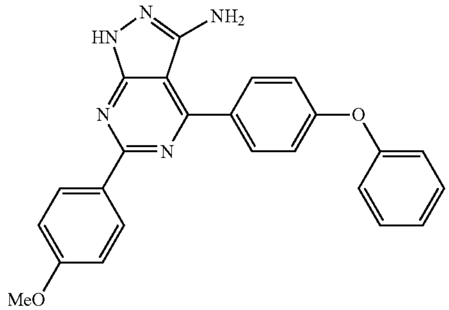 [SMILES: COc1ccc(-c2nc(-c3ccc(Oc4ccccc4)cc3)c3c(N)n[nH]c3n2)cc1] | $^1$H NMR (400 MHz, DMSO-d$_6$) δ ppm 12.67 (1 H, br. s), 8.45 (2 H, δ, J = 8.53 Hz), 8.05 (2 H, δ, J = 8.53 Hz), 7.47 (2 H, t, J = 7.65 Hz), 7.11-7.32 (5 H, m), 7.08 (2 H, δ, J = 8.78 Hz), 5.14 (2 H, br. s), 3.84 (3 H, s); MS (ES+) m/z: 410 (M + H); LC retention time: 4.573 min. |
| Example 117: 6-(3-Methoxyphenyl)-4-(4-phenoxyphenyl)-1H-pyrazolo[3,4-δ]pyrimidin-3-amine | 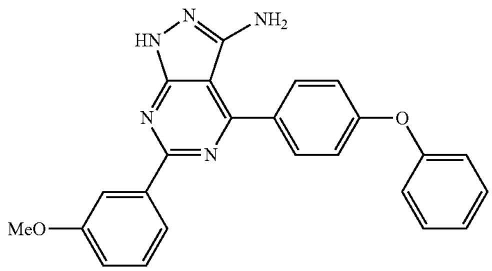 [SMILES: COc1cccc(-c2nc(-c3ccc(Oc4ccccc4)cc3)c3c(N)n[nH]c3n2)c1] | $^1$H NMR (500 MHz, methanol-d$_4$) δ ppm 7.95-8.06 (4 H, m), 738-7.48 (3 H, m), 7.19-7.28 (3 H, m), 7.08-7.18 (3 H, m), 3.89 (3 H, s); MS (ES+) m/z: 410 (M + H); LC retention time: 4.588 min. |
| Example 118: 6-tert-Butyl-4-(4-phenoxyphenyl)-1H-pyrazolo[3,4-δ]pyrimidin-3-amine | 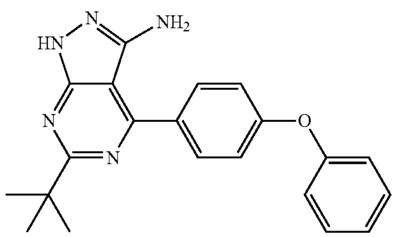 [SMILES: CC(C)(C)c1nc(-c2ccc(Oc3ccccc3)cc2)c2c(N)n[nH]c2n1] | $^1$H NMR (400 MHz, methanol-d$_4$) δ ppm 7.88 (2 H, δ, J = 8.78 Hz), 7.47 (2 H, s), 7.24 (3 H, δ, J = 8.78 Hz), 7.12-7.19 (2 H, m), 1.53 (9 H, s); MS (ES+) m/z: 360 (M + H); LC retention time: 4.551 min. |
| Example 119: 6-(1-Benzothiophen-3-yl)-4-(4-phenoxyphenyl)-1H-pyrazolo[3,4-δ]pyrimidin-3-amine | 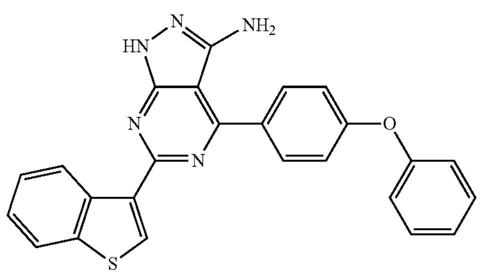 [SMILES: Nc1n[nH]c2nc(-c3csc4ccccc34)nc(-c3ccc(Oc4ccccc4)cc3)c12] | $^1$H NMR (400 MHz, DMSO-d$_6$) δ ppm 12.80 (1 H, br. s), 9.22 (1 H, δ, J = 8.03 Hz), 8.83 (1 H, s), 8.03-8.18 (3 H, m), 7.40-7.62 (4 H, m), 7.13-7.30 (5 H, m), 5.19 (2 H, s); MS (ES+) m/z: 436 (M + H); LC retention time: 4.900 min. |
| Example 120: 4-(4-Phenoxyphenyl)-6-(2-thienyl)-1H-pyrazolo[3,4-δ]pyrimidin-3-amine | 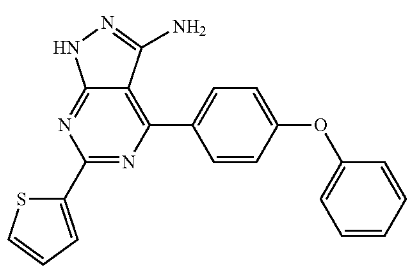 [SMILES: Nc1n[nH]c2nc(-c3cccs3)nc(-c3ccc(Oc4ccccc4)cc3)c12] | $^1$H NMR (400 MHz, DMSO-d$_6$) δ ppm 12.72 (1 H, br. s), 7.94-8.13 (3 H, m), 7.75 (1 H, dd, J = 5.02, 1.25 Hz), 7.38-7.55 (2 H, m), 7.10-7.31 (6 H, m), 5.16 (2 H, s); MS (ES+) m/z: 386 (M + H); LC retention time: 4.526 min. |
| Example 121: 4-(4-Phenoxyphenyl)-6-(3-pyridinyl)-1H-pyrazolo[3,4-δ]pyrimidin-3-amine | 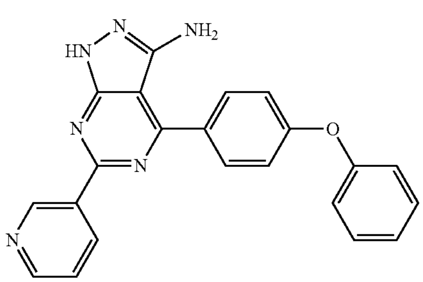 [SMILES: Nc1n[nH]c2nc(-c3cccnc3)nc(-c3ccc(Oc4ccccc4)cc3)c12] | $^1$H NMR (400 MHz, DMSO-d$_6$) δ ppm 12.88 (1 H, s), 9.61 (1 H, δ, J = 2.01 Hz), 8.66-8.86 (2 H, m), 8.09 (2 H, δ, J = 8.53 Hz), 7.57 (1 H, dd, J = 8.03, 4.77 Hz), 7.47 (2 H, t, J = 7.91 Hz), 7.05-7.32 (5 H, m), 5.23 (2 H, s); MS (ES+) m/z: 381 (M + H); LC retention time: 3.628 min. |

-continued

| Example No. | Structure | Spectral data* |
|---|---|---|
| Example 122: 6-(2-Methyl-1,3-thiazol-4-yl)-4-(4-phenoxyphenyl)-1H-pyrazolo[3,4-δ]pyrimidin-3-amine | 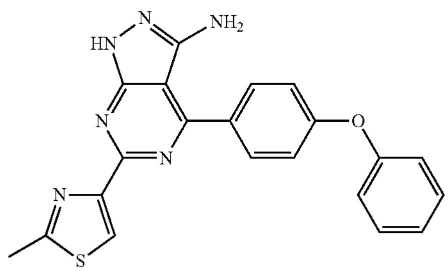 [SMILES: Cc1nc(-c2nc(-c3ccc(Oc4ccccc4)cc3)c3c(N)n[nH]c3n2)cs1] | $^1$H NMR (400 MHz, DMSO-d$_6$) δ ppm 8.47 (1 H, s), 7.98-8.05 (2 H, m), 7.40-7.50 (2 H, m), 7.04-7.28 (5 H, m), 2.83 (3 H, s); MS (ES+) m/z: 401 (M + H); LC retention time: 4.278 min. |
| Example 123: 6-Adamantan-1-yl-4-(4-phenoxyphenyl)-1H-pyrazolo[3,4-d]pyrimidin-3-amine | 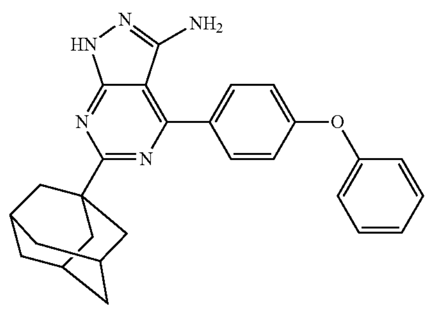 [SMILES: Nc1n[nH]c2nc(C34CC5CC(CC(C5)C3)C4)nc(-c3ccc(Oc4ccccc4)cc3)c12] | $^1$H NMR (400 MHz, DMSO-d$_6$) δ ppm 12.54 (1 H, s), 7.97 (2 H, δ, J = 8.53 Hz), 7.45 (2 H, t, J = 8.03 Hz), 7.06-7.33 (5 H, m), 5.05 (2 H, s), 2.08 (9 H, s), 1.75 (6 H, br. s); MS (ES+) m/z: 438 (M + H); LC retention time: 5.195 min. |
| Example 124: 4-(4-Phenoxyphenyl)-N$^6$-phenyl-1H-pyrazolo[3,4-δ]pyrimidine-3,6-diamine | 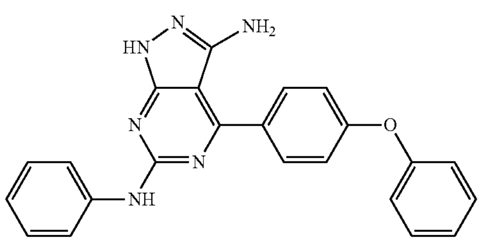 [SMILES: Nc1n[nH]c2nc(Nc3ccccc3)nc(-c3ccc(Oc4ccccc4)cc3)c12] | $^1$H NMR (400 MHz, DMSO-d$_6$) δ ppm 12.10 (1 H, br. s), 9.64 (1 H, s), 7.78-8.04 (4 H, m), 7.46 (2 H, t, J = 8.03 Hz), 7.04-7.36 (7 H, m), 6.81-7.00 (1 H, m), 4.88 (2 H, s); MS (ES+) m/z: 395 (M + H); LC retention time: 4.193 min. |
| Example 125: N$^6$-Methyl-4-(4-phenoxyphenyl)-1H-pyrazolo[3,4-δ]pyrimidine-3,6-diamine | 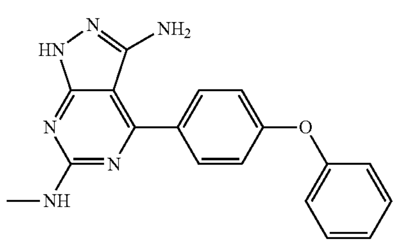 [SMILES: CNc1nc(-c2ccc(Oc3ccccc3)cc2)c2c(N)n[nH]c2n1] | $^1$H NMR (400 MHz, methanol-d$_4$) δ ppm 7.87 (2 H, δ, J = 8.53 Hz), 7.46 (2 H, t, J = 8.03 Hz), 7.25 (1 H, t, J = 7.40 Hz), 7.19 (2 H, δ, J = 8.78 Hz), 7.14 (2 H, δ, J = 7.78 Hz), 3.08 (3 H, s); MS (ES+) m/z: 333 (M + H); LC retention time: 3.115 min. |
| Example 126: 6-(4-Morpholinyl)-4-(4-phenoxyphenyl)-1H-pyrazolo[3,4-d]pyrimidin-3-amine | 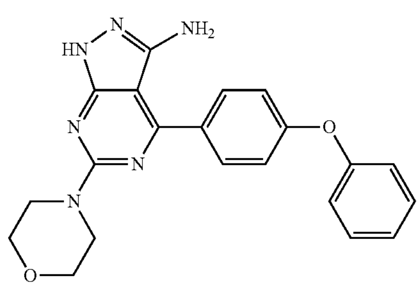 [SMILES: Nc1n[nH]c2nc(N3CCOCC3)nc(-c3ccc(Oc4ccccc4)cc3)c12] | $^1$H NMR (400 MHz, methanol-d$_4$) δ ppm 7.83 (2 H, δ, J = 8.53 Hz), 7.42 (2 H, t, J = 7.91 Hz), 7.21 (1 H, t, J = 7.40 Hz), 7.12 (4 H, t, J = 8.91 Hz), 3.95 (4 H, t, J = 4.77 Hz), 3.75 (4 H, t, J = 4.77 Hz); MS (ES+) m/z: 389 (M + H); LC retention time: 4.026 min. |

| Example No. | Structure | Spectral data* |
|---|---|---|
| Example 127:<br>6-(3,5-Dichlorobenzyl)-4-(4-phenoxyphenyl)-1H-pyrazolo[3,4-d]pyrimidin-3-amine | 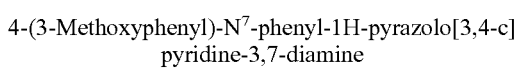 | ¹H NMR (400 MHz, methanol-d₄) δ 7.83-8.00 (2 H, m), 7.40-7.53 (4 H, m), 7.20-7.37 (4 H, m), 7.16 (2 H, d, J = 7.53 Hz), 4.76 (2 H, s); MS (ES+) m/z: 462 (M + H); LC retention time: 4.571 min. |

*Analytical HPLC Method B

Example 128

4-(3-Methoxyphenyl)-N⁷-phenyl-1H-pyrazolo[3,4-c]pyridine-3,7-diamine

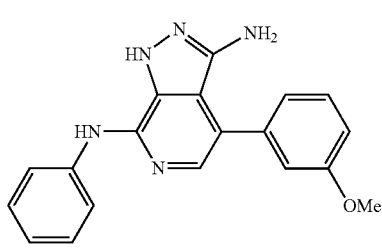 [SMILES: COc1cccc(-c2cnc(Nc3ccccc3)c3[nH]nc(N)c23)c1]

Step 1:

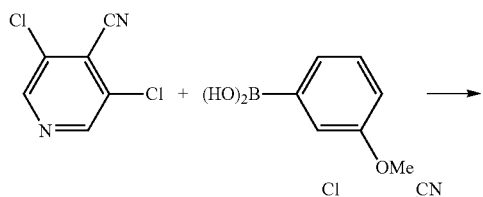

A mixture of 3,5-dichloroisonicotinonitrile (2 g, 11.56 mmol), 3-methoxyphenylboronic acid (1.932 g, 12.72 mmol), potassium phosphate (4.91 g, 23.12 mmol) and palladium tetrakis(triphenylphosphine) (0.668 g, 0.578 mmol) was pumped and backfilled with nitrogen 3 times. N,N-dimethylacetamide (30 mL) was added. The mixture was again pumped and backfilled with nitrogen 3 times. After heating to 110° C. for 15 h, the mixture was diluted with ethyl acetate (300 mL), washed with water (50 mL), brine (50 mL) and dried (MgSO₄) and concentrated. Silica gel chromatography, loading with dichloromethane-hexanes (1:1) and eluting with 5-30% ethyl acetate in hexanes, gave 3-chloro-5-(3-methoxyphenyl)isonicotinonitrile as white solid (1.20 g, 43% yield). MS (ES+) m/z: 245 (M+H); LC retention time: 3.13 min (analytical HPLC Method A).

Step 2:

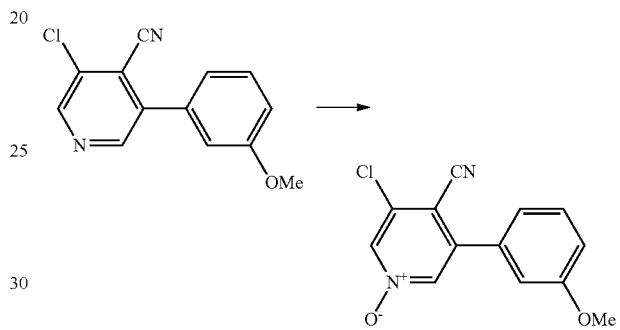

A solution of 3-chloro-5-(3-methoxyphenyl)isonicotinonitrile (1.60 g, 6.54 mmol) and 77% 3-chloroperbenzoic acid (5.86 g, 26.2 mmol) in dichloromethane (60 mL) was stirred at room temperature for 16 h. The mixture was diluted with dichloromethane (100 mL), washed with 1 M sodium sulfite (25 mL), 1 N NaOH (2×25 mL), brined (25 mL), dried (MgSO₄) and concentrated to give crude 3-chloro-4-cyano-5-(3-methoxyphenyl)pyridine 1-oxide as white solid (1.60 g). The crude material was used in the next step without purification. MS (ES+) m/z: 261 (M+H); LC retention time: 2.933 min (analytical HPLC Method A).

Step 3:

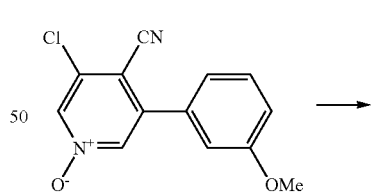

A mixture of crude 3-chloro-4-cyano-5-(3-methoxyphenyl)pyridine 1-oxide from Step 2 and phosphorus oxychloride (15 mL) in a sealed tube was placed in a 100° C. bath. After 1 h at 100° C., HPLC analysis indicated that a 2:1 mixture of products was formed. The mixture was concentrated. Recrystallization from ethyl acetate/hexanes (10 mL/10 mL) gave 2,3-dichloro-5-(3-methoxyphenyl)isonicotinonitrile as white solid (200 mg). The mother liquor was purified by reverse phase HPLC, using Sunfire S10 30×250 mm column and eluting with 80-100% solvent B (90% methanol-10% water-0.1% TFA) in solvent A (10% methanol-90% water-0.1% TFA), to give additional 2,3-dichloro-5-(3-methoxyphenyl)isonicotinonitrile (400 mg). $^1$H NMR (500 MHz, methanol-d$_4$) δ ppm 8.54 (1H, s), 7.45 (1H, t, J=7.97 Hz), 6.77-7.28 (3H, m), 3.86 (3H, s); MS (ES+) m/z: 279 (M+H); LC retention time: 3.768 min (analytical HPLC Method A). No attempt was made to isolate the undesired 2,5-dichloro-3-(3-methoxyphenyl)isonicotinonitrile isomer.

Step 4:

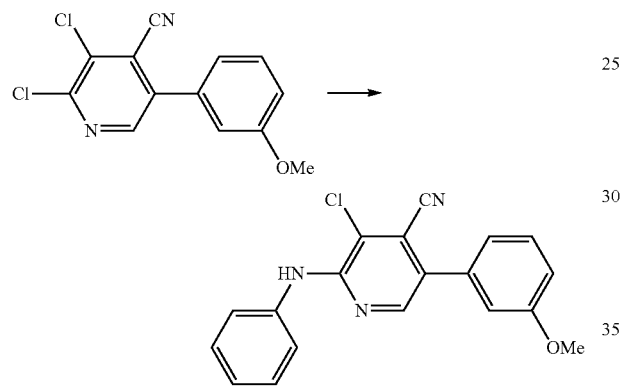

A mixture of 2,3-dichloro-5-(3-methoxyphenyl)isonicotinonitrile (60 mg, 0.215 mmol) and aniline (1.000 g, 10.74 mmol) was heated to 140° C. for 15 h. After cooling to room temperature, the mixture was diluted with ethyl acetate (60 mL), washed with 1N HCl (10 mL), water (10 mL), brine (10 mL), dried (MgSO$_4$) and concentrated. Purification by reverse phase HPLC (Sunfire S10 30×250 mm column), eluting with 60-100% solvent B (10% methanol-90% water-0.1% TFA) in solvent A (90% methanol-10% water-0.1% TFA), gave 3-chloro-5-(3-methoxyphenyl)-2-(phenylamino)isonicotinonitrile TFA salt as yellow solid (45 mg, 47% yield). $^1$H NMR (400 MHz, CDCl$_3$) δ ppm 8.31 (1H, s), 7.49-7.74 (2H, m), 7.33-7.51 (3H, m), 6.93-7.22 (4H, m), 3.87 (3H, s); MS (ES+) m/z: 336 (M+H); LC retention time: 4.046 min (analytical HPLC Method A).

Step 5:

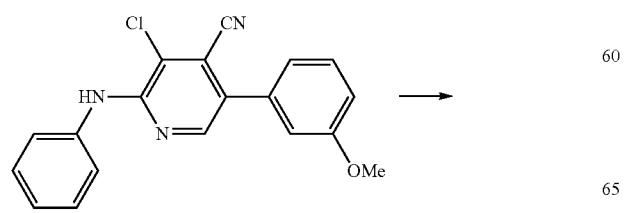

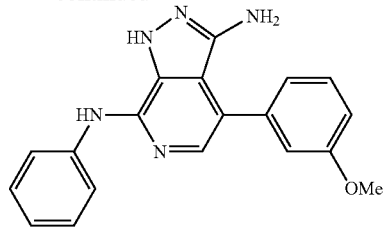

A mixture of 3-chloro-5-(3-methoxyphenyl)-2-(phenylamino)isonicotinonitrile TFA salt (20 mg, 0.044 mmol) and 35% aqueous hydrazine (0.080 mL, 0.889 mmol) in 2-propanol (1 mL) in a microwave tube was sealed and heated to 160° C. under microwave for 2 h. HPLC and LCMS analysis indicated that the reaction was ~40% complete. Purification by reverse phase HPLC (Sunfire S10 30×250 mm column), eluting with 60-100% solvent B (10% methanol-90% water-0.1% TFA) in solvent A (90% methanol-10% water-0.1% TFA), gave Example 128 as yellow solid (7 mg, 28% yield). $^1$H NMR (500 MHz, methanol-d$_4$) δ ppm 7.55-7.69 (2H, m), 7.49-7.56 (3H, m), 7.40-7.47 (1H, m), 7.00-7.12 (3H, m), 6.81 (1H, s), 3.85 (3H, s); MS (ES+) m/z: 332 (M+H); LC retention time: 2.567 min (analytical HPLC Method A).

Example 129

4-(3-Methoxyphenyl)-N$^7$-(2-methylphenyl)-1H-pyrazolo[3,4-c]pyridine-3,7-diamine

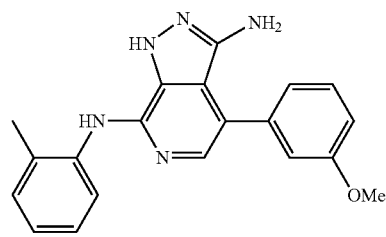 [SMILES: COc1cccc(-c2cnc(Nc3ccccc3C)c3[nH]nc(N)c23)c1]

Step 1:

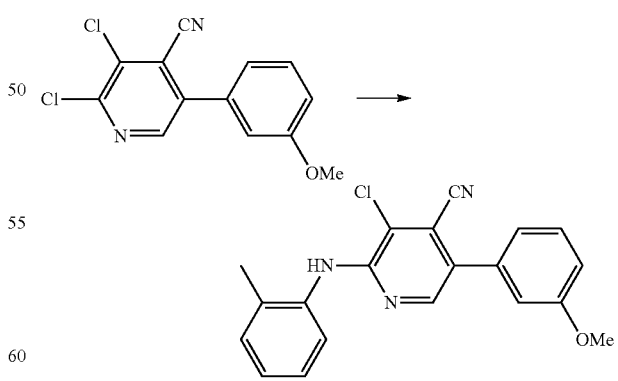

A mixture of 2,3-dichloro-5-(3-methoxyphenyl)isonicotinonitrile (50 mg, 0.179 mmol, from Step 3 of Example 128) and o-toluidine (384 mg, 3.58 mmol) in DMSO (1 mL) was heated to 180° C. under microwave for 1 h. LCMS and HPLC analysis indicated that the reaction was ~25% complete. The mixture was cooled to room temperature, diluted with ethyl acetate (60 mL), washed with 1 N HCl (5 mL), water (5 mL), brine (5 mL), dried (MgSO₄) and concentrated. Purification by reverse phase HPLC (Sunfire S10 30×250 mm column), eluting with 80-100% solvent B (10% methanol-90% water-0.1% TFA) in solvent A (90% methanol-10% water-0.1% TFA), gave 3-chloro-5-(3-methoxyphenyl)-2-(o-tolylamino) isonicotinonitrile as yellow solid, assumed as TFA salt (7 mg, 8% yield). ¹H NMR (400 MHz, methanol-d₄) δ ppm 8.13 (1H, s), 7.38-7.54 (2H, m), 7.28-735 (1H, m), 7.15-7.27 (2H, m), 7.07-7.14 (2H, m), 6.97-7.05 (1H, m), 3.87 (3H, s), 2.27 (3H, s); MS (ES+) m/z: 350 (M+H); LC retention time: 3.848 min (analytical HPLC Method A).

Step 2:

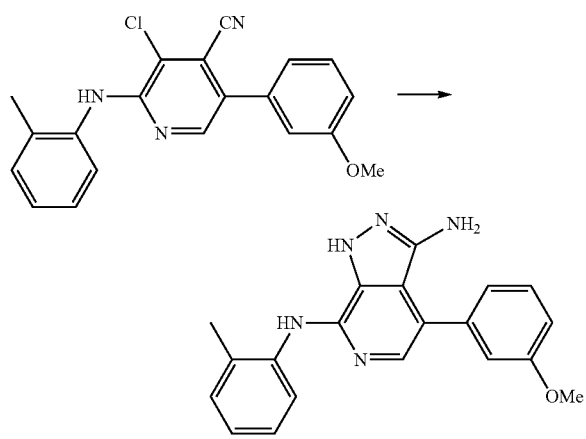

A mixture of 3-chloro-5-(3-methoxyphenyl)-2-(o-tolylamino)isonicotinonitrile TFA salt (7 mg, 0.015 mmol) and 35% aqueous hydrazine (0.027 mL, 0.302 mmol) in N,N-dimethylacetamide (0.5 mL) in a microwave tube was sealed and heated to 180° C. under microwave for 1 h. Purification by reverse phase HPLC (Sunfire S10 30×250 mm column), eluting with 60-100% solvent B (10% methanol-90% water-0.1% TFA) in solvent A (90% methanol-10% water-0.1% TFA), gave Example 129 as yellow solid (4 mg, 46% yield). ¹H NMR (400 MHz, methanol-d₄) δ ppm 7.26-7.75 (5H, m), 6.82-7.19 (3H, m), 6.73 (1H, s), 3.82 (3H, s), 2.31 (3H, s); MS (ES+) m/z: 346 (M+H); LC retention time: 2.34 min (analytical HPLC Method A).

Example 130

N⁷-(2-Chlorophenyl)-4-(3-methoxyphenyl)-1H-pyrazolo[3,4-c]pyridine-3,7-diamine

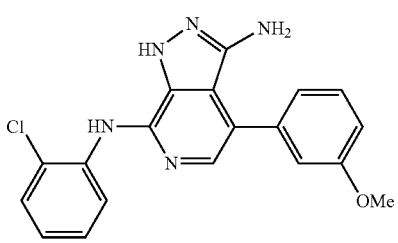 [SMILES: COc1cccc(-c2cnc(Nc3ccccc3Cl)c3[nH]nc(N)c23)c1]

Step 1:

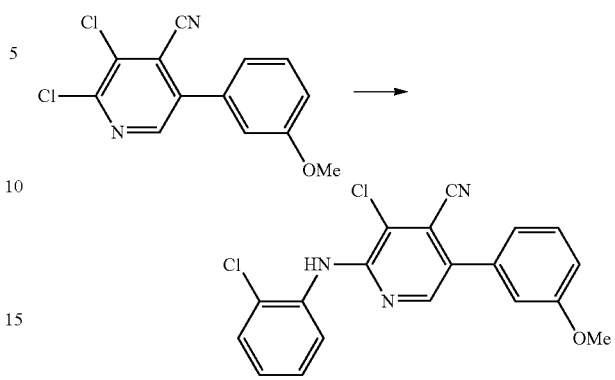

A 1 M solution of lithium bis(trimethylsilyl)amide (0.573 mL, 0.573 mmol) was added to a solution of 2,3-dichloro-5-(3-methoxyphenyl)isonicotinonitrile (40 mg, 0.143 mmol, from Step 3 of Example 128) and 2-chloroaniline (36.6 mg, 0.287 mmol) in THF (2 mL) at room temperature. After 1 h at room temperature, LCMS and HPLC analysis indicated that a 1:2 mixture of two products were formed. The reaction mixture was quenched with saturated sodium bicarbonate (5 mL) and diluted with ethyl acetate (60 mL), washed with water (5 mL), brine (5 mL), dried (MgSO₄) and concentrated. Silica gel chromatography, loading with dichloromethane-hexanes (1:1) and eluting with 5-20% ethyl acetate in hexanes, gave 3-chloro-2-(2-chlorophenylamino)-5-(3-methoxyphenyl) isonicotinonitrile as yellow solid (11 mg, 21% yield). ¹H NMR (400 MHz, CDCl₃) δ ppm 8.51-8.63 (1H, m), 8.35 (1H, s), 7.87 (1H, s), 7.38-7.51 (2H, m), 7.29-7.37 (1H, m), 6.97-7.16 (4H, m), 3.88 (3H, s); MS (ES+) m/z: 370 (M+H); LC retention time: 4.28 min (analytical HPLC Method A). The minor product was found to be 2-chloro-3-(2-chlorophenylamino)-5-(3-methoxyphenyl)isonicotinonitrile.

Step 2:

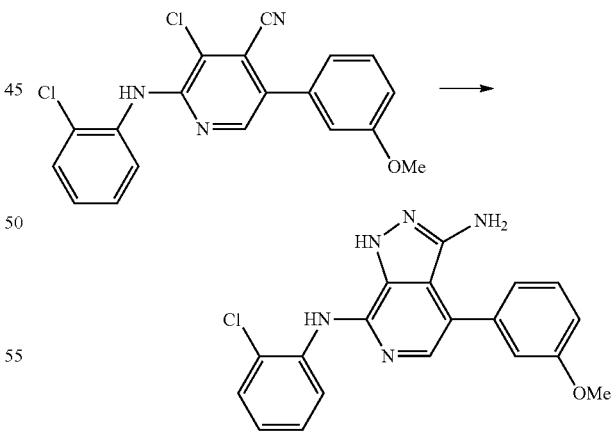

A mixture of 3-chloro-2-(2-chlorophenylamino)-5-(3-methoxyphenyl)isonicotinonitrile (10 mg, 0.027 mmol) and 35% aqueous hydrazine (0.048 mL, 0.540 mmol) in N,N-dimethylacetamide (0.5 mL) in a microwave tube was sealed and heated to 180° C. under microwave for 1.5 h. Purification by reverse phase HPLC (Sunfire S10 30×250 mm column), eluting with 50-100% solvent B (10% methanol-90% water-0.1% TFA) in solvent A (90% methanol-10% water-0.1%

TEA), gave the Example 130 as yellow solid (8 mg, 50% yield). $^1$H NMR (400 MHz, methanol-d$_4$) δ ppm 7.73-7.83 (1H, m), 7.64-7.70 (1H, m), 7.53-7.64 (2H, m), 7.41-7.54 (1H, m), 7.03-7.21 (3H, m), 6.84 (1H, s), 3.88 (3H, s); MS (ES+) m/z: 366 (M+H); LC retention time: 2.40 min (analytical HPLC Method A).

Example 131

3-(3-Amino-7-((2-methylphenyl)amino)-1H-pyrazolo[3,4-c]pyridin-4-yl)phenol

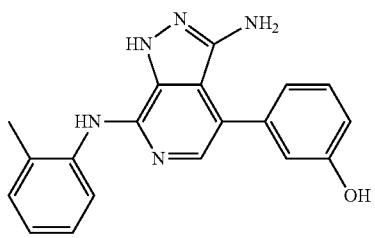 [SMILES: Cc1ccccc1Nc1ncc(-c2cccc(O)c2)c2c(N)n[nH]c12]

A 1.0 M dichloromethane solution of boron tribromide (0.044 mL, 0.044 mmol) was added to a solution of Example 129 (5 mg, 8.72 μmol) in dichloromethane (1 mL) at room temperature. After 1 h at room temperature, the mixture was quenched with saturated sodium bicarbonate (2 mL), diluted with ethyl acetate (60 mL), washed with water (5 mL), brine (5 mL), dried (MgSO$_4$) and concentrated. Purification by reverse phase HPLC (Sunfire S10 30×250 mm column), eluting with 40-100% solvent B (10% methanol-90% water-0.1% TFA) in solvent A (90% methanol-10% water-0.1% TFA), gave Example 131 as yellow solid (3 mg, 62% yield). $^1$H NMR (400 MHz, methanol-d$_4$) δ ppm 7.41-7.59 (4H, m), 7.26-7.43 (1H, m), 6.86-7.01 (3H, m), 6.74 (1H, s), 2.35 (3H, s); MS (ES+) m/z: 332 (M+H); LC retention time: 2.06 min (analytical HPLC Method A).

Example 132

4-(4-Methoxyphenyl)-N$^7$-(2-methylphenyl)-1H-pyrazolo[3,4-c]pyridine-3,7-diamine

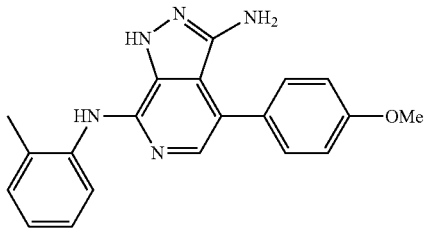 [SMILES: COc1ccc(-c2cnc(Nc3ccccc3C)c3[nH]nc(N)c23)cc1]

Step 1:

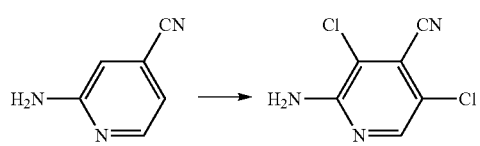 [SMILES: N#Cc1ccnc(N)c1 ; N#Cc1c(Cl)cnc(N)c1Cl]

A solution of 2-aminoisonicotinonitrile (10.98 g, 92 mmol) and N-chlorosuccinimide (25.8 g, 194 mmol) in N,N-dimethylformamide (100 mL) was heated to 55° C. for 3 h. The mixture was concentrated. The residue was stirred vigorously in water (800 mL) and ethyl acetate (600 mL) for 2 h and filtered to remove the insoluble material. The two phases of the filtrate were separated. The aqueous phase was extracted with 1:1 mixture of ethyl acetate-hexanes (2×200 mL). The combined organic extracts were washed with water (2×100 mL), brine (100 mL), dried (MgSO$_4$) and concentrated to give crude 2-amino-3,5-dichloroisonicotinonitrileas (19 g) with approximately 85% purity. The crude material was used in the next reaction without purification.

Step 2:

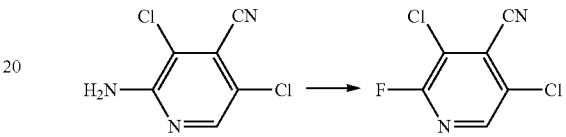

Sodium nitrite (3.17 g, 46.0 mmol) was added in small portions to a suspension of crude 2-amino-3,5-dichloroisonicotinonitrile (4.32 g) in tetrafluoroboric acid (60 mL, 806 mmol) at −10° C. over 1 h. The resultant mixture was stirred at −10° C. for 1 h, carefully quenched with ice and solid Na$_2$CO$_3$ and extracted with ethyl acetate (3×150 mL). The combined organic layers were washed with brine (100 mL), dried (MgSO$_4$), concentrated to ~20 mL in volume, triturated with dichloromethane (30 mL) and filtered. The filtrate was concentrated and purified by silica gel chromatography, loading with dichloromethane-hexanes (1:1) and eluting with 5 to 30% ethyl acetate in hexanes, to give 3,5-dichloro-2-fluoroisonicotinonitrile (1.60 g, 36% yield for 2 steps). $^1$H NMR (400 MHz, CDCl$_3$) δ ppm 8.29 (1H, s); LC retention time: 2.758 min (analytical HPLC Method A).

Step 3:

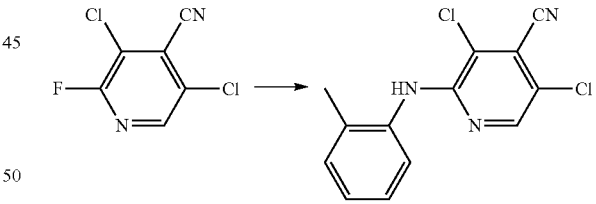

A mixture of 3,5-dichloro-2-fluoroisonicotinonitrile (1.00 g, 5.24 mmol) and o-toluidine (10 g, 93 mmol) was heated to 150° C. for 20 h. After cooling to room temperature, the mixture was diluted with ethyl acetate (200 mL), washed with 1 N HCl (2×20 mL), saturated sodium bicarbonate (20 mL), and brine (20 mL), dried (MgSO$_4$) and concentrated. Silica gel chromatography, loading with dichloromethane-hexanes (1:1) and eluting with 0 to 20% ethyl acetate in hexanes, gave 3,5-dichloro-2-(o-tolylamino)isonicotinonitrile as yellow solid (1.10 g, 76% yield). $^1$H NMR (400 MHz, CDCl$_3$) δ ppm 8.18 (1H, s), 7.71 (1H, δ, J=7.78 Hz), 7.23-7.40 (2H, m), 7.01-7.13 (1H, m), 6.70-6.94 (1H, m), 2.29 (3H, s); MS (ES+) m/z: 278 (M+H); LC retention time: 3.68 min (analytical HPLC Method A).

Step 4:

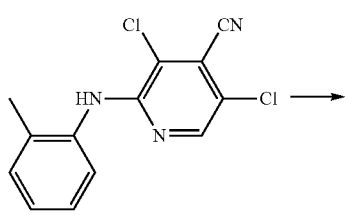

A mixture of 3,5-dichloro-2-(o-tolylamino)isonicotinonitrile (700 mg, 2.52 mmol) and acetic anhydride (10 mL, 106 mmol) was heated in a sealed tube to 180° C. for 20 h. The mixture was cooled to room temperature and concentrated. Silica gel chromatography, loading with dichloromethane-hexanes (1:1) and eluting with 5 to 30% ethyl acetate in hexanes, gave N-(3,5-dichloro-4-cyanopyridin-2-yl)-N-o-tolylacetamide (700 mg, 87% yield). $^1$H NMR (400 MHz, CDCl$_3$) δ ppm 8.44 (1H, s), 7.28-7.43 (4H, m), 2.41 (3H, br. s), 2.04 (3H, s); MS (ES+) m/z: 320 (M+H); LC retention time: 3.38 min (analytical HPLC Method A).

Step 5:

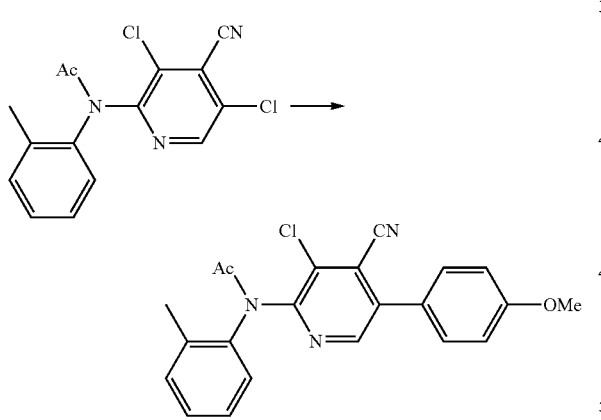

A mixture of N-(3,5-dichloro-4-cyanopyridin-2-yl)-N-o-tolylacetamide (25 mg, 0.078 mmol) and 4-methoxyphenylboronic acid (13.05 mg, 0.086 mmol), potassium phosphate tribasic (49.7 mg, 0.234 mmol) and palladium tetrakis(triphenylphosphine) (9.02 mg, 7.81 µmol) in toluene (2 mL) was pumped and backfilled with nitrogen 3 times, sealed and heated to 100° C. for 3 h. HPLC and LCMS analysis indicated a 2 to 1 mixture of two product isomers. The reaction mixture was diluted with ethyl acetate (60 mL), washed with saturated sodium bicarbonate (5 mL), water (5 mL), brine (5 mL), dried (MgSO$_4$) and concentrated. Purification by reverse phase HPLC (Sunfire S10 30×250 mm column), eluting with 60-100% solvent B (10% methanol-90% water-0.1% TFA) in solvent A (90% methanol-10% water-0.1% TFA), gave N-(3-chloro-4-cyano-5-(3-methoxyphenyl)pyridin-2-yl)-N-o-tolylacetamide as TFA salt (8 mg, 26% yield). $^1$H NMR (400 MHz, CDCl$_3$) δ ppm 8.47 (1H, s), 7.49 (2H, δ, J=8.78 Hz), 7.13-7.45 (4H, m), 6.93-7.09 (2H, m), 3.87 (3H, s), 2.53 (3H, s), 2.09 (3H, s); MS (ES+) m/z: 392 (M+H); LC retention time: 3.68 min (analytical HPLC Method A).

Step 6:

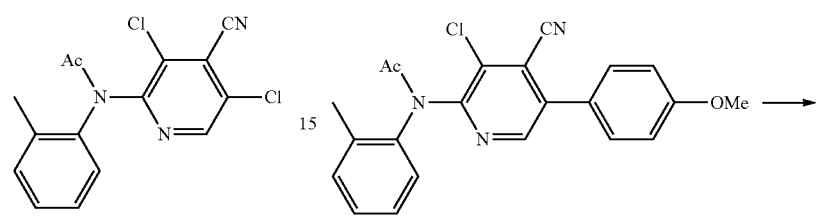

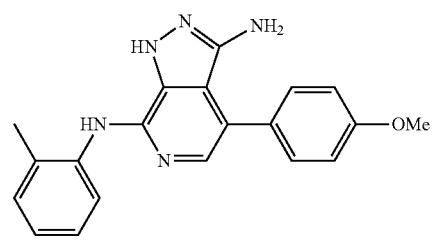

A mixture of N-(3-chloro-4-cyano-5-(4-methoxyphenyl)pyridin-2-yl)-N-o-tolylacetamide TFA salt (8 mg, 0.016 mmol) and hydrazine (9.93 µL, 0.316 mmol) in N,N-dimethylacetamide (0.5 mL) was heated to 180° C. under microwave for 2 h. HPLC and LCMS showed that the reaction was roughly 20% complete. The mixture was then heated to 190° C. under microwave for 1 h. Purification by reverse phase HPLC (Sunfire S10 30×250 mm column), eluting with 40-100% solvent B (10% methanol-90% water-0.1% TFA) in solvent A (90% methanol-10% water-0.1% TFA), to give Example 132 as yellow solid (2 mg, 22%). $^1$H NMR (400 MHz, methanol-d$_4$) δ ppm 7.39-7.62 (5H, m), 7.05-7.19 (3H, m), 6.72 (1H, s), 3.89 (3H, s), 2.37 (3H, s); MS (ES+) m/z: 346 (M+H); LC retention time: 2.57 min (analytical HPLC Method A).

Example 133

N-((3R)-1-(3-Amino-7-((2-methylphenyl)amino)-1H-pyrazolo[3,4-c]pyridin-4-yl)-3-piperidinyl)benzamide

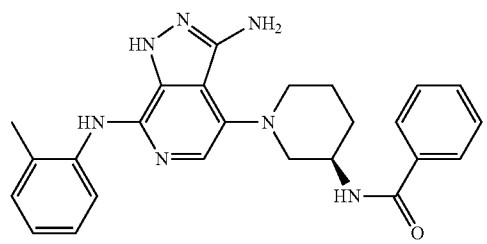 [SMILES: Cc1ccccc1Nc1ncc(N2CCC[C@@H](NC(=O)c3ccccc3)C2)c2c(N)n[nH]c12]

Step 1:

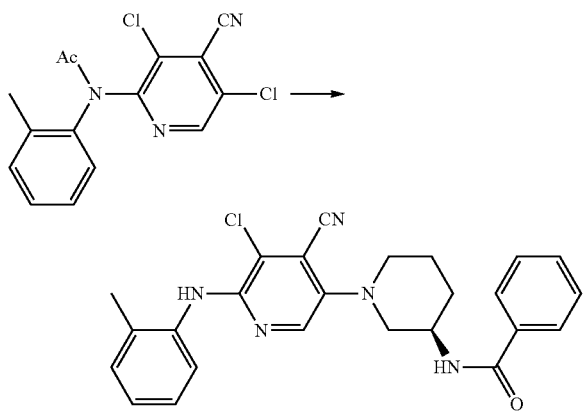

A mixture of N-(3,5-dichloro-4-cyanopyridin-2-yl)-N-o-tolylacetamide (20 mg, 0.062 mmol, from Step 4 of Example 132), (R)—N-(piperidin-3-yl)benzamide (15.31 mg, 0.075 mmol) and triethylamine (0.026 mL, 0.187 mmol) in N,N-dimethylacetamide (1 mL) was heated to 100° C. After 16 h at 100° C., the mixture was diluted with ethyl acetate (80 mL), washed with saturated sodium bicarbonate (5 mL), brine (5 mL), dried (MgSO$_4$) and concentrated. Purification by reverse phase HPLC (Sunfire S10 30×250 mm column), eluting with 60-100% solvent B (10% methanol-90% water-0.1% TFA) in solvent A (90% methanol-10% water-0.1% TFA), gave (R)—N-(1-(5-chloro-4-cyano-6-(N-o-tolylacetamido)pyridin-3-yl)piperidin-3-yl)benzamide TFA salt as white solid (12 mg, 39% yield). $^1$H NMR (400 MHz, CDCl$_3$) δ ppm 8.18 (1H, s), 7.83 (2H, δ, J=7.28 Hz), 7.50-7.60 (1H, m), 7.40-7.51 (2H, m), 7.17-7.40 (4H, m), 4.32-4.54 (1H, m), 3.30-3.47 (3H, m), 3.09-3.25 (1H, m), 2.23-2.63 (2H, m), 1.70-2.03 (2H, m); MS (ES+) m/z: 488 (M+H); LC retention time: 3.57 min (analytical HPLC Method A).

Step 2:

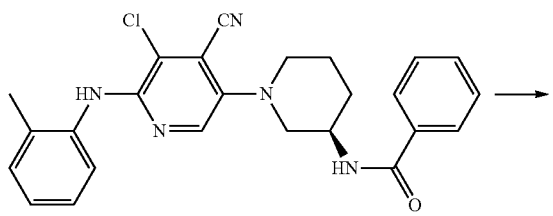

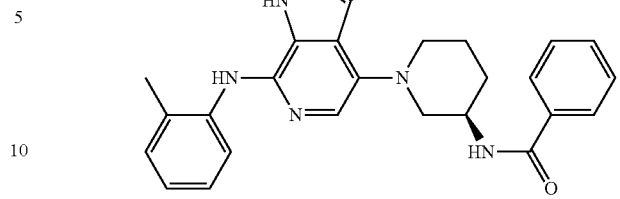

A mixture of (R)—N-(1-(5-chloro-4-cyano-6-(N-o-tolylacetamido)pyridin-3-yl)piperidin-3-yl)benzamide (14 mg, 0.029 mmol) and hydrazine (0.018 mL, 0.574 mmol) in N,N-dimethylacetamide (0.5 mL) was heated to 180° C. under microwave for 2 h. Purification by reverse phase HPLC (Sunfire S10 30×250 mm column), eluting with 40-100% solvent B (10% methanol-90% water-0.1% TFA) in solvent A (90% methanol-10% water-0.1% TFA), gave Example 133 as yellow solid (3 mg, 13% yield). $^1$H NMR (400 MHz, methanol-d$_4$) δ ppm 7.73-7.91 (2H, m), 7.26-7.62 (7H, m), 6.39 (1H, s), 4.13-4.42 (1H, m), 3.41-3.59 (2H, m), 3.20-3.40 (2H, m), 2.49-2.65 (1H, m), 2.22-2.42 (1H, m), 2.02-2.16 (1H, m), 1.89-2.00 (1H, m); MS (ES+) m/z: 442 (M+H); LC retention time: 2.63 min (analytical HPLC Method A).

Examples 134 to 151

Examples 134 to 147 were prepared from N-(3,5-dichloro-4-cyanopyridin-2-yl)-N-o-tolylacetamide (from Step 4 of Example 132) and the corresponding boronic acids following conditions similar to Steps 5 and 6 of Example 132. Example 148 was prepared from N-(3,5-dichloro-4-cyanopyridin-2-yl)-N-o-tolylacetamide (from Step 4 of Example 132) and 6-phenyl-2-(pyridin-2-yl)-1,3,6,2-dioxazaborocane following conditions similar to Steps 5 and 6 of Example 132. Example 149 was prepared from N-(3,5-dichloro-4-cyanopyridin-2-yl)-N-o-tolylacetamide following conditions described in Steps 1 and 2 of Example 133. Examples 150 and 151 were prepared from 3,5-dichloro-2-fluoroisonicotinonitrile (from Step 2 of Example 132) following conditions described in Steps 3 to 6 of Example 132 using appropriately substituted anilines.

| Example No. | Structure | Spectral data* |
|---|---|---|
| Example 134:<br>4-(2-Methoxy-4-pyridinyl)-N$^7$-(2-methylphenyl)-1H-pyrazolo[3,4-c]pyridine-3,7-diamine | | $^1$H NMR (400 MHz,Methanol-d$_4$) δ ppm 8.02-8.45 (1 H, m), 7.35-7.73 (4 H, m), 7.14-7.27 (1 H, m), 6.95-7.11 (1 H, m), 6.89 (1 H, s), 4.02 (3 H, s), 2.37 (3 H, s); MS (ES+) m/z: 347 (M + H); LC retention time: 2.12 min. |

-continued

| Example No. | Structure | Spectral data* |
|---|---|---|
| Example 135: 4-(3-Ethoxyphenyl)-N[7]-(2-methylphenyl)-1H-pyrazolo[3,4-c]pyridine-3,7-diamine | 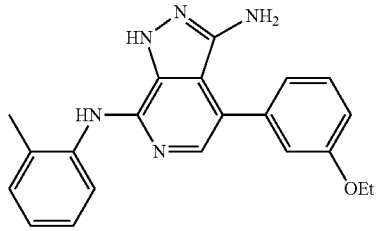 [SMILES: CCOc1cccc(-c2cnc(Nc3ccccc3C)c3[nH]nc(N)c23)c1] | $^1$H NMR (400 MHz, methanol-d$_4$) δ ppm 7.33-7.63 (5 H, m), 6.95-7.16 (3 H, m), 6.76 (1 H, s), 4.10 (2 H, q), 2.35 (3 H, s), 1.41 (3 H, t, J = 7.03 Hz); MS (ES+) m/z: 360 (M + H); LC retention time: 2.76 min. |
| Example 136: N[7]-(2-Methylphenyl)-4-phenyl-1H-pyrazolo[3,4-c]pyridine-3,7-diamine | 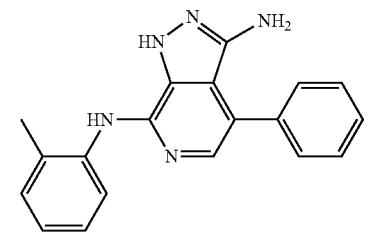 [SMILES: Cc1ccccc1Nc1ncc(-c2ccccc2)c2c(N)n[nH]c12] | $^1$H NMR (400 MHz, methanol-d$_4$) δ ppm δ ppm 7.22-8.03 (9 H, m), 6.77 (1 H, s), 2.37 (3 H, s); MS (ES+) m/z: 316 (M + H); LC retention time: 2.36 min. |
| Example 137: 4-(3-Isopropoxyphenyl)-N[7]-(2-methylphenyl)-1H-pyrazolo[3,4-c]pyridine-3,7-diamine | 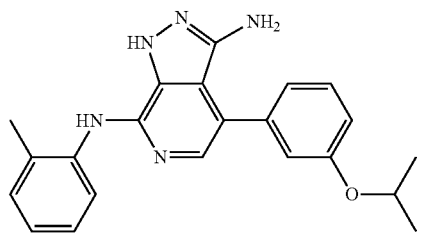 [SMILES: Cc1ccccc1Nc1ncc(-c2cccc(OC(C)C)c2)c2c(N)n[nH]c12] | $^1$H NMR (400 MHz, methanol-d$_4$) δ ppm δ ppm 7.31-7.68 (5 H, m), 6.91-7.22 (3 H, m), 6.78 (1 H, m), 4.54-4.85 (1 H, m), 2.37 (3 H, s), 1.36 (6 H, δ, J = 6.02 Hz); MS (ES+) m/z: 374 (M + H); LC retention time: 2.69 min. |
| Example 138: 4-(1H-Indazol-5-yl)-N[7]-(2-methylphenyl)-1H-pyrazolo[3,4-c]pyridine-3,7-diamine | 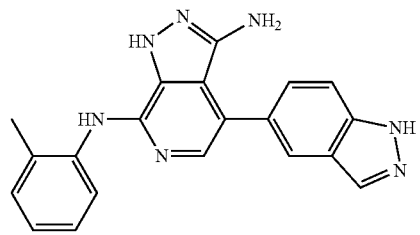 [SMILES: Cc1ccccc1Nc1ncc(-c2ccc3[nH]ncc3c2)c2c(N)n[nH]c12] | $^1$H NMR (400 MHz, methanol-d$_4$) δ ppm δ ppm 8.18 (1 H, s), 7.87-8.03 (1 H, m), 7.68-7.83 (1 H, m), 7.33-7.63 (5 H, m), 6.82 (1 H, m), 2.39 (3 H, s); MS (ES+) m/z: 356 (M + H); LC retention time: 2.23 min. |
| Example 139: 3-(3-Amino-7-((2-methylphenyl)amino)-1H-pyrazolo[3,4-c]pyridin-4-yl)-N-methylbenzamide | 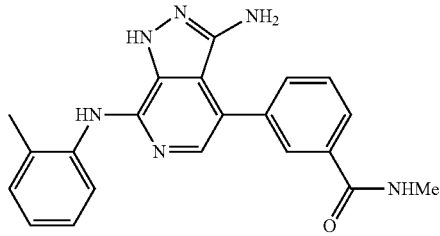 [SMILES: CNC(=O)c1cccc(-c2cnc(Nc3ccccc3C)c3[nH]nc(N)c23)c1] | $^1$H NMR (400 MHz, methanol-d$_4$) δ ppm δ ppm 7.84-8.12 (2 H, m), 7.61-7.80 (2 H, m), 7.35-7.60 (4 H, m), 6.83 (1 H, s), 2.97 (3 H, s), 2.40 (3 H, s); MS (ES+) m/z: 373 (M + H); LC retention time: 2.10 min. |
| Example 140: 4-(2-Methoxyphenyl)-N[7]-(2-methylphenyl)-1H-pyrazolo[3,4-c]pyridine-3,7-diamine | 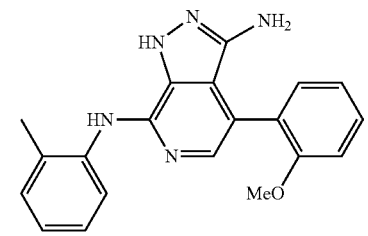 [SMILES: COc1ccccc1-c1cnc(Nc2ccccc2C)c2[nH]nc(N)c12] | $^1$H NMR (400 MHz, methanol-d$_4$) δ ppm δ ppm 7.36-7.63 (5 H, m), 7.25-7.37 (1 H, m), 7.14-7.24 (1 H, m), 6.97-7.13 (1 H, m), 6.69 (1 H, s), 3.82 (3 H, s), 2.36 (3 H, s); MS (ES+) m/z: 346 (M + H); LC retention time: 2.42 min. |

-continued

| Example No. | Structure | Spectral data* |
|---|---|---|
| Example 141: 4-(3-Amino-7-((2-methylphenyl)amino)-1H-pyrazolo[3,4-c]pyridin-4-yl)-N-methylbenzamide | 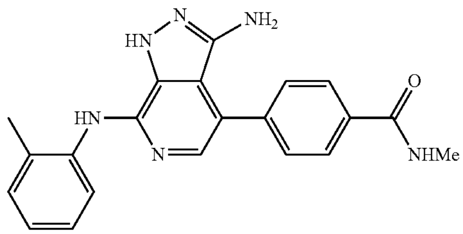 [SMILES: CNC(=O)c1ccc(-c2cnc(Nc3ccccc3C)c3[nH]nc(N)c23)cc1] | $^1$H NMR (500 MHz, methanol-d$_4$) δ ppm 7.97 (2 H, δ, J = 8.25 Hz), 7.63 (2 H, δ, J = 8.25 Hz), 7.37-7.55 (4 H, m), 6.81 (1 H, s), 2.95 (3 H, s), 2.35 (3 H, s); MS (ES+) m/z: 373 (M + H); LC retention time: 2.03 min. |
| Example 142: N$^7$-(2-Methylphenyl)-4-(4-phenoxyphenyl)-1H-pyrazolo[3,4-c]pyridine-3,7-diamine | 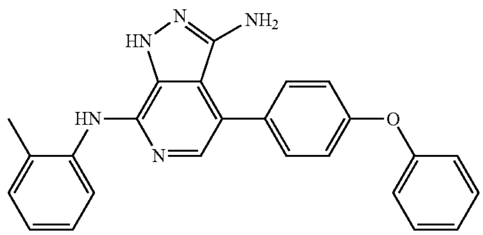 [SMILES: Cc1ccccc1Nc1ncc(-c2ccc(Oc3ccccc3)cc2)c2c(N)n[nH]c12] | $^1$H NMR (400 MHz, methanol-d$_4$) δ ppm 7.31-7.73 (8 H, m), 7.00-7.28 (5 H, m), 6.77 (1 H, s), 2.37 (3 H, s); MS (ES+) m/z: 408 (M + H); LC retention time: 3.18 min. |
| Example 143: N$^7$-(2-Methylphenyl)-4-(2-naphthyl)-1H-pyrazolo[3,4-c]pyridine-3,7-diamine | 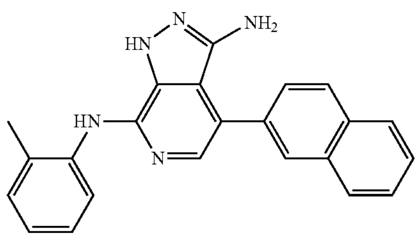 [SMILES: Cc1ccccc1Nc1ncc(-c2ccc3ccccc3c2)c2c(N)n[nH]c12] | $^1$H NMR (500 MHz, methanol-d$_4$) δ ppm 8.00-8.10 (2 H, m), 7.88-8.01 (2 H, m), 7.58-7.72 (2 H, m), 7.54-7.60 (2 H, m), 7.49-7.57 (1 H, m), 7.42-7.50 (2 H, m), 6.87 (1 H, s), 2.36 (3 H, s); MS (ES+) m/z: 366 (M + H); LC retention time: 2.96 min. |
| Example 144: 4-(3-Aminophenyl)-N$^7$-(2-methylphenyl)-1H-pyrazolo[3,4-c]pyridine-3,7-diamine | 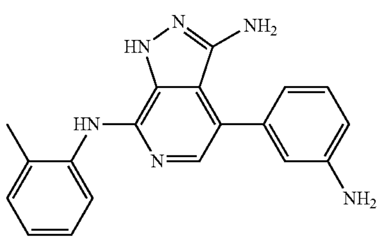 [SMILES: Cc1ccccc1Nc1ncc(-c2cccc(N)c2)c2c(N)n[nH]c12] | $^1$H NMR (400 MHz, methanol-d$_4$) δ ppm 7.33-7.75 (6 H, m), 6.95-7.19 (2 H, m), 6.76 (1 H, s), 2.35 (3 H, s); MS (ES+) m/z: 331 (M + H); LC retention time: 1.38 min. |
| Example 145: N$^7$-(2-Methylphenyl)-4-(3-(trifluoromethoxy)phenyl)-1H-pyrazolo[3,4-c]pyridine-3,7-diamine | 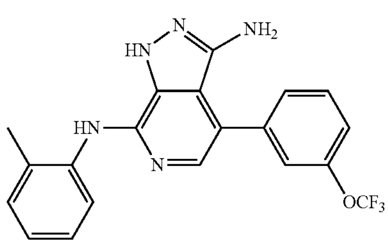 [SMILES: Cc1ccccc1Nc1ncc(-c2cccc(OC(F)(F)F)c2)c2c(N)n[nH]c12] | $^1$H NMR (400 MHz, methanol-d$_4$) δ ppm 7.59-7.72 (1 H, m), 7.30-7.58 (7 H, m), 6.80 (1 H, s), 2.35 (3 H, s); MS (ES+) m/z: 400 (M + H); LC retention time: 2.93 min. |
| Example 146: (3-(3-Amino-7-((2-methylphenyl)amino)-1H-pyrazolo[3,4-c]pyridin-4-yl)phenyl)methanol | 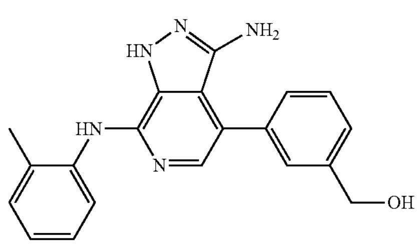 [SMILES: Cc1ccccc1Nc1ncc(-c2cccc(CO)c2)c2c(N)n[nH]c12] | $^1$H NMR (400 MHz, methanol-d$_4$) δ ppm 7.17-7.95 (8 H, m), 6.78 (1 H, s), 4.72 (2 H, s), 2.38 (3 H, s); MS (ES+) m/z: 346 (M + H); LC retention time: 2.00 min. |

-continued

| Example No. | Structure | Spectral data* |
|---|---|---|
| Example 147: N⁴-(2-Methylphenyl)-7-(6-quinolinyl)-1H-pyrazolo[4,3-c]pyridine-3,4-diamine | | ¹H NMR (400 MHz, methanol-d₄) δ ppm 9.07 (1 H, br. s.), 8.80-8.97 (1 H, m), 8.29 (1 H, d, J = 1.76 Hz), 8.16-8.26 (1 H, m), 8.04-8.18 (1 H, m), 7.81-7.98 (1 H, m), 7.31-7.50 (4 H, m), 6.86 (1 H, s), 2.27 (3 H, s); MS (ES+) m/z: 367 (M + H); LC retention time: 1.47 min. |
| Example 148: N⁷-(2-Methylphenyl)-4-(2-pyridinyl)-1H-pyrazolo[3,4-c]pyridine-3,7-diamine | | ¹H NMR (500 MHz, methanol-d₄) δ ppm 8.72 (1 H, d, J = 4.12 Hz), 7.88-8.02 (1 H, m), 7.84 (1 H, d, J = 7.97 Hz), 7.40-7.61 (5 H, m), 7.25 (1 H, s), 2.34 (3 H, s); MS (ES+) m/z: 317 (M + H); LC retention time: 1.78 min. |
| Example 149: N⁷-(2-Methylphenyl)-4-(1-piperidinyl)-1H-pyrazolo[3,4-c]pyridine-3,7-diamine | | ¹H NMR (400 MHz, methanol-d₄) δ ppm 7.06-7.71 (4 H, m), 6.34 (1 H, s), 2.73-3.02 (4 H, m), 2.26 (3 H, s), 1.45-1.93 (6 H, m); MS (ES+) m/z: 323 (M + H); LC retention time: 2.34 min. |
| Example 150: N⁷-(2,4-Dimethylphenyl)-4-(3-methoxyphenyl)-1H-pyrazolo[3,4-c]pyridine-3,7-diamine | | ¹H NMR (400 MHz, methanol-d₄) δ ppm 7.41-7.54 (1 H, m), 7.20-7.41 (3 H, m), 6.96-7.16 (3 H, m), 6.77 (1 H, s), 3.88 (3 H, s), 2.44 (3 H, s), 2.32 (3 H, s); MS (ES+) m/z: 360 (M + H); LC retention time: 2.32 min. |
| Example 151: N⁷-Mesityl-4-(3-methoxyphenyl)-1H-pyrazolo[3,4-c]pyridine-3,7-diamine | | ¹H NMR (400 MHz, methanol-d₄) δ ppm 7.38-7.63 (1 H, m), 7.15-7.29 (2 H, m), 6.98-7.12 (3 H, m), 6.75 (1 H, s), 3.88 (3 H, s), 2.40 (3 H, s), 2.28 (6 H, s); MS (ES+) m/z: 374 (M + H); LC retention time: 2.69 min. |

*Analytical HPLC Method A

Example 152

6-(4-Methoxyphenyl)-4-(4-phenoxyphenyl)-1H-pyrazolo[4,3-c]pyridin-3-amine

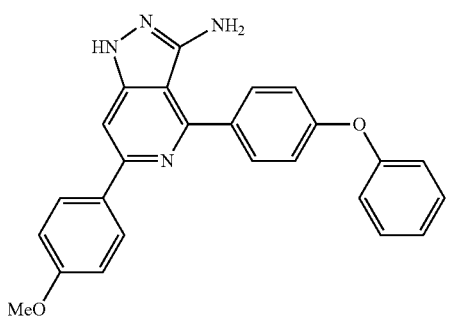

Step 1:

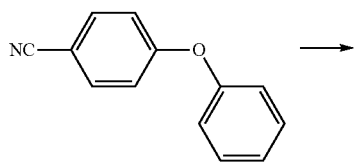

A 2.5 M THF solution of n-BuLi (20.49 mL, 51.2 mmol) was added to a solution of diisopropylamine (7.30 mL, 51.2 mmol) in THF (165 mL) at −78° C. The mixture was stirred at 0° C. for 20 min and cooled to −78° C. Acetonitrile (2.68 mL, 51.2 mmol) was added to give a white cloudy solution. After 30 min at −78° C., a solution of 4-phenoxybenzonitrile (10 g, 51.2 mmol) in THF (35 mL) was added. After 1.5 h at −78° C., saturated ammonium chloride (50 mL), water (25 mL) and 1 N HCl (25 mL) were added. The THF was evaporated in vacuo. The residue was extracted with ethyl acetate (200 mL). The ethyl acetate phase was washed with 0.1 N HCl (50 mL) and brine (10 mL), dried (MgSO$_4$) and concentrated. The resulting mixture was triturated with a mixture of dichloromethane and hexanes. Filtration of the suspension gave 3-amino-3-(4-phenoxyphenyl)acrylonitrile as white solid (7.364 g). The filtrate was concentrated to a small volume and filtered to give additional product (2.501 g). The total amount of the product was 9.865 g (82% yield). $^1$H NMR (400 MHz, CDCl$_3$) δ ppm 7.44-7.50 (2H, m), 7.39 (2H, t, J=7.91 Hz), 7.18 (1H, t, J=7.40 Hz), 6.98-7.08 (4H, m), 4.88 (2H, br. s), 4.22 (1H, s); MS (ES+) m/z: 237 (M+H).

Step 2:

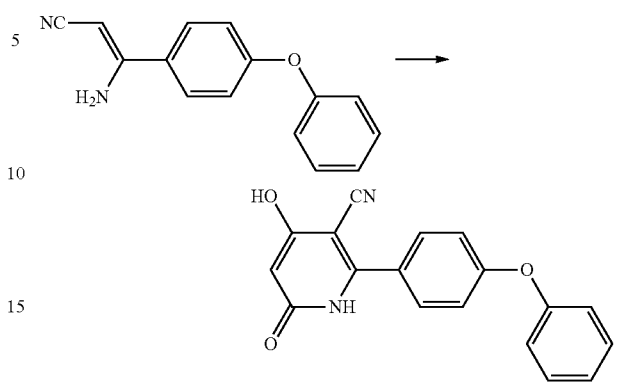

3-Amino-3-(4-phenoxyphenyl)acrylonitrile (720 mg, 3.05 mmol) in diethyl malonate (9 mL, 59.3 mmol) was microwaved at 250° C. for 10 min. After cooling to room temperature, the solid was collected by filtration, washed with 20% isopropanol in heptanes and dried under vacuum to give 4-hydroxy-6-oxo-2-(4-phenoxyphenyl)-1,6-dihydropyridine-3-carbonitrile (688 mg, 74% yield). $^1$H NMR (400 MHz, DMSO-d$_6$) δ ppm 11.95 (1H, br. s), 7.67 (2H, δ, J=8.53 Hz), 7.48 (2H, t, J=7.91 Hz), 7.25 (1H, t, J=7.40 Hz), 7.11 (4H, dd, J=19.70, 8.16 Hz), 5.52-5.74 (1H, m); MS (ES+) m/z: 305 (M+H); LC retention time: 3.546 min (analytical HPLC Method A).

Step 3:

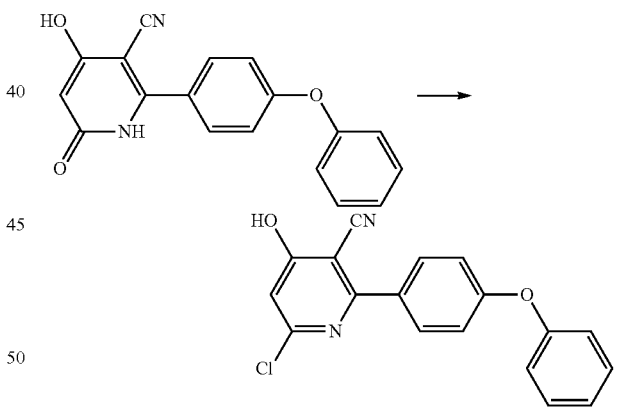

A mixture of 4-hydroxy-6-oxo-2-(4-phenoxyphenyl)-1,6-dihydropyridine-3-carbonitrile (687.6 mg, 2.260 mmol) and phosphoryl trichloride (6 mL, 65.5 mmol) was heated to 90° C. for 2 h. After cooling to room temperature, the mixture was concentrated and treated with 0.5 N NaOH (10 mL). The mixture was sonicated to give a fine suspension. The solid was collected by filtration to give 4,6-dichloro-2-(4-phenoxyphenyl)nicotinonitrile (731.6 mg, 95% yield). $^1$H NMR (500 MHz, CDCl$_3$) δ ppm 7.93-7.98 (2H, m), 7.46 (1H, s), 7.37-7.44 (2H, m), 7.20 (1H, t, J=7.56 Hz), 7.07-7.13 (4H, m); MS (ES+) m/z: 341 (M+H); LC retention time: 4.665 min (analytical HPLC Method A).

Step 4:

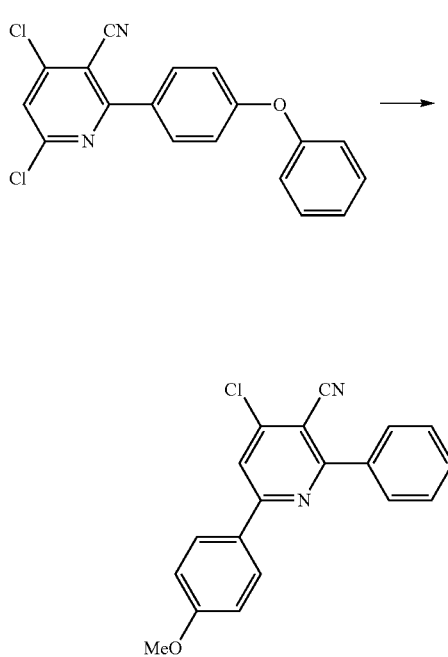

A mixture of 4,6-dichloro-2-(4-phenoxyphenyl)nicotinonitrile (56.8 mg, 0.166 mmol), 4-methoxyphenylboronic acid (26.2 mg, 0.172 mmol), potassium phosphate (0.052 mL, 0.629 mmol) and palladium tetrakis(triphenylphosphine) (9.5 mg, 8.22 µmol) in N,N-dimethylformamide (2 mL) was pumped under vacuum and backfilled with nitrogen twice, and heated to 90° C. under nitrogen. After 19 h at 90° C., the mixture was concentrated. The residue was purified by preparative TLC (30% ethyl acetate in hexanes, Whatman PARTISEL® PLK5F, Silica Gel 150 A with Fluorescent Indicator, size: 20×20 cm, layer thickness: 1000 µM) to give 4-chloro-6-(4-methoxyphenyl)-2-(4-phenoxyphenyl)nicotinonitrile as white solid (17.5 mg, 26% yield). $^1$H NMR (400 MHz, CDCl$_3$) δ ppm 8.10 (2H, δ, J=9.04 Hz), 7.99-8.05 (2H, m), 7.76 (1H, s), 7.40 (2H, t, J=7.91 Hz), 7.19 (1H, t, J=7.40 Hz), 7.12 (4H, dd, J=8.16, 4.14 Hz), 7.02 (2H, δ, J=9.03 Hz), 3.89 (3H, s); MS (ES+) m/z: 413 (M+H); LC retention time: 4.488 min (analytical HPLC Method A).

Step 5:

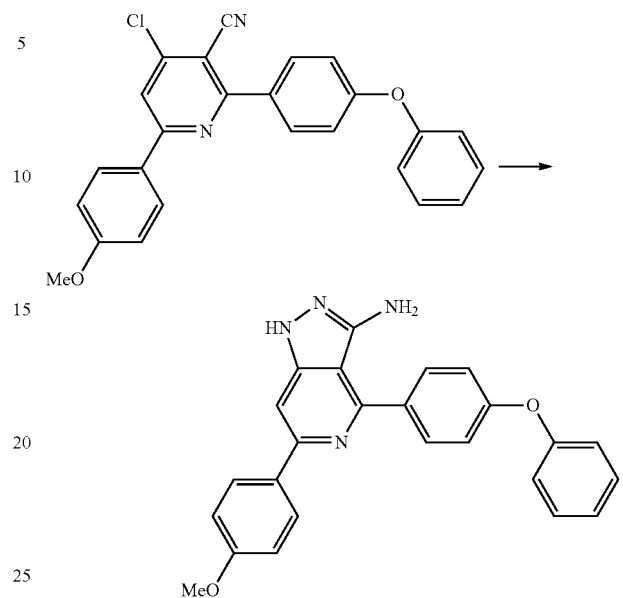

A mixture of 4-chloro-6-(4-methoxyphenyl)-2-(4-phenoxyphenyl)nicotinonitrile (17.5 mg, 0.028 mmol), 35% aqueous hydrazine (100 µL, 1.114 mmol) and 1-propanol (1 mL) was heated to 140° C. in a sealed tube for 3 h. Purification by reverse phase HPLC (Sunfire S10 30×250 mm column), eluting with 50-70% solvent B (10% methanol-90% water-0.1% TFA) in solvent A (90% methanol-10% water-0.1% TEA), gave Example 152 as yellow solid (18.5 mg, 95% yield). $^1$H NMR (400 MHz, CDCl$_3$) δ ppm 7.54-7.63 (4H, m), 7.40-7.48 (3H, m), 7.21-7.25 (1H, m), 7.11 (4H, δ, J=8.78 Hz), 6.88 (2H, δ, J=9.03 Hz), 3.80 (3H, s); MS (ES+) m/z: 409 (M+H); LC retention time: 3.325 min (analytical HPLC Method A).

Examples 153 to 159

Examples 153 to 158 were prepared from 4,6-dichloro-2-(4-phenoxyphenyl)nicotinonitrile (from Step 3 of Example 152) following conditions described in Steps 4 and 5 of Example 152. Example 159 was prepared from Example 152 using conditions described for the synthesis of Example 131.

| Example No. | Structure | Spectral data* |
|---|---|---|
| Example 153: 6-(3-Methoxyphenyl)-4-(4-phenoxyphenyl)-1H-pyrazolo[4,3-c]pyridin-3-amine | 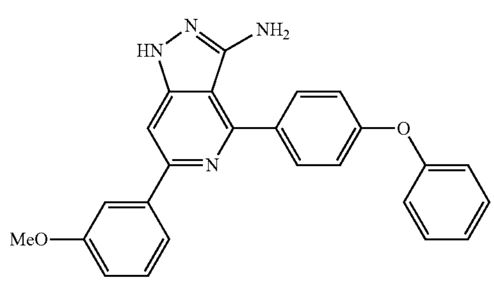 [SMILES: COc1cccc(-c2cc3[nH]nc(N)c3c(-c3ccc(Oc4ccccc4)cc3)n2)c1] | $^1$H NMR (400 MHz, CDCl$_3$) δ ppm 7.51-7.59 (3 H, m), 7.40-7.47 (2 H, m), 7.21-7.30 (2 H, m), 7.16-7.20 (2 H, m), 7.07-7.13 (4 H, m), 6.96 (1 H, dd, J = 8.28, 1.51 Hz), 3.75 (3 H, s); MS (ES+) m/z: 409 (M + H); LC retention time: 3.363 min. |

-continued

| Example No. | Structure | Spectral data* |
|---|---|---|
| Example 154:<br>4,6-Bis(4-phenoxyphenyl)-1H-pyrazolo[4,3-c]pyridin-3-amine | | $^1$H NMR (400 MHz, CDCl$_3$) δ ppm 7.59 (4 H, δ, J = 7.78 Hz), 7.31-7.47 (5 H, m), 7.14-7.25 (2 H, m), 7.05-7.12 (4 H, m), 6.98 (4 H, dd, J = 15.81, 8.28 Hz); MS (ES+) m/z: 471 (M + H); LC retention time: 3.843 min. |
| Example 155:<br>6-(2-Naphthyl)-4-(4-phenoxyphenyl)-1H-pyrazolo[4,3-c]pyridin-3-amine | | $^1$H NMR (400 MHz, CDCl$_3$) δ ppm 8.62 (1 H, d, J = 1.10 Hz), 8.23 (1 H, dd, J = 8.66, 1.79 Hz), 7.92-7.98 (2 H, m), 7.86-7.91 (3 H, m), 7.70 (1 H, s), 7.49-7.52 (2 H, m), 7.38-7.43 (2 H, m), 7.15-7.22 (3 H, m), 7.12 (2 H, d, J = 7.42 Hz), 4.19 (2 H, br. s.); MS (ES+) m/z: 429.4 (M + H); LC retention time: 3.731 min. |
| Example 156:<br>4-(3-Amino-4-(4-phenoxyphenyl)-1H-pyrazolo[4,3-c]pyridin-6-yl)-N,N-dimethylbenzamide | | $^1$H NMR (400 MHz, CDCl$_3$) δ ppm 7.75 (2 H, δ, J = 8.28 Hz), 7.70 (2 H, δ, J = 8.78 Hz), 7.54 (2 H, δ, J = 8.28 Hz), 7.38-7.45 (2 H, m), 7.19-7.25 (1 H, m), 7.14 (2 H, δ, J = 8.78 Hz), 7.10 (2 H, δ, J = 7.78 Hz), 6.60 (1 H, s), 3.21 (3 H, s), 3.00 (3 H, s); MS (ES+) m/z: 450 (M + H); LC retention time: 3.118 min. |
| Example 157:<br>6-(1-Benzyl-1H-pyrazol-4-yl)-4-(4-phenoxyphenyl)-1H-pyrazolo[4,3-c]pyridin-3-amine | | $^1$H NMR (400 MHz, methanol-d$_4$) δ ppm 8.46 (1 H, s), 8.18 (1 H, s), 7.81-7.85 (2 H, m), 7.73 (1 H, s), 7.44-7.50 (2 H, m), 7.32-7.38 (5 H, m), 7.24-7.28 (3 H, m), 7.15-7.19 (2 H, m), 5.44 (2 H, s); MS (ES+) m/z: 459 (M + H); LC retention time: 3.443 min. |
| Example 158:<br>4-(4-Phenoxyphenyl)-6-(4-pyridinyl)-1H-pyrazolo[4,3-c]pyridin-3-amine | | $^1$H NMR (400 MHz, methanol-d$_4$) δ ppm 8.87 (2 H, δ, J = 6.78 Hz), 8.68 (2 H, δ, J = 6.78 Hz), 8.15 (1 H, s), 7.87-7.91 (2 H, m), 7.41-7.48 (2 H, m), 7.19-7.25 (3 H, m), 7.12-7.17 (2 H, m); MS (ES+) m/z: 380 (M + H); LC retention time: 3.188 min. |

| Example No. | Structure | Spectral data* |
|---|---|---|
| Example 159:<br>4-(3-Amino-4-(4-phenoxyphenyl)-1H-pyrazolo[4,3-c]pyridin-6-yl)phenol | | $^1$H NMR (400 MHz, methanol-$d_4$) δ ppm 7.85-7.89 (2 H, m), 7.68-7.73 (2 H, m), 7.65 (1 H, s), 7.44-7.49 (2 H, m), 7.24-7.29 (3 H, m), 7.14-7.19 (2 H, m), 6.97-7.03 (2 H, m); MS (ES+) m/z: 395 (M + H); LC retention time: 3.136 min. |

*Analytical HPLC Method A

Example 160

4-(4-Phenoxyphenyl)-7-phenyl-1H-1-pyrazolo[4,3-c]pyridin-3-amine

Step 1:

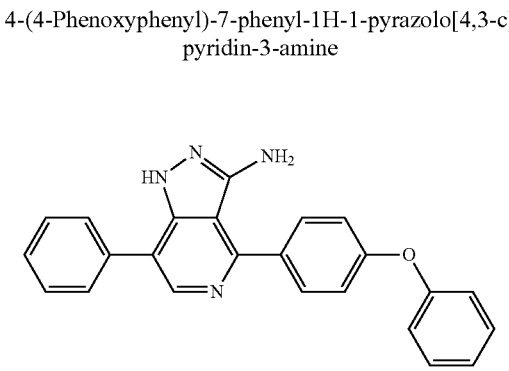

A mixture of (Z)-3-amino-3-(4-phenoxyphenyl)acrylonitrile (717 mg, 3.03 mmol) in diethyl 2-phenylmalonate (8 mL, 37.1 mmol) was microwaved at 250° C. for 15 min. After cooling to room temperature, the resulting suspension was filtered. The solid was washed with 20% isopropyl alcohol in heptanes and dried under vacuum to give 4-hydroxy-6-oxo-2-(4-phenoxyphenyl)-5-phenyl-1,6-dihydropyridine-3-carbonitrile (714 mg, 62% yield). $^1$H NMR (500 MHz, DMSO-$d_6$) δ ppm 12.23 (1H, br. s), 10.76 (1H, br. s), 7.72 (2H, δ, J=8.80 Hz), 7.46-7.51 (2H, m), 7.39-7.44 (2H, m), 7.30-7.36 (3H, m), 7.26 (1H, t, J=7.42 Hz), 7.15 (2H, δ, J=7.70 Hz), 7.10 (2H, δ, J=8.80 Hz); MS (ES+) m/z: 381 (M+H); LC retention time: 3.820 min (analytical HPLC Method A).

Step 2:

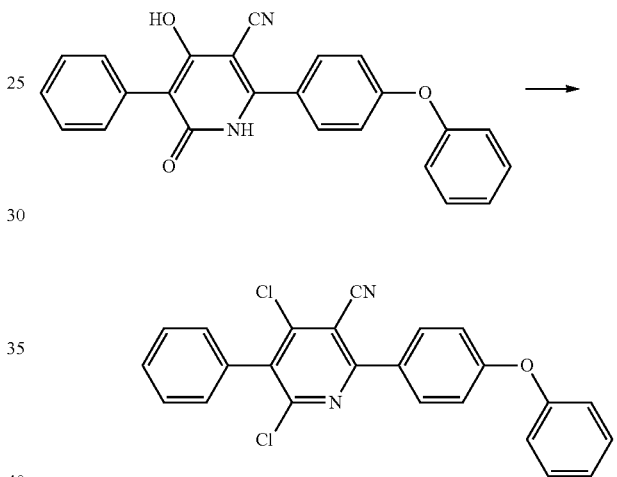

A mixture of 4-hydroxy-6-oxo-2-(4-phenoxyphenyl)-5-phenyl-1,6-dihydropyridine-3-carbonitrile (204 mg, 0.536 mmol) and phosphoryl trichloride (1 mL) was heated to 100° C. for 3 h. The mixture was concentrated and treated with slow addition of water to give a suspension. The white solid was collected by filtration, washed with water and dried under vacuum to give 4,6-dichloro-2-(4-phenoxyphenyl)-5-phenylnicotinonitrile as a brown solid (224 mg, 100% yield). $^1$H NMR (400 MHz, CDCl$_3$) δ ppm 7.96-8.04 (2H, m), 7.50-7.58 (3H, m), 7.37-7.44 (2H, m), 7.28-7.34 (2H, m), 7.17-7.24 (1H, m), 7.08-7.16 (4H, m); MS (ES+) m/z: 417 (M+H); LC retention time: 4.951 min (analytical HPLC Method A).

Step 3:

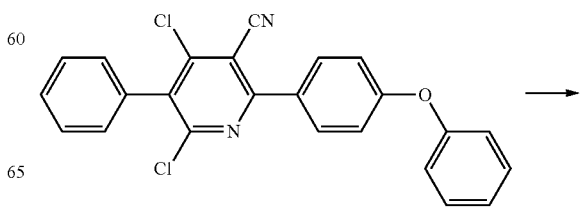

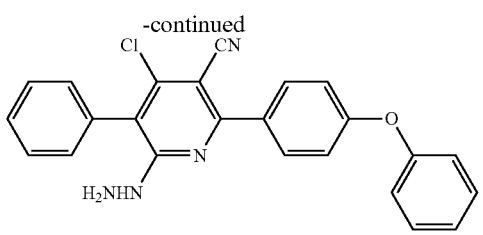

A mixture of 4,6-dichloro-2-(4-phenoxyphenyl)-5-phenylnicotinonitrile (106 mg, 0.254 mmol), 35% aqueous hydrazine (0.114 mL, 1.270 mmol) and ethanol (1.5 mL) was stirred at room temperature for 40 min and at 100° C. for 50 min. Purification by reverse phase HPLC (Sunfire S10 30×250 mm column), eluting with 70-95% solvent B (10% methanol-90% water-0.1% TFA) in solvent A (90% methanol-10% water-0.1% TFA), gave 4-chloro-6-hydrazinyl-2-(4-phenoxyphenyl)-5-phenylnicotinonitrile TFA salt, as brown solid (72.6 mg, 52% yield). $^1$H NMR (400 MHz, CDCl$_3$) δ ppm 8.50 (3H, br. s), 7.83-7.93 (2H, m), 7.47-7.55 (3H, m), 7.37-7.45 (2H, m), 7.19-7.25 (3H, m), 7.06-7.14 (4H, m); MS (ES+) m/z: 413 (M+H); LC retention time: 3.935 min (analytical HPLC Method A).

Step 4:

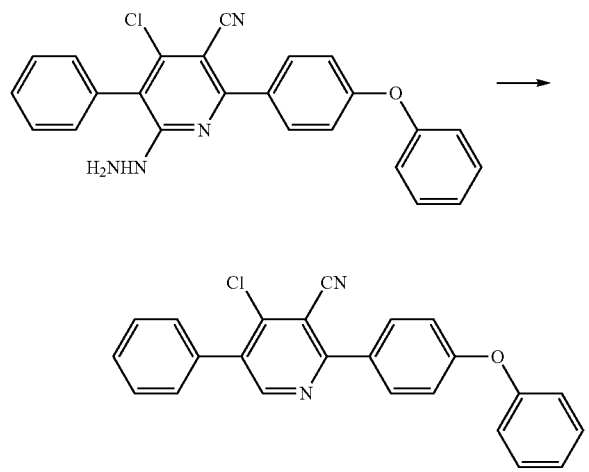

A mixture of 4-chloro-6-hydrazinyl-2-(4-phenoxyphenyl)-5-phenylnicotinonitrile TFA salt (72.6 mg, 0.138 mmol), 1.0 M aqueous copper(II) sulfate (0.276 mL, 0.276 mmol) and 1-propanol (1 mL) was heated to 100° C. in a sealed tube for 2 h. After cooling to room temperature, the mixture was filtered. The filtrate was concentrated and purified by reverse phase HPLC (isocratic 100% solvent B for 25 min, 40 mL/min, Sunfire 30×250 mm to give 4-chloro-2-(4-phenoxyphenyl)-5-phenylnicotinonitrile TFA salt as white solid (17.9 mg, 26% yield). $^1$H NMR (400 MHz, CDCl$_3$) δ ppm 8.78 (1H, s), 7.87-7.96 (2H, m), 7.46-7.56 (5H, m), 7.37-7.45 (2H, m), 7.20 (1H, t, J=7.40 Hz), 7.09-7.17 (4H, m); MS (ES+) m/z: 383 (M+H); LC retention time: 4.790 min (analytical HPLC Method A).

Step 5:

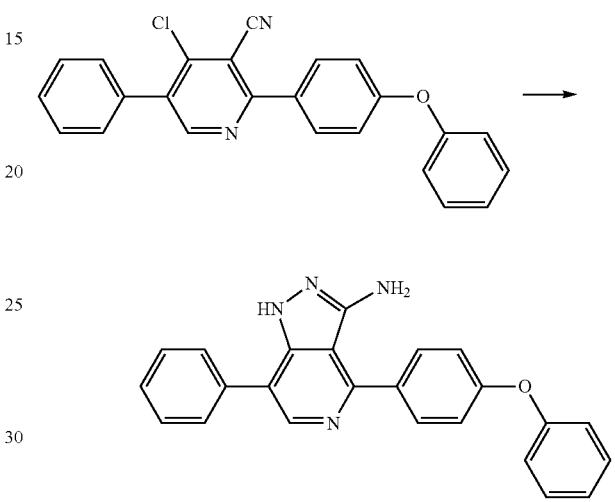

A mixture of 4-chloro-2-(4-phenoxyphenyl)-5-phenylnicotinonitrile (17.9 mg, 0.047 mmol), 35% aqueous hydrazine (200 µL, 2.228 mmol) and 1-propanol (2 mL) was heated to 120° C. in a sealed tube for 3 h. Purification by reverse phase HPLC (Sunfire S10 30×250 mm column), eluting with 55-85% solvent B (10% methanol-90% water-0.1% TFA) in solvent A (90% methanol-10% water-0.1% TFA), gave Example 160 as yellow solid (15.9 mg, 56% yield). $^1$H NMR (400 MHz, methanol-d$_4$) δ ppm 8.19 (1H, s), 7.78-7.92 (4H, m), 7.57-7.69 (3H, m), 7.44-7.53 (2H, m), 7.24-7.34 (3H, m), 7.14-7.23 (2H, m); MS (ES+) m/z: 379 (M+H); LC retention time: 3.263 min (analytical HPLC Method. A).

Examples 161 to 167

Examples 161 to 167 were prepared from appropriately substituted malonates following conditions described for synthesis of Example 160.

| Example No. | Structure | Spectral data* |
|---|---|---|
| Example 161: 6-Chloro-4-(4-phenoxyphenyl)-1H-pyrazolo[4,3-c]pyridin-3-amine | 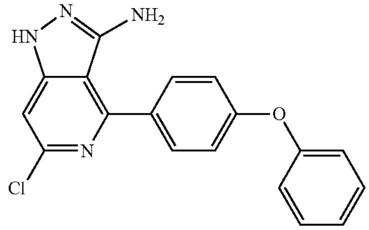 [SMILES: Nc1n[nH]c2cc(Cl)nc(-c3ccc(Oc4ccccc4)cc3)c12] | $^1$H NMR (400 MHz, methanol-d$_4$) δ ppm 7.68-7.74 (2 H, m), 7.39-7.47 (2 H, m), 7.35 (1 H, s), 7.20 (1 H, t, J = 7.42 Hz), 7.14-7.18 (2 H, m), 7.12 (2 H, δ, J = 7.42 Hz); MS (ES+) m/z: 337 (M + H); LC retention time: 3.895 min. |

-continued

| Example No. | Structure | Spectral data* |
|---|---|---|
| Example 162: 6-Chloro-7-methyl-4-(4-phenoxyphenyl)-1H-pyrazolo[4,3-c]pyridin-3-amine | 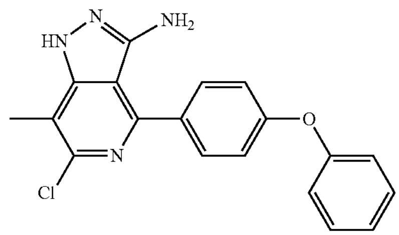 [SMILES: Cc1c(Cl)nc(-c2ccc(Oc3ccccc3)cc2)c2c(N)n[nH]c12] | $^1$H NMR (500 MHz, methanol-$d_4$) δ ppm 7.69-7.72 (2 H, m), 7.43 (2 H, t, J = 7.97 Hz), 7.22 (1 H, t, J = 7.42 Hz), 7.18 (2 H, δ, J = 8.80 Hz), 7.13 (2 H, δ, J = 7.70 Hz), 2.53 (3 H, s); MS (ES+) m/z: 351 (M + H); LC retention time: 4.028 min. |
| Example 163: 6-Chloro-7-methoxy-4-(4-phenoxyphenyl)-1H-pyrazolo[4,3-c]pyridin-3-amine | 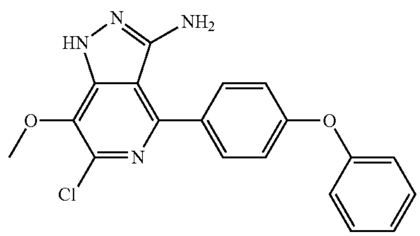 [SMILES: COc1c(Cl)nc(-c2ccc(Oc3ccccc3)cc2)c2c(N)n[nH]c12] | $^1$H NMR (400 MHz, methanol-$d_4$) δ ppm 7.65-7.70 (2 H, m), 7.39-7.45 (2 H, m), 7.09-7.23 (5 H, m), 4.06 (3 H, s); MS (ES+) m/z: 367 (M + H); LC retention time: 3.991 min. |
| Example 164: 4-(4-Phenoxyphenyl)-1H-pyrazolo[4,3-c]pyridin-3-amine | 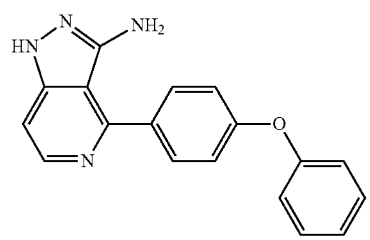 [SMILES: Nc1n[nH]c2ccnc(-c3ccc(Oc4ccccc4)cc3)c12] | $^1$H NMR (400 MHz, methanol-$d_4$) δ ppm 8.16 (1 H, δ, J = 7.03 Hz), 7.80-7.86 (2 H, m), 7.66 (1 H, δ, J = 7.03 Hz), 7.43-7.52 (2 H, m), 7.24-7.30 (3 H, m), 7.15-7.21 (2 H, m); MS (ES+) m/z: 303 (M + H); LC retention time: 2.738 min. |
| Example 165: 7-Methyl-4-(4-phenoxyphenyl)-1H-pyrazolo[4,3-c]pyridin-3-amine | 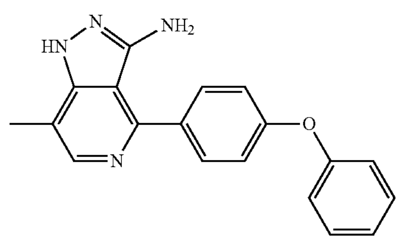 [SMILES: Cc1cnc(-c2ccc(Oc3ccccc3)cc2)c2c(N)n[nH]c12] | $^1$H NMR (400 MHz, methanol-$d_4$) δ ppm 8.01 (1 H, δ, J = 1.00 Hz), 7.77-7.82 (2 H, m), 7.43-7.51 (2 H, m), 7.23-7.30 (3 H, m), 7.14-7.19 (2 H, m), 2.58 (3 H, s); MS (ES+) m/z: 317 (M + H); LC retention time: 2.888 min. |
| Example 166: 7-Methoxy-4-(4-phenoxyphenyl)-1H-pyrazolo[4,3-c]pyridin-3-amine | 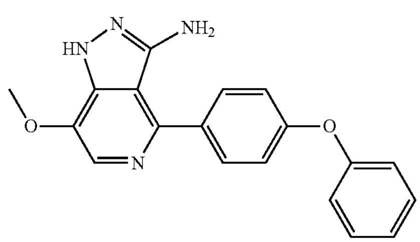 [SMILES: COc1cnc(-c2ccc(Oc3ccccc3)cc2)c2c(N)n[nH]c12] | $^1$H NMR (400 MHz, methanol-$d_4$) δ ppm 7.82 (1 H, s), 735-7.78 (2 H, m), 7.44-7.49 (2 H, m), 7.22-7.29 (3 H, m), 7.14-7.18 (2 H, m), 4.15 (3 H, s); MS (ES+) m/z: 333 (M + H); LC retention time: 2.910 min. |
| Example 167: 7-Benzyl-4-(4-phenoxyphenyl)-1H-pyrazolo[4,3-c]pyridin-3-amine | 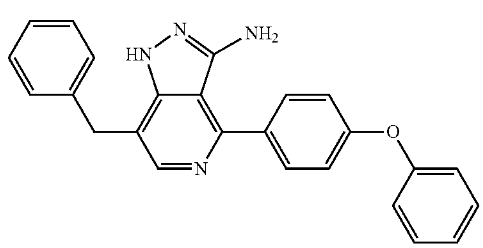 [SMILES: Nc1n[nH]c2c(Cc3ccccc3)cnc(-c3ccc(Oc4ccccc4)cc3)c12] | $^1$H NMR (400 MHz, methanol-$d_4$) δ ppm 7.77-7.83 (3 H, m), 7.43-7.50 (2 H, m), 7.36 (4 H, m), 7.27-7.23 (4H, m), 7.13-7.19 (2 H, m), 4.30 (2 H, s); MS (ES+) m/z: 393 (M + H); LC retention time: 3.338 min. |

*Analytical HPLC Method A

Example 168

4-(4-Phenoxyphenyl)-1H-pyrazolo[4,3-c]quinolin-3-amine

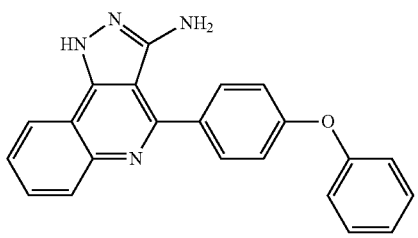 [SMILES: Nc1n[nH]c2c1c(-c1ccc(Oc3ccccc3)cc1)nc1ccccc12]

Step 1:

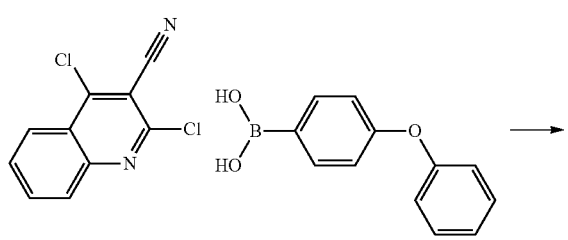

A mixture of 2,4-dichloroquinoline-3-carbonitrile (51.5 mg, 0.231 mmol), 4-phenoxyphenylboronic acid (51 mg, 0.238 mmol), palladium tetrakis(triphenylphosphine) (19.5 mg, 0.017 mmol), potassium phosphate (0.098 mL, 1.187 mmol) and N,N-dimethylformamide (2 mL) was pumped and backfilled with nitrogen twice, and heated to 85° C. for 2 h. The mixture was concentrated, treated with water and extracted with dichloromethane. The dichloromethane phase was concentrated. Purification by reverse phase HPLC (Sunfire S10 30×250 mm column), eluting with 85-100% solvent B (10% methanol-90% water-0.1% TFA) in solvent A (90% methanol-10% water-0.1% TFA), gave 4-chloro-2-(4-phenoxyphenyl)quinoline-3-carbonitrile TFA salt (3.7 mg, 3% yield). $^1$H NMR (400 MHz, CDCl$_3$) δ ppm 8.31 (1H, δ, J=7.53 Hz), 8.20 (1H, δ, J=8.28 Hz), 7.91-8.00 (3H, m), 7.72-7.79 (2H, m), 7.37-7.43 (2H, m), 7.09-7.18 (4H, m); MS (ES+) m/z: 357 (M+H); LC retention time: 4.731 min (analytical HPLC Method A).

Step 2:

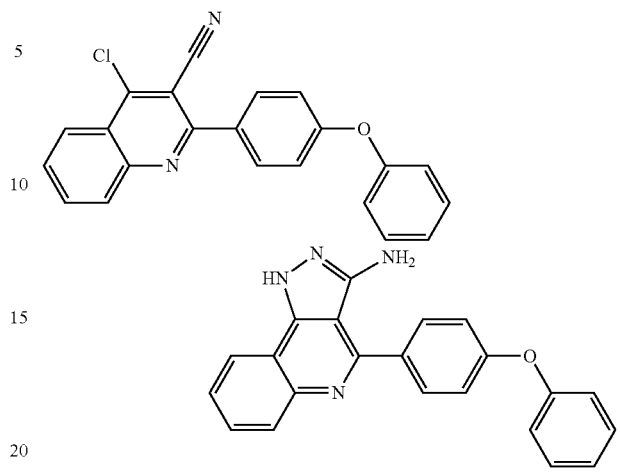

Following conditions similar to Step 5 of Example 160, Example 168 was prepared. $^1$H NMR (400 MHz, methanol-d$_4$) δ ppm 8.43-8.47 (1H, m), 8.03 (1H, δ, J=8.28 Hz), 7.88-7.91 (3H, m), 7.82 (1H, t, J=7.65 Hz), 7.46-7.51 (2H, m), 7.27-7.32 (3H, m), 7.18-7.21 (2H, m); MS (ES+) m/z: 353 (M+H); LC retention time: 3.173 min (analytical HPLC Method A).

Example 169

(1-(3-Amino-4-(4-phenoxyphenyl)-1H-pyrazolo[4,3-c]pyridin-6-yl)-2-pyrrolidinyl)methanol

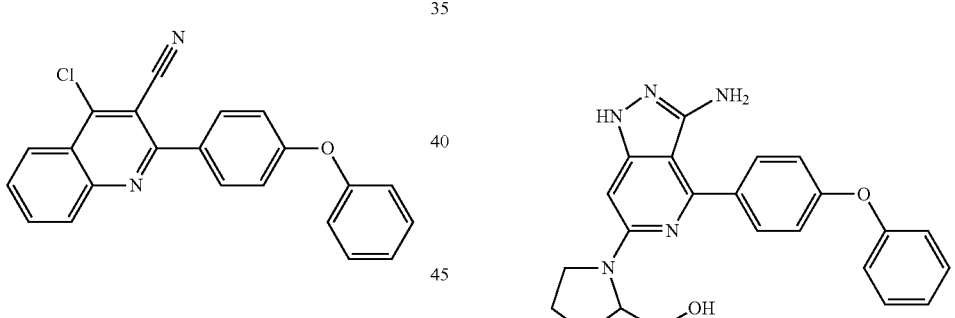

A mixture of 6-chloro-4-(4-phenoxyphenyl)-1H-pyrazolo[4,3-c]pyridin-3-amine bis-TFA salt (6.1 mg, 10.80 μmol, from Example 161), (S)-pyrrolidin-2-ylmethanol (160 μL, 1.639 mmol) and (R)-pyrrolidin-2-ylmethanol (160 μL, 1.639 mmol) in N,N-dimethylacetamide (0.3 mL) was microwaved at 180° C. for 15 min and at 220° C. for 15 min. LC-MS analysis showed trace amount of product. Additional (S)-pyrrolidin-2-ylmethanol (85 mg) and (R)-pyrrolidin-2-ylmethanol (85 mg) were added. The mixture was microwaved at 250° C. for 2.25 h. Purification by reverse phase HPLC (Sunfire S10 30×250 mm column), eluting with 50-80% solvent B (10% methanol-90% water-0.1% TFA) in solvent A (90% methanol-10% water-0.1% TFA), gave Example 169 (5 mg, 71% yield). $^1$H NMR (400 MHz, methanol-d$_4$) δ ppm 7.80-7.85 (2H, m), 7.43-7.49 (2H, m), 7.25-7.29 (1H, m), 7.20-7.25 (2H, m), 7.13-7.1.7 (2H, m), 6.48 (1H, s), 4.14-4.22 (1H, m), 3.78-3.83 (1H, m), 3.67 (1H, t, J=10.29 Hz), 3.55-3.62 (1H, m), 3.45-3.54 (1H, m), 2.87 (1H, s), 2.19-2.27 (1H, m), 2.05-2.16 (2H, m), 1.86-1.93 (1H, m); MS (ES+) m/z: 402 (M+H); LC retention time: 3.181 min (analytical HPLC Method A).

Example 170

(1-(3-Amino-4-(4-phenoxyphenyl)-1H-pyrazolo[4,3-c]pyridin-6-yl)-3-piperidinyl)methanol

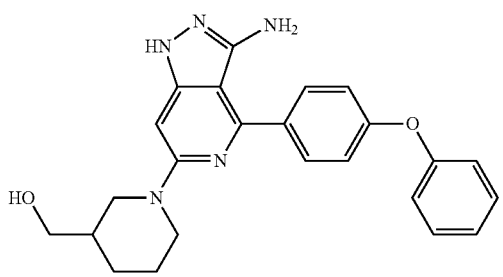 [SMILES: Nc1n[nH]c2cc(N3CCCC(CO)C3)nc(-c3ccc(Oc4ccccc4)cc3)c12]

A solution of 6-chloro-4-(4-phenoxyphenyl)-1H-pyrazolo[4,3-c]pyridin-3-amine bis-TFA salt (7 mg, 0.012 mmol, from Example 161) and piperidin-3-ylmethanol (15 mg, 0.130 mmol) in N,N-dimethylacetamide (0.3 mL) was microwaved at 250° C. for 3 h. LCMS analysis showed only trace amount of product. Additional piperidin-3-ylmethanol (226.4 mg) was added and the mixture was microwaved at 250° C. for 2 h. The mixture was diluted with water (1 mL) and methanol (0.5 mL), filtered and purified by reverse phase HPLC (Sunfire S10 30×250 mm column), eluting with 50-80% solvent B (10% methanol-90% water-0.1% TFA) in solvent A (90% methanol-10% water-0.1% TFA), to give Example 170 as yellow solid, assumed as bis-TFA salt (3.8 mg, 46% yield). $^1$H NMR (400 MHz, CDCl$_3$) δ ppm 7.63 (2H, δ, J=8.78 Hz), 7.39-7.45 (2H, m), 7.20-7.25 (1H, m), 7.09-7.16 (4H, m), 6.40 (1H, s), 3.90 (1H, δ), 3.70-3.80 (1H, m), 3.65 (1H, dd, J=11.04, 5.27 Hz), 3.44-3.57 (2H, m), 3.32-3.41 (1H, 2.02 (1H, m), 1.74-1.91 (2H, m), 1.66 (1H, m), 1.39 (1H, m); MS (ES+) m/z: 416 (M+H); LC retention time: 3.178 min (analytical HPLC Method A).

Example 171

(1-(3-Amino-4-(4-phenoxyphenyl)-1H-pyrazolo[4,3-c]pyridin-6-yl)-4-piperidinyl)methanol

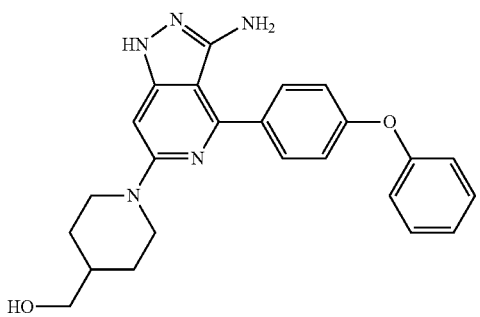 [SMILES: Nc1n[nH]c2cc(N3CCC(CO)CC3)nc(-c3ccc(Oc4ccccc4)cc3)c12]

A solution of 6-chloro-4-(4-phenoxyphenyl)-1H-pyrazolo[4,3-c]pyridin-3-amine bis-TFA salt (7.4 mg, 0.013 mmol, from Example 161) and piperidin-4-ylmethanol (79.7 mg, 0.692 mmol) in N,N-dimethylacetamide (0.15 mL) was microwaved at 250° C. for 2 h. Purification by reverse phase HPLC (Sunfire S10 30×250 mm column), eluting with 50-70% solvent B (10% methanol-90% water-0.1% TFA) in solvent A (90% methanol-10% water-0.1% TFA), gave Example 171 as yellow powder, assumed as bis-TFA salt (7.4 mg, 88% yield). $^1$H NMR (500 MHz, methanol-d$_4$) δ ppm 7.75-7.79 (2H, m), 7.46 (2H, dd, J=8.52, 7.42 Hz), 7.22-7.28 (3H, m), 7.15 (2H, δ, J=7.42 Hz), 6.72-6.75 (1H, m), 4.35 (1H, δ, J=6.32 Hz), 3.92 (2H, t, J=12.37 Hz), 3.48 (1H, 8, J=6.05 Hz), 3.07 (2H, qd, J=12.28, 2.20 Hz), 1.91 (2H, δ, J=10.45 Hz), 1.69-1.80 (1H, m), 1.56 (1H, qd, J=12.46, 4.12 Hz), 1.45 (1H, qd, J=12.46, 4.12 Hz); MS (ES+) m/z: 416 (M+H); LC retention time: 3.096 min (analytical HPLC Method A).

Example 172

6-(3-Bromophenyl)-4-(4-phenoxyphenyl)-1H-pyrazolo[4,3-e]pyridin-3-amine

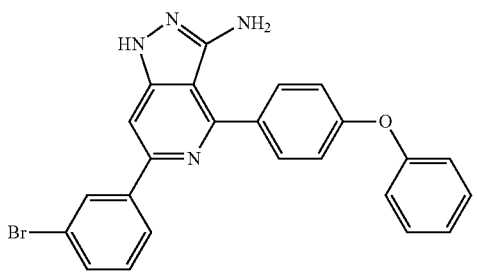 [SMILES: Nc1n[nH]c2cc(-c3cccc(Br)c3)nc(-c3ccc(Oc4ccccc4)cc3)c12]

Step 1:

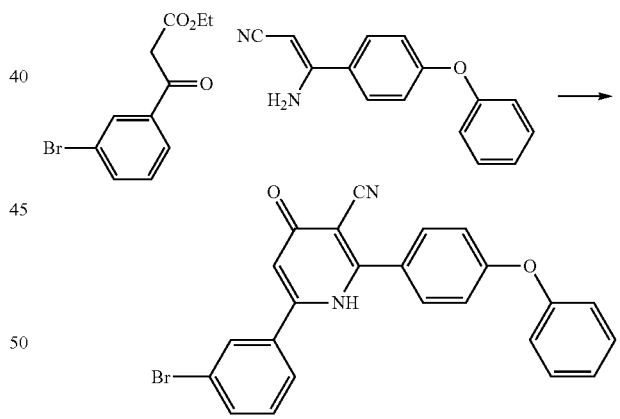

A mixture of 3-amino-3-(4-phenoxyphenyl)acrylonitrile (0.553 g, 2342 mmol) and ethyl 3-(3-bromophenyl)-3-oxopropanoate (2.540 g, 9.37 mmol) was microwaved at 230° C. for 20 min. After cooling to room temperature, the mixture was diluted with water and extracted with ethyl acetate (100 mL). The ethyl acetate phase was washed with saturated ammonium chloride, brine, dried (MgSO$_4$), and concentrated. Silica gel chromatography, eluting with 0-80% ethyl acetate in hexanes, gave 6-(3-bromophenyl)-4-oxo-2-(4-phenoxyphenyl)-1,4-dihydropyridine-3-carbonitrile as brown solid (0.909 g, 88% yield). $^1$H NMR (400 MHz, CDCl$_3$) δ ppm 7.81 (1H, br. s), 7.70 (2H, δ, J=8.28 Hz), 7.62 (2H, δ, J=7.28 Hz), 7.35 (3H, t, J=7.40 Hz), 7.18 (1H, t, J=7.28 Hz), 7.03 (4H, dd, J=11.92, 8.66 Hz), 6.68 (1H, br. s); MS (ES+) m/z: 443,445 (M+H); LC retention time: 4.361 min (analytical HPLC Method A).

Step 2:

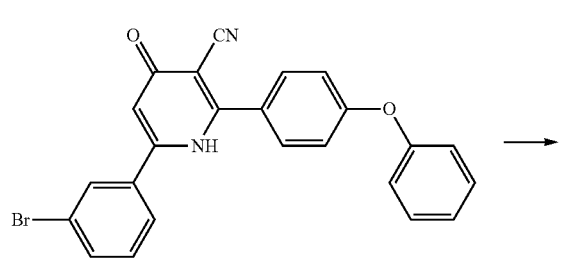

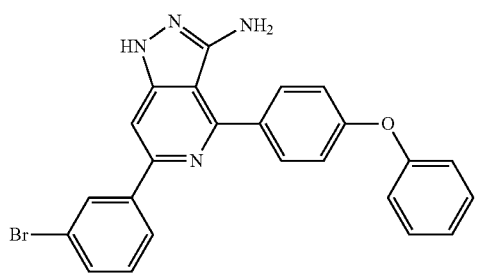

A mixture of 6-(3-bromophenyl)-4-hydroxy-2-(4-phenoxyphenyl)nicotinonitrile (38.8 mg, 0.070 mmol) and phosphoryl trichloride (0.5 mL, 5.38 mmol) was heated to 90° C. for 17 h, then concentrated to give crude 6-(3-bromophenyl)-4-chloro-2-(4-phenoxyphenyl)nicotinonitrile, which was used in the next reaction without purification. MS (ES+) m/z: 461, 463 (M+H); LC retention time: 4.821 min (analytical HPLC Method A).

Step 3:

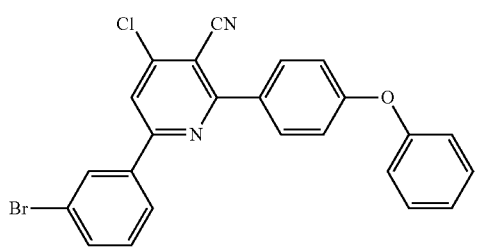

A mixture of crude 6-(3-bromophenyl)-4-chloro-2-(4-phenoxyphenyl)nicotinonitrile from Step 2, 35% aqueous hydrazine (200 μL, 2.228 mmol) and 1-propanol (1.5 mL) was heated to 100° C. in a sealed vial for 22 h. The mixture was concentrated, dissolved in 5% TFA in methanol, filtered and purified by reverse phase HPLC (Sunfire S10 30×250 mm column), eluting with 65-95% solvent B (10% methanol-90% water-0.1% TFA) in solvent A (90% methanol-10% water 0.1% TFA), to give Example 172 as yellow solid, assumed bis-TFA salt (43 mg, 90% yield for 2 steps). $^1$H NMR (400 MHz, methanol-$d_4$) δ ppm 8.09 (1H, t, J=1.76 Hz), 7.87-7.92 (2H, m), 7.84 (1H, dd, J=7.78, 1.76 Hz), 7.77-7.81 (2H, m), 7.54 (1H, t, J=7.91 Hz), 7.43-7.50 (2H, m), 7.25-7.30 (3H, m), 7.17 (2H, 6); MS (ES+) m/z: 457, 459 (M+H); LC retention time: 3.793 min (analytical HPLC Method A).

Examples 173 to 184

Examples 173 to 182 were prepared from appropriately substituted β-ketoester and 3-(3-bromophenyl)-3-oxopropanoate following conditions similar to Steps 1 to 3 of Example 172 Examples 182 to 184 were prepared from diethyl 3-oxopentanedioate and 3-(3-bromophenyl)-3-oxopropanoate using similar sequence followed by subsequent functional group manipulation.

| Example No. | Structure | Spectral data* |
|---|---|---|
| Example 173: 4-(3-Amino-4-(4-phenoxyphenyl)-1H-pyrazolo[4,3-c]pyridin-6-yl)benzonitrile | 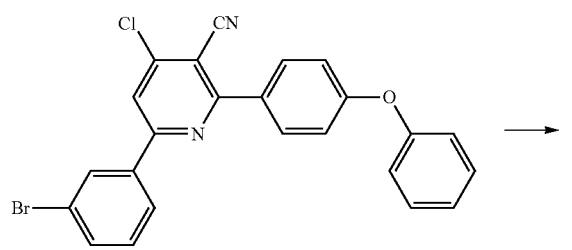 | $^1$H NMR (400 MHz, methanol-$d_4$) δ ppm 8.05-8.10 (2 H, m), 7.95-7.99 (2 H, m), 7.88-7.93 (2 H, m), 7.84 (1 H, s), 7.44-7.50 (2 H, m), 7.25-7.31 (3 H, m), 7.17 (2 H, dd, J = 8.66, 1.13 Hz); MS (ES+) m/z: 404 (M + H); LC retention time: 3.528 min. |

-continued

| Example No. | Structure | Spectral data* |
|---|---|---|
| Example 174: 6-(3-Nitrophenyl)-4-(4-phenoxyphenyl)-1H-pyrazolo[4,3-c]pyridin-3-amine | 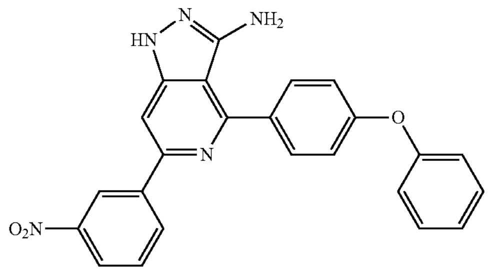 [SMILES: Nc1n[nH]c2cc(-c3cccc([N+](=O)[O-])c3)nc(-c3ccc(Oc4ccccc4)cc3)c12] | $^1$H NMR (400 MHz, CDCl$_3$) δ ppm 8.72 (1 H, s), 8.23-8.33 (2 H, m), 7.74 (2 H, δ, J = 8.78 Hz), 7.65-7.71 (2 H, m), 7.42 (2 H, t, J = 8.03 Hz), 7.23 (1 H, t, J = 7.40 Hz), 7.18 (2 H, δ, J = 8.78 Hz), 7.11 (2 H, δ, J = 7.53 Hz); MS (ES+) m/z: 424 (M + H); LC retention time: 3.780 min. |
| Example 175: 4-(4-Phenoxyphenyl)-6-(3-pyridinyl)-1H-pyrazolo[4,3-c]pyridin-3-amine | 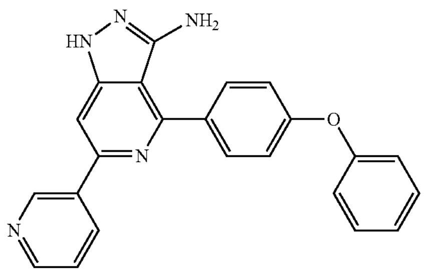 [SMILES: Nc1n[nH]c2cc(-c3cccnc3)nc(-c3ccc(Oc4ccccc4)cc3)c12] | $^1$H NMR (400 MHz, methanol-d$_4$) δ ppm 9.29 (1 H, δ, J = 1.51 Hz), 8.85 (1 H, δ, J = 5.27 Hz), 8.76 (1 H, dt, J = 8.09, 1.85 Hz), 7.86-7.96 (4 H, m), 7.42-7.50 (2 H, m), 7.22-7.29 (3 H, m), 7.13-7.19 (2 H, m); MS (ES+) m/z: 480 (M + H); LC retention time: 3.061 min. |
| Example 176: 6-(4-(Dimethylamino)phenyl)-4-(4-phenoxyphenyl)-1H-pyrazolo[4,3-c]pyridin-3-amine | 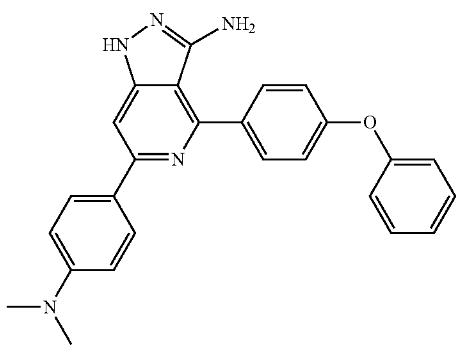 [SMILES: CN(C)c1ccc(-c2cc3[nH]nc(N)c3c(-c3ccc(Oc4ccccc4)cc3)n2)cc1] | $^1$H NMR (400 MHz, methanol-d$_4$) δ ppm 7.84-7.90 (2 H, m), 7.70-7.75 (2 H, m), 7.62 (1 H, s), 7.44-7.51 (2 H, m), 7.25-7.30 (3 H, m), 7.15-7.20 (2 H, m), 6.90-6.95 (2 H, m), 3.08 (6 H, s); MS (ES+) m/z: 422 (M + H); LC retention time: 3.403 min. |
| Example 177: 4-(4-Phenoxyphenyl)-6-(2-pyridinyl)-1H-pyrazolo[4,3-c]pyridin-3-amine | 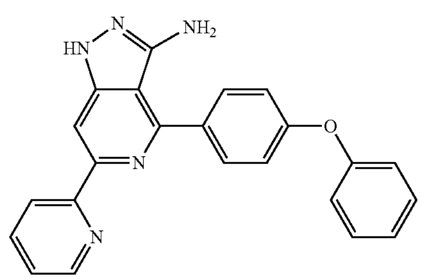 [SMILES: Nc1n[nH]c2cc(-c3ccccn3)nc(-c3ccc(Oc4ccccc4)cc3)c12] | $^1$H NMR (400 MHz, methanol-d$_4$) δ ppm 8.77 (1 H, δ, J = 4.52 Hz), 8.35 (1 H, δ, J = 8.03 Hz), 8.24 (1 H, s), 8.13 (1 H, t, J =7.28 Hz), 7.89 (2 H, δ, J = 8.53 Hz), 7.63 (1 H, dd, J = 7.03, 5.27 Hz), 7.44 (2 H, t, J = 7.78 Hz), 7.19-7.29 (3 H, m), 7.14 (2 H, δ, J = 7.78 Hz); MS (ES+) m/z: 380 (M + H); LC retention time: 3.236 min. |
| Example 178: 6-(5-Bromo-3-pyridinyl)-4-(4-phenoxyphenyl)-1H-pyrazolo[4,3-c]pyridin-3-amine | 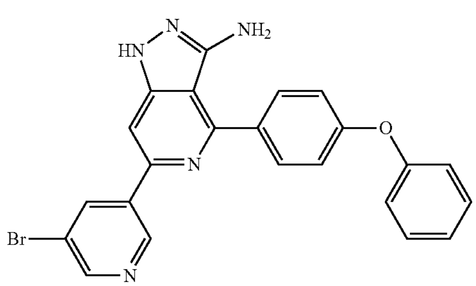 [SMILES: Nc1n[nH]c2cc(-c3cncc(Br)c3)nc(-c3ccc(Oc4ccccc4)cc3)c12] | $^1$H NMR (400 MHz, CDCl$_3$) δ ppm 9.21 (1 H, br. s), 8.77 (1 H, br. s), 8.75 (1 H, s), 7.70-7.76 (3 H, m), 7.43 (2 H, t, J = 7.91 Hz), 7.20-7.25 (1 H, m), 7.19 (2 H, δ, J = 8.78 Hz), 7.12 (2 H, δ, J = 7.53 Hz); MS (ES+) m/z: 458, 460 (M + H); LC retention time: 4.036 min. |

| Example No. | Structure | Spectral data* |
|---|---|---|
| Example 179:<br>4,6-Bis(4-methoxyphenyl)-1H-pyrazolo[4,3-c]pyridin-3-amine | 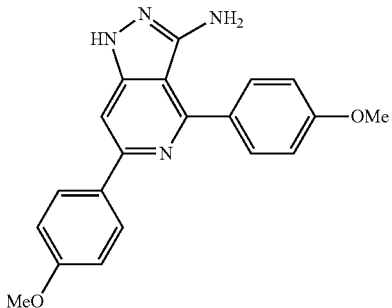 [SMILES: COc1ccc(-c2cc3[nH]nc(N)c3c(-c3ccc(OC)cc3)n2)cc1] | ¹H NMR (400 MHz, methanol-d₄) δ ppm 7.85 (2 H, d, J = 8.78 Hz), 7.80 (2 H, d, J = 9.03 Hz), 7.66 (1 H, s), 7.28 (2 H, d, J = 8.78 Hz), 7.15 (2 H, d, J = 8.78 Hz), 3.96 (3 H, s), 3.90 (3 H, s); MS (ES+) m/z: 347.2 (M + H); LC retention time: 2.552 min. |
| Example 180:<br>6-(3-Bromophenyl)-4-(4-methoxyphenyl)-1H-pyrazolo[4,3-c]pyridin-3-amine | 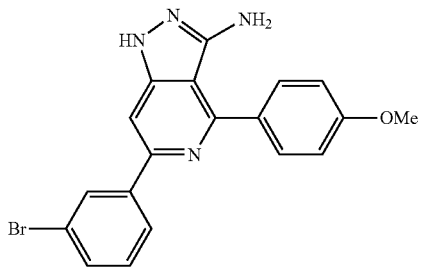 [SMILES: COc1ccc(-c2nc(-c3cccc(Br)c3)cc3[nH]nc(N)c23)cc1] | ¹H NMR (400 MHz, methanol-d₄) δ ppm 8.09 (1 H, t, J = 1.88 Hz), 7.82-7.93 (3 H, m), 7.77-7.82 (1 H, m), 7.76 (1 H, s), 7.54 (1 H, t, J = 8.03 Hz), 7.28 (2 H, d, J = 9.03 Hz), 3.96 (3 H, s); MS (ES+) m/z: 395, 397 (M + H); LC retention time: 2.881 min. |
| Example 181:<br>3-(3-Amino-4-(4-methoxyphenyl)-1H-pyrazolo[4,3-c]pyridin-6-yl)benzonitrile | 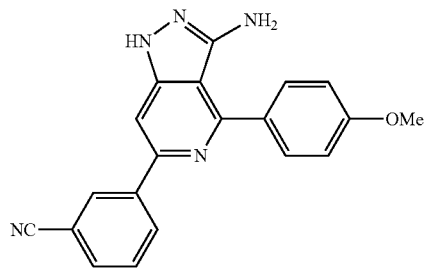 [SMILES: COc1ccc(-c2nc(-c3cccc(C#N)c3)cc3[nH]nc(N)c23)cc1] | ¹H NMR (400 MHz, methanol-d₄) δ ppm 8.30 (1 H, s), 8.17 (1 H, dt, J = 8.03, 1.51 Hz), 7.94-8.02 (1 H, m), 7.84-7.92 (2 H, m), 7.74-7.83 (2 H, m), 7.23-7.34 (2 H, m), 3.96 (3 H, s); MS (ES+) m/z: 342.2 (M + H); LC retention time: 2.412 min. |
| Example 182:<br>(3-Amino-4-(4-phenoxyphenyl)-1H-pyrazolo[4,3-c]pyridin-6-yl)acetic acid | 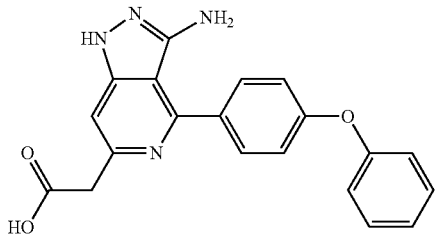 [SMILES: Nc1n[nH]c2cc(CC(=O)O)nc(-c3ccc(Oc4ccccc4)cc3)c12] | ¹H NMR (400 MHz, methanol-d₄) δ ppm 7.77-7.83 (2 H, m), 7.58 (1 H, s), 7.44-7.50 (2 H, m), 7.24-7.30 (3 H, m), 7.17 (2 H, dd, J = 8.66, 1.13 Hz), 4.11 (2 H, s); MS (ES+) m/z: 361.2 (M + H); LC retention time: 2.650 min. |
| Example 183:<br>2-(3-Amino-4-(4-phenoxyphenyl)-1H-pyrazolo[4,3-c]pyridin-6-yl)acetohydrazide | 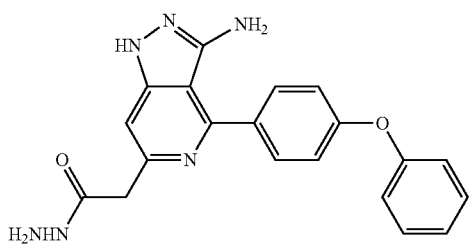 | ¹H NMR (400 MHz, methanol-d₄) δ ppm 7.79-7.84 (2 H, m), 7.56 (1 H, s), 7.45-7.50 (2 H, m), 7.24-7.30 (3 H, m), 7.17 (2 H, dd, J = 8.66, 1.13 Hz), 4.07 (2 H, s); MS (ES+) m/z: 375.2 (M +H); LC retention time: 2.303 min. |

| Example No. | Structure | Spectral data* |
|---|---|---|
| Example 184:<br>6-(2-(4-Morpholinyl)-2-oxoethyl)-4-(4-phenoxyphenyl)-1H-pyrazolo[4,3-c]pyridin-3-amine | | $^1$H NMR (400 MHz, methanol-d$_4$) δ ppm 7.79-7.82 (2 H, m), 7.51 (1 H, s), 7.45-7.50 (2 H, m), 7.24-7.29 (3 H, m), 7.15-7.18 (2 H, m), 4.22 (2 H, s), 3.74-3.78 (2 H, m), 3.70 (2 H, t, J = 4.52 Hz), 3.60-3.66 (4 H, m); MS (ES+) m/z: 430.2 (M + H); LC retention time: 2.803 min. |

*Analytical HPLC Method A

Example 185

4-(3-Amino-4-(4-phenoxyphenyl)-1H-pyrazolo pyridin-6-yl)benzamide

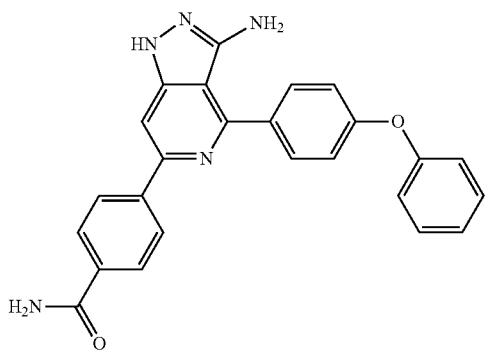 [SMILES: NC(=O)c1ccc(-c2cc3[nH]nc(N)c3c(-c3ccc(Oc4ccccc4)cc3)n2)cc1]

A 30% aqueous solution of hydrogen peroxide (100 μL, 3.26 mmol) was added to a mixture of 4-(3-amino-4-(4-phenoxyphenyl)-1H-pyrazolo[4,3-c]pyridin-6-yl)benzonitrile bis-TFA salt (22.8 mg, 0.036 mmol, from Example 173) and potassium carbonate (81.7 mg, 0.591 mmol) in DMSO (0.8 mL). After 3 days at room temperature, the mixture was diluted with methanol (1.2 mL), filtered and purified by reverse phase HPLC (Sunfire S10 30×250 mm column), eluting with 45-75% solvent B (10% methanol-90% water-0.1% TFA) in solvent A (90% methanol-10% water-0.1% TFA), to give Example 185 as yellow solid, assumed bis-TFA salt (10.8 mg, 46% yield). $^1$H NMR (400 MHz, methanol-d$_4$) δ ppm 8.10 (2H, δ, J=8.53 Hz), 7.96-8.02 (2H, m), 7.87-7.93 (2H, m), 7.82 (1H, s), 7.44-7.51 (2H, m), 7.24-7.30 (3H, m), 7.15-7.20 (2 in); MS (ES+) m/z: 422 (M+H); LC retention time: 3.068 min (analytical HPLC Method A).

Example 186

5-(3-Amino-4-(4-phenoxyphenyl)-1H-pyrazolo[4,3-c]pyridin-6-yl)-2-methoxybenzoic acid

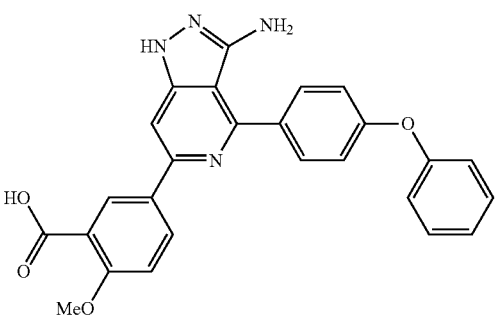 [SMILES: COc1ccc(-c2cc3[nH]nc(N)c3c(-c3ccc(Oc4ccccc4)cc3)n2)cc1C(=O)O]

Step 1:

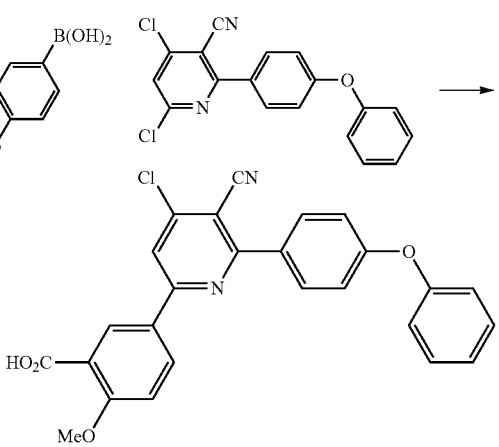

A mixture of 4,6-dichloro-2-(4-phenoxyphenyl)nicotinonitrile (41.2 mg, 0.121 mmol, from Step 3 of Example 152), 5-borono-2-methoxybenzoic acid (18.9 mg, 0.096 mmol), palladium(II) acetate (4 mg, 0.018 mmol), potassium phosphate (125.8 mg, 0.593 mmol) and 1,1'-bis(di-t-butylphosphino)ferrocene (8.3 mg, 0.017 mmol) in N,N-dimethylformamide (0.5 mL) was pumped and backfilled with nitrogen twice. The reaction vial was then sealed and heated to 85° C.

for 3 h. The crude material was poured into a mixture of ethyl acetate (20 mL) and diluted HCl (1 mmol, 5 mL). The aqueous pH was tested as pH 5. The ethyl acetate phase was concentrated and purified by reverse phase HPLC (Sunfire S10 30×250 mm column), eluting with 80-100% solvent B (10% methanol-90% water-0.1% TFA) in solvent A (90% methanol-10% water-0.1% TFA), to give impure 5-(4-chloro-5-cyano-6-(4-phenoxyphenyl)pyridin-2-yl)-2-methoxybenzoic acid (43 mg). This material was taken to next reaction without further purification. MS (ES+) m/z: 457 (M+H).

Step 2:

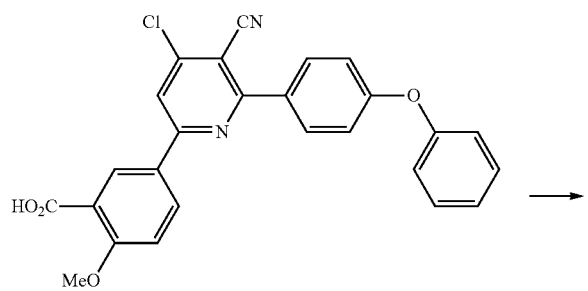

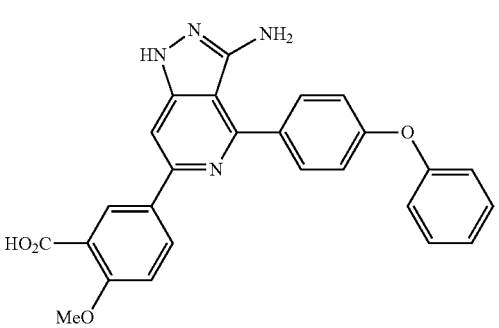

Hydrazine (173 µL, 5.51 mmol) was added to a solution of impure 5-(4-chloro-5-cyano-6-(4-phenoxyphenyl)pyridin-2-yl)-2-methoxybenzoic acid in methanol (0.500 mL) and dichloromethane (0.5 mL). The mixture was stirred at room temperature for 4 h and at 60° C. for 18 h. LCMS analysis showed that the starting material was consumed. The mixture was concentrated, treated with methanol (2 mL) and TFA (0.5 mL) and stirred at room temperature for 90 min. The crude was diluted with water (1 mL) and filtered. The filtrate was purified by reverse phase HPLC (Sunfire S10 30×250 mm column), eluting with 50-65% solvent B (10% methanol-90% water-0.1% TFA) in solvent A (90% methanol-10% water-0.1% TFA), to give Example 186 as yellow solid, assumed as bis-TFA salt (8.5 mg, 21% yield for 2 steps). $^1$H NMR (400 MHz, methanol-$d_4$) δ ppm 8.30 (1H, δ, J=2.51 Hz), 8.03 (1H, dd, J=8.78, 2.51 Hz), 7.89 (2H, δ, J=8.78 Hz), 7.74 (1H, s), 7.47 (2H, t, J=8.03 Hz), 7.37 (1H, δ, J=8.78 Hz), 7.24-7.30 (3H, m), 7.17 (2H, δ, J=7.78 Hz), 4.01 (3H, s); MS (ES+) m/z: 453 (M+H); LC retention time: 3.058 min (analytical HPLC Method A).

Example 187

Benzyl 3-(3-amino-4-(4-phenoxyphenyl)-1H-pyrazolo[4,3-e]pyridin-6-yl)-1-piperidinecarboxylate

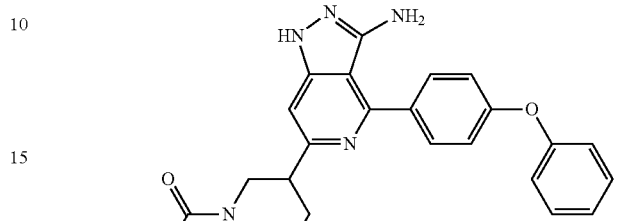

Step 1:

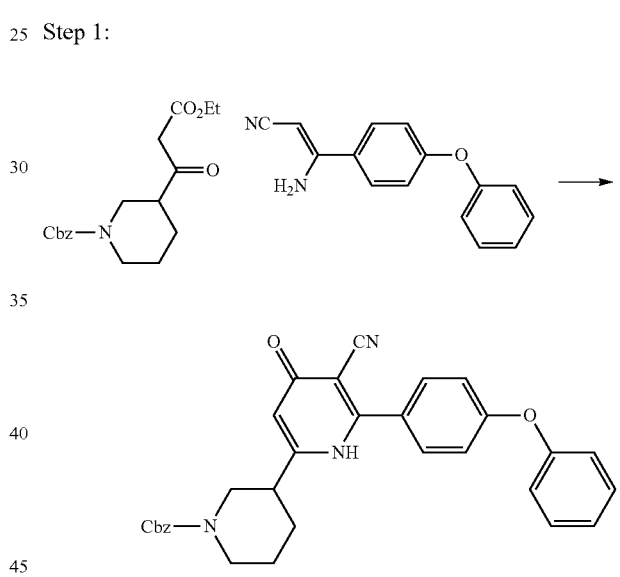

A mixture of 3-amino-3-(4-phenoxyphenyl)acrylonitrile (133 mg, 0.563 mmol) and benzyl 3-(3-ethoxy-3-oxopropanoyl)piperidine-1-carboxylate (323 mg, 0.969 mmol) in N,N-dimethylacetamide (1 mL) was microwaved at 250° C. for 10 min. Purification by reverse phase HPLC (Sunfire S10 30×250 mm column), eluting with 75-100% solvent B (10% methanol-90% water-0.1% TFA) in solvent A (90% methanol-10% water-0.1% TFA), gave benzyl 3-(5-cyano-4-hydroxy-6-(4-phenoxyphenyl)pyridin-2-yl)piperidine-1-carboxylate TFA salt as yellow solid (167.8 mg, 48% yield). $^1$H NMR (400 MHz, methanol-$d_4$) δ pm 7.67 (2H, br. s), 7.38-7.45 (2H, m), 7.32 (5H, br. s), 7.21 (1H, t, J=7.40 Hz), 7.04-7.14 (4H, m), 6.44 (1H, s), 5.11 (2H, s), 4.25 (1H, δ, J=12.30 Hz), 4.08 (1H, δ, J=13.05 Hz), 2.89-3.16 (2H, m), 2.75-2.85 (1H, m, J=10.82, 10.82, 3.58, 3.39 Hz), 2.09 (1H, δ, J=12.55 Hz), 1.67-1.85 (2H, m), 1.56 (1H, t); MS (ES+) m/z: 506 (M+H); LC retention time: 4.131 min (analytical HPLC Method A).

Step 2:

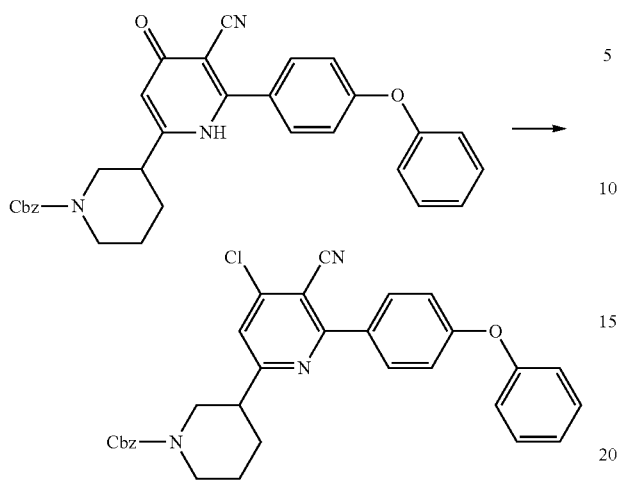

A solution of N-benzyl-3-(5-cyano-4-oxo-6-(4-phenoxyphenyl)-1,4-dihydropyridin-2-yl)piperidine-1-carboxamide (167.9 mg, 0.333 mmol) and phosphorus oxychloride (0.093 mL, 0.998 mmol) in N,N-dimethylformamide (1 mL) was heated to 90° C. in a sealed tube for 50 min. The mixture was concentrated. The residue was dissolved in dichloromethane, washed with saturated sodium bicarbonate and concentrated. Silica gel chromatography, eluting with 0-50% ethyl acetate in hexanes, gave N-benzyl-3-(4-chloro-5-cyano-6-(4-phenoxyphenyl)pyridin-2-yl)piperidine-1-carboxamide as white solid (144.4 mg, 83% yield). $^1$H NMR (400 MHz, CDCl$_3$) δ ppm 7.92 (2H, δ, J=8.53 Hz), 7.28-7.46 (8H, m), 7.19 (1H, t, J=7.40 Hz), 7.06-7.14 (4H, m), 5.15 (2H, s), 4.36 (1H, hr. s), 4.12-4.25 (1H, m), 3.16 (1H, br. s), 2.92 (2H, br. s), 2.07 (1H, br. s), 1.84 (2H, hr. s), 1.58-1.70 (1H, m); MS (ES+) m/z: 524 (M+H); LC retention time: 4.330 min (analytical HPLC Method A).

Step 3:

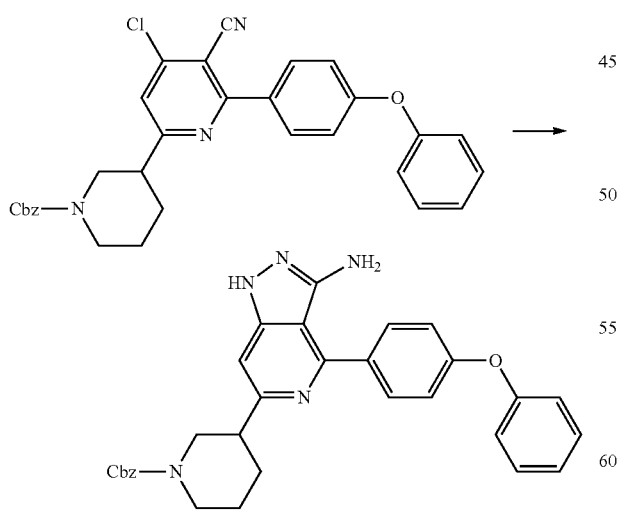

A solution of benzyl 3-(4-chloro-5-cyano-6-(4-phenoxyphenyl)pyridin-2-yl)-piperidine-1-carboxylate (144.4 mg, 0.276 mmol) and hydrazine (45 μL, 1.432 mmol) in N,N-dimethylformamide (0.5 mL) was heated to 110° C. in a sealed tube for 90 min. After cooling to room temperature, TFA (150 μL) was added. The mixture was stirred at room temperature for 1.5 h, and concentrated. Silica gel chromatography, eluting with 0-10% methanol in dichloromethane, gave Example 187 as yellow solid (110.1 mg, 76% yield). $^1$H NMR (400 MHz, methanol-d$_4$) δ ppm 7.78 (2H, br. s), 7.51 (1H, s), 7.47 (2H, t, J=7.78 Hz), 7.20-7.40 (8H, m), 7.16 (2H, δ, J=8.03 Hz), 5.14 (2H, s), 4.34 (1H, δ, J=11.80 Hz), 4.13 (1H, δ, J=13.05 Hz), 3.15 (1H, br. s), 3.14 (2H, t, J=10.67 Hz), 2.22 (1H, δ, J=11.54 Hz), 1.82-1.99 (2H, 1.65 (1H, t, J=11.80 Hz); MS (ES+) m/z: 520 (M+H); LC retention time: 3.583 min (analytical HPLC Method A).

Example 188

Benzyl 4-(3-amino-4-(4-phenoxyphenyl)-1H-pyrazolo[4,3-c]pyridin-6-yl)-1-piperidinecarboxylate

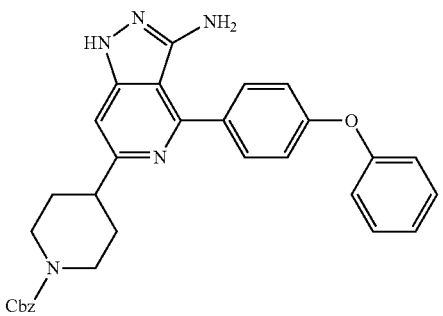 [SMILES: Nc1n[nH]c2cc(C3CCN(C(=O)OCc4ccccc4)CC3)nc(-c3ccc(Oc4ccccc4)cc3)c12]

Following conditions similar to Steps 1 to 3 of Example 187, Example 188 was prepared from the isomeric benzyl 4-(3-ethoxy-3-oxopropanoyl)piperidine-1-carboxylate and 3-amino-3-(4-phenoxyphenyl)acrylonitrile. $^1$H NMR (400 MHz, methanol-d$_4$) δ ppm 7.78-7.81 (2 FT, m), 7.45-7.50 (4H, m), 7.36-7.39 (4H, m), 7.25-7.28 (3H, m), 7.15-7.18 (2H, m), 5.15 (2H, s), 4.35 (2H, br. s), 3.15-3.21 (2H, m), 2.99 (1H, br. s), 2.06 (2H, br. s), 1.79 (2H, δ, J=8.28 Hz); MS (ES+) m/z: 520 (M+H); LC retention time: 3.575 min (analytical HPLC Method A).

Example 189

5-(3-Amino-4-(4-phenoxyphenyl)-1H-pyrazolo[4,3-c]pyridin-6-yl)nicotinonitrile

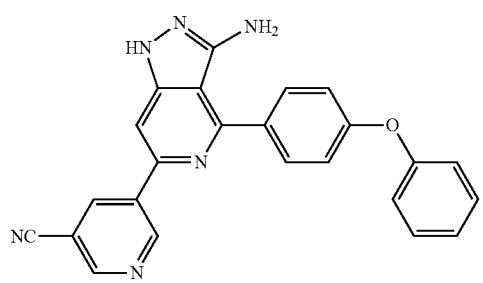 [SMILES: N#Cc1cncc(-c2cc3[nH]nc(N)c3c(-c3ccc(Oc4ccccc4)cc3)n2)c1]

A mixture of 5'-bromo-4-hydrazinyl-6-(4-phenoxyphenyl)-2,3'-bipyridine-5-carbonitrile tris-TFA salt (45.4 mg, 0.057 mmol, from Example 178), zinc cyanide (66.8 mg, 0.569 mmol), palladium tetrakis(triphenylphosphine) (12.3 mg, 0.011 mmol) and N,N-dimethylformamide (1 mL) was pumped under vacuum and backfilled with nitrogen twice. The sealed tube was then heated to 120° C. under nitrogen for 90 min. After addition of water (0.4 mL) and methanol (0.6 mL), the mixture was filtered. The solid was found to contain the expected product but impure (76.2 mg). The filtrate also contains product and was purified by reverse phase HPLC (Sunfire S10 30×250 mm column), eluting with 65-95% solvent B (10% methanol-90% water-0.1% TFA) in solvent A (90% methanol-10% water-0.1% TEA) to give Example 189 as yellow solid (9.7 mg). $^1$H NMR (400 MHz, methanol-$d_4$) δ ppm 9.32 (1H, δ, J=2.26 Hz), 9.09 (1H, δ, J=2.01 Hz), 8.77 (1H, t, J=2.01 Hz), 7.88-7.93 (3H, m), 7.44-7.49 (2H, m), 7.23-7.29 (3H, m), 7.16 (2H, δ, J=7.53 Hz); MS (ES+) m/z: 405 (M+H); LC retention time: 3.751 min (analytical HPLC Method A).

Example 190

5-(3-Amino-4-(4-phenoxyphenyl)-1H-pyrazolo[4,3-c]pyridin-6-yl)nicotinic acid

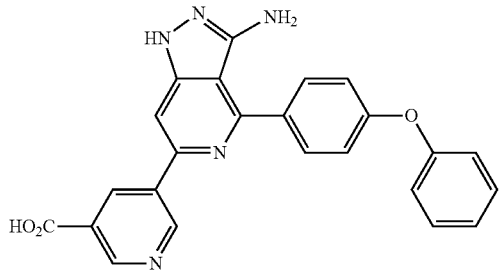 [SMILES: Nc1n[nH]c2cc(-c3cncc(C(=O)O)c3)nc(-c3ccc(Oc4ccccc4)cc3)c12]

A mixture of the impure product from Example 189 (12.7 mg) and concentrated HCl (0.5 mL) was heated to 100° C. in a sealed tube for 30 min. Purification by reverse phase HPLC (Sunfire S10 30×250 mm column), eluting with 50-80% solvent B (10% methanol-90% water-0.1% TEA) in solvent A (90% methanol-10% water-0.1% TFA), gave Example 190 as yellow solid (2.0 mg). $^1$H NMR (400 MHz, methanol-$d_4$) δ ppm 9.32 (1H, δ, J=1.25 Hz), 9.25 (1H, δ, J=1.76 Hz), 8.89 (1H, t, J=2.13 Hz), 7.90-7.93 (3H, m), 7.44-7.50 (2H, m), 7.26-7.31 (3H, m), 7.16-7.20 (2H, m); MS (ES+) m/z: 424 (M+H); LC retention time: 3.283 min (analytical HPLC Method A).

Example 191

4-(4-Phenoxyphenyl)-6-(5-(1H-tetrazol-5-yl)-3-pyridinyl)-1H-pyrazolo[4,3-c]pyridin-3-amine

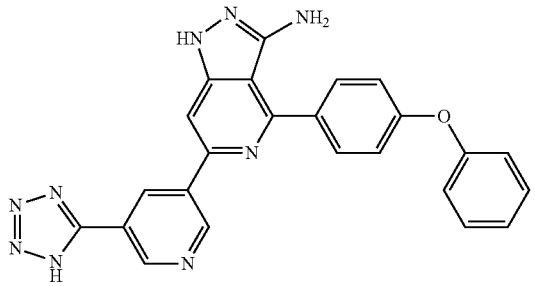 [SMILES: Nc1n[nH]c2cc(-c3cncc(-c4nnn[nH]4)c3)nc(-c3ccc(Oc4ccccc4)cc3)c12]

A mixture of impure 5-(3-amino-4-(4-phenoxyphenyl)-1H-pyrazolo[4,3-c]pyridin-6-yl)nicotinonitrile tris-TFA salt (10.7 mg, from Example 189), sodium azide (18 mg, 0.277 mmol) and ammonium chloride (17.5 mg, 0.327 mmol) in N,N-dimethylacetamide (0.3 mL) was heated to 110° C. in a sealed tube for 3 h. The mixture was diluted with water (0.5 mL) and methanol (1 mL), filtered and concentrated. Purification by reverse phase HPLC (Sunfire S10 30×250 mm column), eluting with 55-85% solvent B (10% methanol-90% water-0.1% TFA) in solvent A (90% methanol-10% water-0.1% TFA), gave Example 191 as yellow solid (5.8 mg). $^1$H NMR (400 MHz, methanol-$d_4$) δ ppm 9.43 (1H, s), 9.23 (1H, s), 9.02 (1H, δ, J=1.76 Hz), 7.91-7.98 (3H, m), 7.47 (2H, t, 5=7.15 Hz), 7.24-7.31 (3H, m), 7.18 (2H, δ, J=7.78 Hz); MS (ES+) m/z: 448 (M+H); LC retention time: 3.458 min (analytical HPLC Method A).

Example 192

Methyl 4-(3-amino-4-(4-phenoxyphenyl)-1H-pyrazolo[4,3-c]pyridin-6-yl)benzoate

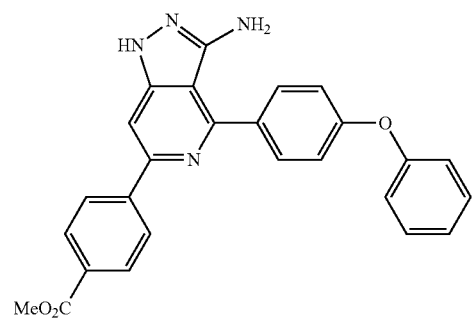 [SMILES: COC(=O)c1ccc(-c2cc3[nH]nc(N)c3c(-c3ccc(Oc4ccccc4)cc3)n2)cc1]

Step 1:

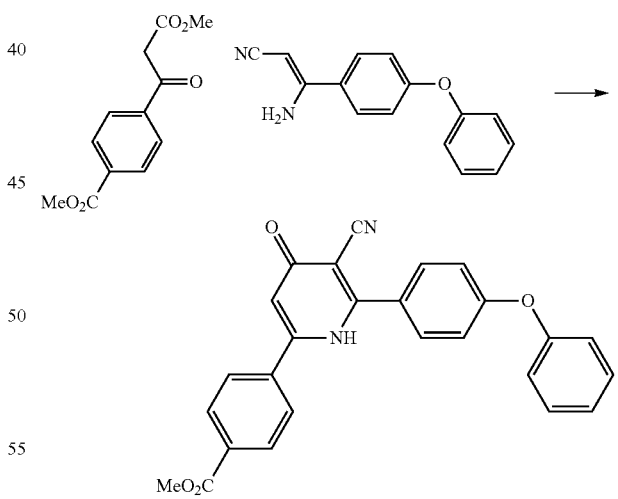

A mixture of 3-amino-3-(4-phenoxyphenyl)acrylonitrile (0.517 g, 2.188 mmol) and methyl 4-(3-methoxy-3-oxopropanoyl)benzoate (2.068 g, 8.75 mmol) was microwaved at 230° C. for 20 min. After cooling to room temperature, the mixture was poured into saturated ammonium chloride (25 mL) and extracted with ethyl acetate (80 mL). The ethyl acetate phase was washed with saturated ammonium chloride (10 mL), water (10 mL), brine (5 mL), dried (MgSO$_4$) and concentrated. Silica gel chromatography, eluting with 0-80% ethyl acetate in hexanes, gave impure products. The material was triturated with dichloromethane. The white solid was collected by filtration to give methyl 4-(5-cyano-4-oxo-6-(4-phenoxyphenyl)-1,4-dihydropyridin-2-yl)benzoate (0.598 g, 65% yield). $^1$H NMR (400 MHz, CDCl$_3$) δ ppm 9.25 (1H, br. s), 8.17 (2H, br. s), 8.02 (1H, br. s), 7.71 (2H, br. s), 7.40 (2H, t, J=7.91 Hz), 7.24 (1H, br. s), 7.03-7.16 (4H, m), 6.62 (1H, br. s), 3.95 (3H, s); MS (ES+) m/z: 423 (M–H); LC retention time: 4.118 min (analytical HPLC Method A).

Step 2:

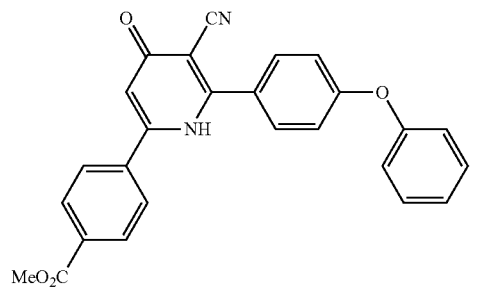

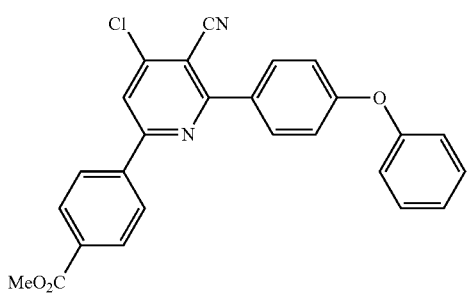

A mixture of methyl 4-(5-cyano-4-oxo-6-(4-phenoxyphenyl)-1,4-dihydropyridin-2-yl)benzoate (598.2 mg, 1.416 mmol) and phosphoryl trichloride (12 mL) was heated to 90° C. for 1 h then concentrated. The residue was dissolved in dichloromethane, washed with water and concentrated. Silica gel chromatography, eluting with 0-20% ethyl acetate in hexanes, gave methyl 4-(4-chloro-5-cyano-6-(4-phenoxyphenyl)pyridin-2-yl)benzoate as white solid (0.5582 g, 89% yield). $^1$H NMR (400 MHz, CDCl$_3$) δ ppm 8.19 (4H, s), 8.01-8.06 (2H, m), 7.89 (1H, s), 7.38-7.44 (2H, m), 7.20 (1H, t, J=7.40 Hz), 7.10-7.17 (4H, m), 3.97 (3H, s), MS (ES+) m/z: 441 (M+H); LC retention time: 4.333 min (analytical HPLC Method A).

Step 3:

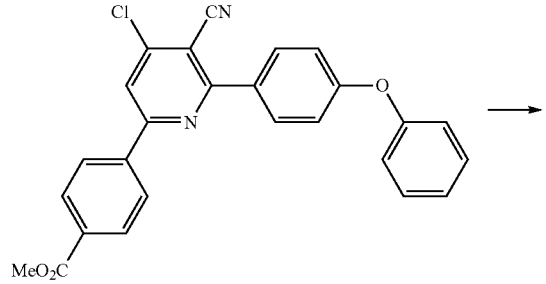

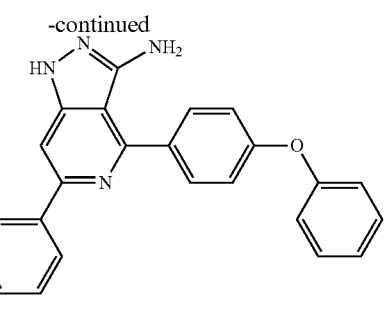

Batch 1: A solution of methyl 4-(4-chloro-5-cyano-6-(4-phenoxyphenyl)pyridin-2-yl)benzoate (52.8 mg, 0.120 mmol) and hydrazine (76 μL, 2.421 mmol) in N,N-dimethylformamide (0.5 mL) was stirred room temperature for 2.5 h and concentrated. Batch 2: A solution of methyl 4-(4-chloro-5-cyano-6-(4-phenoxyphenyl)pyridin-2-yl)benzoate (266.5 mg, 0.604 mmol) and hydrazine (190 μL, 6.06 mmol) in N,N-dimethylformamide (3 mL) was stirred room temperature for 3 days and concentrated. LCMS analysis showed that the starting material disappeared in both batches, but with mixtures of cyclized and un-cyclized products. The two batches were combined, dissolved in methanol (4 mL) and TFA (2 mL), stirred at room temperature for 2 h and concentrated. The residue was treated with dichloromethane (6 mL) and stirred overnight to give a suspension. The mixture was filtered and the filtrate was concentrated and purified by silica gel chromatography, eluting with 0-8% methanol in dichloromethane, to give Example 192 as yellow solid (0.3146 g, 99% yield). $^1$H NMR (400 MHz, methanol-d$_4$) δ ppm 8.23 (2H, δ, J=8.53 Hz), 7.98-8.04 (2H, m), 7.88-7.93 (2H, m), 7.83 (1H, s), 7.44-7.51 (2H, m), 7.25-7.30 (3H, m), 7.15-7.20 (2H, m), 3.97 (3H, s); MS (ES+) m/z: 437 (M+H); LC retention time: 3.598 min (analytical HPLC Method A).

Example 193

4-(3-Amino-4-(4-phenoxyphenyl)-1H-pyrazolo[4,3-e]pyridin-6-yl)benzoic acid

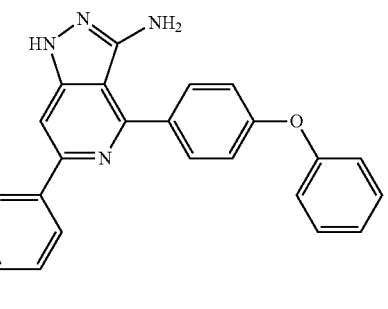

A mixture of methyl 4-(3-amino-4-(4-phenoxyphenyl)-1H-pyrazolo[4,3-c]pyridin-6-yl)benzoate (161.2 mg, 0.369 mmol, from Example 192), 2 M aqueous NaOH (0.5 mL, 1.000 mmol), DMSO (1 mL) and methanol (1 mL) was stirred at room temperature for 1 h. Solid NaOH (50 mg) was added. After additional 4 h at room temperature, the methanol solvent was evaporated in vacuo. The residue was neutralized to pH 5-6 with 1 N HCl. The solid was collected by filtration to give Example 193 as light brown solid (118.5 mg, 76% yield). $^1$H NMR (400 MHz, methanol-$d_4$) δ ppm 8.16-8.20 (2H, m), 8.11-8.15 (2H, m), 7.82-7.86 (2H, m), 7.73 (1H, s), 7.40-7.45 (2H, m), 7.16-7.22 (3H, m), 7.13 (2H, dd, J=8.78, 1.00 Hz); MS (ES+) 111/Z: 423 (M+H); LC retention time: 3.306 min (analytical HPLC Method A).

Example 194

4-(3-Amino-4-(4-phenoxyphenyl)-1H-pyrazolo[4,3-c]pyridin-6-yl)benzohydrazide

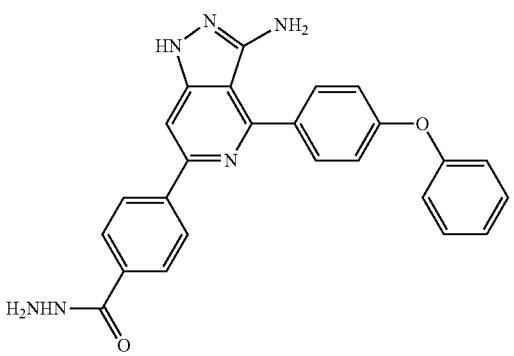

A solution of methyl 4-(3-amino-4-(4-phenoxyphenyl)-1H-pyrazolo[4,3-c]pyridin-6-yl)benzoate (28 mg, 0.064 mmol, from Example 192) and hydrazine (20 μL 0.637 mmol) in N,N-dimethylformamide (0.5 mL) was stirred at 100° C. for 3 h. LC-MS showed that only small amount of the desired product was formed. A 35% aqueous solution of hydrazine (0.5 mL) was added. After additional 1 h at 100° C., the mixture was cooled to give a suspension. Water was added and the mixture filtered. The solid was washed with water, dried under vacuum to give Example 194 (19 mg, 67% yield). $^1$H NMR (400 MHz, methanol-$d_4$) δ ppm 8.18 (2H, δ, J=8.53 Hz), 7.91 (2H, δ, J=8.53 Hz), 7.81-7.85 (2H, m), 7.71 (1H, s), 7.42 (2H, t, J=8.03 Hz), 7.16-7.22 (3H, m), 7.13 (2H, dd, J=8.66, 1.13 Hz); MS (ES+) m/z: 437 (M+H); LC retention time: 2.801 min (analytical HPLC Method A).

Example 195

(4-(3-Amino-4-(4-phenoxyphenyl)-1H-pyrazolo[4,3-c]pyridin-6-yl)phenyl)methanol

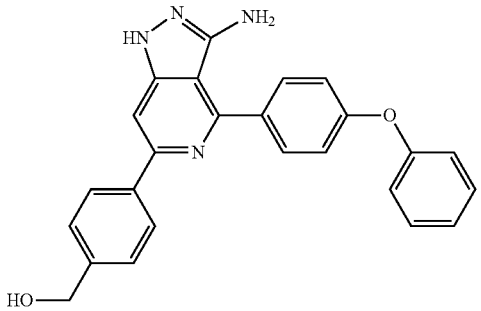 [SMILES: Nc1n[nH]c2cc(-c3ccc(CO)cc3)nc(-c3ccc(Oc4ccccc4)cc3)c12]

A 1 M THF solution of lithium aluminum hydride (0.15 mL, 0.150 mmol) was added to a solution of 4-(3-amino-4-(4-phenoxyphenyl)-1H-pyrazolo[4,3-c]pyridin-6-yl)benzoic acid (12.1 mg, 0.029 mmol, from Example 193) in THF (0.5 mL) at room temperature for 16 h, quenched with saturated ammonium chloride and extracted with ethyl acetate. The organic phase was concentrated and purified by reverse phase HPLC (Sunfire S10 30×250 mm column), eluting with 45-75% solvent B (10% methanol-0.90% water-0.1% TFA) in solvent A (90% methanol-10% water-0.1% TFA), to give Example 195 as yellow solid (4.5 mg). $^1$H NMR (400 MHz, methanol-$d_4$) δ ppm 7.88-7.92 (2H, m), 7.85 (2H, δ, J=8.28 Hz), 7.75 (1H, s), 7.61 (2H, δ, J=8.28 Hz), 7.47 (2H, t, J=8.03 Hz), 7.28 (3H, δ, J=8.53 Hz), 7.16-7.20 (2H, m), 4.73 (2H, s); MS (ES+) m/z: 409 (M+H); LC retention time: 3.121 min (analytical HPLC Method A).

Example 196 tert-Butyl N-(4-(3-amino-4-(4-phenoxyphenyl)-1H-pyrazolo[4,3-c]pyridin-6-yl)benzoyl)glycinate

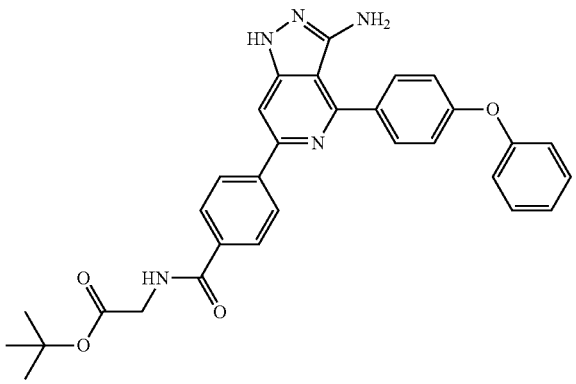 [SMILES: CC(C)(C)OC(=O)CNC(=O)c1ccc(-c2cc3[nH]nc(N)c3c(-c3ccc(Oc4ccccc4)cc3)n2)cc1]

A solution of 4-(3-amino-4-(4-phenoxyphenyl)-1H-pyrazolo[4,3-c]pyridin-6-yl)benzoic acid TFA salt (20.9 mg, 0.039 mmol, from Example 193), tert-butyl 2-aminoacetate (19.2 mg, 0.146 mmol), N-(3-dimethylaminopropyl)N'-methylcarbodiimide hydrochloride (23.4 mg, 0.122 mmol) and 4-(N,N-dimethylamino)pyridine (10.7 mg, 0.088 mmol) in N,N-dimethylformamide (0.45 mL) was stirred at room temperature for 3.5 h, diluted with small amount of water and methanol and filtered. Purification by reverse phase HPLC (Sunfire S10 30×250 mm column), eluting with 60-90% solvent B (10% methanol-90% water-0.1% TFA) in solvent A (90% methanol-10% water-0.1% TFA), gave Example 196 as yellow solid (12.4 mg, 41% yield). $^1$H NMR (400 MHz, methanol-$d_4$) δ ppm 8.09 (2H, δ, J=8.28 Hz), 7.99 (2H, δ, J=8.28 Hz), 7.91 (2H, δ, J=8.78 Hz), 7.84 (1H, s), 7.47 (2H, t, J=7.91 Hz), 7.24-7.31 (3H, m), 7.17 (2H, δ, J=8.03 Hz), 4.05 (2H, s), 1.50 (9H, s); MS (ES+) m/z: 536 (M+H); LC retention time: 3.505 min (analytical HPLC Method A).

Example 197

6-(4-(4-Morpholinylcarbonyl)phenyl)-4-(4-phenoxyphenyl)-1H-pyrazolo[4,3-c]pyridin-3-amine

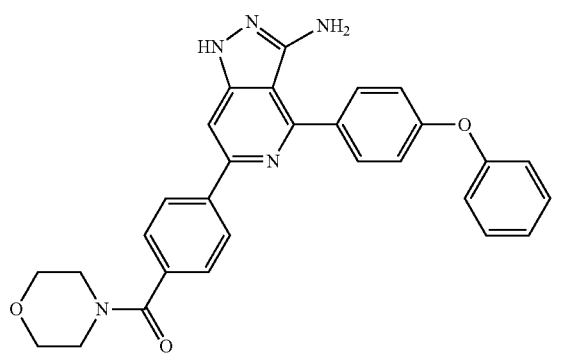 [SMILES: Nc1n[nH]c2cc(-c3ccc(C(=O)N4CCOCC4)cc3)nc(-c3ccc(Oc4ccccc4)cc3)c12]

A mixture of methyl 4-(3-amino-4-(4-phenoxyphenyl)-1H-pyrazolo[4,3-c]pyridin-6-yl)benzoate (18 mg, 0.041 mmol, from Example 192) and morpholine (0.359 mL) was stirred at 100° C. for 6 h, at 150° C. for 17 h, then concentrated. Purification by reverse phase HPLC (Sunfire S10 30×250 min column), eluting with 45-75% solvent B (10% methanol-90% water-0.1% TFA) in solvent A (90% methanol-10% water-0.1% TFA), gave Example 197 as yellow solid (1.5 mg, 5% yield). $^1$H NMR (500 MHz, methanol-$d_4$) δ ppm 7.97 (2H, δ, J=8.25 Hz), 7.89-7.93 (2H, m), 7.81 (1H, s), 7.67 (2H, δ, J=7.97 Hz), 7.48 (2H, dd, J=8.52, 7.42 Hz), 7.24-7.31 (3H, m), 7.18 (2H, 6, J=7.70 Hz), 3.80 (4H, br. s), 3.65 (2H, br. s), 3.49 (2H, br. s); MS (ES+) m/z: 492 (M+H); LC retention time: 3.135 min (analytical HPLC Method A).

Example 198

4-(3-Amino-4-(4-phenoxyphenyl)-1H-pyrazolo[4,3-c]pyridin-6-yl)-N-(2-hydroxyethyl)benzamide

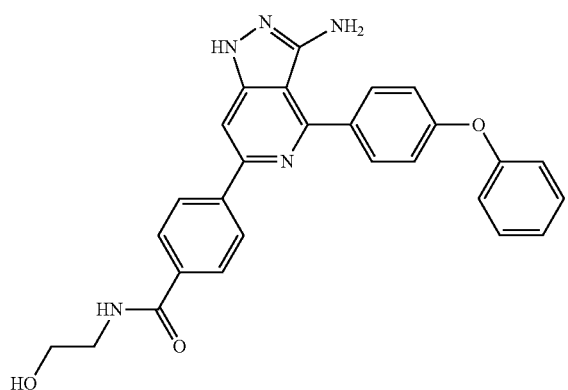 [SMILES: Nc1n[nH]c2cc(-c3ccc(C(=O)NCCO)cc3)nc(-c3ccc(Oc4ccccc4)cc3)c12]

A solution of methyl 4-(3-amino-4-(4-phenoxyphenyl)-1H-pyrazolo[4,3-c]pyridin-6-yl)benzoate (19 mg, 0.044 mmol, from Example 192) and 2-aminoethanol (52 μL, 0.862 mmol) in N,N-dimethylacetamide (0.3 mL) was stirred at 150° C. for 5 h. The mixture was diluted with water (1 mL), methanol (0.5 mL) and filtered. Purification by reverse phase HPLC (Sunfire S10 30×250 mm column), eluting with 45-75% solvent B (10% methanol-90% water-0.1% TFA) in solvent A (90% methanol-10% water-0.1% TFA), gave Example 198 as yellow solid (5.4 mg, 18% yield). $^1$H NMR (500 MHz, methanol-$d_4$) δ ppm 8.07 (2H, δ, J=8.52 Hz), 7.98 (2H, δ, J=8.52 Hz), 7.89-7.92 (2H, m), 7.82 (1H, s), 7.47 (2H, t, J=8.11 Hz), 7.25-7.30 (3H, 7.18 (2H, δ, J=7.70 Hz), 3.74 (2H, δ, J=5.77 Hz), 3.55 (2H, t, J=5.77 Hz); MS (ES+) m/z: 466 (M+H); LC retention time: 3.030 min (analytical HPLC Method A).

Example 199

6-(4-Aminophenyl)-4-(4-phenoxyphenyl)-1H-pyrazolo[4,3-c]pyridin-3-amine

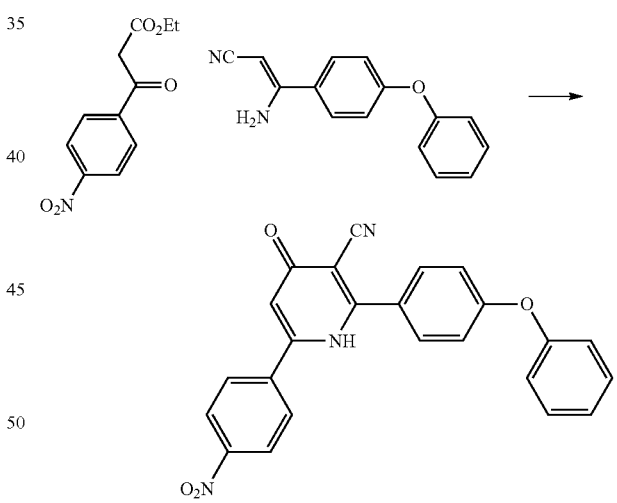

Step 1:

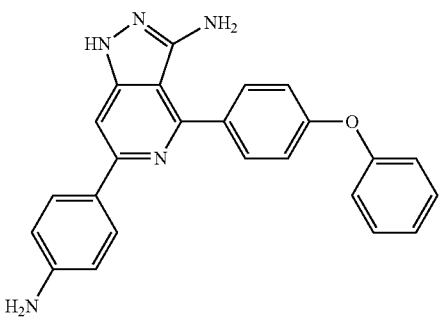 [SMILES: Nc1ccc(-c2cc3[nH]nc(N)c3c(-c3ccc(Oc4ccccc4)cc3)n2)cc1]

A mixture of 3-amino-3-(4-phenoxyphenyl)acrylonitrile (101 mg, 0.427 mmol) and ethyl 3-(4-nitrophenyl)-3-oxopropanoate (312.8 mg, 1.319 mmol) in N,N-dimethylacetamide (1 mL) was microwaved at 230° C. for 20 min, cooled to room temperature, and concentrated. Silica gel chromatography, eluting with 0-5% methanol in dichloromethane, gave 6-(4-nitrophenyl)-4-oxo-2-(4-phenoxyphenyl)-1,4-dihydropyridine-3-carbonitrile as brown solid (211 mg, 100% yield). $^1$H NMR (400 MHz, CDCl$_3$) δ ppm 8.31 (2H, δ, J=8.78 Hz), 8.19 (2H, br. s), 7.96 (2H, br. s), 7.39 (2H, t, J=7.91 Hz), 7.18 (1H, t, J=7.40 Hz), 7.06-7.13 (3H, m); MS (ES+) m/z: 410 (M+H); LC retention time: 4.275 min (analytical HPLC Method A).

Step 2:

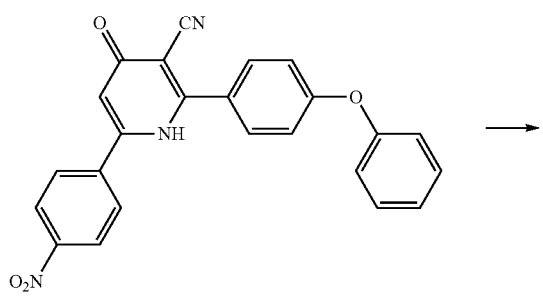

A mixture of 6-(4-nitrophenyl)-4-oxo-2-(4-phenoxyphenyl)-1,4-dihydropyridine-3-carbonitrile (211 mg, 0.515 mmol) and phosphoryl trichloride (1 mL, 10.92 mmol) was heated to 95° C. for 30 min, then concentrated. The residue was dissolved in dichloromethane (2 mL) and washed with saturated sodium bicarbonate. Silica gel chromatography, eluting with 0-100% ethyl acetate in hexanes, gave 4-chloro-6-(4-nitrophenyl)-2-(4-phenoxyphenyl)nicotinonitrile as white solid (136.3 mg, 62% yield). $^1$H NMR (400 MHz, CDCl$_3$) δ ppm 8.35-8.41 (2H, m), 8.27-8.33 (2H, m), 8.00-8.06 (2H, m), 7.91 (1H, s), 7.38-7.46 (2H, m), 7.21 (1H, t, J=7.40 Hz), 7.10-7.18 (4H, m); MS (ES+) m/z: 428 (M+14); LC retention time: 4.141 min (analytical HPLC Method A).

Step 3:

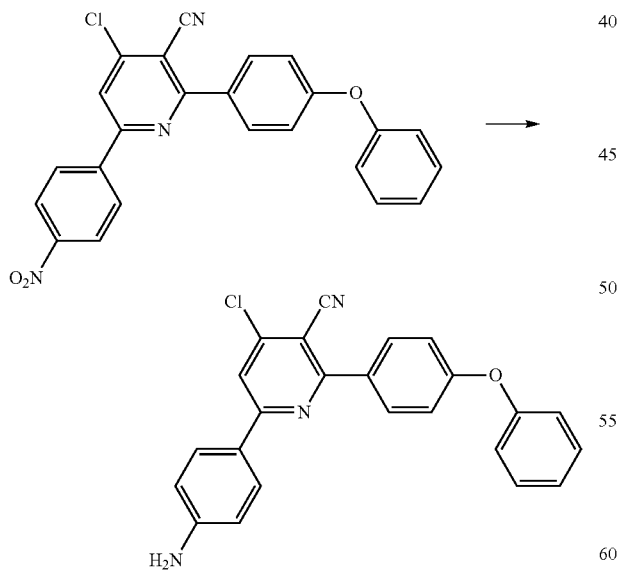

A mixture of 4-chloro-6-(4-nitrophenyl)-2-(4-phenoxyphenyl)nicotinonitrile (136.3 mg, 0.319 mmol), zinc dust (312 mg, 4.78 mmol), ammonium chloride (256 mg, 4.78 mmol), THF (3 mL) and methanol (3 mL) was stirred at room temperature for 15 min, and filtered. The filtrate was concentrated and partitioned with dichloromethane and saturated sodium bicarbonate. The organic layer was separated and concentrated. Silica gel chromatography, eluting with 0-40% ethyl acetate in hexanes, gave pure 6-(4-aminophenyl)-4-chloro-2-(4-phenoxyphenyl)nicotinonitrile as yellow solid (51 mg). $^1$H NMR (400 MHz, CDCl$_3$) δ ppm 7.96-8.04 (4H, m), 7.70 (1H, s), 7.40 (2H, t, J=8.03 Hz), 7.18 (1H, t, J=7.40 Hz), 7.08-7.14 (4H, m), 6.76 (2H, δ, J=8.78 Hz), 4.04 (2H, s); MS (ES+) m/z: 398 (M+H); LC retention time: 4.551 min (analytical HPLC Method A). Additional impure product was also obtained from the chromatography (48.1 mg).

Step 4:

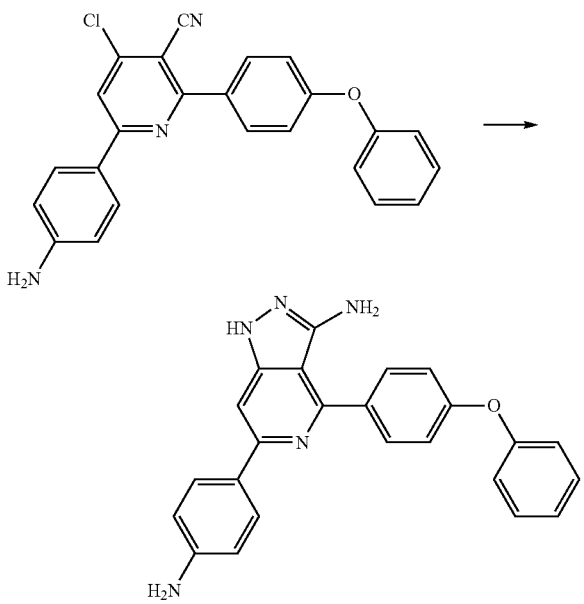

A solution of 6-(4-aminophenyl)-4-chloro-2-(4-phenoxyphenyl)nicotinonitrile (13.1 mg, 0.033 mmol) and hydrazine (40 μL, 1.273 mmol) in N,N-dimethylacetamide (0.25 mL) was heated to 150° C. in a sealed tube for 2 h, cooled to room temperature and diluted with water. The precipitate was filtration, washed with water and dried. Further purification with silica gel chromatography, eluting with 0-8% methanol in dichloromethane, gave Example 199 as white solid (6.1 mg, 47% yield). $^1$H NMR (400 MHz, methanol-d$_4$) δ ppm 7.80 (4H, t, J=8.41 Hz), 7.45 (1H, s), 7.42 (2H, t, Hz), 7.15-7.21 (3H, m), 7.12 (2H, δ, J=8.78 Hz), 6.80 (2H, δ, J=8.53 Hz); MS (ES+) m/z: 394 (M+H); LC retention time: 2.960 min (analytical HPLC Method A).

Example 200

N-(4-(3-Amino-4-(4-phenoxyphenyl)-1H-pyrazolo[4,3-c]pyridin-6-yl)phenyl)acetamide

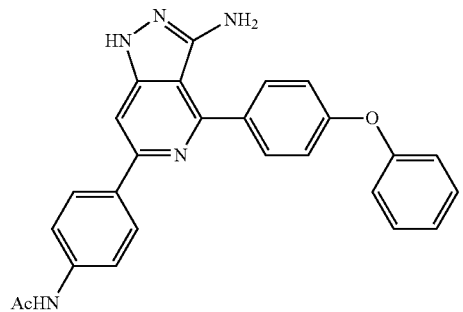

Step 1:

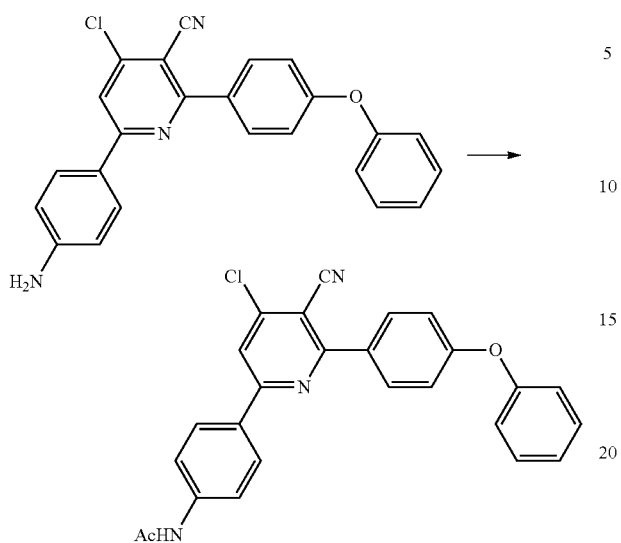

Acetyl chloride (0.013 mL, 0.181 mmol) was added to a suspension of 6-(4-aminophenyl)-4-chloro-2-(4-phenoxyphenyl)nicotinonitrile (48 mg, 0.121 mmol, from Step 3 of Example 199) and Hunig's base (0.084 mL, 0.483 mmol) in dichloromethane (1 mL) at room temperature. After 90 min at room temperature, additional acetyl chloride (0.05 mL) was added. After additional 23 h, the reaction was stopped and the mixture purified by silica gel chromatography, eluting with 0-60% ethyl acetate in hexanes, to give N-(4-(4-chloro-5-cyano-6-(4-phenoxyphenyl)pyridin-2-yl)phenyl)acetamide as yellow solid (24.9 mg, 47% yield). $^1$H NMR (400 MHz, CDCl$_3$) δ ppm 8.11 (2H, δ, J=8.78 Hz), 8.00-8.03 (2H, m), 7.79 (1H, s), 7.68 (2H, δ, J=8.53 Hz), 7.35-7.44 (3H, m), 7.19 (1H, t, J=7.40 Hz), 7.08-7.15 (4H, m), 2.23 (3H, s); MS (ES+) m/z: 440 (M+H); LC retention time: 4.668 min (analytical HPLC Method A). Unreacted starting material was also recovered (13.7 mg).

Step 2:

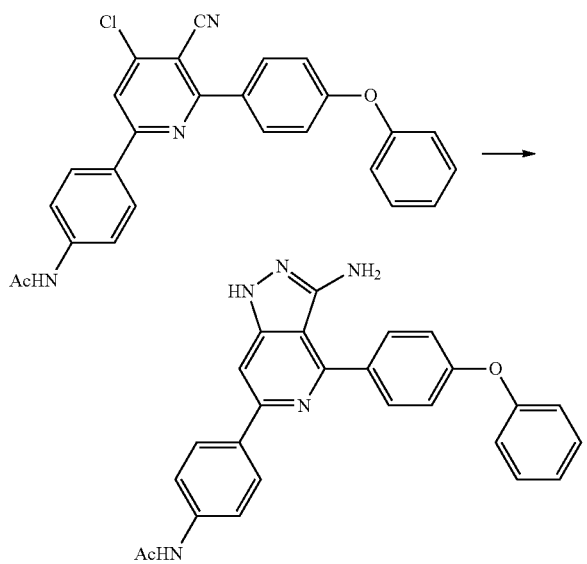

A mixture of N-(4-(4-chloro-5-cyano-6-(4-phenoxyphenyl)pyridin-2-yl)phenyl)acetamide (24.9 mg, 0.057 mmol), 35% aqueous hydrazine (20 μL, 0.637 mmol) and N,N-dimethylformamide (0.5 mL) in a sealed tube was heated to 100° C. for 3 h, 120° C. for 6 h and concentrated. Silica gel chromatography, eluting with 0-10% methanol in dichloromethane, gave the desired product. The material was triturated with dichloromethane and filtered to give Example 200 as light yellow solid (9.4 mg, 38% yield). $^1$H NMR (400 MHz, DMSO-d$_6$) δ ppm 12.20 (1H, s), 10.08 (1H, s), 8.11 (2H, δ, J=8.78 Hz), 7.81-7.84 (2H, m), 7.69 (2H, δ, J=8.78 Hz), 7.63 (1H, s), 7.43-7.48 (2H, m), 7.13-7.23 (5H, m), 4.83 (2H, s), 2.07 (3H, s); MS (ES+) m/z: 436 (M+H); LC retention time: 3.200 min (analytical HPLC Method A).

Example 201

1-(4-(3-Amino-4-(4-phenoxyphenyl)-1H-pyrazolo[4,3-c]pyridin-6-yl)phenyl)-3-phenylurea

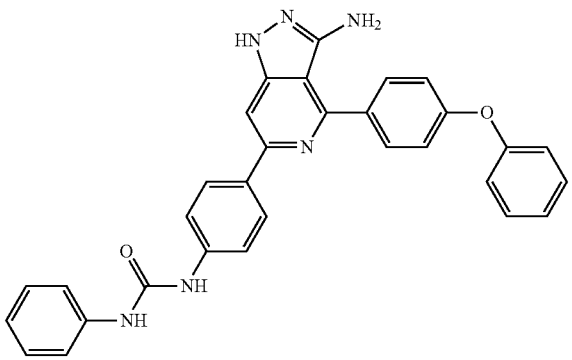 [SMILES: Nc1n[nH]c2cc(-c3ccc(NC(=O)Nc4ccccc4)cc3)nc(-c3ccc(Oc4ccccc4)cc3)c12]

A mixture of 6-(4-aminophenyl)-4-(4-phenoxyphenyl)-1H-pyrazolo[4,3-c]pyridin-3-amine tris-TFA salt (4.3 mg, 5.85 mol, from Example 199), Hunig's base (10 μL, 0.057 mmol) and phenyl isocyanate (2 μL, 0.018 mmol) in dichloromethane (0.3 mL) was stirred at room temperature for a total of 46 h, with addition of two more batches of phenyl isocyanate (2 μL each) at 4.5 h and 23 h time points. The mixture was concentrated, dissolved in methanol and purified by reverse phase HPLC (Sunfire S10 30×250 mm column), eluting with 60-90% solvent B (10% methanol-90% water-0.1% TFA) in solvent A (90% methanol-10% water-0.1% TFA), to give Example 201 as yellow solid, assumed bis-TFA salt (1.0 mg, 22% yield). $^1$H NMR (500 MHz, methanol-d$_4$) δ ppm 7.88-7.91 (2H, δ, J=8.80 Hz), 7.81 (2H, δ, J=8.80 Hz), 7.70-7.74 (3H, m), 7.44-7.50 (4H, m), 7.26-7.34 (6H, m), 7.18 (2H, δ, J=7.70 Hz); MS (ES+) m/z: 513 (M+H); LC retention time: 3.636 min (analytical HPLC Method A).

Example 202

N-(4-(3-Amino-4-(4-phenoxyphenyl)-1H-pyrazolo[4,3-c]pyridin-6-yl)phenyl)benzamide

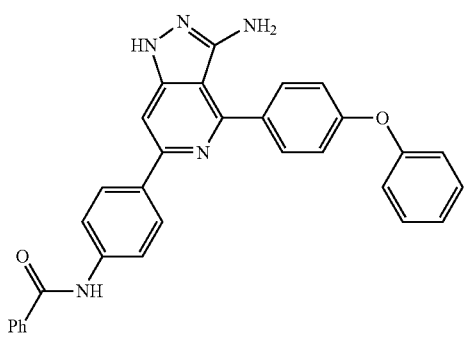 [SMILES: Nc1n[nH]c2cc(-c3ccc(NC(=O)c4ccccc4)cc3)nc(-c3ccc(Oc4ccccc4)cc3)c12]

Step 1:

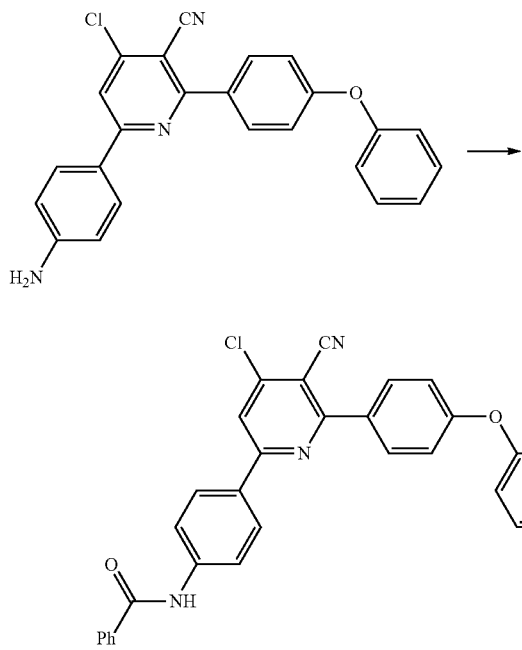

Benzoyl chloride (10 µL, 0.086 mmol was added to a mixture of 6-(4-aminophenyl)-4-chloro-2-(4-phenoxyphenyl)nicotinonitrile (13 mg, 0.033 mmol, from Step 3 of Example 199) and Hunig's base (30 µL, 0.172 mmol) in dichloromethane (0.6 mL). After 16 h at room temperature, the reaction was complete as judged by LCMS analysis. Silica gel chromatography, eluting with 0-50% ethyl acetate in hexanes, gave N-(4-(4-chloro-5-cyano-6-(4-phenoxyphenyl)pyridin-2-yl)phenyl)benzamide as yellow solid (17.6 mg, 100% yield). $^1$H NMR (400 MHz, CDCl$_3$) δ ppm 8.18 (2H, δ, J=8.53 Hz), 8.02-8.06 (2H, m), 7.97 (1H, s), 7.91 (2H, δ, J=7.28 Hz), 7.80-7.87 (3H, m), 7.57-7.63 (1H, m), 7.53 (2H, t, J=7.40 Hz), 7.38-7.44 (2H, m), 7.19 (1H, t, J=7.40 Hz), 7.09-7.17 (4H, m); MS (ES+) m/z: 502 (M+H); LC retention time: 4.923 min (analytical HPLC Method A).

Step 2:

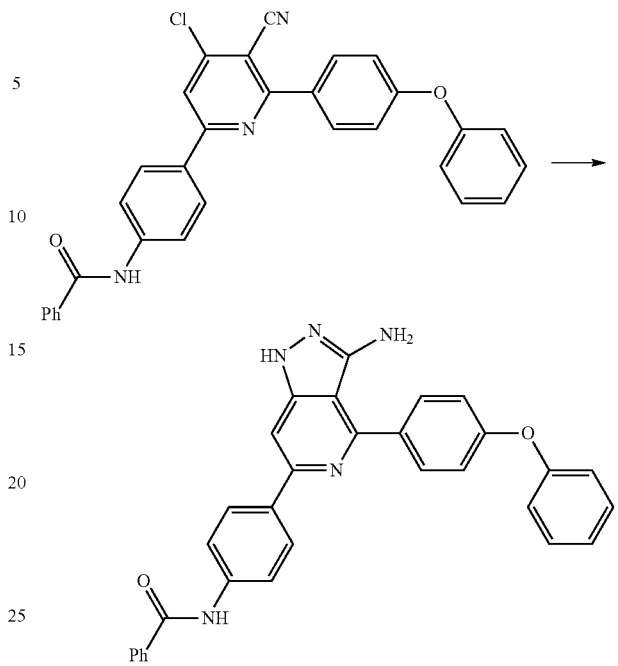

A mixture of N-(4-(4-chloro-5-cyano-6-(4-phenoxyphenyl)pyridin-2-yl)phenyl)benzamide (16.4 mg, 0.033 mmol), 35% aqueous hydrazine (10 µL, 0.318 mmol) and N,N-dimethylformamide (0.3 mL) was heated to 120° C. in a sealed tube for 18 h. N,N-dimethylformamide was evaporated in vacuo. The residue was treated with water to give a suspension. The white solid was collected by filtration and dried under vacuum to give Example 202 as off-white solid (14.9 mg, 82% yield). $^1$H NMR (500 MHz, methanol-d$_4$) δ ppm 8.09 (2H, δ, J=8.80 Hz), 7.96 (2H, δ, J=7.15 Hz), 7.85 (2H, δ, J=8.80 Hz), 7.83 (2H, δ, J=8.52 Hz), 7.63 (1H, s), 7.58-7.62 (1H, m), 7.53 (2H, t, J=7.56 Hz), 7.40-7.45 (2H, m), 7.16-7.21 (3H, m), 7.13 (2H, δ, J=7.70 Hz); MS (ES+) m/z: 498 (M+H); LC retention time: 3.511 min (analytical HPLC Method A).

Examples 203 and 204

1-(4-(3-Amino-4-(4-phenoxyphenyl)-1H-pyrazolo[4,3-c]pyridin-6-yl)phenyl)-3-methylurea, and

N-(4-(3-Amino-4-(4-phenoxyphenyl)-1H-pyrazolo[4,3-c]pyridin-6-yl)phenyl)hydrazinecarboxamide, respectively

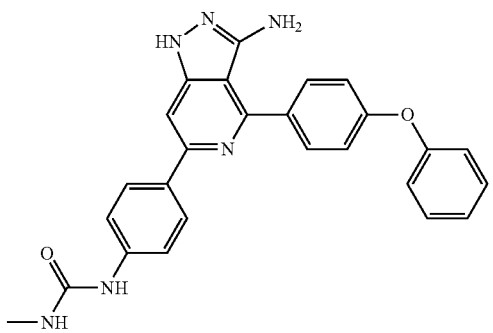

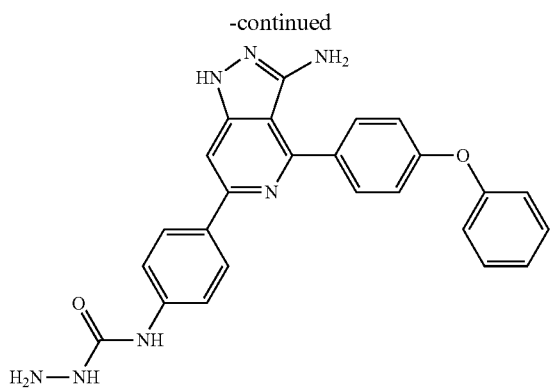

Methyl isocyanate (1.4 mg, 0.025 mmol) was added to a solution of 6-(4-aminophenyl)-4-chloro-2-(4-phenoxyphenyl)nicotinonitrile (10 mg, 0.025 mmol, from Step 3 of Example 199) in THF (0.5 mL) at room temperature. After 18 h at room temperature, LCMS analysis showed that the first step was complete. The mixture was concentrated. The solid residue was treated with hydrazine (40 µL, 1.274 mmol) and N,N-dimethylacetamide (500 µL). The mixture was heated to 120° C. for 6 h and at 150° C. for 1 h. The crude material was diluted with water (0.5 mL) and methanol (1 mL) and purified by reverse phase HPLC (Sunfire S10 30×250 mm column), eluting with 40-70% solvent B (10% methanol-90% water-0.1% TFA) in solvent A (90% methanol-10% water-0.1% TFA). Example 203 was obtained as yellow solid (2.6 mg, 15% yield).

$^{1}$H NMR (400 MHz, methanol-$d_4$) δ ppm 7.88 (2H, δ, J=8.28 Hz), 7.76 (2H, δ, J=8.53 Hz), 7.69 (1H, s), 7.64 (2H, δ, J=8.53 Hz), 7.47 (2H, t, J=7.53 Hz), 7.28 (3H, δ, J=8.28 Hz), 7.17 (2H, δ, J=8.53 Hz), 2.80 (3H, s); MS (ES+) m/z: 451 (M+H); LC retention time: 3.218 min (analytical HPLC Method A). Example 204 was obtained as yellow solid (4.8 mg, 24% yield).

$^{1}$H NMR (400 MHz, methanol-$d_4$) δ ppm 7.89 (2H, dd, J=8.78, 2.51 Hz), 7.80-7.85 (3H, m), 7.71-7.77 (2H, m), 7.47 (2H, t, J=7.91 Hz), 7.28 (3H, δ, J=7.03 Hz), 7.17 (2H, δ, J=8.03 Hz); MS (ES+) m/z: 452 (M+H); LC retention time: 2.796 min (analytical HPLC Method A).

Example 205

4-(4-Phenoxyphenyl)-6-phenyl-1H-pyrazolo[4,3-c]pyridin-3-amine

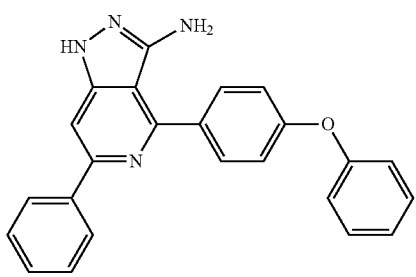 [SMILES: Nc1n[nH]c2cc(-c3ccccc3)nc(-c3ccc(Oc4ccccc4)cc3)c12]

Step 1:

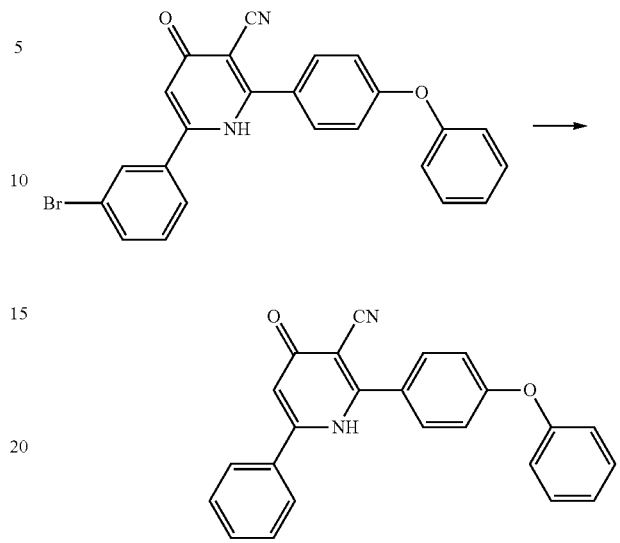

A mixture of 6-(3-bromophenyl)-4-hydroxy-2-(4-phenoxyphenyl)nicotinonitrile (12.9 mg, 0.029 mmol, from Step 1 of Example 172), Pd/C (3.4 mg, 3.19 µmol) in ethanol (1 mL) and N,N-dimethylacetamide (0.1 mL) was hydrogenated in 50 psi hydrogen for 40 min and filtered. The filtrate was concentrated and used in the next reaction without purification.

Step 2:

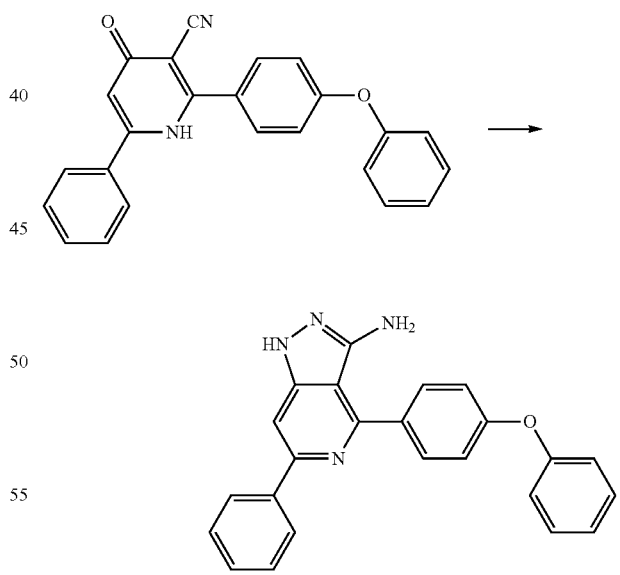

Following conditions similar to Steps 2 and 3 of Example 172, Example 205 was prepared using the crude material from Step 1. $^{1}$H NMR (400 MHz, methanol-$d_4$) δ ppm 7.83-7.92 (4H, m), 7.76 (1H, s), 7.61-7.65 (3H, m), 7.47 (2H, t, J=7.91 Hz), 7.23-7.30 (3H, m), 7.18 (2H, δ, J=7.78 Hz); MS (ES+) m/z: 379 (M+H); LC retention time: 3.236 min (analytical HPLC Method A).

Example 206

6-(4-Aminophenyl)-4-(4-methoxyphenyl)-1H-pyrazolo[4,3-c]pyridin-3-amine

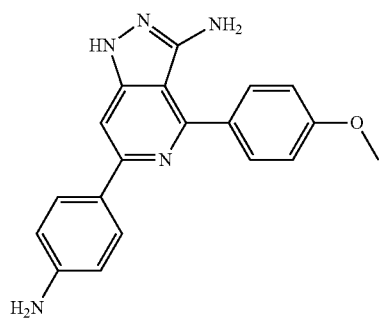 [SMILES: COc1ccc(-c2nc(-c3ccc(N)cc3)cc3[nH]nc(N)c23)cc1]

Example 206 was prepared from tert-butyl 3-(4-acetamidophenyl)-3-oxopropanoate and 3-amino-3-(4-methoxyphenyl)acrylonitrile using conditions similar to Steps 1 to 3 of Example 172. The synthesis of 3-amino-3-(4-methoxyphenyl)acrylonitrile was analogous to Step 1 of Example 152. Characterization of Example 206: $^1$H NMR (400 MHz, DMSO-d$_6$) δ ppm 7.81-7.87 (4H, m), 7.72 (1H, s), 7.25 (3H, δ, J=8.78 Hz), 7.14-7.20 (3H, m), 3.90 (3H, s); MS (ES+) m/z: 332 (M+H); LC retention time: 1.928 min (analytical HPLC Method A).

Example 207

Methyl 3-(3-amino-4-(4-phenoxyphenyl)-1H-pyrazolo[4,3-c]pyridin-6-yl)benzoate

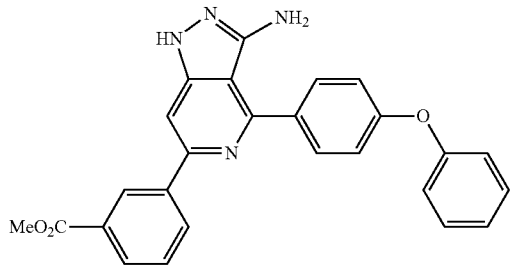 [SMILES: COC(=O)c1cccc(-c2cc3[nH]nc(N)c3c(-c3ccc(Oc4ccccc4)cc3)n2)c1]

Step 1:

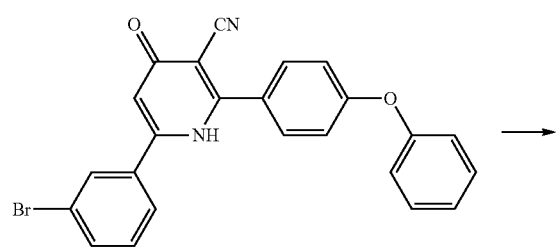

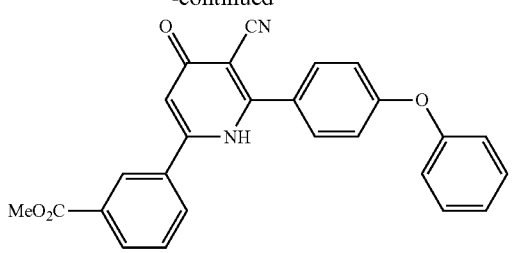

A N,N-dimethylacetamide (0.5 mL) suspension of 6-(3-bromophenyl)-4-hydroxy-2-(4-phenoxyphenyl)nicotinonitrile (46.3 mg, 0.104 mmol, from Step 1 of Example 172), PdCl$_2$(dppf)-dichloromethane adduct (19.1 mg, 0.023 mmol), methanol (120 µL, 2.97 mmol) and TEA (120 µL, 0.861 mmol) in a microwave vial was filled with carbon monoxide and sealed. The vial was microwaved at 120° C. for 30 min then concentrated. Purification by reverse phase HPLC (Sunfire S10 30×250 mm column), eluting with 80-100% solvent B (10% methanol-90% water-0.1% TFA) in solvent A (90% methanol-10% water-0.1% TFA), game methyl 3-(5-cyano-4-hydroxy-6-(4-phenoxyphenyl)pyridin-2-yl)benzoate TFA salt as yellow solid (18.5 mg, 33% yield). $^1$H NMR (400 MHz, CDCl$_3$) δ ppm 8.32 (1H, br. s), 8.16 (1H, br. s), 7.89 (1H, br. s), 7.51-7.79 (3H, m), 7.31-7.43 (2H, m), 6.96-723 (5H, m), 6.88 (1H, br. s), 3.88 (3H, br. s); MS (ES+) m/z: 423 (M+H); LC retention time: 4.071 min (analytical HPLC Method A).

Steps 2 and 3:

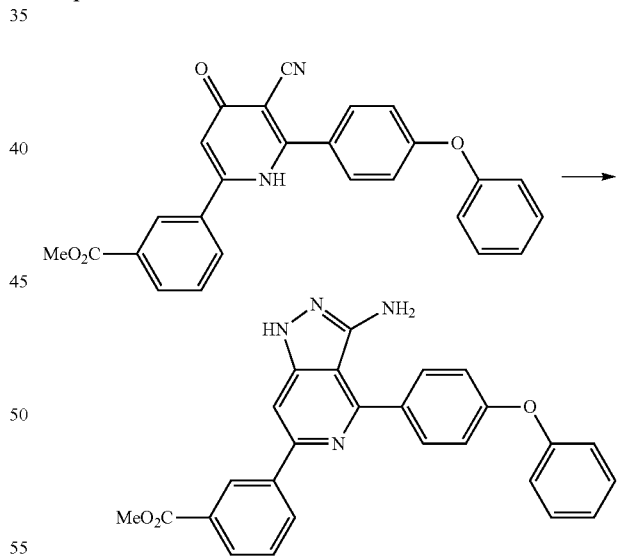

Following conditions similar to Steps 2 and 3 of Example 172, methyl 3-(5-cyano-4-hydroxy-6-(4-phenoxyphenyl)pyridin-2-yl)benzoate was converted to Example 207. $^1$H NMR (400 MHz, CDCl$_3$) δ ppm 8.71 (1H, t, J=1.63 Hz), 8.38 (1H, dt, J=7.78, 1.51 Hz), 8.07 (1H, ddd, J=7.91, 1.38, 1.26 Hz), 7.82-7.88 (2H, m), 7.63 (1H, s), 7.55 (1H, t, J=7.78 Hz), 7.35-7.44 (2H, m), 7.14-7.22 (3H, m), 7.08-7.14 (2H, m), 3.97 (3H, s); MS (ES+) m/z: 437 (M+H); LC retention time: 3.460 min (analytical HPLC Method A).

Example 208

3-(3-Amino-4-(4-phenoxyphenyl)-1H-pyrazolo[4,3-c]pyridin-6-yl)benzoic acid

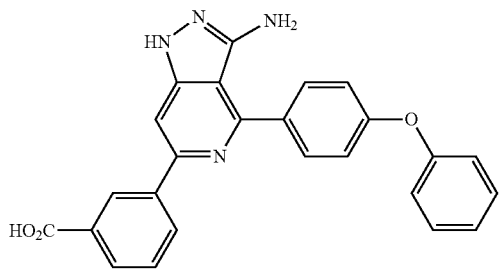 [SMILES: Nc1n[nH]c2cc(-c3cccc(C(=O)O)c3)nc(-c3ccc(Oc4ccccc4)cc3)c12]

Following conditions described for synthesis of Example 193, Example 207 was hydrolyzed to give Example 208. $^1$H NMR (500 MHz, methanol-$d_4$) δ ppm 8.50 (1H, t, J=1.65 Hz), 8.25-8.29 (1H, m), 8.07-8.11 (1H, m), 7.88-7.92 (2H, m), 7.82 (1H, s), 7.74 (1H, t, J=7.84 Hz), 7.44-7.49 (2H, m), 7.24-7.31 (3H, m), 7.15-7.19 (2H, m); MS (ES+) m/z: 423 (M+H); LC retention time: 3.233 min (analytical HPLC Method A).

Examples 209 to 219

Example 209 was prepared from methyl 3-oxo-3-(pyridin-3-yl)propanoate and 3-amino-3-(4-methoxyphenyl)acrylonitrile following conditions similar to Steps 1 to 3 of Example 172. Example 210 was prepared from Example 209 following conditions similar to synthesis of Example 131. Example 211 was prepared from Example 174 following conditions similar to Step 3 of Example 199. Example 212 was prepared from Example 211 following conditions described for Example 201. Examples 213 and 214 were prepared by coupling appropriate amines with Example 208, following conditions similar to synthesis of Example 196. Example 215 was prepared from ethyl 3-oxo-3-phenylpropanoate and 3-amino-3-phenylacrylonitrile following conditions similar to Steps 1 to 3 of Example 172. Examples 216 and 217 were prepared from Example 193 and appropriate amines following similar conditions in the synthesis of Example 196. Example 218 was prepared from Example 207 following conditions described for the synthesis of Example 195. Example 219 was prepared from Example 196 by treatment with acid.

| Example No. | Structure | Spectral data* |
|---|---|---|
| Example 209:<br>4-(4-Methoxyphenyl)-6-(3-pyridinyl)-1H-pyrazolo[4,3-c]pyridin-3-amine | | $^1$H NMR (400 MHz, methanol-$d_4$) δ ppm 9.24 (1 H, δ, J = 1.76 Hz), 8.87 (1 H, dd, J = 5.27, 1.25 Hz), 8.69 (1 H, ddd, J = 8.47, 1.82, 1.51 Hz), 7.91-7.94 (1 H, m), 7.89-7.90 (1 H, m), 7.85-7.89 (2 H, m), 7.24-7.29 (2 H, m), 3.95 (3 H, s); MS (ES+) m/z: 318 (M + H); LC retention time: 1.910 min. |
| Example 210:<br>4-(3-Amino-6-(3-pyridinyl)-1H-pyrazolo[4,3-c]pyridin-4-yl)phenol | | $^1$H NMR (400 MHz, methanol-$d_4$) δ ppm 9.50 (1 H, δ, J = 1.51 Hz), 9.04-9.11 (2 H, m), 8.28 (1 H, dd, J = 7.78, 6.02 Hz), 8.00 (1 H, s), 7.82-7.86 (2 H, m), 7.12-7.16 (2 H, m); MS (ES+) m/z: 304 (M + H); LC retention time: 1.403 min. |
| Example 211:<br>6-(3-Aminophenyl)-4-(4-phenoxyphenyl)-1H-pyrazolo[4,3-c]pyridin-3-amine | | $^1$H NMR (500 MHz, methanol-$d_4$) δ ppm 7.76-7.80 (2 H, m), 7.53 (1 H, s), 7.38-7.44 (3 H, m), 7.33 (1 H, δ, J = 8.25 Hz), 7.20 (1 H, t, J = 7.70 Hz), 7.14-7.18 (3 H, m), 7.11 (2 H, δ, J = 7.42 Hz), 6.78 (1 H, dd); MS (ES+) m/z: 394 (M + H); LC retention time: 2.818 min. |

| Example No. | Structure | Spectral data* |
|---|---|---|
| Example 212: 1-(3-(3-Amino-4-(4-phenoxyphenyl)-1H-pyrazolo[4,3-c]pyridin-6-yl)phenyl)-3-phenylurea | 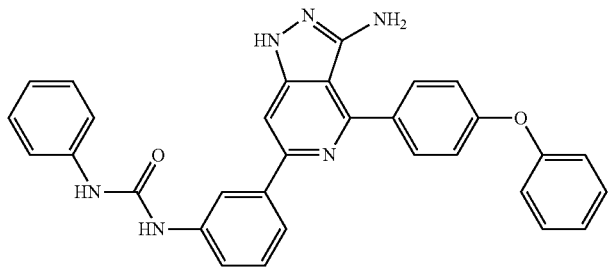 [SMILES: Nc1n[nH]c2cc(-c3cccc(NC(=O)Nc4ccccc4)c3)nc(-c3ccc(Oc4ccccc4)cc3)c12] | $^1$H NMR (400 MHz, methanol-$d_4$) δ ppm 8.14 (1 H, t, J = 1.76 Hz), 7.87-7.92 (2 H, m), 7.77 (1 H, s), 7.43-7.55 (8 H, m), 7.25-7.33 (6 H, m), 7.15-7.20 (2 H, m), 7.05 (1 H, t, J = 7.40 Hz); MS (ES+) m/z: 513 (M + H); LC retention time: 3.680 min. |
| Example 213: 3-(3-Amino-4-(4-phenoxyphenyl)-1H-pyrazolo[4,3-c]pyridin-6-yl)-N-cyclopropylbenzamide | 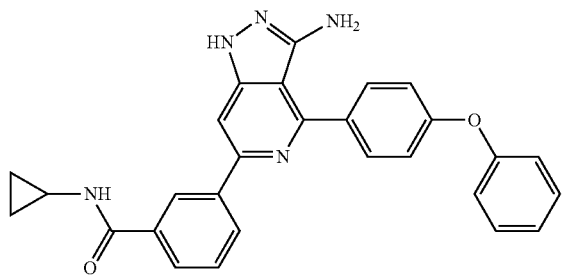 [SMILES: Nc1n[nH]c2cc(-c3cccc(C(=O)NC4CC4)c3)nc(-c3ccc(Oc4ccccc4)cc3)c12] | $^1$H NMR (400 MHz, methanol-$d_4$) δ ppm 8.48 (1 H, s), 8.23 (1 H, δ, J = 7.78 Hz), 7.80-7.86 (3 H, m), 7.70 (1 H, s), 7.57 (1 H, t, J = 7.78 Hz), 7.42 (2 H, t, J = 7.91 Hz), 7.16-7.22 (3 H, m), 7.13 (2 H, δ, J = 8.53 Hz), 2.84-2.92 (1 H, m), 0.80-0.87 (2 H, m), 0.63-0.70 (2 H, m); MS (ES+) m/z: 462 (M + H); LC retention time: 3.226 min. |
| Example 214: 3-(3-Amino-4-(4-phenoxyphenyl)-1H-pyrazolo[4,3-c]pyridin-6-yl)-N-(methylsulfonyl)benzamide | 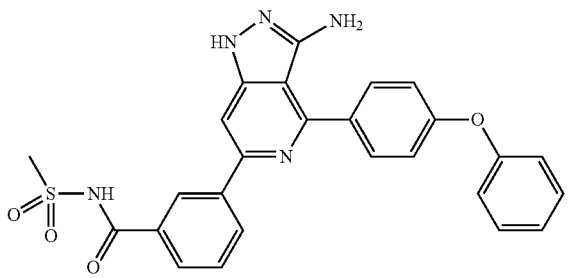 [SMILES: CS(=O)(=O)NC(=O)c1cccc(-c2cc3[nH]nc(N)c3c(-c3ccc(Oc4ccccc4)cc3)n2)c1] | $^1$H NMR (500 MHz, methanol-$d_4$) δ ppm 8.41 (1 H, s), 8.14 (2 H, dt, J = 7.90, 1.68 Hz), 7.90 (2 H, δ, J = 8.52 Hz), 7.84 (1 H, s), 7.78 (1 H, t, J = 7.84 Hz), 7.47 (2 H, t, J = 7.84 Hz), 7.26-7.31 (3 H, m), 7.17 (2 H, δ, J = 7.97 Hz), 3.41 (3 H, s); MS (ES+) m/z: 5-- (M + H); LC retention time: 3.128 min. |
| Example 215: 4,6-Diphenyl-1H-pyrazolo[4,3-c]pyridin-3-amine | 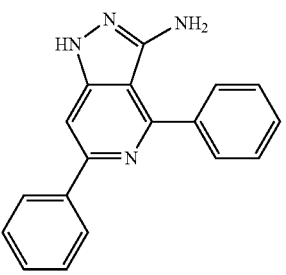 [SMILES: Nc1n[nH]c2cc(-c3ccccc3)nc(-c3ccccc3)c12] | $^1$H NMR (400 MHz, methanol-$d_4$) δ ppm 7.88-7.92 (2 H, m), 7.84-7.88 (2 H, m), 7.73-7.81 (4 H, m), 7.61-7.65 (3 H, m); MS (ES+) m/z: 287 (M + H); LC retention time: 2.280 min. |
| Example 216: 4-(3-Amino-4-(4-phenoxyphenyl)-1H-pyrazolo[4,3-c]pyridin-6-yl)-N-methylbenzamide | 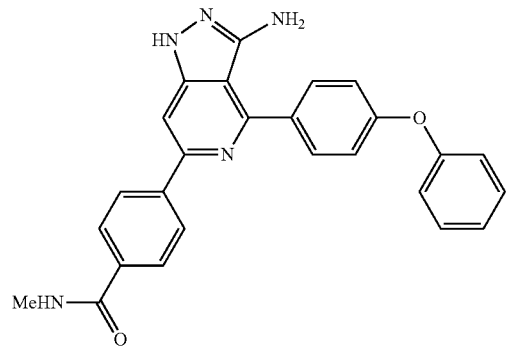 [SMILES: CNC(=O)c1ccc(-c2cc3[nH]nc(N)c3c(-c3ccc(Oc4ccccc4)cc3)n2)cc1] | $^1$H NMR (400 MHz, methanol-$d_4$) δ ppm 8.02-8.07 (2 H, m), 7.95-8.00 (2 H, m), 7.90 (2 H, δ, J = 8.78 Hz), 7.82 (1 H, s), 7.47 (2 H, t, J = 7.91 Hz), 7.24-7.31 (3 H, m), 7.15-7.20 (2 H, m), 2.96 (3 H, s); MS (ES+) m/z: 436 (M + H); LC retention time: 3.090 min. |

| Example No. | Structure | Spectral data* |
|---|---|---|
| Example 217:<br>4-(3-Amino-4-(4-phenoxyphenyl)-1H-pyrazolo[4,3-c]pyridin-6-yl)-N-1H-tetrazol-5-ylbenzamide | | ¹H NMR (500 MHz, methanol-d₄) δ ppm 8.28 (2 H, δ, J = 8.52 Hz), 8.08 (2 H, δ, J = 8.52 Hz), 7.92 (2 H, δ, J = 8.80 Hz), 7.86 (1 H, s), 7.48 (2 H, t, J = 7.97 Hz), 7.27-7.30 (3 H, m), 7.18 (2 H, δ, J = 7.70 Hz); MS (ES+) m/z: 490 (M + H); LC retention time: 3.213 min. |
| Example 218:<br>(3-(3-Amino-4-(4-phenoxyphenyl)-1H-pyrazolo[4,3-c]pyridin-6-yl)phenyl)methanol | | ¹H NMR (400 MHz, methanol-d₄) δ ppm 7.88-7.92 (2 H, m), 7.85 (1 H, s), 7.74-7.79 (2 H, m), 7.57-7.64 (2 H, m), 7.44-7.51 (2 H, m), 7.24-7.30 (3 H, m), 7.15-7.20 (2 H, m), 4.75 (2 H, s); MS (ES+) m/z: 409 (M + H); LC retention time: 3.080 min. |
| Example 219:<br>N-(4-(3-Amino-4-(4-phenoxyphenyl)-1H-pyrazolo[4,3-c]pyridin-6-yl)benzoyl)glycine | | ¹H NMR (400 MHz, methanol-d₄) δ ppm 8.09 (2 H, d, J = 7.53 Hz), 7.99 (2 H, d, J = 7.53 Hz), 7.91 (2 H, d, J = 8.28 Hz), 7.83 (1 H, s), 7.47 (2 H, t, J = 7.78 Hz), 7.24-7.31 (3 H, m), 7.17 (2 H, d, J = 8.03 Hz), 4.14 (2 H, s); MS (ES+) m/z: 480.2 (M + H); LC retention time: 2.976 min. |

*Analytical HPLC Method A

Example 220

3-(3-Amino-4-(4-phenoxyphenyl)-1H-pyrazolo[4,3-c]pyridin-6-yl)-N-1,3,4-thiadiazol-2-ylbenzamide Step 1:

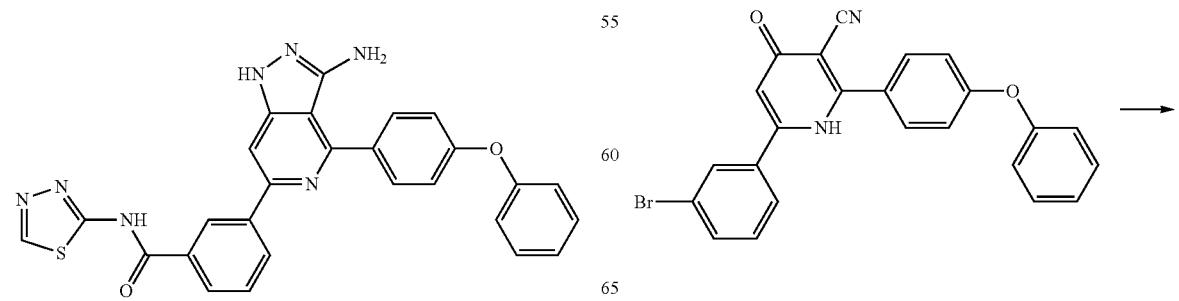

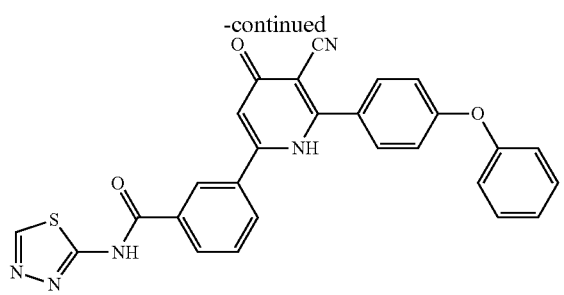

A mixture of 6-(3-bromophenyl)-4-oxo-2-(4-phenoxyphenyl)-1,4-dihydropyridine-3-carbonitrile (25.6 mg, 0.058 mmol, from Step 1 of Example 172), PdCl$_2$(dppf)-dichloromethane adduct (11.8 mg, 0.014 mmol), 1,3,4-thiadiazol-2-amine (19.4 mg, 0.192 mmol) and N,N-dimethylacetamide (0.5 mL) was purged with carbon monoxide, sealed in a microwaved vial and microwaved at 110° C. for 15 min. Additional Pd catalyst (11.8 mg) was added. The vial was re-filled with carbon monoxide gas and microwaved at 110° C. for additional 15 min. Another portions of 1,3,4-thiadiazol-2-amine (39 mg) and the Pd catalyst (0.9 mg) were added. The vial was then filled with carbon monoxide gas and microwaved at 110° C. for 30 min. The mixture was concentrated and purified by reverse phase HPLC (Sunfire S10 30×250 mm column), eluting with 70-100% solvent B (10% methanol-90% water-0.1% TFA) in solvent A (90% methanol-10% water-0.1% TFA), to give 3-(5-cyano-4-oxo-6-(4-phenoxyphenyl)-1,4-dihydropyridin-2-yl)-N-(1,3,4-thiadiazol-2-yl)benzamide TFA salt (8.0 mg, 42% yield). $^1$H NMR (400 MHz, methanol-d$_4$) δ ppm 9.15 (1H, br. s), 8.54 (1H, br. s), 8.11-8.18 (2H, m), 7.84-7.92 (2H, m), 7.72-7.78 (1H, m), 7.43 (2H, t, J=7.65 Hz), 7.18-7.25 (1. H, m), 7.13 (3H, dd, J=16.69, 8.16 Hz), 7.02 (1H, s); MS (ES+) m/z: 492 (M+H); LC retention time: 3.948 min (analytical HPLC Method A).

Step 2:

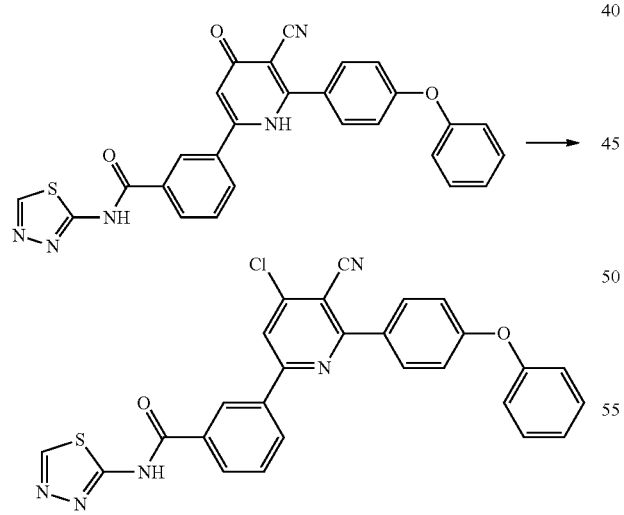

Following conditions similar to Step 2 of Example 172, 3-(5-cyano-4-oxo-6-(4-phenoxyphenyl)-1,4-dihydropyridin-2-yl)-N-(1,3,4-thiadiazol-2-yl)benzamide was concerted to 3-(4-chloro-5-cyano-6-(4-phenoxyphenyl)pyridin-2-yl)-N-(1,3,4-thiadiazol-2-yl)benzamide. $^1$H NMR (400 MHz, CDCl$_3$) δ ppm 8.89 (2H, br. s), 8.52 (1H, br. s), 8.33 (1H, br. s), 8.09 (1H, br. s), 7.96-8.05 (2H, m), 7.76 (1H, br. s), 7.37-7.45 (2H, m), 7.17-7.23 (1H, m), 7.13 (4H, δ, J=7.78 Hz); MS (ES+) m/z: 510 (M+H); LC retention time: 4.743 min (analytical HPLC Method A).

Step 3:

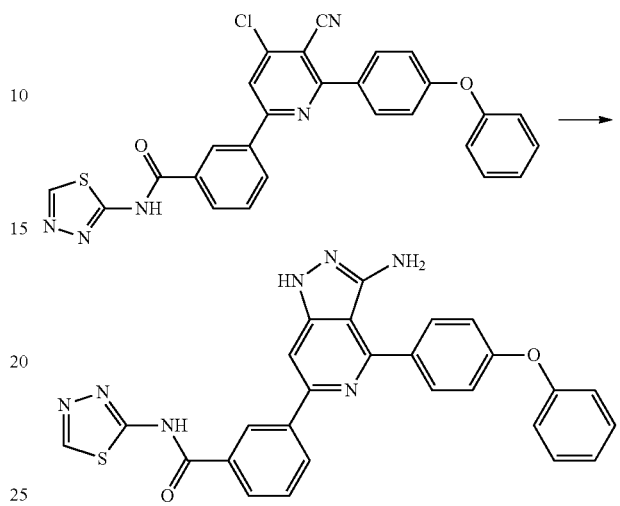

A mixture of 3-(4-chloro-5-cyano-6-(4-phenoxyphenyl)pyridin-2-yl)-N-(1,3,4-thiadiazol-2-yl)benzamide (5.2 mg, 10.20 μmol), 35% aqueous hydrazine (10 μL, 0.111 mmol), 1-propanol (0.5 mL) and ethyl acetate (0.5 mL) was stirred at 90° C. for 90 min.

Additional hydrazine (100 μL) was added. After additional 90 min at 90° C., the mixture was concentrated, dissolved in n-propanol (0.5 mL) and TFA (50 μL) and heated to 40° C. for 30 min. The crude mixture was purified by reverse phase HPLC (Sunfire S10 30×250 mm column), eluting with 55-85% solvent B (10% methanol-90% water-0.1% TFA) in solvent A (90% methanol-10% water-0.1% TFA), to give Example 220 as yellow solid, assumed bis-TFA salt (1.2 mg, 16% yield). $^1$H NMR (400 MHz, methanol-d$_4$) δ ppm 9.14 (1H, s), 8.58 (1H, t, J=1.63 Hz), 8.31 (1H, δ, J=7.78 Hz), 8.18 (1H, δ, J=8.53 Hz), 7.90-7.95 (2H, m), 7.89 (1H, s), 7.83 (1H, t, J=7.78 Hz), 7.45-7.51 (2H, m), 7.26-7.32 (3H, m), 7.18 (2H, δ, J=7.53 Hz); MS (ES+) m/z: 506 (M+H); LC retention time: 3.398 min (analytical HPLC Method A).

Example 221

3-(3-Amino-4-(4-phenoxyphenyl)-1H-1-pyrazolo[4,3-c]pyridin-6-yl)benzonitrile

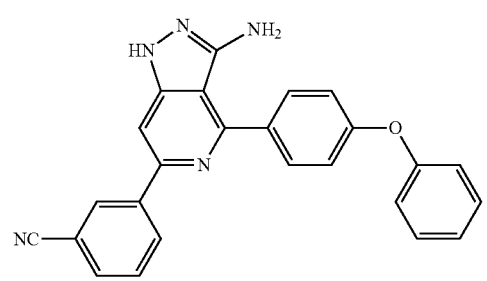 [SMILES: N#Cc1cccc(-c2cc3[nH]nc(N)c3c(-c3ccc(Oc4ccccc4)cc3)n2)c1]

Step 1:

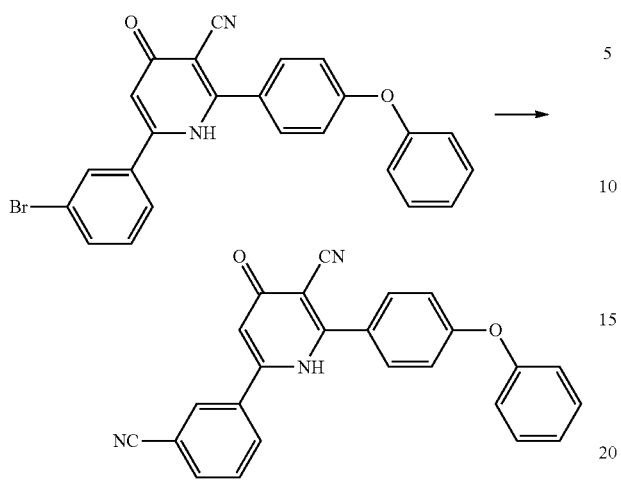

A mixture of 6-(3-bromophenyl)-4-oxo-2-(4-phenoxyphenyl)-1,4-dihydropyridine-3-carbonitrile (168.6 mg, 0.380 mmol, from Step 1 of Example 172), copper(I) cyanide (195.3 mg, 2.181 mmol) and N,N-dimethylacetamide (1.5 mL) was microwaved at 220° C. for 90 min, cooled to room temperature, and diluted with ethyl acetate (10 mL), ammonium hydroxide (2 mL) and saturated ammonium chloride (0.2 mL). The resulting two-phase system was stirred vigorously under air for 3 h then filtered. The ethyl acetate phase from the filtrate was collected and concentrated. Purification by reverse phase HPLC (Sunfire S10 30×250 mm column), eluting with 70-90% solvent B (10% methanol-90% water-0.1% TFA) in solvent A (90% methanol-10% water-0.1% TFA), gave 6-(3-cyanophenyl)-4-oxo-2-(4-phenoxyphenyl)-1,4-dihydropyridine-3-carbonitrile TFA salt as yellow solid (72.9 mg, 38% yield). $^1$H NMR (500 MHz, CDCl$_3$) δ ppm 8.04 (1H, s), 7.98 (1H, δ, J=7.97 Hz), 7.77 (1H, δ, J=7.70 Hz), 7.72 (2H, δ, J=8.25 Hz), 7.64 (1H, t, J=7.84 Hz), 7.35 (2H, t, J=7.84 Hz), 7.18 (1H, t, J=7.42 Hz), 7.05 (2H, δ, J=8.52 Hz), 7.00 (2H, δ, J=8.25 Hz), 6.85 (1H, s); MS (ES+) m/z: 390 (M+H); LC retention time: 4.031 min (analytical HPLC Method A).

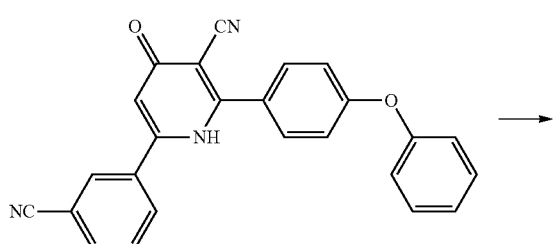

Step 2:

Following conditions similar to Step 2 of Example 172, 6-(3-cyanophenyl)-4-oxo-2-(4-phenoxyphenyl)-1,4-dihydropyridine-3-carbonitrile was concerted to 4-chloro-6-(3-cyanophenyl)-2-(4-phenoxyphenyl)nicotinonitrile. $^1$H NMR (400 MHz, CDCl$_3$) δ ppm 8.45-8.48 (1H, m), 8.32 (1H, ddd, J=8.28, 1.51, 1.25 Hz), 8.00-8.05 (2H, m), 7.85 (1H, s), 7.79-7.83 (1H, m), 7.66 (1H, t, J=7.91 Hz), 7.39-7.45 (2H, m), 7.21 (1H, t, J=7.40 Hz), 7.11-7.18 (4H, m); MS (ES+) m/z: 408 (M+H); LC retention time: 4.718 min (analytical HPLC Method A).

Step 3:

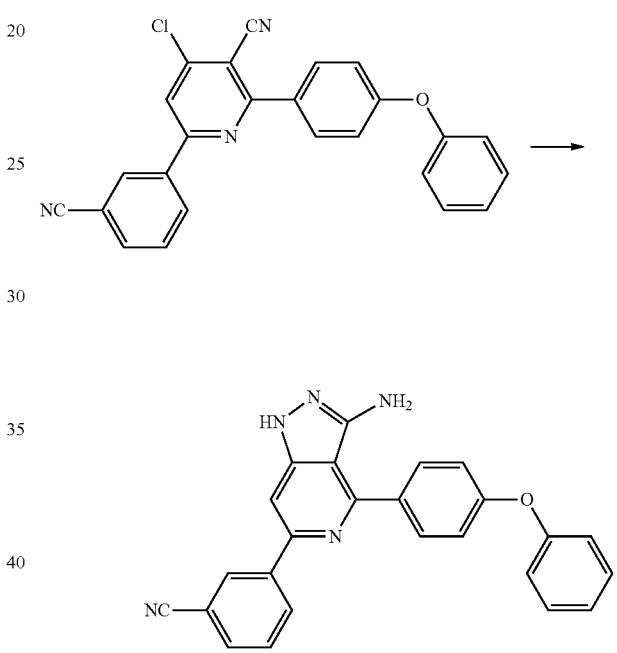

Following conditions similar to Step 3 of Example 220, 4-chloro-6-(3-cyanophenyl)-2-(4-phenoxyphenyl)nicotinonitrile was converted to Example 221. $^1$H NMR (400 MHz, methanol-d$_4$) δ ppm 8.31 (1H, t, J=1.51 Hz), 8.16-8.20 (1H, m), 7.98 (1H, ddd, J=7.91, 1.38, 1.25 Hz), 7.89-7.93 (2H, m), 7.84 (1H, s), 7.80 (1H, t, J=7.91 Hz), 7.44-7.50 (2H, m), 7.24-7.30 (3H, m), 7.15-7.20 (2H, m); MS (ES+) m/z: 404 (M+H); LC retention time: 3.513 min (analytical HPLC Method A).

Examples 222 to 224

Following conditions similar to synthesis of Example 191, Examples 222 and 223 were prepared from Examples 221 and 173, respectively. Following conditions similar to synthesis of Example 185, Example 224 was prepared from Example 221.

| Example No. | Structure | Spectral data* |
|---|---|---|
| Example 222:<br>4-(4-Phenoxyphenyl)-6-(3-(1H-tetrazol-5-yl)phenyl)-1H-pyrazolo[4,3-c]pyridin-3-amine | | $^1$H NMR (500 MHz, methanol-$d_4$) δ ppm 8.57 (1 H, t, J = 1.65 Hz), 8.27 (1 H, δ, J = 7.97 Hz), 8.06-8.10 (1 H, m), 7.91-7.95 (2 H, m), 7.87 (1 H, s), 7.84 (1 H, t, J = 7.84 Hz), 7.45-7.50 (2 H, m), 7.24-7.31 (3 H, m), 7.16-7.20 (2 H, m); MS (ES+) m/z: 447 (M + H); LC retention time: 3.263 min. |
| Example 223:<br>4-(4-Phenoxyphenyl)-6-(4-(1H-tetrazol-5-yl)phenyl)-1H-pyrazolo[4,3-c]pyridin-3-amine | | $^1$H NMR (400 MHz, methanol-$d_4$) δ ppm 8.30 (2 H, δ, J = 8.28 Hz), 8.10 (2 H, δ, J = 8.28 Hz), 7.92 (2 H, δ, J = 8.78 Hz), 7.87 (1 H, s), 7.48 (2 H, t, J = 8.03 Hz), 7.26-7.31 (4 H, m), 7.18 (2 H, δ, J = 8.78 Hz); MS (ES+) m/z: 447 (M + H); LC retention time: 3.320 min. |
| Example 224:<br>3-(3-Amino-4-(4-phenoxyphenyl)-1H-pyrazolo[4,3-c]pyridin-6-yl)benzamide | | $^1$H NMR (500 MHz, methanol-$d_4$) δ ppm 8.36 (1 H, t, J = 1.65 Hz), 8.10-8.14 (1 H, m), 8.03-8.07 (1 H, m), 7.89-7.94 (2 H, m), 7.83 (1 H, s), 7.73 (1 H, t, J = 7.84 Hz), 7.45-7.50 (2 H, m), 7.25-7.31 (3 H, m), 7.16-7.19 (2 H, m); MS (ES+) m/z: 422 (M + H); LC retention time: 3.006 min. |

*Analytical HPLC Method A

Example 225

4-(4-Phenoxyphenyl)-7-(2-pyridinyl)-1H-pyrazolo[4,3-c]pyridin-3-amine

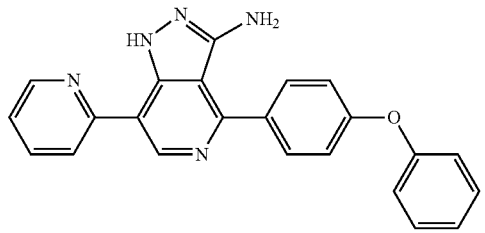 [SMILES: Nc1n[nH]c2c(-c3ccccn3)cnc(-c3ccc(Oc4ccccc4)cc3)c12]

Step 1:

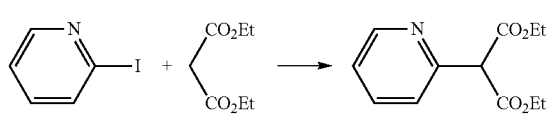 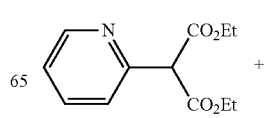

A mixture of 2-iodopyridine (1.00 g, 4.88 mmol), picolinic acid (0.060 g, 0.488 mmol), copper(I) iodide (0.046 g, 0.244 mmol), cesium carbonate (4.77 g, 14.63 mmol) and diethyl malonate (1.563 g, 9.76 mmol) in dioxane (10 mL) was stirred under nitrogen at room temperature for 15 h. The mixture was diluted with ethyl acetate (200 mL), washed with saturated ammonium chloride (20 mL), water (20 mL), brine (20 mL), dried (MgSO$_4$) and concentrated. Silica gel chromatography, loading with dichloromethane-hexanes (1:1) and eluting with 5 to 30% ethyl acetate in hexanes, gave diethyl 2-(pyridin-2-yl)malonate (700 mg, 42% yield). $^1$H NMR (400 MHz, CDCl$_3$) δ ppm 8.58 (1H, δ, J=4.77 Hz), 7.71 (1H, dd, J=7.78, 1.51 Hz), 7.50 (1H, δ, J=7.78 Hz), 7.18-7.24 (1H, m), 4.94 (1H, s), 4.14-4.32 (4H, m, J=7.15, 7.15, 7.03, 3.51 Hz), 1.19-1.35 (6H, m); MS (ES+) m/z: 238 (M+H); LC retention time: 1.88 min (analytical HPLC Method A).

Steps 2 and 3:

-continued

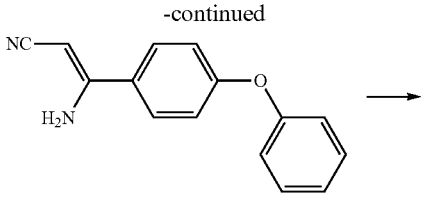

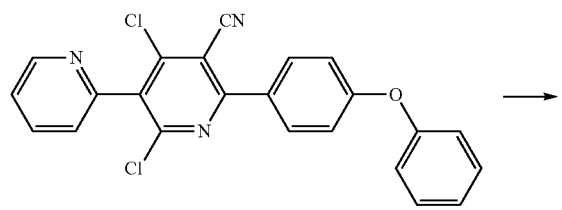

Following conditions similar to Steps 1 and 2 of Example 160, diethyl 2-(pyridin-2-yl)malonate was converted to 2',4'-dichloro-6'-(4-phenoxyphenyl)-2,3'-bipyridine-5'-carbonitrile. $^1$H NMR (400 MHz, CDCl$_3$) δ ppm 8.80 (1H, δ, J=4.27 Hz), 7.95-8.08 (2H, m), 7.78-7.95 (1H, m), 7.35-7.53 (4H, m), 7.16-7.24 (1H, m), 7.03-7.18 (4H, m); MS (ES+) m/z: 418 (M+H); LC retention time: 3.92 min (analytical HPLC Method A).

Step 4:

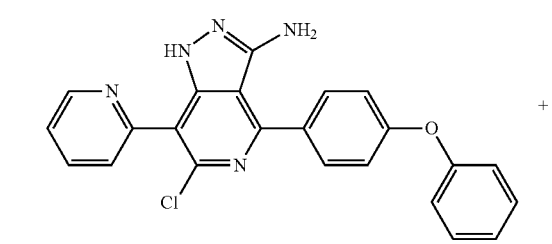

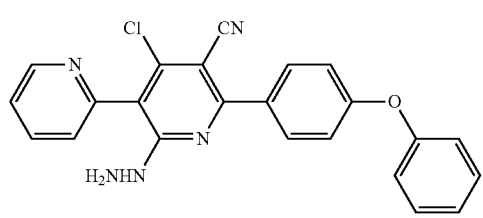

A mixture of 2',4'-dichloro-6'-(4-phenoxyphenyl)-2,3'-bipyridine-5'-carbonitrile (40 mg, 0.096 mmol) and hydrazine (0.2 mL, 4.14 mmol) in isopropanol (2 mL) was heated to 90° C. for 1 h and cooled to room temperature. Purification by reverse phase HPLC (Sunfire S10 30×250 mm column), eluting with 40-100% solvent B (10% methanol-90% water-0.1% TFA) in solvent A (90% methanol-10% water-0.1% TFA), gave 4'-chloro-2'-hydrazinyl-6'-(4-phenoxyphenyl)-2,3'-bipyridine-5'-carbonitrile bis-TFA salt (10 mg, 16% yield) and 6-chloro-4-(4-phenoxyphenyl)-7-(pyridin-2-yl)-1H-pyrazolo[4,3-c]pyridin-3-amine bis-TFA salt (15 mg, 24% yield). Characterization of the chloro product: $^1$H NMR (400 MHz, methanol-d$_4$) δ ppm 8.91 (1H, δ, J=4.52 Hz), 8.21-8.45 (1H, m), 8.10 (1H, δ, J=8.03 Hz), 7.69-7.93 (3H, m, 3-6.59, 2.64, 2.42, 2.42 Hz), 7.39-7.55 (2H, m), 6.99-7.36 (6H, m); MS (ES+) m/z: 414 (M+H); LC retention time: 3.38 min (analytical HPLC Method A).

Step 5:

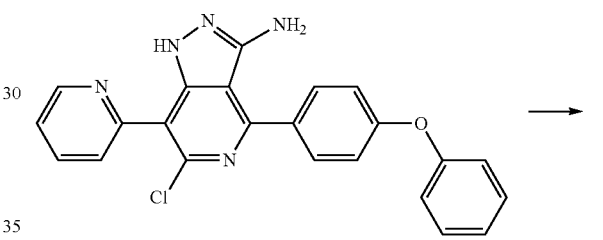

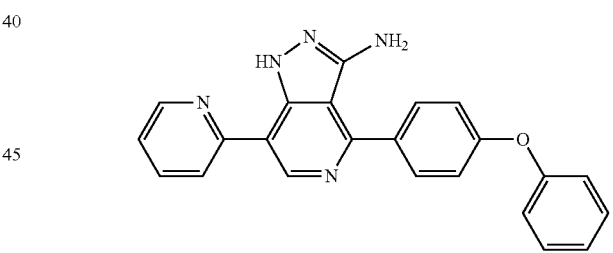

A mixture of 6-chloro-4-(4-phenoxyphenyl)-7-(pyridin-2-yl)-1H-pyrazolo[4,3-c]pyridin-3-amine bis-TFA salt (10 mg, 0.016 mmol) and zinc dust (10.19 mg, 0.156 mmol) in acetic acid (1 mL) was heated to 70° C. for 1 h. The mixture was filtered and the filtrate concentrated. Purification by reverse phase HPLC (Sunfire S10 30×250 mm column), eluting with 40-100% solvent B (10% methanol-90% water-0.1% TFA) in solvent A (90% methanol-10% water-0.1% TFA), gave Example 225 as yellow solid (2 mg, 18% yield). $^1$H NMR (400 MHz, methanol-d$_4$) δ ppm 8.70-9.04 (2H, m), 8.29 (1H, br. s), 7.92-8.20 (1H, m), 7.75-7.94 (2H, m), 7.41-7.65 (3H, m), 7.23-7.36 (3H, m), 7.18 (2H, δ, J=7.78 Hz); MS (ES+) m/z: 380 (M+H); LC retention time: 2.65 min (analytical HPLC Method A).

Examples 226 to 230

Following conditions similar to synthesis of Example 225, Examples 226 to 230 were prepared.

| Example No | Structure | Spectral data* |
|---|---|---|
| Example 226:<br>3-(3-Amino-4-(4-phenoxyphenyl)-1H-pyrazolo[4,3-c]pyridin-7-yl)benzohydrazide | | $^1$H NMR (500 MHz, methanol-$d_4$) δ ppm 8.40 (1 H, s), 8.26 (1 H, s), 8.16 (1 H, d, J = 7.78 Hz), 8.07 (1 H, d, J = 7.78 Hz), 7.83-7.97 (2 H, m), 7.78 (1 H, t, J = 7.78 Hz), 7.49 (2 H, t, J = 8.03 Hz), 7.24-7.37 (3 H, m), 7.14-7.25 (2 H, m); MS (ES+) m/z: 437 (M + H); LC retention time: 2.43 min. |
| Example 227:<br>3-(3-Amino-4-(4-phenoxyphenyl)-1H-pyrazolo[4,3-c]pyridin-7-yl)benzoic acid | | $^1$H NMR (500 MHz, methanol-$d_4$) δ ppm 8.51 (1 H, s), 8.18-8.29 (2 H, m), 8.10 (1 H, d, J = 7.78 Hz), 7.88 (2 H, d, J = 8.53 Hz), 7.76 (1 H, t, J = 7.78 Hz), 7.45-7.58 (2 H, m), 7.25-7.37 (3 H, m), 7.21 (2 H, d, J = 7.78 Hz); MS (ES+) m/z: 423 (M + H); LC retention time: 2.77 min. |
| Example 228:<br>3-(3-Amino-4-(4-phenoxyphenyl)-1H-pyrazolo[4,3-c]pyridin-7-yl)-N,N-dimethylbenzamide | | $^1$H NMR (500 MHz, methanol-$d_4$) δ ppm 8.26 (1 H, s), 7.91-8.01 (2 H, m), 7.82-7.92 (2 H, m), 7.70-7.78 (1 H, m), 7.62-7.69 (1 H, m), 7.50 (2 H, t, J = 7.91 Hz), 7.28-7.39 (3 H, m), 7.21 (2 H, d, J = 7.53 Hz), 3.18 (3 H, s), 3.12 (3 H, s); MS (ES+) m/z: 450 (M + H); LC retention time: 2.55 min. |
| Example 229:<br>3-(3-Amino-4-(4-phenoxyphenyl)-1H-pyrazolo[4,3-c]pyridin-7-yl)-N-benzylbenzamide | | $^1$H NMR (500 MHz, methanol-$d_4$) δ ppm 8.28 (1 H, s), 8.26-8.39 (1 H, m), 8.26-8.32 (1 H, m), 8.26-8.32 (1 H, m), 8.21-828 (1 H, m), 8.24 (1 H, s), 7.96-8.06 (2 H, m), 8.02 (3 H, t, J = 7.29 Hz), 7.80-7.89 (2 H, m), 7.84 (3 H, d, J = 8.80 Hz), 7.72 (1 H, t, J = 7.70 Hz), 7.47 (2 H, t, J = 8.11 Hz), 7.37-7.42 (3 H, m), 7.33 (2 H, t, J = 7.56 Hz), 7.23-7.31 (3 H, m), 7.18 (2 H, d, J = 7.70 Hz), 4.62 (2 H, s); MS (ES+) m/z: 512 (M + H); LC retention time: 2.94 min. |
| Example 230:<br>7-(3-(4-Morpholinylcarbonyl)phenyl)-4-(4-phenoxyphenyl)-1H-pyrazolo[4,3-c]pyridin-3-amine | | $^1$H NMR (500 MHz, methanol-$d_4$) δ ppm 8.22 (1 H, s), 7.90-8.02 (2 H, m), 7.79-7.88 (2 H, m), 7.71 (1 H, t, J = 7.84 Hz), 7.57-7.67 (1 H, m), 7.39-7.52 (2 H, m), 7.24-7.33 (3 H, m), 7.18 (2 H, d, J = 7.70 Hz), 3.73-3.92 (4 H, m), 3.61-3.75 (2 H, m), 3.48-3.62 (2 H, m); MS (ES+) m/z: 492 (M + H); LC retention time: 2.66 min. |

*Analytical HPLC Method A

Example 231

2-(3-(3-Amino-4-(4-phenoxyphenyl)-1H-pyrazolo[4,3-c]pyridin-6-yl)phenyl)acetohydrazide

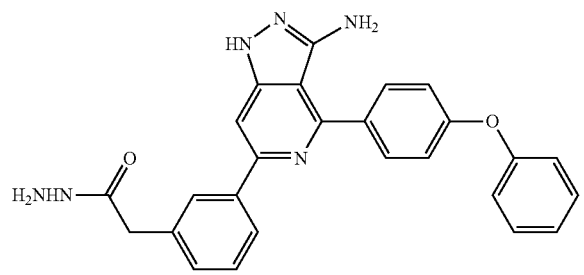

Step 1:

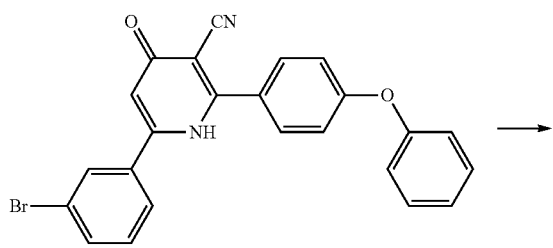

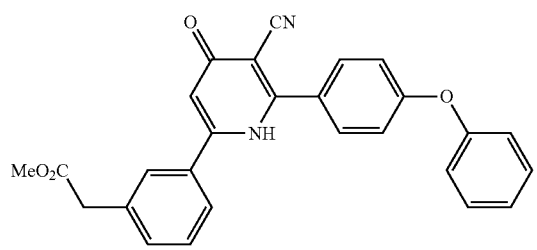

A mixture of 6-(3-bromophenyl)-4-oxo-2-(4-phenoxyphenyl)-1,4-dihydropyridine-3-carbonitrile (118 mg, 0.266 mmol, from Step 1 of Example 172), diethyl malonate (100 μL, 0.659 mmol), cesium carbonate (867 mg, 2.66 mmol), Pd$_2$(dba)$_3$ (12 mg, 0.013 mmol), bis(tri-t-butylphosphine) palladium(0) (7 mg, 0.014 mmol) and 1,2-dimethoxyethane (2 mL) was pumped under vacuum and backfilled with nitrogen twice. The sealed tube was heated to 100° C. 17 h. LC-MS showed that the desired product was formed. The solvent was evaporated. The residue was dissolved in methanol and purified by reverse phase HPLC (Sunfire S10 30×250 mm column), eluting with 65-95% solvent B (10% methanol-90% water-0.1% TFA) in solvent A (90% methanol-10% water-0.1% TFA), to give methyl 2-(3-(5-cyano-4-oxo-6-(4-phenoxyphenyl)-1,4-dihydropyridin-2-yl)phenyl) acetate TFA salt as yellow oil (172 mg, 12% yield). The trans esterification probably took place when methanol was added to make solution for HPLC injection, in the presence of cesium carbonate. $^1$H NMR (400 MHz, CDCl$_3$) δ ppm 7.71 (1H, s), 7.68 (1H, s), 7.35-7.60 (7H, m), 7.22 (1H, t, J=7.40 Hz), 7.01-7.12 (6H, m), 3.68-3.71 (3H, m); MS (ES+) m/z: 437 (M+H); LC retention time: 3.890 min (analytical HPLC Method A).

Step 2:

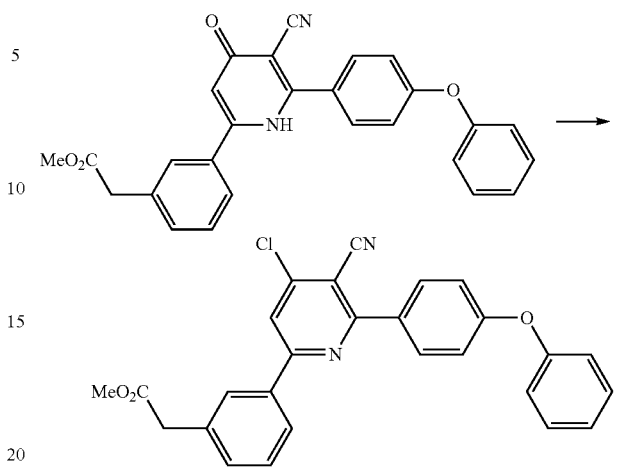

Following conditions similar to Step 2 of Example 160, methyl 2-(3-(5-cyano-4-oxo-6-(4-phenoxyphenyl)-1,4-dihydropyridin-2-yl)phenyl) acetate was converted to methyl 2-(3-(4-chloro-5-cyano-6-(4-phenoxyphenyl)pyridin-2-yl) phenyl) acetate. $^1$H NMR (400 MHz, CDCl$_3$) δ ppm 8.00-8.06 (4H, m), 7.84 (1H, s), 7.38-7.53 (4H, m), 7.19 (1H, t, J=7.53 Hz), 7.10-7.16 (4H, m), 3.74 (2H, s), 3.72 (3H, s); MS (ES+) m/z: 455 (M+H); LC retention time: 4.776 min (analytical HPLC Method A).

Step 3:

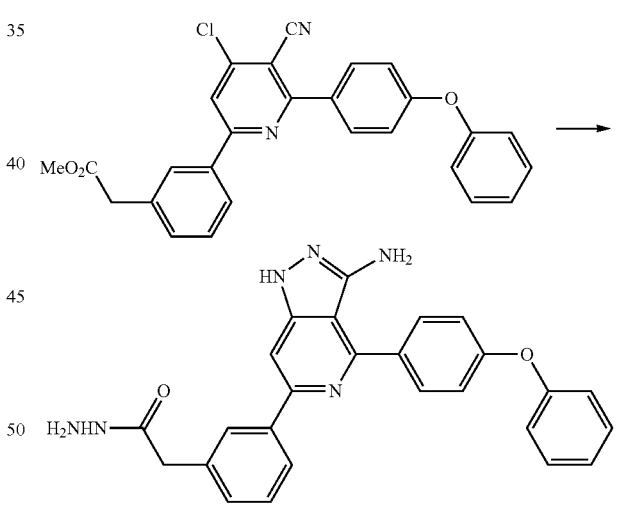

A mixture of methyl 2-(3-(4-chloro-5-cyano-6-(4-phenoxyphenyl)pyridin-2-yl)phenyl) acetate (7.3 mg, 0.016 mmol), hydrazine (50.4 μL, 1.606 mmol) and dichloromethane (1 mL) the mixture was stirred at room temperature for 1 h. Additional hydrazine (200 μL) was added. After 24 h at room temperature, the mixture was concentrated. The white solid was dissolved in methanol (2 mL) and TFA (188 μL). After 3 h at room temperature, the mixture was concentrated. Purification by reverse phase HPLC (Sunfire S10 30×250 mm column), eluting with 40-70% solvent B (10% methanol-90% water-0.1% TFA) in solvent A (90% methanol-10% water-0.1% TFA), gave Example 231 as yellow solid (6.5 mg, 50% yield). $^1$H NMR (400 MHz, methanol-d$_4$) δ ppm 7.88-7.93

(2H, m), 7.78-7.84 (2H, m), 7.77 (1H, s), 7.53-7.62 (2H, m), 7.45-7.50 (2H, m), 7.24-7.30 (3H, m), 7.17 (2H, δ, J=7.53 Hz), 3.75 (2H, s); MS (ES+) m/z: 451 (M+H); LC retention time: 2.775 min (analytical HPLC Method A).

Example 232

(2-(3-Amino-6-(3-pyridinyl)-1H-pyrazolo[4,3-c]pyridin-4-yl)-5-methoxyphenyl)methanol

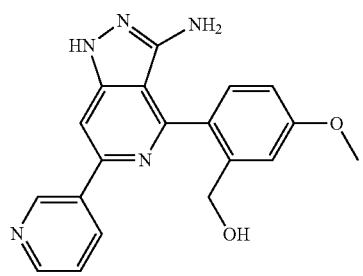 [SMILES: COc1ccc(-c2nc(-c3cccnc3)cc3[nH]nc(N)c23)c(CO)c1]

Step 1:

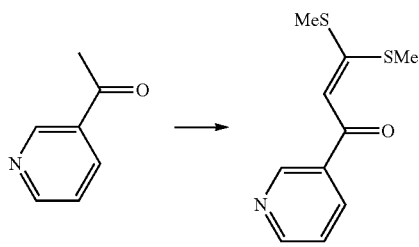

1-(Pyridin-3-yl)ethanone (4.54 mL, 41.3 mmol) was added to a mixture of sodium hydride (3.30 g, 83 mmol, 60% in mineral oil) and benzene (66 mL) at room temperature. After 5 min, carbon disulfide (3.73 mL, 61.9 mmol) was added. After 5 min, iodomethane (7.74 mL, 124 mmol) was added. After another 5 min, N,N-dimethylacetamide (8.12 mL, 87 mmol) was added. The mixture was stirred for 50 min at room temperature, and quenched with water. The precipitate was collected by filtration and washed with water to give 3,3-bis(methylthio)-1-(pyridin-3-yl)prop-2-en-1-one as pale yellow solid (3.0582 g). The aqueous filtrate was extracted with ethyl acetate (2×100 mL). The combined extracts were washed with brine (20 mL), dried (MgSO$_4$), and concentrated. The brown solid residue was triturated with ethyl acetate-hexanes. The yellow solid was collected by filtration to give additional product (1.3683 g). The filtrate was concentrated and triturated again to give another batch of the desired product (1.2859 g). $^1$H NMR (400 MHz, CDCl$_3$) δ ppm 9.13 (1H, δ, J=1.51 Hz), 8.72 (1H, dd, J=4.77, 1.76 Hz), 8.23 (1H, ddd, J=7.91, 2.13, 2.01 Hz), 7.41 (1H, dd, J=8.41, 4.39 Hz), 6.73 (1H, s), 2.59 (3H, s), 2.56 (3H, s); MS (ES+) m/z: 226 (M+H); LC retention time: 1.950 min (analytical HPLC Method A).

Step 2:

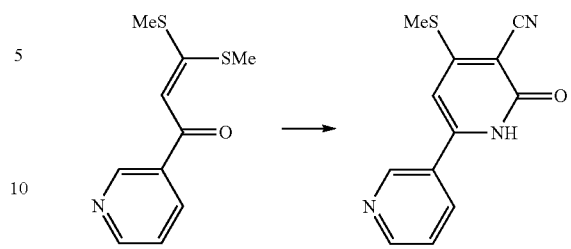

Sodium (0.408 g, 17.75 mmol) was added to 2-propanol (100 mL) and the mixture was stirred at room temperature under nitrogen for 24 h. Additional sodium (0.25 g) was added. After 17 h at room temperature, the mixture was heated to 60° C. for 1 h to dissolve the rest of the Na metal and then cooled to room temperature. 2-Cyanoacetamide (2.15 g, 25.6 mmol) was added. After 30 min at room temperature, 3,3-bis(methylthio)-1-(pyridin-3-yl)prop-2-en-1-one (5.7124 g, 25.4 mmol) was added. The mixture was stirred at room temperature for 30 min, at reflux for 2 h, and concentrated. The solid residue was dissolved in water (100 mL) and acidified with aqueous HCl (0.3 N, 100 mL) to give a suspension. The brown solid was collected by filtration and dried under vacuum to give 4-(methylthio)-2-oxo-6-(pyridin-3-yl)-1,2-dihydropyridine-3-carbonitrile (5.1267 g, 83% yield). $^1$H NMR (400 MHz, DMSO-d$_6$) δ ppm 12.68 (1H, br. s), 9.03 (1H, s), 8.74 (1H, dd, J=4.77, 1.51 Hz), 8.24 (1H, δ, J=8.03 Hz), 7.59 (1H, dd, J=8.03, 4.77 Hz), 6.70 (1H, br. s), 2.71 (3H, s); MS (ES+) m/z: 244 (M+H); LC retention time: 1.912 min (analytical HPLC Method A).

Step 3:

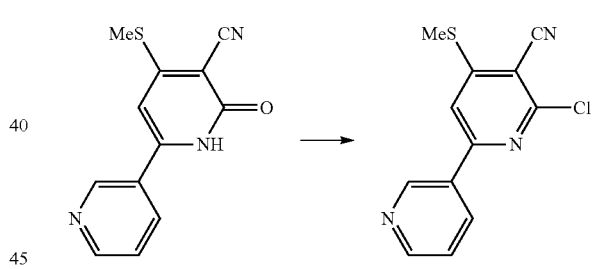

Following conditions similar to Step 2 of Example 160, 4-(methylthio)-2-oxo-6-(pyridin-3-yl)-1,2-dihydropyridine-3-carbonitrile was converted to 6-chloro-4-(methylthio)-2,3'-bipyridine-5-carbonitrile. $^1$H NMR (400 MHz, DMSO-d$_6$) δ ppm 9.48 (1H, δ, J=1.76 Hz), 8.87 (1H, dd, J=5.14, 1.38 Hz), 8.79-8.83 (1H, m), 8.05 (1H, s), 7.85 (1H, dd), 2.85 (3H, s); MS (ES+) m/z: 261 (M+H); LC retention time: 2.933 min (analytical HPLC Method A).

Step 4:

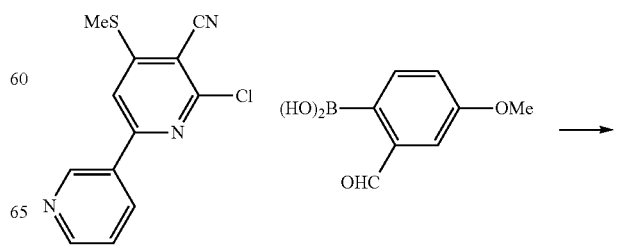

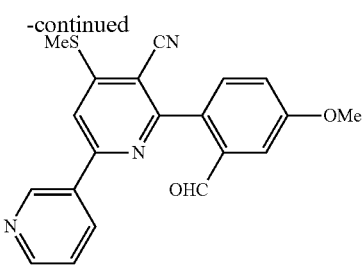

A mixture of 6-chloro-4-(methylthio)-2,3'-bipyridine-5-carbonitrile (57.7 mg, 0.220 mmol), 2-formyl-4-methoxyphenylboronic acid (83.4 mg, 0.463 mmol), aqueous potassium phosphate (550 μL, 1.100 mmol) and palladium tetrakis (triphenylphosphine) (16.1 mg, 0.014 mmol) in N,N-dimethylformamide (1 mL) was pumped under vacuum and backfilled with nitrogen twice. After 2 h at 90° C., the mixture was cooled to room temperature, diluted with methanol (2 mL) and filtered to give 6-(2-formyl-4-methoxyphenyl)-4-(methylthio)-2,3'-bipyridine-5-carbonitrile as brown solid (56.9 mg, 62% yield). $^1$H NMR (500 MHz, CDCl$_3$) δ ppm 9.99 (1H, s), 9.20 (1H, δ, J=1.92 Hz), 8.72 (1H, dd, J=4.67, 1.65 Hz), 8.34 (1H, dt, J=7.97, 1.92 Hz), 7.71 (1H, δ, J=8.52 Hz), 7.57 (1H, δ, J=2.75 Hz), 7.56 (1H, s), 7.45-7.49 (1H, m), 7.44 (1H, dd, J=8.11, 4.81 Hz), 3.95 (3H, s), 2.74 (3H, s); MS (ES+) m/z: 362 (M+H); LC retention time: 3.088 min (analytical HPLC Method A).
Step 5:

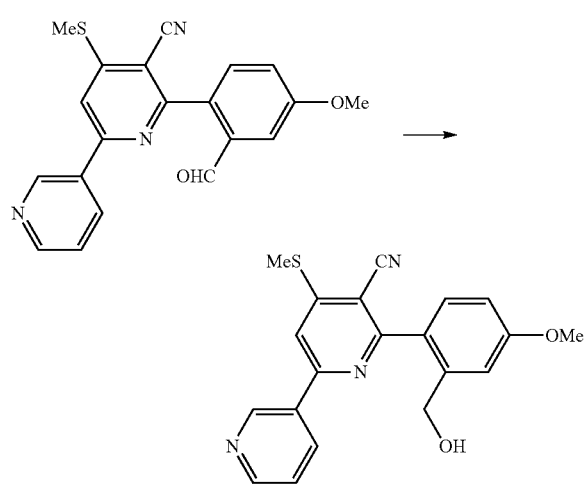

Sodium borohydride (2.2 mg, 0.058 mmol) was added to a solution of 6-(2-formyl-4-methoxyphenyl)-4-(methylthio)-2,3'-bipyridine-5-carbonitrile (4.3 mg, 0.012 mmol) in methanol (0.45 mL) and dichloromethane (0.450 mL) at room temperature. After 20 min at ambient temperature, the mixture was quenched with TEA (10 μL) and concentrated. Silica gel chromatography, eluting with 0-10% methanol in dichloromethane, gave 6-(2-(hydroxymethyl)-4-methoxyphenyl)-4-(methylthio)-2,3'-bipyridine-5-carbonitrile as white solid (2.8 mg, 65% yield). $^1$H NMR (400 MHz, CDCl$_3$) δ ppm 9.12 (1H, δ, J=2.01 Hz), 8.72-8.77 (1H, m), 822-8.28 (1H, m), 7.60-7.65 (1H, m), 7.43-7.49 (2H, m), 7.11 (1H, δ, J=2.76 Hz), 6.97-7.02 (1H, m), 4.44 (2H, s), 3.90 (3H, s), 2.72 (3H, s); MS (ES+) 111/Z: 364 (M+H); LC retention time: 3.061 min (analytical HPLC Method A).
Step 6:

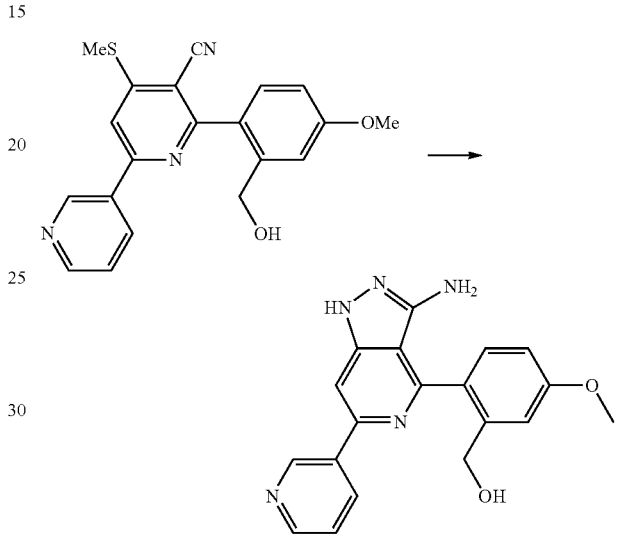

Following conditions similar to Step 3 of Example 172, 6-(2-(hydroxymethyl)-4-methoxyphenyl)-4-(methylthio)-2,3'-bipyridine-5-carbonitrile was converted to Example 232. $^1$H NMR (500 MHz, methanol-d$_4$) δ ppm 9.12 (1H, br. s), 8.79 (1H, 8, J=4.40 Hz), 8.48 (1H, δ, J=7.97 Hz), 7.90 (1H, s), 7.76 (1H, dd, J=7.84, 5.09 Hz), 7.59 (1H, δ, J=8.52 Hz), 7.29 (1H, t, J=2.47 Hz), 7.17 (1H, dd, J=8.39, 2.61 Hz), 4.62 (2H, s), 3.95 (3H, s); MS (ES+) m/z: 348 (M+H); LC retention time: 1.192 min (analytical HPLC Method A).

Examples 233 to 244

Examples 233 to 239 were prepared from Example 187. Examples 240 to 242 were prepared from Example 188. Examples 243 and 244 were prepared using similar sequence to Examples 187 and 233 to 239.

| Example No. | Structure | Spectral data* |
|---|---|---|
| Example 233:<br>4-(4-Phenoxyphenyl)-6-(3-piperidinyl)-1H-pyrazolo[4,3-c]pyridin-3-amine | ![structure] | $^1$H NMR (400 MHz, methanol-d$_4$) δ ppm 7.81 (2 H, d, J = 8.78 Hz), 7.52-7.56 (1 H, m), 7.47 (2 H, t, J = 8.03 Hz), 7.23-7.30 (3 H, m), 7.17 (2 H, d, J = 7.78 Hz), 3.72 (1 H, d, J = 11.80 Hz), 3.49 (2 H, d, J = 11.04 Hz), 3.39 (1 H, t, J = 12.05 Hz), 3.04-3.14 (1 H, m), 2.29 (1 H, d, J = 7.03 Hz), 2.14 (1 H, d, J = 7.78 Hz), 1.90-2.02 (2 H, m); MS (ES+) m/z: 386 (M + H); LC retention time: 2.273 min. |

-continued

| Example No. | Structure | Spectral data* |
|---|---|---|
| Example 234:<br>6-(1-Methyl-3-piperidinyl)-4-(4-phenoxyphenyl)-1H-pyrazolo[4,3-c]pyridin-3-amine | | ¹H NMR (500 MHz, methanol-d₄) δ ppm 7.79-7.82 (2 H, m), 7.45-7.50 (3 H, m), 7.24-7.29 (3 H, m), 7.16 (2 H, d, J = 7.70 Hz), 3.82 (1 H, d), 3.61 (1 H, d), 3.51 (1 H, t), 3.39 (1 H, t, J = 12.10 Hz), 3.07 (1 H, t), 2.97 (3 H, s), 2.26 (1 H, d), 2.17 (1 H, d), 1.82-2.04 (2 H, m); MS (ES+) m/z: 400.3 (M + H); LC retention time: 2.293 min. |
| Example 235:<br>6-(1-Benzoyl-3-piperidinyl)-4-(4-phenoxyphenyl)-1H-pyrazolo[4,3-c]pyridin-3-amine | | ¹H NMR (500 MHz, methanol-d₄) δ ppm 7.80-7.88 (2 H, m), 7.58 (1 H, br. s.), 7.48 (5 H, dd, J = 8.52, 7.42 Hz), 7.24-7.31 (4 H, m), 7.17 (3 H, d, J = 7.97 Hz), 4.02 (1 H, br. s.), 3.75-3.85 (2 H, m), 2.26-2.33 (2 H, m), 1.96-2.11 (2 H, m), 1.84 (1 H, br. s.), 1.68 (1 H, br. s.); MS (ES+) m/z: 490.3 (M + H); LC retention time: 3.306 min. |
| Example 236:<br>3-(3-Amino-4-(4-phenoxyphenyl)-1H-pyrazolo[4,3-c]pyridin-6-yl)-N-phenyl-1-piperidinecarboxamide | | ¹H NMR (500 MHz, methanol-d₄) δ ppm 7.79-7.85 (2 H, m), 7.55 (1 H, s), 7.47 (2 H, t, J = 7.97 Hz), 7.32-7.36 (2 H, m), 7.23-7.30 (5 H, m), 7.17 (2 H, d, J = 7.70 Hz), 7.03 (1 H, t, J = 7.29 Hz), 4.38 (1 H, d, J = 9.90 Hz), 4.13 (1 H, d, J = 13.75 Hz), 3.17-3.26 (3 H, m), 2.25-2.31 (1 H, m), 1.97-2.07 (1 H, m), 1.90-1.97 (1 H, m), 1.69-1.80 (1 H, m); MS (ES+) m/z: 505.3 (M + H); LC retention time: 3.420 min. |
| Example 237:<br>6-(1-Acryloyl-3-piperidinyl)-4-(4-phenoxyphenyl)-1H-pyrazolo[4,3-c]pyridin-3-amine | | ¹H NMR (500 MHz, methanol-d₄) δ ppm 7.82 (2 H, d, J = 8.52 Hz), 7.52-7.57 (1 H, m), 7.45-7.50 (2 H, m), 7.24-7.30 (3 H, m), 7.17 (2 H, d, J = 7.70 Hz), 6.83 (1 H, dd, J = 16.77, 10.72 Hz), 6.25 (1 H, d, J = 16.77 Hz), 5.80 (1 H, d, J = 10.45 Hz), 4.69 (1 H, d), 4.16 (1 H, d, J = 13.47 Hz), 3.11-3.20 (2 H, m), 2.23-2.31 (1 H, m), 1.91-2.10 (2 H, m), 1.60-1.73 (1 H, m); MS (ES+) m/z: 440.3 (M + H); LC retention time: 2.996 min. |
| Example 238:<br>Methyl(3-(3-amino-4-(4-phenoxyphenyl)-1H-pyrazolo[4,3-c]pyridin-6-yl)-1-piperidinyl)(oxo)acetate | | ¹H NMR (500 MHz, methanol-d₄): 2:1 mixture of two conformers; MS (ES+) m/z: 472.3 (M + H); LC retention time: 2.978 min. |

| Example No. | Structure | Spectral data* |
|---|---|---|
| Example 239: (3-(3-Amino-4-(4-phenoxyphenyl)-1H-pyrazolo[4,3-c]pyridin-6-yl)-1-piperidinyl)(oxo) acetic acid | 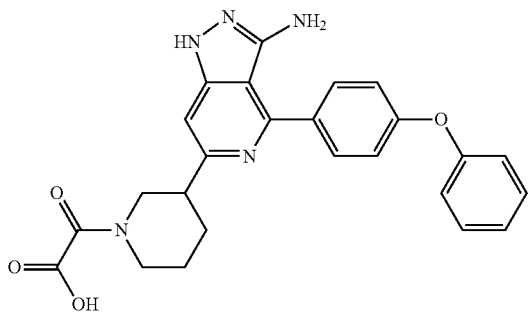 [SMILES: Nc1n[nH]c2cc(C3CCCN(C(=O)C(=O)O)C3)nc(-c3ccc(Oc4ccccc4)cc3)c12] | $^1$H NMR (500 MHz, methanol-d$_4$): 2:1 mixture of two conformers; MS (ES+) m/z: 458.2 (M + H); LC retention time: 2.948 min. |
| Example 240: 4-(4-Phenoxyphenyl)-6-(4-piperidinyl)-1H-pyrazolo[4,3-c]pyridin-3-amine | 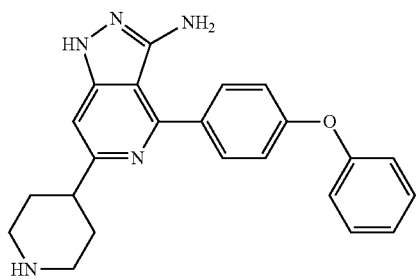 [SMILES: Nc1n[nH]c2cc(C3CCNCC3)nc(-c3ccc(Oc4ccccc4)cc3)c12] | $^1$H NMR (400 MHz, methanol-d$_4$) δ ppm 7.79-7.84 (2 H, m), 7.45-7.51 (3 H, m), 7.24-7.29 (3 H, m), 7.17 (2 H, dd, J = 8.66, 1.13 Hz), 3.61 (2 H, d, J = 12.80 Hz), 3.32-3.38 (1 H, m), 3.18 (2 H, td, J = 12.92, 2.76 Hz), 2.34 (2 H, d, J = 13.80 Hz), 2.08 (2 H, qd, J = 13.18, 3.89 Hz); MS (ES+) m/z: 386.2 (M + H); LC retention time: 2.207 min. |
| Example 241: 6-(1-Benzoyl-4-piperidinyl)-4-(4-phenoxyphenyl)-1H-pyrazolo[4,3-c]pyridin-3-amine | 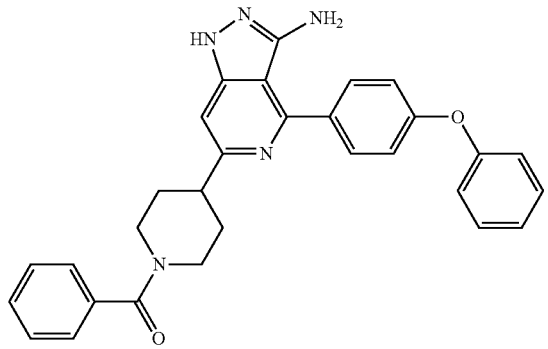 [SMILES: Nc1n[nH]c2cc(C3CCN(C(=O)c4ccccc4)CC3)nc(-c3ccc(Oc4ccccc4)cc3)c12] | $^1$H NMR (500 MHz, methanol-d$_4$) δ ppm 7.78-7.82 (2 H, m), 7.44-7.54 (8 H, m), 7.25-7.29 (3 H, m), 7.15-7.18 (2 H, m), 3.93 (2 H, br. s.), 3.02 (2 H, br. s.), 2.20 (2 H, br. s.), 1.99 (2 H, br. s.), 1.91 (4 H, br. s.); MS (ES+) m/z: 490.1 (M + H); LC retention time: 3.215 min. |
| Example 242: 4-(3-Amino-4-(4-phenoxyphenyl)-1H-pyrazolo[4,3-c]pyridin-6-yl)-N-phenyl-1-piperidinecarboxamide | 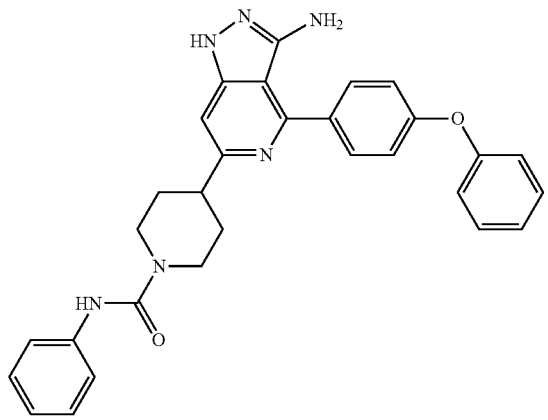 [SMILES: Nc1n[nH]c2cc(C3CCN(C(=O)Nc4ccccc4)CC3)nc(-c3ccc(Oc4ccccc4)cc3)c12] | $^1$H NMR (400 MHz, methanol-d$_4$) δ ppm 7.79-7.83 (2 H, m), 7.45-7.50 (3 H, m), 7.35-7.39 (2 H, m), 7.25-7.30 (5 H, m), 7.15-7.19 (2 H, m), 7.01-7.06 (1 H, m), 4.37-4.45 (2 H, br. d), 3.15-3.23 (1 H, m), 3.01-3.11 (2 H, m), 2.12 (2 H, br. d), 1.81-1.94 (2 H, m); MS (ES+) m/z: 505.2 (M + H); LC retention time: 3.216 min. |

-continued

| Example No. | Structure | Spectral data* |
|---|---|---|
| Example 243:<br>3-(3-Amino-4-(4-phenoxyphenyl)-1H-pyrazolo[4,3-c]pyridin-6-yl)-1-pyrrolidinecarbaldehyde | 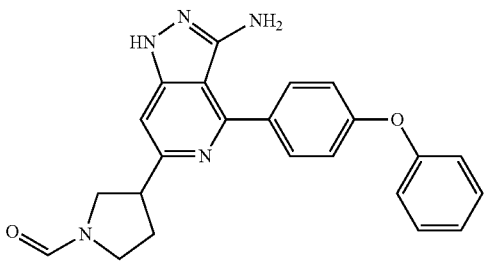 [SMILES: Nc1n[nH]c2cc(C3CCN(C=O)C3)nc(-c3ccc(Oc4ccccc4)cc3)c12] | $^1$H NMR (400 MHz, methanol-$d_4$): a mixture of different conformers; MS (ES+) m/z: 400.5 (M + H); LC retention time: 2.760 min. |
| Example 244:<br>6-(1-Benzoyl-3-pyrrolidinyl)-4-(4-phenoxyphenyl)-1H-pyrazolo[4,3-c]pyridin-3-amine | 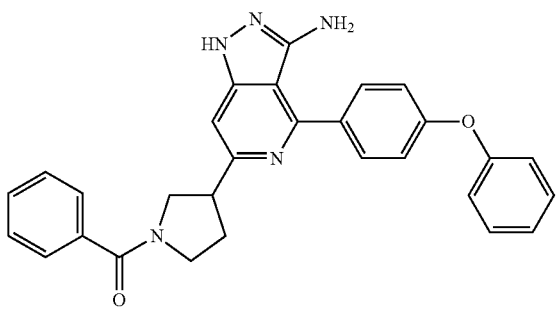 [SMILES: Nc1n[nH]c2cc(C3CCN(C(=O)c4ccccc4)C3)nc(-c3ccc(Oc4ccccc4)cc3)c12] | $^1$H NMR (500 MHz, methanol-$d_4$) δ ppm 7.83 (1 H, d, J = 8.80 Hz), 7.76 (1 H, d, J = 8.52 Hz), 7.57-7.62 (2 H, m), 7.43-7.55 (6 H, m), 7.22-7.31 (3 H, m), 7.16 (2 H, dd, J = 11.41, 8.11 Hz), 4.01-4.19 (1 H, m), 3.86-3.96 (2 H, m), 3.76-3.85 (1 H, m), 3.69-3.75 (1 H, m), 2.45-2.63 (1 H, m), 2.27-2.45 (1 H, m); MS (ES+) m/z: 476.5 (M + H); LC retention time: 3.268 min. |

*Analytical HPLC Method A

Example 245

4-(3-Amino-4-(4-phenoxyphenyl)-1H-pyrazolo[4,3-c]pyridin-6-yl)-2-fluorobenzoic acid

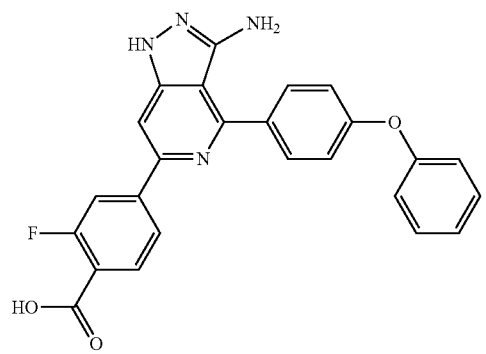 [SMILES: Nc1n[nH]c2cc(-c3ccc(C(=O)O)c(F)c3)nc(-c3ccc(Oc4ccccc4)cc3)c12]

Step 1:

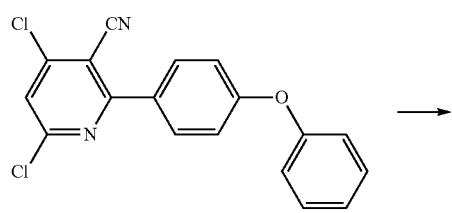

→

-continued

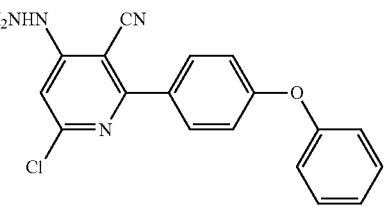

A

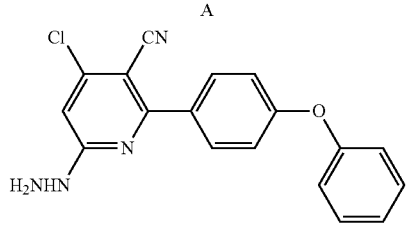

B

Hydrazine (0.1 mL, 3.19 mmol) was added to a solution of 4,6-dichloro-2-(4-phenoxyphenyl)nicotinonitrile (218.8 mg, 0.641 mmol, from Step 3 of Example 152) in dichloromethane (2 mL). After 3 h at room temperature, additional hydrazine (0.2 mL) was added. The mixture was stirred for 3 days, and purified by silica gel chromatography, eluting with 30-80% EtOAc in hexanes, to give 6-chloro-4-hydrazinyl-2-(4-phenoxyphenyl)nicotinonitrile (product A) as white solid (91.6 mg, 42% yield). $^1$H NMR (400 MHz, DMSO-$d_6$) δ ppm 8.76 (1H, s), 7.75-7.79 (2H, m), 7.42-7.48 (2H, m), 7.22 (1H, t, J=7.40 Hz), 7.07-7.14 (5H, m), 4.65 (2H, s); MS (ES+) m/z: 337.1 (M+H); LC retention time: 4.010 min (analytical HPLC Method A). 4-Chloro-6-hydrazinyl-2-(4-phenoxyphenyl)nicotinonitrile (product B) was also obtained (103.4 mg, 48% yield).

Step 2:

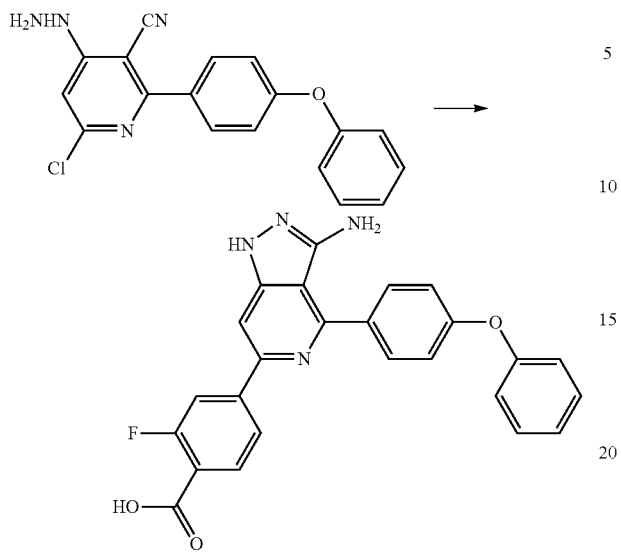

A solution of 6-chloro-4-hydrazinyl-2-(4-phenoxyphenyl)nicotinonitrile (9.5 mg, 0.028 mmol), 4-borono-2-fluorobenzoic acid (14.5 mg, 0.079 mmol), 2 M aqueous potassium phosphate (0.071 mL, 0.141 mmol) and $PdCl_2$(dppf)-$CH_2Cl_2$ adduct (4.6 mg, 5.63 μmol) in DMF (0.45 mL) was degassed by vacuum-$N_2$ refill cycle twice. The sealed tube was then heated at 85° C. under $N_2$. After 1.5 h, no desired product was detected. Additional 4-borono-2-fluorobenzoic acid (21.4 mg), $PdCl_2$(dppf)-$CH_2Cl_2$ adduct (11 mg), potassium phosphate (0.14 mL) and DMF (0.3 mL) were added. The mixture was again degassed by vacuum-$N_2$ refill cycle twice and stirred at 85° C. for 20 h. The mixture was diluted with 1 N aqueous HCl (0.7 mL) and MeOH (0.8 mL), and purified by reverse phase HPLC (Sunfire S10 30×250 mm column), eluting with 60-90% solvent B (10% methanol-90% water-0.1% TFA) in solvent A (90% methanol-10% water-0.1% TFA), to give Example 245 as yellow powder (2.7 mg, 14% yield), assumed as bis-TFA salt. $^1$H NMR (400 MHz, methanol-$d_4$) δ ppm 8.15 (1H, t, J=7.65 Hz), 7.89-7.93 (2H, m), 7.86 (1H, s), 7.77-7.84 (2H, m), 7.44-7.50 (2H, m), 7.24-7.30 (3H, m), 7.15-7.19 (2H, m); MS (ES+) m/z: 441.2 (M+H); LC retention time: 3.438 min (analytical HPLC Method A).

Example 246

(4-(3-Amino-4-(4-phenoxyphenyl)-1H-pyrazolo[4,3-c]pyridin-6-yl)-1H-pyrazol-1-yl)acetic acid

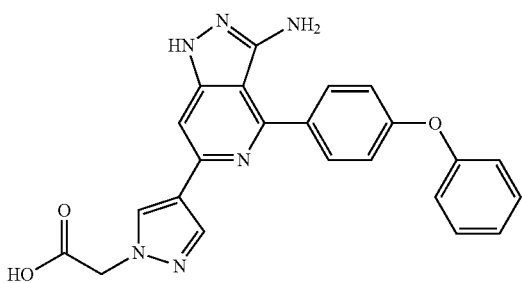 [SMILES: Nc1n[nH]c2cc(-c3cnn(CC(=O)O)c3)nc(-c3ccc(Oc4ccccc4)cc3)c12]

The title compound was prepared from 6-chloro-4-hydrazinyl-2-(4-phenoxyphenyl)nicotinonitrile (product A from Step 1 of Example 245) following conditions similar to Step 2 of Example 245. $^1$H NMR (400 MHz, methanol-$d_4$) δ ppm 8.44 (1H, s), 8.18 (1H, s), 7.83-7.87 (2H, m), 7.74 (1H, s), 7.45-7.50 (2H, m), 7.24-7.30 (3H, m), 7.17 (2H, d, J=7.53 Hz), 5.11 (2H, s); MS (ES+) m/z: 427.2 (M+H); LC retention time: 2.890 min (analytical HPLC Method A).

Example 247

5-(3-Amino-4-(4-phenoxyphenyl)-1H-pyrazolo[4,3-c]pyridin-6-yl)-2-thiophenecarboxylic acid

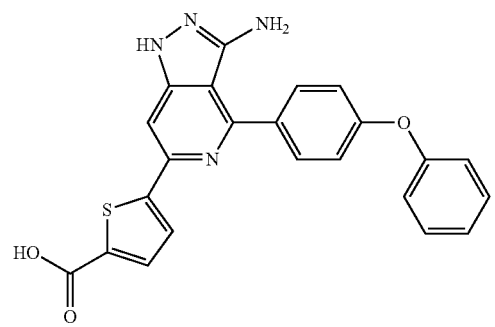 [SMILES: Nc1n[nH]c2cc(-c3ccc(C(=O)O)s3)nc(-c3ccc(Oc4ccccc4)cc3)c12]

The title compound was prepared from 6-chloro-4-hydrazinyl-2-(4-phenoxyphenyl)nicotinonitrile (product A from Step 1 of Example 245) following conditions similar to Step 2 of Example 245. $^1$H NMR (400 MHz, methanol-$d_4$) δ ppm 7.83-7.88 (2H, m), 7.81 (1H, d, J=4.02 Hz), 7.74-7.77 (2H, m), 7.42-7.48 (2H, m), 7.19-7.25 (3H, m), 7.13-7.18 (2H, m); MS (ES+) m/z: 429.2 (M+H); LC retention time: 3.841 min (analytical HPLC Method A).

Example 248

(3-((3-Amino-4-(4-phenoxyphenyl)-1H-pyrazolo[4,3-c]pyridin-6-yl)amino)-1H-pyrazol-1-yl)acetic acid

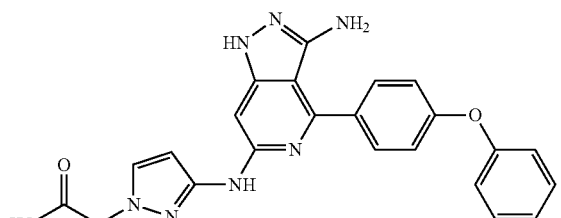

Step 1:

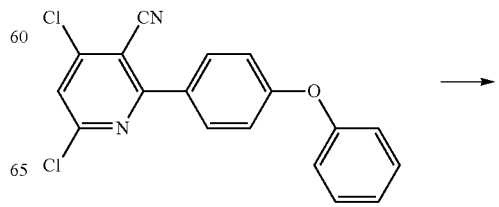

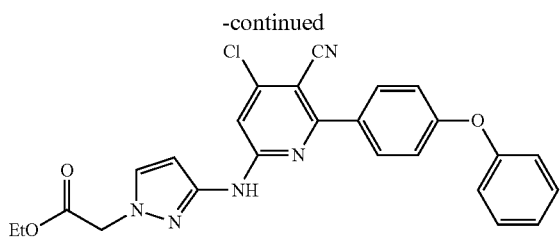

A solution of 4,6-dichloro-2-(4-phenoxyphenyl)nicotinonitrile (52.4 mg, 0.154 mmol, from Step 3 of Example 152), ethyl 2-(3-amino-1H-pyrazol-1-yl) acetate (30.6 mg, 0.181 mmol), Cs$_2$CO$_3$ (75.9 mg, 0.233 mmol), Pd$_2$(dba)$_3$ (14.8 mg, 0.016 mmol) and Xantphos (20.2 mg, 0.035 mmol) in dioxane (1 mL) was degassed by vacuum-N$_2$ refill cycle twice. The sealed tube was then heated to 80° C. for 16 h. The mixture was purified by silica gel chromatography, eluting with 0-60% EtOAc in hexanes, gave ethyl 2-(3-(4-chloro-5-cyano-6-(4-phenoxyphenyl)pyridin-2-ylamino)-1H-pyrazol-1-yl) acetate as white solid (15.8 mg) along with some impure material.). $^1$H NMR (400 MHz, CDCl$_3$) δ ppm 7.86-7.91 (2H, m), 7.45 (1H, s), 7.36-7.44 (4H, m), 7.17 (1H, t, J=7.40 Hz), 7.06-7.12 (4H, m), 6.27 (1H, br. s), 4.85 (2H, s), 4.27 (2H, q, J=7.28 Hz), 1.31 (3H, t, J=7.15 Hz); MS (ES+) m/z: 474.4 (M+H); LC retention time: 3.235 min (analytical HPLC Method A).

Step 2:

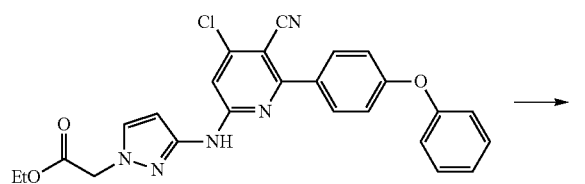

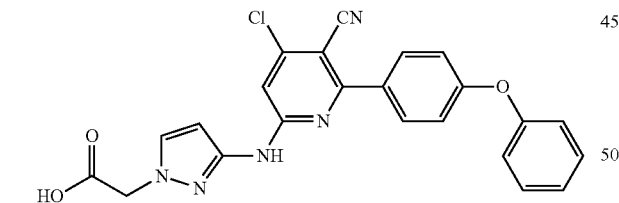

To a solution of ethyl 2-(3-(4-chloro-5-cyano-6-(4-phenoxyphenyl)pyridin-2-ylamino)-1H-pyrazol-1-yl) acetate (9.2 mg, 0.019 mmol) in MeOH (0.15 mL)-DMSO (0.15 mL) was added 1 N aqueous NaOH (0.15 mL, 7.7 eq). After 1 h at room temperature, the mixture was concentrated, treated with water (0.3 mL) and 1 N HCl (0.15 mL). A white suspension was formed. The precipitate was collected by filtration to give 2-(3-(4-chloro-5-cyano-6-(4-phenoxyphenyl)pyridin-2-ylamino)-1H-pyrazol-1-yl)acetic acid as light yellow solid (0.0070 g), which was taken to next reaction without further purification. MS (ES+) m/z: 446.4 (M+H); LC retention time: 2.708 min (analytical HPLC Method A).

Step 3:

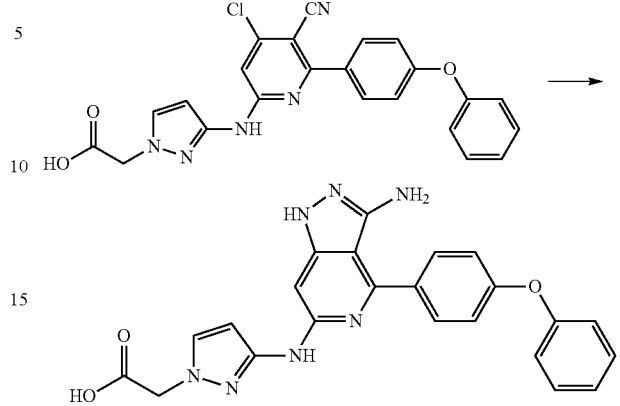

A solution of 2-(3-(4-chloro-5-cyano-6-(4-phenoxyphenyl)pyridin-2-ylamino)-1H-pyrazol-1-yl)acetic acid (7 mg, 9.42 μmol) and hydrazine (11 μL, 0.350 mmol) in N,N-Dimethylacetamide (0.15 mL) was heated to 100° C. for 3 h. The mixture was cooled to room temperature, diluted with MeOH (0.30 mL), and purified by reverse phase HPLC (Sunfire S10 30×250 mm column), eluting with 55-85% solvent B (10% methanol-90% water-0.1% TFA) in solvent A (90% methanol-10% water-0.1% TFA), to give Example 248 as yellow solid (1.4 mg, 21% yield), assumed as bis-TFA salt. $^1$H NMR (400 MHz, methanol-d$_4$) δ ppm 7.92-7.97 (2H, m), 7.71 (1H, d, J=2.51 Hz), 7.44-7.51 (2H, m), 7.24-7.32 (3H, m), 7.16-7.20 (2H, m), 6.81 (1H, s), 6.05 (1H, d, J=2.51 Hz), 4.92 (2H, s); MS (ES+) m/z: 442.4 (M+H); LC retention time: 3.390 min (analytical HPLC Method A).

Example 249

2-(3-((3-Amino-4-(4-phenoxyphenyl)-1H-pyrazolo[4,3-c]pyridin-6-yl)amino)-1H-pyrazol-1-yl)-N,N-dimethylacetamide

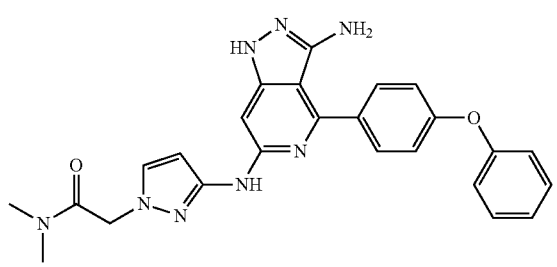 [SMILES: CN(C)C(=O)Cn1ccc(Nc2cc3[nH]nc(N)c3c(-c3ccc(Oc4ccccc4)cc3)n2)n1]

The acid from Step 2 of Example 248 and dimethylamine were coupled with HATU and subsequently reacted with hydrazine following conditions in Step 3 of Example 248 to give Example 249. $^1$H NMR (400 MHz, methanol-d$_4$) δ ppm 7.91-7.97 (2H, m), 7.65 (1H, d, J=2.51 Hz), 7.47-7.54 (2H, m), 7.31 (1H, t, J=7.40 Hz), 7.18-7.24 (4H, m), 6.78 (1H, s), 6.05 (1H, d, J=2.26 Hz), 5.09 (2H, s), 3.03 (3H, s), 2.86 (3H, s); MS (ES+) m/z: 469.5 (M+H); LC retention time: 3.238 min (analytical HPLC Method A).

Example 250

4-(3-Amino-4-(6-methoxy-2-naphthyl)-1H-pyrazolo[4,3-e]pyridin-6-yl)benzoic acid

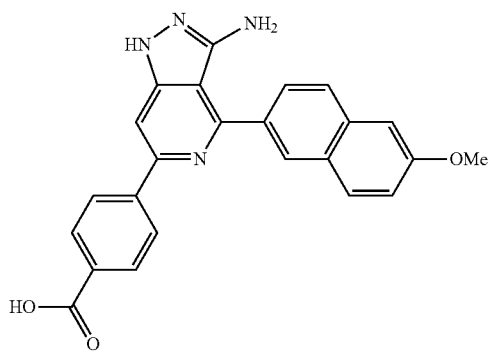 [SMILES: COc1ccc2cc(-c3nc(-c4ccc(C(=O)O)cc4)cc4[nH]nc(N)c34)ccc2c1]

Step 1:

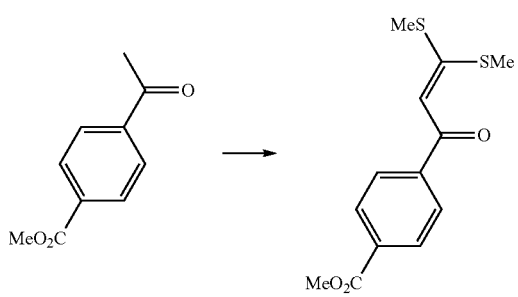 [SMILES: COC(=O)c1ccc(C(C)=O)cc1 ; COC(=O)c1ccc(C(=O)C=C(SC)SC)cc1]

Methyl 4-acetylbenzoate (4.2 g, 23.57 mmol) was added to a mixture of sodium hydride (1.886 g, 47.1 mmol, 60% in mineral oil) and benzene (80 mL) at room temperature. After 5 min, carbon disulfide (2.131 mL, 35.4 mmol) was added. After another 5 min, iodomethane (4.42 mL, 70.7 mmol) was added. After another 5 min, N,N-dimethylacetamide (4.64 mL, 49.5 mmol) was added. The mixture was stirred for 30 min at room temperature, and quenched with water 20 mL). The brown precipitate was collected by filtration and washed with water (10 mL) to give methyl 4-(3,3-bis(methylthio)acryloyl)benzoate (2.50 g). The filtrate was extracted with ethyl acetate (3×100 mL). The combined organic extracts were washed with brine (30 mL), dried ($MgSO_4$) and concentrated. The brown solid was titrated with ethyl acetate-hexanes. The solid was collected by filtration and dried under vacuum to give additional product (2.0 g). The total yield of the reaction was 67%. $^1$H NMR (400 MHz, $CDCl_3$) δ ppm 8.10 (2H, d, J=8.52 Hz), 7.96 (2H, d, J=8.52 Hz), 6.75 (1H, s), 3.94 (3H, s), 2.37-2.68 (6H, m); MS (ES+) m/z: 283 (M+H); LC retention time: 3.19 min (analytical HPLC Method A).

Step 2:

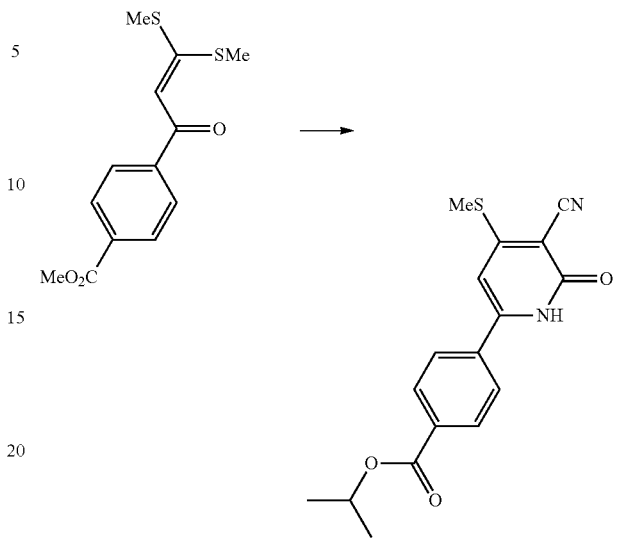

A 12% isopropanol suspension of sodium isopropoxide (9.08 g, 13.28 mmol) was added to a mixture of methyl 4-(3,3-bis(methylthio)acryloyl)benzoate (2.5 g, 8.85 mmol) and 2-cyanoacetamide (0.744 g, 8.85 mmol) in isopropanol (50 mL). The resultant mixture was heated to 100° C. for 3 h, cooled to room temperature and quenched with 0.3 N HCl (50 mL). The brown precipitate was collected by filtration, washed with water (10 mL) and dried under vacuum to give isopropyl 4-(5-cyano-4-(methylthio)-6-oxo-1,6-dihydropyridin-2-yl)benzoate (2.3 g, 63% yield). $^1$H NMR (400 MHz, DMSO-$d_6$) δ ppm 7.70-8.42 (4H, m), 6.67 (1H, br. s), 4.89-5.43 (1H, m), 1.10-1.64 (6H, m); MS (ES+) m/z: 329 (M+H); LC retention time: 3.18 min (analytical HPLC Method A).

Step 3:

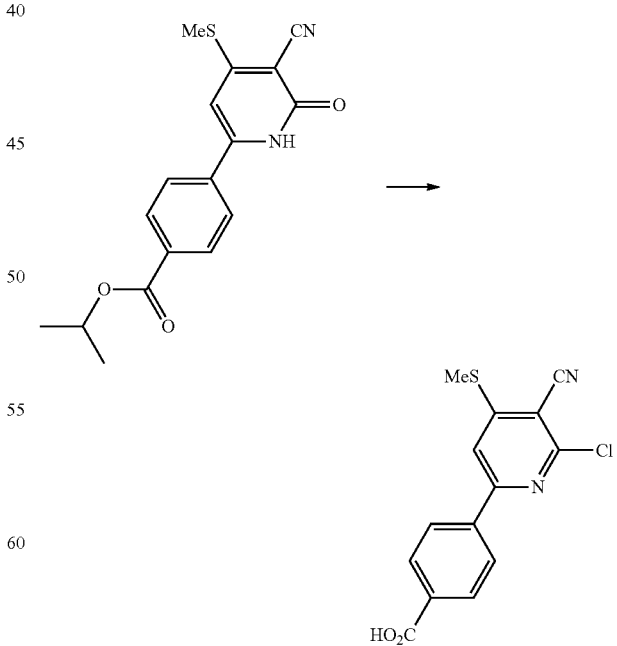

A suspension of isopropyl 4-(5-cyano-4-(methylthio)-6-oxo-1,6-dihydropyridin-2-yl)benzoate (1.6 g, 4.87 mmol) in phosphoryl trichloride (14.94 g, 97 mmol) was heated to 110° C. for 60 h, cooled to room temperature and carefully added to cold water (50 mL). The resultant mixture was carefully quenched with saturated. NaHCO$_3$(200 mL), and extracted with ethyl acetate (3×200 mL). The combined organic extracts were washed with brine (100 mL), dried (MgSO$_4$) and concentrated to give a mixture of acid and ester. The material was treated with DMF (10 ml) and 6 N HCl (10 ml), heated to 100° C. for 1 h, cooled to room temperature and diluted with water (50 ml) and filtered. The solid was washed with water (10 ml), dried under vacuum to give 4-(6-chloro-5-cyano-4-(methylthio)pyridin-2-yl)benzoic acid (1.45 g. 70% yield). $^1$H NMR (400 MHz, DMSO-d$_6$) δ ppm 8.31 (2H, d, J=8.53 Hz), 8.10 (2H, d, J=8.53 Hz), 7.95 (1H, s), 2.87 (3H, s); MS (ES+) m/z: 305 (M+H); LC retention time: 3.45 min (analytical HPLC Method A).

Step 4:

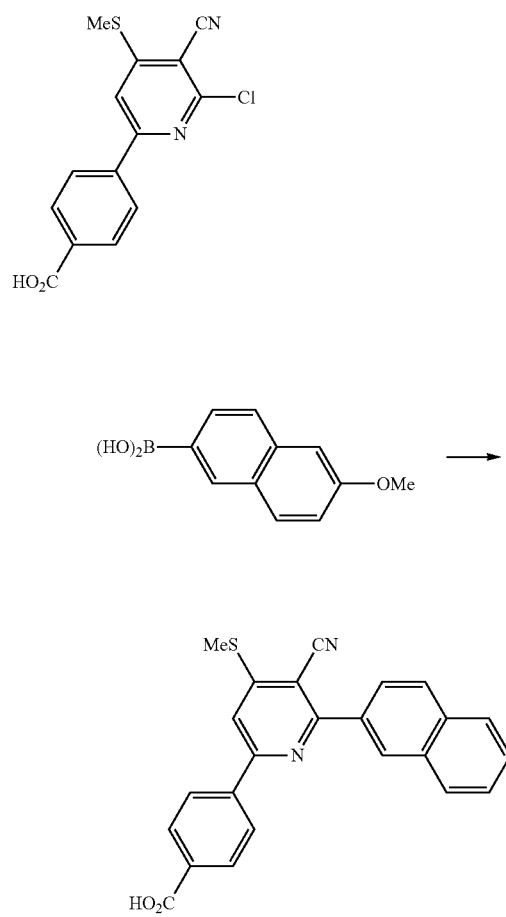

A mixture of 4-(6-chloro-5-cyano-4-(methylthio)pyridin-2-yl)benzoic acid (50 mg, 0.164 mmol) and 6-methoxynaphthalen-2-ylboronic acid (49.7 mg, 0.246 mmol), potassium phosphate (139 mg, 0.656 mmol) and palladium tetrakis(triphenylphosphine) (18.96 mg, 0.016 mmol) in N,N-dimethylacetamide (2 mL) was pumped under vacuum and backfilled with nitrogen three times. After 2 h at 100° C., the mixture was cooled to room temperature, diluted with EtOAc (60 mL), washed with saturated NH$_4$Cl (5 mL), water (5 ml), brine (5 mL), dried (MgSO$_4$) and concentrated. The residue was triturated with MeOH (10 ml) and filtered. The yellow solid was collected and dried under vacuum to give 4-(5-cyano-6-(6-methoxynaphthalen-2-yl)-4-(methylthio)pyridin-2-yl)benzoic acid (45 mg, 51% yield). $^1$H NMR (400 MHz, DMSO-d$_6$) δ ppm 8.34-8.53 (2H, m), 8.21-8.34 (1H, m), 7.99-8.19 (4H, m), 7.85-7.98 (1H, m), 7.41-7.54 (1H, m), 7.18-7.37 (2H, m), 3.94 (3H, s); MS (ES+) m/z: 427 (M+H); LC retention time: 4.01 min (analytical HPLC Method A).

Step 5:

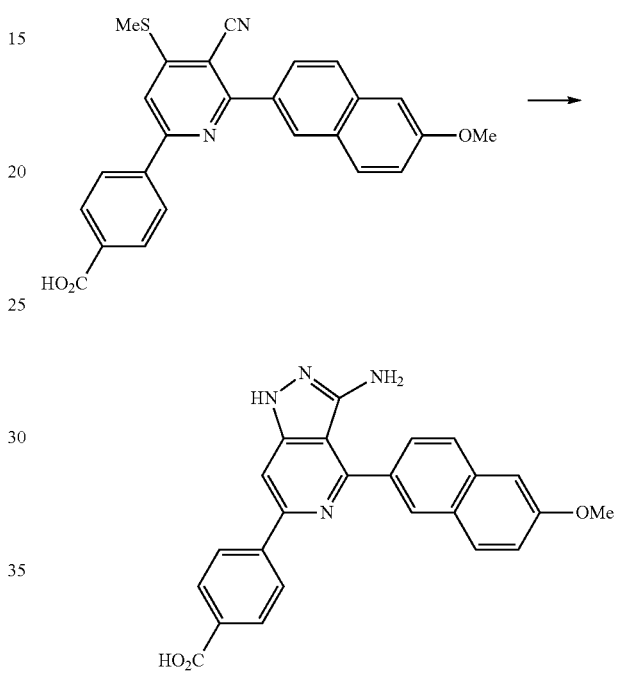

A mixture of 4-(5-cyano-6-(6-methoxynaphthalen-2-yl)-4-(methylthio)pyridin-2-yl)benzoic acid (15 mg, 0.035 mmol) and 65% aqueous hydrazine (0.2 ml, 4.14 mmol) in DMA (0.4 mL) was heated to 180° C. under microwave for 1 h. The mixture was purified by reverse phase HPLC (Sunfire S10 30×250 mm column), eluting with 40-100% solvent B (10% methanol-90% water-0.1% TFA) in solvent A (90% methanol-10% water-0.1% TFA), to give Example 250 as yellow solid (5 mg, 22% yield), assumed bis-TFA salt. $^1$H NMR (400 MHz, methanol-d$_4$) δ ppm 8.45 (1H, d, J=1.51 Hz), 8.22-8.33 (2H, m), 8.17 (1H, d, J=8.53 Hz), 7.97-8.09 (3H, m), 7.91-7.96 (1H, m), 7.89 (1H, s), 7.48 (1H, d, J=2.51 Hz), 7.20-7.42 (1H, m), 4.02 (3H, s); MS (ES+) m/z: 411 (M+H); LC retention time: 2.67 min (analytical HPLC Method A).

Examples 251 to 263

Examples 251 to 262 were prepared from 4-(6-chloro-5-cyano-4-(methylthio)pyridin-2-yl)benzoic acid (Step 3 of Example 250) using analogous conditions to the synthesis of Example 250. Example 263 was prepared from Example 252 by treatment with BBr$_3$.

| Example No. | Structure | Spectral data* |
|---|---|---|
| Example 251: 4-(3-Amino-4-dibenzo[b,d]thiophen-2-yl-1H-pyrazolo[4,3-c]pyridin-6-yl)benzoic acid | 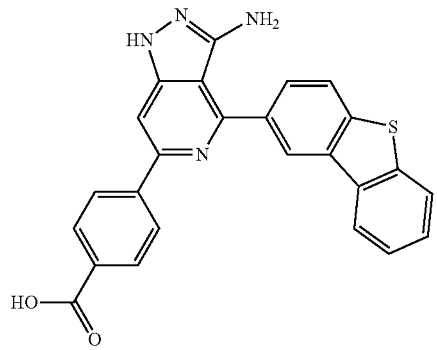 [SMILES: Nc1n[nH]c2cc(-c3ccc(C(=O)O)cc3)nc(-c3ccc4sc5ccccc5c4c3)c12] | $^1$H NMR (400 MHz, DMSO-d$_6$) δ ppm 8.83 (1 H, s), 8.41-8.60 (1 H, m), 8.23-8.41 (3 H, m), 8.04-8.20 (3 H, m), 7.95-8.04 (1 H, m), 7.92 (1 H, s), 7.50-7.67 (2 H, m); MS (ES+) m/z: 437 (M + H); LC retention time: 2.84 min. |
| Example 252: 4-(3-Amino-4-(4-methoxyphenyl)-1H-pyrazolo[4,3-c]pyridin-6-yl)benzoic acid | 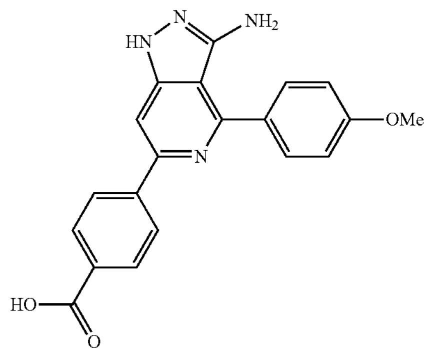 [SMILES: COc1ccc(-c2nc(-c3ccc(C(=O)O)cc3)cc3[nH]nc(N)c23)cc1] | $^1$H NMR (400 MHz, DMSO-d$_6$) δ ppm 8.15-8.34 (2 H, m), 8.07 (2 H, d, J = 8.53 Hz), 7.58-7.94 (3 H, m), 7.19 (2 H, d, J = 8.53 Hz), 3.88 (3 H, s); MS (ES+) m/z: 361 (M + H); LC retention time: 2.67 min. |
| Example 253: 4-(3-Amino-4-phenyl-1H-pyrazolo[4,3-c]pyridin-6-yl)benzoic acid | 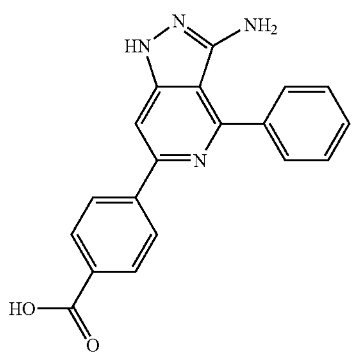 [SMILES: Nc1n[nH]c2cc(-c3ccc(C(=O)O)cc3)nc(-c3ccccc3)c12] | $^1$H NMR (400 MHz, methanol-d$_4$) δ ppm 8.26 (2 H, d, J = 8.78 Hz), 8.01 (2 H, d, J = 8.53 Hz), 7.91-7.96 (2 H, m), 7.88 (1 H, s), 7.71-7.86 (3 H, m); MS (ES+) m/z: 331 (M + H); LC retention time: 1.84 min. |
| Example 254: 4-(3-Amino-4-(4-ethoxyphenyl)-1H-pyrazolo[4,3-c]pyridin-6-yl)benzoic acid | 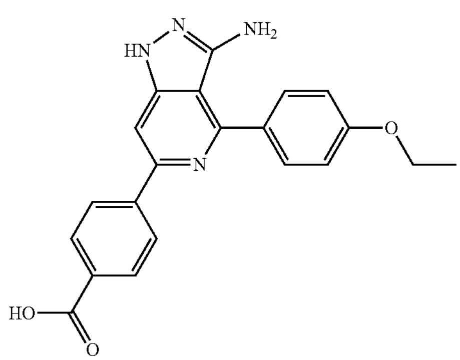 [SMILES: CCOc1ccc(-c2nc(-c3ccc(C(=O)O)cc3)cc3[nH]nc(N)c23)cc1] | $^1$H NMR (400 MHz, methanol-d$_4$) δ ppm 8.21-8.36 (2 H, m), 7.97-8.07 (2 H, m), 7.85-7.95 (2 H, m), 7.82 (1 H, s), 7.28 (2 H, d, J = 8.78 Hz), 4.17-4.31 (2 H, m), 1.49 (3 H, t, J = 6.90 Hz); MS (ES+) m/z: 375 (M + H); LC retention time: 2.34 min. |

-continued

| Example No. | Structure | Spectral data* |
|---|---|---|
| Example 255: 4-(3-Amino-4-(4-isopropoxyphenyl)-1H-pyrazolo[4,3-c]pyridin-6-yl)benzoic acid | 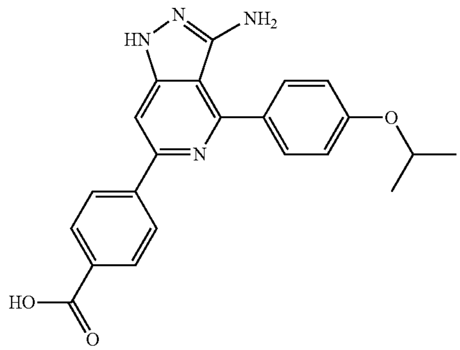 [SMILES: CC(C)Oc1ccc(-c2nc(-c3ccc(C(=O)O)cc3)cc3[nH]nc(N)c23)cc1] | $^1$H NMR (400 MHz, methanol-d$_4$) δ ppm 8.18-8.35 (2 H, m), 7.96-8.08 (2 H, m), 7.86-7.94 (2 H, m), 7.82 (1 H, s), 7.16-7.36 (2 H, m), 4.75-4.88 (1 H, m), 1.42 (6 H, d, J = 6.02 Hz); MS (ES+) m/z: 389 (M + H); LC retention time: 2.41 min. |
| Example 256: 4-(3-Amino-4-(4-(methylsulfanyl)phenyl)-1H-pyrazolo[4,3-c]pyridin-6-yl)benzoic acid | 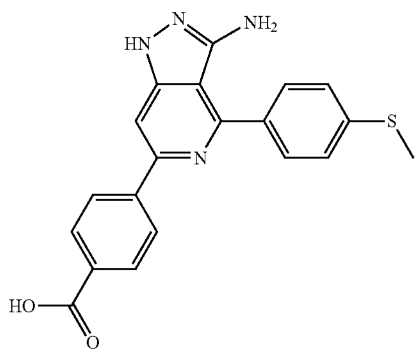 [SMILES: CSc1ccc(-c2nc(-c3ccc(C(=O)O)cc3)cc3[nH]nc(N)c23)cc1] | $^1$H NMR (500 MHz, DMSO-d$_6$) δ ppm 8.06-8.27 (2 H, m), 7.86-8.04 (2 H, m), 7.76 (1 H, s), 7.60-7.73 (2 H, m), 7.23-7.52 (2 H, m), 2.47 (3 H, s); MS (ES+) m/z: 377 (M + H); LC retention time: 2.18 min. |
| Example 257: 4-(3-Amino-4-(3-fluoro-4-methoxyphenyl)-1H-pyrazolo[4,3-c]pyridin-6-yl)benzoic acid | 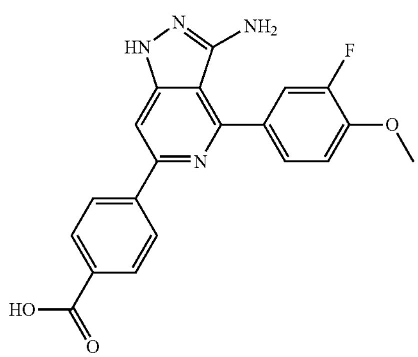 [SMILES: COc1ccc(-c2nc(-c3ccc(C(=O)O)cc3)cc3[nH]nc(N)c23)cc1F] | $^1$H NMR (500 MHz, methanol-d$_4$) δ ppm 8.20 (2 H, d, J = 8.25 Hz), 7.95 (2 H, d, J = 8.25 Hz), 7.80 (1 H, s), 7.70-7.78 (1 H, m), 7.67 (1 H, d, J = 8.52 Hz), 7.34-7.47 (1 H, m), 4.00 (3 H, s); MS (ES+) m/z: 379 (M + H); LC retention time: 2.15 min. |
| Example 258: 4-(3-Amino-4-(2-naphthyl)-1H-pyrazolo[4,3-c]pyridin-6-yl)benzoic acid | 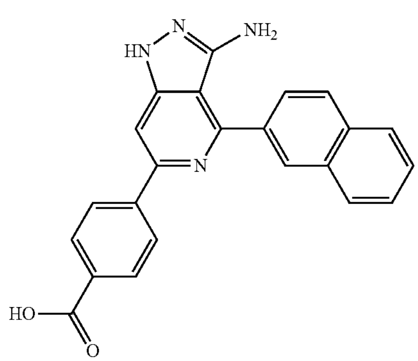 [SMILES: Nc1n[nH]c2cc(-c3ccc(C(=O)O)cc3)nc(-c3ccc4ccccc4c3)c12] | $^1$H NMR (500 MHz, methanol-d$_4$) δ ppm 8.50 (1 H, s), 8.20-8.28 (3 H, m), 8.13 (1 H, d, J = 7.97 Hz), 8.08 (1 H, d, J = 7.97 Hz), 7.98-8.04 (2 H, m), 7.92-7.97 (1 H, m), 7.89 (1 H, s), 7.67-7.76 (2 H, m); MS (ES+) m/z: 381 (M + H); LC retention time: 2.56 min. |

-continued

| Example No. | Structure | Spectral data* |
|---|---|---|
| Example 259:<br>4-(3-Amino-4-(3-furyl)-<br>1H-pyrazolo[4,3-c]<br>pyridin-6-yl)benzoic<br>acid | | ¹H NMR (400 MHz, methanol-d₄) δ ppm 8.42 (1 H, s), 8.25 (2 H, d, J = 8.53 Hz), 8.02 (2 H, d, J = 8.78 Hz), 7.87-7.96 (1 H, m), 7.81 (1 H, s), 6.98-7.25 (1 H, m); MS (ES+) m/z: 321 (M + H); LC retention time: 1.54 min. |
| Example 260:<br>4-(3-Amino-4-(3-<br>thienyl)-1H-pyrazolo<br>[4,3-c]pyridin-6-<br>yl)benzoic acid | | ¹H NMR (400 MHz, methanol-d₄) δ ppm 8.29-8.40 (1 H, m), 8.24 (2 H, d, J = 8.53 Hz), 8.03 (2 H, d, J = 8.53 Hz), 7.84-7.88 (1 H, m), 7.83 (1 H, s), 7.60-7.75 (1 H, m); MS (ES+) m/z: 337 (M + H); LC retention time: 1.65 min. |
| Example 261:<br>4-(3-Amino-4-(1H-<br>pyrazol-3-yl)-1H-<br>pyrazolo[4,3-c]pyridin-<br>6-yl)benzoic acid | | ¹H NMR (400 MHz, methanol-d₄) δ ppm 8.24 (2 H, d, J = 8.28 Hz), 7.94-8.14 (3 H, m), 7.60-7.77 (1 H, m), 7.35-7.55 (1 H, m); MS (ES+) m/z: 321 (M + H); LC retention time: 1.84 min. |
| Example 262:<br>4-(3-Amino-4-(4-(3-<br>fluorophenoxy)phenyl)-<br>1H-pyrazolo[4,3-c]<br>pyridin-6-yl)benzoic<br>acid | | ¹H NMR (400 MHz, methanol-d₄) δ ppm 8.24 (2 H, d, J = 8.53 Hz), 8.01 (2 H, d, J = 8.78 Hz), 7.94 (2 H, d, J = 8.78 Hz), 7.84 (1 H, s), 7.38-7.54 (1 H, m), 7.34 (2 H, d, J = 8.78 Hz), 7.00 (3 H, d, J = 8.28 Hz); MS (ES+) m/z: 441 (M + H); LC retention time: 2.93 min. |

-continued

| Example No. | Structure | Spectral data* |
|---|---|---|
| Example 263: 4-(3-Amino-4-(4-hydroxyphenyl)-1H-pyrazolo[4,3-c]pyridin-6-yl)benzoic acid | 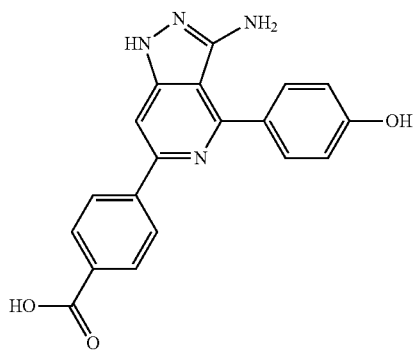 [SMILES: Nc1n[nH]c2cc(-c3ccc(C(=O)O)cc3)nc(-c3ccc(O)cc3)c12] | $^1$H NMR (400 MHz, methanol-$d_4$) δ ppm 8.14 (2 H, d, J = 8.53 Hz), 7.87 (2 H, d, J = 8.53 Hz), 7.55-7.78 (3 H, m), 6.94-7.15 (2 H, m); MS (ES+) m/z: 347 (M + H); LC retention time: 1.80 min. |

*Analytical HPLC Method A

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:
1. A compound of formula (I):

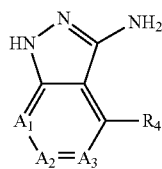

or a pharmaceutically acceptable salt thereof, wherein
$A_1$ is selected from N and $CR_1$;
$A_2$ is selected from N and $CR_2$;
$A_3$ is selected from N and $CR_3$; wherein at least one of $A_1$, $A_2$, and $A_3$ is N; and $A_1$ and $A_2$ are not simultaneously N;
$R_1$ is selected from H, F, Cl, Br, $NO_2$, CN, $NR_aR_a$, $C_{1-6}$alkyl substituted with 0-5 $R_{1a}$, $C_{2-6}$alkenyl substituted with 0-5 $R_{1a}$, $C_{2-6}$alkynyl substituted with 0-5 $R_{1a}$, —O—$C_{1-6}$alkyl, —O—(CHR)$_r$-carbocyclyl substituted with 0-5 $R_{1a}$, —(CHR)$_r$-carbocyclyl substituted with 0-5 $R_{1a}$, and —(CHR)$_r$-heterocyclyl substituted with 0-5 $R_{1a}$;
$R_{1a}$, at each occurrence, is independently selected from $C_{1-6}$alkyl substituted with 0-5 $R_e$, $C_{2-6}$alkenyl substituted with 0-5 $R_e$, $C_{2-6}$alkynyl substituted with 0-5 $R_e$, $C_{1-6}$haloalkyl, F, Cl, Br, $NO_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$NR$_a$P(O)$_p$R$_b$, —(CHR)$_r$—$C_{3-6}$-carbocyclyl substituted with 0-5 $R_e$ and/or —(CHR)$_r$-heterocyclyl substituted with 0-5 $R_e$;
$R_2$ is selected from H, F, Cl, Br, $NO_2$, CN, $NR_aR_a$, $C_{1-6}$alkyl substituted with 0-5 $R_{2a}$, $C_{2-6}$alkenyl substituted with 0-5 $R_{2a}$, $C_{2-6}$alkynyl substituted with 0-5 $R_{2a}$, —O—$C_{1-6}$alkyl substituted with 0-5 $R_{2a}$, —O—(CHR)$_r$-carbocyclyl substituted with 0-5 $R_{2a}$, —(CHR)$_r$-carbocyclyl substituted with 0-5 $R_{2a}$, and —(CHR)$_r$-heterocyclyl substituted with 0-5 $R_{2a}$;
$R_{2a}$, at each occurrence, is independently selected from $C_{1-6}$alkyl, $C_{2-6}$alkenyl, $C_{2-6}$alkynyl, $C_{1-6}$haloalkyl, —(CH$_2$)$_r$$C_{3-10}$-cycloalkyl, F, Cl, Br, $NO_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$C(O)C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$(CHR)$_r$C(O)OR$_d$, —(CHR)$_r$-carbocyclyl substituted with 0-5 $R_e$ and/or —(CHR)$_r$-heterocyclyl substituted with 0-5 $R_e$;
$R_3$ is selected from H, F, Cl, Br, $NO_2$, CN, $C_{1-6}$alkyl substituted with 0-5 $R_{3a}$, $C_{2-6}$alkenyl substituted with 0-5 $R_{3a}$, $C_{2-6}$alkynyl substituted with 0-5 $R_{3a}$, —O—$C_{1-6}$alkyl substituted with 0-5 $R_{3a}$, —O-carbocyclyl substituted with 0-5 $R_{3a}$, —(CHR)$_r$-carbocyclyl substituted with 0-5 $R_{3a}$ and —(CHR)$_r$-heterocyclyl substituted with 0-5 $R_{3a}$;
$R_{3a}$, at each occurrence, is independently selected from $C_{1-6}$alkyl, $C_{2-6}$alkenyl, $C_{2-6}$alkynyl, $C_{1-6}$haloalkyl, —(CH$_2$)$_r$$C_{3-10}$cycloalkyl, F, Cl, Br, $NO_2$, CN, —(CHR)$_r$OH, —(CHR)$_r$SH, —(CHR)$_r$—O—(CHR)$_r$R$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$-aryl substituted with 0-5 $R_e$, and/or —(CHR)$_r$-heterocyclyl substituted with 0-5 $R_e$;
alternatively, $R_1$ and $R_2$, or $R_2$ and $R_3$, are taken together with the ring atoms to which they are attached to form a fused carbocyclyl or heterocyclyl;
$R_4$ is selected from carbocyclyl substituted with 0-5 $R_{4a}$ and heterocyclyl substituted with 0-5 $R_{4a}$;

$R_{4a}$, at each occurrence, is independently selected from F, Cl, Br, $NO_2$, CN, $C_{1-6}$alkyl, $C_{2-6}$alkenyl, $C_{2-6}$alkynyl, $C_{1-6}$haloalkyl, —(CHR)$_r$OH, —(CHR)$_r$SH, —(CHR)$_r$—O—(CHR)$_r$R$_c$, —(CHR)$_r$S(O)$_p$(CHR)$_r$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$-$C_{3-6}$-carbocyclyl substituted with 0-5 R$_e$, and/or —(CHR)$_r$-heterocyclyl substituted with 0-5 R$_e$;

R, at each occurrence, is independently selected from H, $C_{1-6}$alkyl, $C_{1-6}$haloalkyl, and/or —(CH$_2$)$_r$-aryl;

$R_a$, at each occurrence, is independently selected from H, $NH_2$, $C_{1-6}$alkyl substituted with 0-3 R$_e$, $C_{2-6}$alkenyl substituted with 0-3 R$_e$, $C_{2-6}$alkynyl substituted with 0-3 R$_e$, $C_{1-6}$haloalkyl, —O—$C_{1-6}$alkyl substituted with 0-3 R$_e$, —(CH$_2$)$_r$OH, (CH$_2$)$_r$$C_{3-10}$ carbocyclyl substituted with 0-3 R$_e$, and/or —(CH$_2$)$_r$-heterocyclyl substituted with 0-3 R$_e$, or $R_a$ and $R_a$, together with the nitrogen atom to which they are both attached, form a heterocyclyl substituted with 0-3 R$_e$;

$R_b$, at each occurrence, is independently selected from $C_{1-6}$alkyl substituted with 0-3 R$_e$, $C_{1-6}$haloalkyl, $C_{2-6}$alkenyl substituted with 0-3 R$_e$, $C_{2-6}$alkynyl substituted with 0-3 R$_e$, —(CH$_2$)$_r$$C_{3-10}$-carbocyclyl substituted with 0-3 R$_e$, and/or —(CH$_2$)$_r$-heterocyclyl substituted with 0-3 R$_e$;

$R_c$, at each occurrence, is independently selected from $C_{1-6}$alkyl substituted with 0-3 R$_g$, $C_{2-6}$alkenyl substituted with 0-3 R$_g$, $C_{2-6}$alkynyl substituted with 0-3 R$_g$, $C_{1-6}$haloalkyl, —(CH$_2$)$_r$OH, —(CH$_2$)$_r$—$C_{3-10}$carbocyclyl substituted with 0-3 R$_g$, and/or —(CH$_2$)$_r$heterocyclyl substituted with 0-3 R$_g$;

$R_d$, at each occurrence, is independently selected from H, $C_{1-6}$alkyl substituted with 0-3 R$_e$, $C_{1-6}$haloalkyl, $C_{2-6}$alkenyl substituted with 0-3 R$_e$, $C_{2-6}$alkynyl substituted with 0-3 R$_e$, —(CH$_2$)$_r$—$C_{3-10}$carbocyclyl substituted with 0-3 R$_e$, and/or —(CH$_2$)$_r$-heterocyclyl substituted with 0-3 R$_e$;

$R_e$, at each occurrence, is independently selected from $C_{1-6}$alkyl, $C_{2-6}$alkenyl, $C_{2-6}$alkynyl, —(CH$_2$)$_r$$C_{3-6}$cycloalkyl, F, Cl, Br, CN, $NO_2$, —(CH$_2$)$_r$CO$_2$H, —(CH$_2$)$_r$OC$_{1-5}$alkyl, OH, SH, —(CH$_2$)$_r$SC$_{1-5}$alkyl, —(CH$_2$)$_r$NR$_f$R$_f$, —(CH$_2$)$_r$C(O)NR$_f$R$_f$, —(CH$_2$)$_r$-phenyl, and/or —(CH$_2$)$_r$-heterocyclyl;

$R_f$, at each occurrence, is independently selected from H, $C_{1-5}$alkyl, and $C_{3-6}$cycloalkyl, and/or phenyl;

$R_g$, at each occurrence, is independently selected from $C_{1-6}$alkyl, (CH$_2$)$_r$$C_{3-6}$cycloalkyl, F, Cl, Br, CN, $NO_2$, —(CH$_2$)$_r$CO$_2$H, —(CH$_2$)$_r$OC$_{1-6}$alkyl, OH, —(CH$_2$)$_r$-phenyl, and/or —(CH$_2$)$_r$-heterocyclyl;

p, at each occurrence, is independently selected from 0, 1, and/or 2;

r, at each occurrence, is independently selected from 0, 1, 2, 3, and/or 4;

provided that:
(1) if $A_1$ is N, $A_2$ is $CR_2$, and $A_3$ is N, then $R_4$ is phenyl substituted with 1-4 $R_{4a}$ wherein at least one $R_{4a}$ is —O—(CHR)$_r$-phenyl substituted with 0-5 R$_g$;
(2) if $A_1$ is N, $A_2$ is $CR_2$, and $A_3$ is $CR_3$, then $R_4$ is phenyl substituted with 1-4 $R_{4a}$ wherein at least one $R_{4a}$ is —O—(CHR)$_r$-phenyl substituted with 0-5 R$_g$ and $R_2$ is other than $C_{1-6}$alkyl, cyclohexyl, or 1,4-dioxaspiro[4,5]dec-8-yl each substituted or unsubstituted; and
(3) if $A_1$ is $CR_1$, $A_2$ is N, $A_3$ is $CR_3$, and $R_{4a}$ is $NH_2$ or phenyl, then $R_1$ is not hydrogen.

2. The compound according to claim 1 of the Formula (II) or (III):

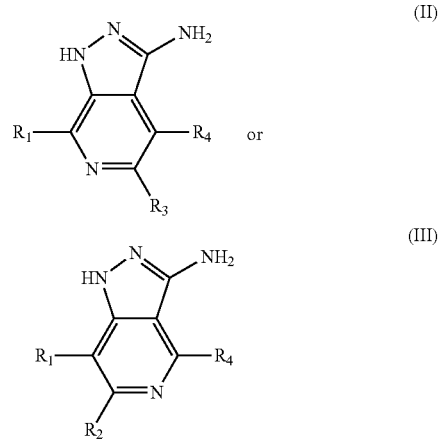

or a pharmaceutically acceptable salt thereof, wherein
$R_1$ is selected from H, F, Cl, Br, $NR_aR_a$, $C_{1-4}$alkyl substituted with 0-3 $R_{1a}$, —O—$C_{1-4}$alkyl, —O-aryl substituted with 0-3 $R_{1a}$, —(CHR)$_r$-aryl substituted with 0-3 $R_{1a}$, —(CHR)$_r$-heterocyclyl substituted with 0-3 $R_{1a}$;

$R_{1a}$, at each occurrence, is independently selected from $C_{1-4}$alkyl substituted with 0-3 R$_e$, $C_{1-4}$haloalkyl, F, Cl, Br, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$—$C_{3-6}$-carbocyclyl substituted with 0-3 R$_e$, and/or —(CH$_2$)$_r$-heterocyclyl substituted with 0-3 R$_e$;

$R_2$ is selected from H, F, Cl, Br, $NO_2$, CN, $NR_aR_a$, $C_{1-4}$alkyl substituted with 0-3 $R_{2a}$, —O—$C_{1-4}$alkyl substituted with 0-3 $R_{2a}$, —O-carbocyclyl substituted with 0-3 $R_{2a}$, —(CHR)$_r$-carbocyclyl substituted with 0-3 $R_{2a}$, and heterocyclyl substituted with 0-3 $R_{2a}$;

$R_{2a}$, at each occurrence, is independently selected from $C_{1-4}$alkyl, $C_{2-4}$alkenyl, $C_{2-4}$alkynyl, $C_{1-4}$haloalkyl, —(CH$_2$)$_r$$C_{3-6}$cycloalkyl, F, Cl, Br, $NO_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$C(O)C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$(CHR)$_r$C(O)OR$_d$, —(CHR)$_r$-carbocyclyl substituted with 0-3 R$_e$ and/or —(CHR)$_r$-heterocyclyl substituted with 0-3 R$_e$;

alternatively, $R_1$ and $R_2$ of Formula (III) are taken together with the ring atoms to which they are attached to form a fused carbocyclyl or heterocyclyl;

$R_3$ is selected from H, F, Cl, Br, $NO_2$, CN, $C_{1-4}$alkyl substituted with 0-3 $R_{3a}$, —O—$C_{1-4}$alkyl substituted with 0-3 $R_{3a}$, —O-aryl substituted with 0-3 $R_{3a}$, —(CHR)$_r$-aryl substituted with 0-3 $R_{3a}$, and —(CHR)$_r$-heterocyclyl substituted with 0-3 $R_{3a}$;

$R_{3a}$, at each occurrence, is independently selected from $C_{1-4}$alkyl, $C_{2-4}$alkenyl, $C_{2-4}$alkynyl, $C_{1-4}$-haloalkyl, —(CH$_2$)$_r$$C_{3-6}$cycloalkyl, F, Cl, Br, $NO_2$, CN, —(CHR)$_r$ OH, —(CHR)$_r$SH, —(CHR)$_r$—O—(CHR)$_r$R$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)R$_d$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$-aryl substituted with 0-3 R$_e$, and/or —(CHR)$_r$-heterocyclyl substituted with 0-3 R$_e$;

R$_4$ is selected from aryl substituted with 0-3 R$_{4a}$ and heterocyclyl substituted with 0-3 R$_{4a}$;

R$_{4a}$, at each occurrence, is independently selected from F, Cl, Br, C$_{1-4}$alkyl, —(CHR)$_r$OH, —(CHR)$_r$OR$_e$, —(CHR)$_r$SR$_b$, —(CHR)$_r$C(O)R$_d$, —(CHR)$_r$NR$_a$R$_a$, —(CHR)$_r$NHC(O)R$_d$—(CHR)$_r$C(O)NR$_a$R$_a$, —(CHR)$_r$—C$_{3-6}$carbocyclyl substituted with 0-3 R$_e$, and/or —(CHR)$_r$-heterocyclyl substituted with 0-3 R$_e$, R, at each occurrence, is independently selected from H, C$_{1-6}$alkyl, and/or C$_{1-6}$haloalkyl;

R$_a$, at each occurrence, is independently selected from H, NH$_2$, C$_{1-4}$alkyl substituted with 0-3 R$_e$, CF$_3$, —O—C$_{1-4}$alkyl, —(CH$_2$)$_r$OH, —(CH$_2$)$_r$C$_{3-6}$cycloalkyl substituted with 0-3 R$_e$, —(CH$_2$)$_r$-phenyl substituted with 0-3 R$_e$, and/or —(CH$_2$)$_r$-heterocyclyl substituted with 0-3 R$_e$, or R$_a$ and R$_a$ together with the nitrogen atom to which they are both attached form a heterocyclyl substituted with 0-3 R$_e$;

R$_b$, at each occurrence, is independently selected from C$_{1-4}$alkyl substituted with 0-3 R$_e$, CF$_3$, phenyl substituted with 0-3 R$_e$, and/or heterocyclyl substituted with 0-3 R$_e$;

R$_c$, at each occurrence, is independently selected from C$_{1-4}$alkyl substituted with 0-3 R$_g$, C$_{2-4}$alkenyl substituted with 0-3 R$_g$, C$_{2-4}$alkynyl substituted with 0-3 R$_g$, C$_{1-4}$-haloalkyl, —(CH$_2$)$_r$OH, —(CH$_2$)$_r$-aryl substituted with 0-3 R$_g$, —(CH$_2$)$_r$—C$_{3-10}$cycloalkyl substituted with 0-3 R$_g$ and/or —(CH$_2$)$_r$-heterocyclyl substituted with 0-3 R$_g$;

R$_d$, at each occurrence, is independently selected from H, C$_{1-4}$alkyl substituted with 0-3 R$_e$, C$_{2-4}$alkenyl substituted with 0-3 R$_e$, C$_{2-4}$alkynyl substituted with 0-3 R$_e$, CF$_3$, —(CH$_2$)$_r$-phenyl substituted with 0-3 R$_e$, and/or heterocyclyl substituted with 0-3 R$_e$;

R$_e$, at each occurrence, is independently selected from C$_{1-4}$alkyl, C$_{3-6}$cycloalkyl, F, Cl, Br, CN, NO$_2$, —(CH$_2$)$_r$CO$_2$H; —(CH$_2$)$_r$C(O)NR$_f$R$_f$; —(CH$_2$)$_r$OC$_{1-4}$alkyl, OH, SH, —(CH$_2$)$_r$SC$_{1-5}$ alkyl, —(CH$_2$)$_r$-phenyl, and/or —(CH$_2$)$_r$-heterocyclyl;

R$_f$, at each occurrence, is independently selected from H and/or C$_{1-5}$alkyl;

R$_g$, at each occurrence, is independently selected from C$_{1-4}$alkyl, —(CH$_2$)$_r$—C$_{3-6}$cycloalkyl, F, Cl, Br, CN, NO$_2$, —(CH$_2$)$_r$OC$_{1-4}$alkyl, OH, and/or —(CH$_2$)$_r$-phenyl; and r, at each occurrence, is independently selected from 0, 1, 2, and/or 3.

3. The compound according to claim 2 or a pharmaceutically acceptable salt thereof, wherein R$_1$ is —NH-aryl substituted with 0-3 R$_e$;

R$_4$ is selected from aryl substituted with 0-3 R$_{4a}$ and heterocyclyl substituted with 0-3 R$_{4a}$;

R$_{4a}$, at each occurrence, is independently selected from —(CH$_2$)$_r$OH, —OR$_e$, C$_{1-4}$alkyl, —NHC(O)R$_d$, —C(O)NHR$_a$, NR$_a$R$_a$, and/or —(CH$_2$)$_r$SR$_b$;

R$_a$, at each occurrence, is independently selected from H, NH$_2$, and/or C$_{1-4}$alkyl substituted with 0-3 R$_e$;

R$_c$, at each occurrence, is independently selected from C$_{1-4}$alkyl substituted with 0-3 R$_g$ and/or aryl substituted with 0-3 R$_g$;

R$_d$, at each occurrence, is independently selected from H, C$_{1-4}$alkyl substituted with 0-3 R$_e$, and/or phenyl substituted with 0-3 R$_e$;

R$_e$, at each occurrence, is independently selected from F, Cl, Br, and C$_{1-4}$alkyl; and R$_g$, at each occurrence, is independently selected from F, Cl, Br, OH, and/or C$_{1-4}$alkyl.

4. The compound according to claim 2 or a pharmaceutically acceptable salt thereof, wherein R$_4$ is substituted with 0-3 R$_{4a}$ and selected from pyrrolyl, pyrazolyl, imidazolyl, oxazolyl, isoxazolyl, thiazolyl, isothiazolyl, furyl, thienyl, piperidinyl, pyridyl, pyrazinyl, pyrimidinyl, triazolyl, indolyl, indazolyl, benzothiazolyl, benzoxazolyl, benzodioxolyl, benzothienyl, quinolinyl, isoquinolinyl, benzimidazolyl, benzofuryl, benzisothiazolyl, benzisoxazolyl, benzodiazinyl, and dibenzothienyl.

5. The compound according to claim 2 or a pharmaceutically acceptable salt thereof, wherein R$_4$ is selected from naphthyl and phenyl, each of which is substituted with 1-3 R$_{4a}$ and;

R$_{4a}$, at each occurrence, is independently selected from F, Cl, Br, C$_{1-4}$alkyl, —(CH$_2$)$_r$OH, —(CH$_2$)$_r$OR, and/or —(CH$_2$)$_r$SR$_b$.

6. The compound according to claim 5 of the Formula (IIa) or (IIIa):

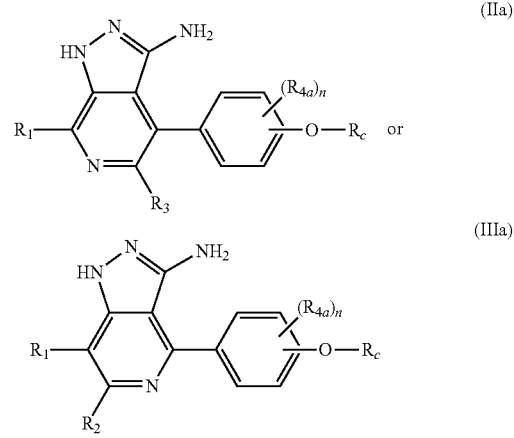

or a pharmaceutically acceptable salt thereof, wherein

R$_1$ is selected from H, NHR$_a$, C$_{1-4}$alkyl substituted with 0-3 R$_{1a}$, —O—C$_{1-4}$alkyl, —O-aryl substituted with 0-3 R$_{1a}$, —(CH$_2$)$_r$aryl substituted with 0-3 R$_{1a}$, heterocyclyl substituted with 0-3 R$_{1a}$;

R$_{1a}$, at each occurrence, is independently selected from C$_{1-4}$alkyl substituted with 0-3 R$_e$, C$_{1-4}$-haloalkyl, F, Cl, Br, —(CH$_2$)$_r$OH, —(CH$_2$)$_r$SH, —(CH$_2$)$_r$OR$_b$, —(CH$_2$)$_r$S(O)$_2$R$_b$, —(CH$_2$)$_r$C(O)R$_d$, —(CHANR$_a$R$_a$, —(CH$_2$)$_r$C(O)NR$_a$R$_a$, —(CH$_2$)$_r$C(O)NHOR$_b$, —(CH$_2$)$_r$NHC(O)R$_d$, —(CH$_2$)$_r$NHC(O)OR$_b$, —(CH$_2$)$_r$OC(O)NR$_a$R$_a$, —(CH$_2$)$_r$C(O)OR$_d$, —(CH$_2$)$_r$S(O)$_2$NR$_a$R$_a$, —(CH$_2$)$_r$NHS(O)$_2$R$_b$, —(CH$_2$)$_r$NHP(O)$_p$R$_b$, —(CH$_2$)$_r$-phenyl substituted with 0-3 R$_e$ and/or —(CH$_2$)$_r$-heterocyclyl substituted with 0-3 R$_e$;

R$_2$ is selected from H, F, Cl, Br, NO$_2$, CN, NR$_a$R$_a$, C$_{1-4}$alkyl substituted with 0-3 R$_{2a}$, —O—C$_{1-4}$alkyl substituted with 0-3 R$_{2a}$, —O-aryl substituted with 0-3 R$_{2a}$, —(CH$_2$)$_r$-phenyl substituted with 0-3 R$_{2a}$, —(CH$_2$)$_r$—C$_{3-10}$ cycloalkyl substituted with 0-3 R$_{2a}$, and heterocyclyl substituted with 0-3 R$_{2a}$;

R$_{2a}$, at each occurrence, is independently selected from C$_{1-4}$alkyl, C$_{1-4}$-haloalkyl, F, Cl, Br, NO$_2$, CN, —(CH$_2$)$_r$OH, —(CH$_2$)$_r$SH, —(CH$_2$)$_r$OR$_b$, —(CH$_2$)$_r$S(O)$_p$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$C(O)NR$_a$OR$_b$, —(CH$_2$)$_r$NHC(O)NR$_a$R$_a$, —(CH$_2$)$_r$NHC(O)OR$_b$, —(CH$_2$)$_r$OC(O)NR$_a$R$_a$, —(CH$_2$)$_r$C(O)OR$_d$, —(CH$_2$)$_r$C(O)C(O)OR$_d$, —(CH$_2$)$_r$S(O)$_2$NR$_a$R$_a$, —(CH$_2$)$_r$NHS(O)$_2$R$_b$, —(CH$_2$)$_r$C(O)NHS(O)$_2$R$_b$, —(CH$_2$)$_r$C(O)NR$_a$(CH$_2$)$_r$C(O)OR$_d$, —(CH$_2$)$_r$C$_{3-6}$cycloalkyl, —(CH$_2$)$_r$phenyl substituted with 0-3 R$_e$, and/or —(CH$_2$)$_r$-heterocyclyl substituted with 0-3 R$_e$;

R$_3$ is selected from H, C$_{1-4}$alkyl substituted with 0-3 R$_{3a}$, aryl substituted with 0-3 R$_{3a}$, and heterocyclyl substituted with 0-3 R$_{3a}$;

R$_{3a}$, at each occurrence, is independently selected from C$_{1-4}$alkyl, C$_{1-4}$-haloalkyl, —(CH$_2$)$_r$OH, —(CH$_2$)$_r$OR$_b$, —(CH$_2$)$_r$S(O)$_2$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$NHC(O)R$_d$, —(CH$_2$)$_r$NHC(O)OR$_b$, —(CH$_2$)$_r$C(O)OR$_d$, —(CH$_2$)$_r$-phenyl substituted with 0-3 R$_e$ and/or —(CH$_2$)$_r$-heterocyclyl substituted with 0-3 R$_e$;

R$_a$, at each occurrence, is independently selected from H, NH$_2$, C$_{1-4}$alkyl substituted with 0-3 R$_e$, CF$_3$, —O—C$_{1-4}$alkyl, —(CH$_2$)$_r$OH, —(CH$_2$)$_r$C$_{3-6}$cycloalkyl substituted with 0-3 R$_e$, —(CH$_2$)$_r$phenyl substituted with 0-3 R$_e$, and/or —(CH$_2$)$_r$ heterocyclyl substituted with 0-3 R$_e$, or R$_a$ and R$_a$ together with the nitrogen atom to which they are both attached form a heterocyclyl substituted with 0-3 R$_e$;

R$_b$, at each occurrence, is independently selected from C$_{1-4}$alkyl substituted with 0-3 R$_e$, phenyl substituted with 0-3 R$_e$, and/or heterocyclyl substituted with 0-3 R$_e$;

R$_c$, at each occurrence, is independently selected from C$_{1-4}$alkyl substituted with 0-3 R$_g$, C$_{1-4}$-haloalkyl, —(CH$_2$)$_r$—C$_{3-6}$cycloalkyl substituted with 0-3 R$_g$, —(CH$_2$)$_r$-aryl substituted with 0-3 R$_g$ and/or —(CH$_2$)$_r$-heterocyclyl substituted with 0-3 R$_g$;

R$_d$, at each occurrence, is independently selected from H, C$_{1-4}$alkyl substituted with 0-3 R$_e$, C$_{2-4}$alkenyl substituted with 0-3 R$_e$, —(CH$_2$)$_r$phenyl substituted with 0-3 R$_e$, and/or heterocyclyl substituted with 0-3 R$_e$;

R$_e$, at each occurrence, is independently selected from C$_{1-4}$alkyl, C$_{3-6}$cycloalkyl, F, Cl, Br, CN, NO$_2$, —(CH$_2$)$_r$CO$_2$H, —(CH$_2$)$_r$C(O)NR/(C$_{1-4}$alkyl), —(CH$_2$)$_r$OC$_{1-5}$alkyl, OH, SH, —(CH$_2$)$_r$SC$_{1-4}$alkyl, —(CH$_2$)$_r$phenyl and/or —(CH$_2$)$_r$heterocyclyl;

R$_g$, at each occurrence, is independently selected from C$_{1-4}$alkyl, F, Cl, Br, CN, NO$_2$, —(CH$_2$)$_r$OC$_{1-4}$alkyl, OH, and/or —(CH$_2$)$_r$phenyl;

r, at each occurrence, is independently selected from 0, 1, and/or 2; and n, at each occurrence, is independently selected from 0, 1, and/or 2.

7. The compound according to claim 6 of the Formula (IIb) or (IIIb):

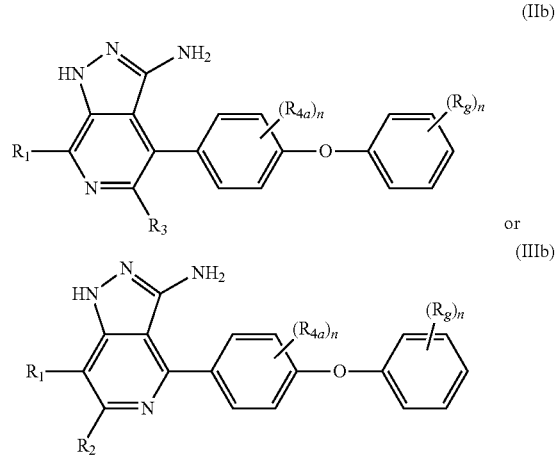

or a pharmaceutically acceptable salt thereof, wherein

R$_1$ is selected from H, NHR$_a$, C$_{1-4}$alkyl substituted with 0-3 R$_{1a}$, —O—C$_{1-4}$alkyl, —(CH$_2$)$_r$aryl substituted with 0-3 R$_{1a}$, and heterocyclyl substituted with 0-3 R$_{1a}$;

R$_{1a}$, at each occurrence, is independently selected from C$_{1-4}$alkyl substituted with 0-3 R$_e$, CF$_3$, F, Cl, Br, —(CH$_2$)$_r$OH, —(CH$_2$)$_r$OR$_b$, —(CH$_2$)$_r$S(O)$_2$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$NHC(O)R$_d$, —(CH$_2$)$_r$NHC(O)OR$_b$, —(CH$_2$)$_r$C(O)OR$_d$, —(CH$_2$)$_r$S(O)$_2$NR$_a$R$_a$, —(CH$_2$)$_r$NHS(O)$_2$R$_b$, —(CH$_2$)$_r$-phenyl substituted with 0-3 R$_e$ and/or —(CH$_2$)$_r$-heterocyclyl substituted with 0-3 R$_e$;

R$_2$ is selected from H, F, Cl, Br, NHR$_a$, C$_{1-4}$alkyl substituted with 0-3 R$_{2a}$, —(CH$_2$)$_r$-aryl substituted with 0-3 R$_{2a}$, —(CH$_2$)$_r$—C$_{3-10}$cycloalkyl substituted with 0-3 R$_{2a}$, and heterocyclyl substituted with 0-3 R$_{2a}$;

R$_{2a}$, at each occurrence, is independently selected from C$_{1-4}$alkyl, C$_{1-4}$-haloalkyl, F, Cl, Br, NO$_2$, CN, —(CH$_2$)$_r$OH, —(CH$_2$)$_r$OR$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$NHC(O)NR$_a$R$_a$, —(CH$_2$)$_r$C(O)OR$_d$, —(CH$_2$)$_r$C(O)C(O)OR$_d$, —(CH$_2$)$_r$C(O)NHS(O)$_2$R$_b$, —(CH$_2$)$_r$C(O)NR$_a$(CH$_2$)$_r$C(O)OR$_d$, —(CH$_2$)$_r$phenyl substituted with 0-3 R$_e$, and/or —(CH$_2$)$_r$-heterocyclyl substituted with 0-3 R$_e$;

R$_3$ is selected from H, C$_{1-4}$alkyl substituted with 0-3 R$_{3a}$, phenyl substituted with 0-3 R$_{3a}$, and heterocyclyl substituted with 0-3 R$_{3a}$;

R$_{3a}$, at each occurrence, is independently selected from —(CH$_2$)$_r$OR$_b$ and —(CH$_2$)$_r$C(O)NR$_a$R$_a$;

R$_a$, at each occurrence, is independently selected from H, NH$_2$, C$_{1-4}$alkyl substituted with 0-3 R$_e$, —(CH$_2$)$_r$OH, —(CHAC$_{3-6}$cycloalkyl substituted with 0-3 R$_e$, —(CH$_2$)$_r$phenyl substituted with 0-3 R$_e$, and/or —(CH$_2$)$_r$heterocyclyl substituted with 0-3 R$_e$, or R$_a$ and R$_a$ together with the nitrogen atom to which they are both attached form a heterocyclyl substituted with 0-3 R$_e$;

R$_b$, at each occurrence, is independently selected from C$_{1-4}$alkyl substituted with 0-3 R$_e$, phenyl substituted with 0-3 R$_e$, and/or heterocyclyl substituted with 0-3 R$_e$;

R$_d$, at each occurrence, is independently selected from H, C$_{1-4}$alkyl substituted with 0-3 R$_e$, C$_{2-4}$alkenyl substituted with 0-3 R$_e$, —(CH$_2$)$_r$phenyl substituted with 0-3 R$_e$, and/or heterocyclyl substituted with 0-3 R$_e$;

R$_e$, at each occurrence, is independently selected from F, Cl, C$_{1-4}$alkyl, —(CH$_2$)$_r$CO$_2$H, and/or —(CH$_2$)$_r$C(O)N(CH$_3$)$_2$, $R_g$, at each occurrence, is independently selected from F, Cl, Br, OH, $C_{1-4}$alkyl, and/or —O$C_{1-4}$alkyl;

r, at each occurrence, is independently selected from 0, 1, and/or 2; and n, at each occurrence, is independently selected from 0, 1, and/or 2.

8. The compound according to claim 1 of the Formula (IV):

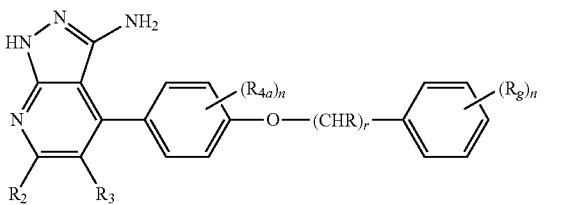

(IV)

or a pharmaceutically acceptable salt thereof, wherein $R_2$ is selected from H, —O-aryl wherein said aryl is substituted with 0-3 $R_{2a}$, —O—$C_{1-4}$alkyl wherein said alkyl is substituted with 0-3 $R_{2a}$, $NR_aR_a$, $C_{3-6}$cycloalkyl substituted with 0-3 $R_{2a}$, aryl substituted with 0-3 $R_{2a}$, and heterocyclyl substituted with 0-3 $R_{2a}$;

$R_{2a}$, at each occurrence, is independently selected from $C_{1-6}$alkyl, $C_{2-6}$alkenyl, $C_{2-6}$alkynyl, $C_{1-6}$haloalkyl, —(CH$_2$)$_r$C$_{3-6}$cycloalkyl, F, Cl, Br, NO$_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$(CHR)$_r$C(O)OR$_d$, —(CHR)$_r$-aryl substituted with 0-5 $R_e$ and/or —(CHR)$_r$-heterocyclyl substituted with 0-5 $R_e$;

$R_3$ is selected from H, F, Cl, Br, NO$_2$, CN, $C_{1-4}$alkyl, —(CHR)$_r$-aryl substituted with 0-3 $R_{3a}$, —O—$C_{1-4}$alkyl, —O-aryl substituted with 0-3 $R_{3a}$, and —(CHR)$_r$-heterocyclyl substituted with 0-3 $R_{3a}$;

$R_{3a}$, at each occurrence, is independently selected from $C_{1-4}$alkyl, $C_{2-4}$alkenyl, $C_{2-4}$alkynyl, $C_{1-4}$haloalkyl, —(CH$_2$)$_r$C$_{3-6}$cycloalkyl, F, Cl, Br, NO$_2$, CN, —(CHR)$_r$OH;

$R_a$, at each occurrence, is independently selected from H, NH$_2$, $C_{1-4}$alkyl substituted with 0-3 $R_e$, CF$_3$, —O—$C_{1-6}$alkyl, —(CH$_2$)$_r$OH, $C_{3-6}$cycloalkyl substituted with 0-3 $R_e$, phenyl substituted with 0-3 $R_e$, and/or heterocyclyl substituted with 0-3 $R_e$, or $R_a$ and $R_a$ together with the nitrogen atom to which they are both attached form a heterocyclyl substituted with 0-3 $R_e$;

$R_b$, at each occurrence, is independently selected from $C_{1-4}$alkyl, CF$_3$, phenyl substituted with 0-3 $R_e$, and/or heterocyclyl substituted with 0-3 $R_e$;

$R_d$, at each occurrence, is independently selected from H, $C_{1-4}$alkyl, CF$_3$, phenyl substituted with 0-3 $R_e$, and/or heterocyclyl substituted with 0-3 $R_e$;

$R_e$, at each occurrence, is independently selected from $C_{1-4}$alkyl, $C_{3-6}$cycloalkyl, F, Cl, Br, CN, NO$_2$, NH$_2$, CO$_2$H, —(CH$_2$)$_r$OC$_{1-5}$alkyl, OH, SH, (CH$_2$)$_r$SC$_{1-5}$alkyl, (CH$_2$)$_r$phenyl and/or (CH$_2$)$_r$heterocyclyl;

$R_g$, at each occurrence, is independently selected from $C_{1-4}$alkyl, F, Cl, Br, CN, NO$_2$, —(CH$_2$)$_r$OC$_{1-4}$alkyl, and/or OH;

r, at each occurrence, is independently selected from 0, 1, and/or 2; and n, at each occurrence, is independently selected from 0, 1, 2, and/or 3.

9. The compound according to claim 8 or a pharmaceutically acceptable salt thereof, wherein $R_2$ is selected from $C_{3-6}$cycloalkyl, —NH—$C_{3-6}$cycloalkyl, —O-phenyl, phenyl, pyrrole, piperidine, piperazine, and pyridine, each ring substituted with 0-2 $R_{2a}$; and $R_{2a}$, at each occurrence, is independently selected from —O—$C_{1-4}$alkyl, OH, NH$_2$, —NHC(O)O—$C_{1-4}$alkyl, —NHC(O)NH-heteroaryl, —NHC(O)-phenyl unsubstituted or substituted with $C_{1-4}$alkyl, —C(O)—$C_{1-4}$alkyl, —C(O)-phenyl, —C(O)NH-phenyl, —C(O)NH—$C_{3-6}$cycloalkyl, —C(O)NH-heterocyclyl, —C(O)NH—NH$_2$, and/or —C(O)NR$_a$R$_a$ wherein $R_a$ and $R_a$ may be taken together with the nitrogen atom to which they are attached to form a 5- to 6-membered heterocyclyl.

10. The compound according to claim 1 of the Formula (V):

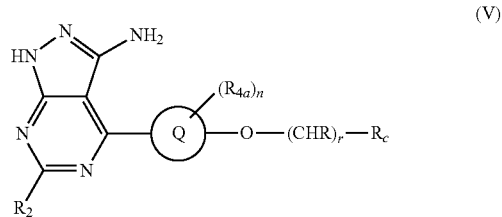

(V)

or a pharmaceutically acceptable salt thereof, wherein $R_2$ is selected from H, F, Cl, Br, NO$_2$, CN, $NR_aR_a$, $C_{1-6}$alkyl, —(CHR)$_r$-carbocyclyl substituted with 0-5 $R_{2a}$, —O—$C_{1-6}$alkyl, —O—(CHR)$_r$-carbocyclyl substituted with 0-5 $R_{2a}$, heterocyclyl substituted with 0-5 $R_{2a}$;

$R_{2a}$, at each occurrence, is independently selected from $C_{1-4}$alkyl, $C_{2-4}$alkenyl, $C_{2-4}$alkynyl, $C_{1-4}$haloalkyl, F, Cl, Br, NO$_2$, CN, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$OR$_b$, —(CHR)$_r$NR$_a$C(O)NR$_a$R$_a$, —(CHR)$_r$NR$_a$C(O)OR$_b$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$C(O)NR$_a$S(O)$_p$R$_b$, —(CHR)$_r$C(O)NR$_a$(CHR)$_r$C(O)OR$_d$, —(CHR)$_r$C$_{3-6}$-carbocyclyl substituted with 0-3 $R_e$ and/or —(CHR)$_r$C$_{3-6}$heterocyclyl substituted with 0-3 $R_e$;

Q is selected from aryl and heteroaryl;

$R_{4a}$ is selected from F, Cl, Br, OH, and $C_{1-6}$alkyl;

$R_a$, at each occurrence, is independently selected from H, NH$_2$, $C_{1-4}$alkyl substituted with 0-3 $R_e$, CF$_3$, —O—$C_{1-6}$alkyl, —(CH$_2$)$_r$OH, $C_{3-6}$cycloalkyl substituted with 0-3 $R_e$, phenyl substituted with 0-3 $R_e$, and/or heterocyclyl substituted with 0-3 $R_e$, or $R_a$ and $R_a$ together with the nitrogen atom to which they are both attached form a heterocyclyl substituted with 0-3 $R_e$;

$R_b$, at each occurrence, is independently selected from $C_{1-4}$alkyl, CF$_3$, phenyl substituted with 0-3 $R_e$, and/or heterocyclyl substituted with 0-3 $R_e$;

$R_c$ is selected from $C_{3-6}$cycloalkyl substituted with 0-3 $R_g$, aryl substituted with 0-3 $R_g$, and heterocyclyl substituted with 0-3 $R_g$;

$R_d$, at each occurrence, is independently selected from H, $C_{1-4}$alkyl, $CF_3$, phenyl substituted with 0-3 $R_e$, and/or heterocyclyl substituted with 0-3 $R_e$;

$R_e$, at each occurrence, is independently selected from $C_{1-4}$alkyl, $C_{3-6}$cycloalkyl, F, Cl, Br, CN, $NO_2$, $CO_2H$, $—(CH_2)_rOC_{1-5}$alkyl, OH, SH, $—(CH_2)_rSC_{1-5}$ alkyl, $—(CH_2)_r$phenyl and/or $—(CH_2)_r$heterocyclyl;

$R_g$, at each occurrence, is independently selected from F, Cl, Br, OH, $C_{1-6}$alkyl, and/or $—OC_{1-5}$alkyl;

n, at each occurrence, is independently selected from 0, 1, and/or 2; and r, at each occurrence, is independently selected from 0, 1, and/or 2.

11. The compound according to claim 10 or a pharmaceutically acceptable salt thereof, wherein Q is phenyl;

$R_2$ is selected from F, Cl, Br, $NO_2$, CN, $NR_aR_a$, $—(CHR)_r$—$C_{3-10}$cycloalkyl substituted with 0-3 $R_{2a}$, $—(CHR)_r$-aryl substituted with 0-3 $R_{2a}$—O—$C_{1-4}$ alkyl, $—O—(CHR)_r$-aryl substituted with 0-3 $R_{2a}$, and heterocyclyl substituted with 0-3 $R_{2a}$;

$R_{2a}$, at each occurrence, is independently selected from $C_{1-4}$alkyl, $C_{1-4}$-haloalkyl, F, Cl, Br, $NO_2$, CN, $—OH$, $—SH$, $—OR_b$, $—S(O)_2R_b$, $—C(O)R_d$, $—NR_aR_a$, $—C(O)NR_aR_a$; $—C(O)NR_aOR_b$, $—NHC(O)NR_aR_a$, $—NHC(O)OR_b$, $—OC(O)NR_aR_a$, $—C(O)OR_d$, $—S(O)_2NR_aR_a$, $—NHS(O)_2R_b$, $—C(O)NHS(O)_2R_b$, $—C(O)NR_a(CH_2)_rC(O)OR_d$, $C_{3-6}$cycloalkyl substituted with 0-3 $R_e$, phenyl substituted with 0-3 $R_e$ and/or heterocyclyl substituted with 0-3 $R_e$;

$R_c$ is phenyl substituted with 0-3 $R_g$; and r, at each occurrence, is independently selected from 0 and/or 1.

12. A pharmaceutical composition comprising one or more compounds according to claim 1 and a pharmaceutically acceptable carrier or diluent.

13. The compound according to claim 8 or a pharmaceutically acceptable salt thereof, wherein said compound is: 6-cyclopentyl-4-(4-phenoxyphenyl)-1H-pyrazolo[3,4-b]pyridin-3-amine (1); 4-(4-(benzyloxy)phenyl)-6-cyclopentyl-1H-pyrazolo[3,4-b]pyridin-3-amine (2); 6-cyclopentyl-4-(4-(2-methylphenoxy)phenyl)-1H-pyrazolo[3,4-b]pyridin-3-amine (3); 6-cyclopentyl-4-(4-(4-methylphenoxy)phenyl)-1H-pyrazolo[3,4-b]pyridin-3-amine (4); 6-cyclopentyl-4-(4-(3-methylphenoxy)phenyl)-1H-pyrazolo[3,4-b]pyridin-3-amine (5); 4-(4-phenoxyphenyl)-1H-pyrazolo[3,4-b]pyridin-3-amine (6); 6-cyclohexyl-4-(4-phenoxyphenyl)-1H-pyrazolo[3,4-b]pyridin-3-amine (7); 6-(4-methoxyphenyl)-4-(4-phenoxyphenyl)-1H-pyrazolo[3,4-b]pyridin-3-amine (8); 4-(4-phenoxyphenyl)-6-(1-piperidinyl)-1H-pyrazolo[3,4-b]pyridin-3-amine (9); 6-phenoxy-4-(4-phenoxyphenyl)-1H-pyrazolo[3,4-b]pyridin-3-amine (10); 4-(4-phenoxyphenyl)-6-(4-pyridinyl)-1H-pyrazolo[3,4-b]pyridin-3-amine (11); 6-(3-methoxyphenyl)-4-(4-phenoxyphenyl)-1H-pyrazolo[3,4-b]pyridin-3-amine (12); 3-(3-amino-4-(4-phenoxyphenyl)-1H-pyrazolo[3,4-b]pyridin-6-yl)benzoic acid (13); 1-(3-(3-amino-4-(4-phenoxyphenyl)-1H-pyrazolo[3,4-b]pyridin-6-yl)phenyl)ethanone (14); 4-(4-phenoxyphenyl)-6-(1-pyrrolidinyl)-1H-pyrazolo[3,4-b]pyridin-3-amine (15); $N^6$-cyclopentyl-4-(4-phenoxyphenyl)-1H-pyrazolo[3,4-b]pyridine-3,6-diamine (16); tert-butyl(1-(3-amino-4-(4-phenoxyphenyl)-1H-pyrazolo[3,4-b]pyridin-6-yl)-3-pyrrolidinyl) carbamate (17); tert-butyl (1-(3-amino-4-(4-phenoxyphenyl)-1H-pyrazolo[3,4-b]pyridin-6-yl)-4-piperidinyl)carbamate (18); 6-(4-benzoyl-1-piperazinyl)-4-(4-phenoxyphenyl)-1H-pyrazolo[3,4-b]pyridin-3-amine (19); 6-(4-methoxyphenoxy)-4-(4-phenoxyphenyl)-1H-pyrazolo[3,4-b]pyridin-3-amine (20); 6-methoxy-4-(4-phenoxyphenyl)-1H-pyrazolo[3,4-b]pyridin-3-amine (21); 4-(3-amino-4-(4-phenoxyphenyl)-1H-pyrazolo[3,4-b]pyridin-6-yl)phenol (22); 3-(3-amino-4-(4-phenoxyphenyl)-1H-pyrazolo[3,4-b]pyridin-6-yl)phenol (23); N-(3-(3-amino-4-(4-phenoxyphenyl)-1H-pyrazolo[3,4-b]pyridin-6-yl)phenyl)acetamide (24); 6-(3-aminophenyl)-4-(4-phenoxyphenyl)-1H-pyrazolo[3,4-b]pyridin-3-amine (25); 6-(3-amino-1-pyrrolidinyl)-4-(4-phenoxyphenyl)-1H-pyrazolo[3,4-b]pyridin-3-amine (26); 1-(3-(3-amino-4-(4-phenoxyphenyl)-1H-pyrazolo[3,4-b]pyridin-6-yl)phenyl)-3-(4-methyl-1,3-thiazol-2-yl)urea (27); 6-(4-aminophenyl)-4-(4-phenoxyphenyl)-1H-pyrazolo[3,4-b]pyridin-3-amine (28); N-(4-(3-amino-4-(4-phenoxyphenyl)-1H-pyrazolo[3,4-b]pyridin-6-yl)phenyl)acetamide (29); 6-(4-amino-1-piperidinyl)-4-(4-phenoxyphenyl)-1H-pyrazolo[3,4-b]pyridin-3-amine (30); 1-(1-(3-amino-4-(4-phenoxyphenyl)-1H-pyrazolo[3,4-b]pyridin-6-yl)-3-pyrrolidinyl)-3-(4-methyl-1,3-thiazol-2-yl)urea (31); 3-(3-amino-4-(4-phenoxyphenyl)-1H-pyrazolo[3,4-b]pyridin-6-yl) benzohydrazide (33); 3-(3-amino-4-(4-phenoxyphenyl)-1H-pyrazolo[3,4-b]pyridin-6-yl)-N-phenylbenzamide (34); 6-(3-(4-morpholinylcarbonyl)phenyl)-4-(4-phenoxyphenyl)-1H-pyrazolo[3,4-b]pyridin-3-amine (35); 3-(3-amino-4-(4-phenoxyphenyl)-1H-pyrazolo[3,4-b]pyridin-6-yl)-N-cyclopropylbenzamide (36); or 3-(3-amino-4-(4-phenoxyphenyl)-1H-pyrazolo[3,4-b]pyridin-6-yl)-N-1H-indol-2-ylbenzamide (37).

14. The compound according to claim 2 or a pharmaceutically acceptable salt thereof, wherein said compound is: 4-(2-Naphthyl)-1H-pyrazolo[3,4-c]pyridin-3-amine (38); 4-(4-Methoxyphenyl)-1H-pyrazolo[3,4-c]pyridin-3-amine (39); 4-(3-Methoxyphenyl)-1H-pyrazolo[3,4-c]pyridin-3-amine (40); 4-(4-Phenoxyphenyl)-1H-pyrazolo[3,4-c]pyridin-3-amine (41); 4-(1,3-Benzodioxol-5-yl)-1H-pyrazolo[3,4-c]pyridin-3-amine (42); 4-(4-Isopropoxyphenyl)-1H-pyrazolo[3,4-c]pyridin-3-amine (43);

4-(4-(Cyclopentyloxy)phenyl)-1H-pyrazolo[3,4-c]pyridin-3-amine (44); 4-(4-(Methylsulfanyl)phenyl)-1H-pyrazolo[3,4-c]pyridin-3-amine (45); 4-(4-(Trifluoromethoxy)phenyl)-1H-pyrazolo[3,4-c]pyridin-3-amine (46); 4-(4-(1-Pyrrolidinylcarbonyl)phenyl)-1H-pyrazolo[3,4-c]pyridin-3-amine (47); 4-Dibenzo[b,d]thiophen-2-yl-1H-pyrazolo[3,4-c]pyridin-3-amine (48); 4-(6-Methoxy-2-naphthyl)-1H-pyrazolo[3,4-c]pyridin-3-amine (49); 4-(4-(4-Methoxyphenoxy)phenyl)-1H-pyrazolo[3,4-c]pyridin-3-amine (50); 4-(4-(3-Methoxyphenoxy)phenyl)-1H-pyrazolo[3,4-c]pyridin-3-amine (51); 4-(4-(3-Ethoxyphenoxy)phenyl)-1H-pyrazolo[3,4-c]pyridin-3-amine (52); 4-(4-(3,5-Dimethylphenoxy)phenyl)-1H-pyrazolo[3,4-c]pyridin-3-amine (53); 4-(3-Amino-1H-pyrazolo[3,4-c]pyridin-4-yl)-2-methylphenol (54); 4-(3-Methyl-4-phenoxyphenyl)-1H-pyrazolo[3,4-c]pyridin-3-amine (55); 4-(3-Fluoro-4-phenoxyphenyl)-1H-pyrazolo[3,4-c]pyridin-3-amine (56); 4-(4-(3-Amino-1H-pyrazolo[3,4-c]pyridin-4-yl)phenoxy)phenol (57); 4-(4-Benzylphenyl)-1H-pyrazolo[3,4-c]pyridin-3-amine (58); 4-(4-Phenoxyphenyl)-7-phenyl-1H-pyrazolo[3,4-c]pyridin-3-amine (59); 7-(4-(4-Morpholinylcarbonyl)phenyl)-4-(4-phenoxyphenyl)-1H-pyrazolo[3,4-c]pyridin-3-amine (60); N-(4-(3-Amino-4-(4-phenoxyphenyl)-1H-pyrazolo[3,4-c]pyridin-7-yl)phenyl)benzamide (61); N-(3-(3-Amino-4-(4-phenoxyphenyl)-1H-pyrazolo[3,4-c]pyridin-7-yl)phenyl)methanesulfonamide (62); 4-(4-Phenoxyphenyl)-7-(4-(1-pyrrolidinylcarbonyl)phenyl)-1H-pyrazolo[3,4-c]pyridin-3-amine (63); 7-(3-(Methylsulfonyl)phenyl)-4-(4-phenoxyphenyl)-1H-pyrazolo[3,4-c]pyridin-3-amine (64); 7-(3-(Methoxymethyl)phenyl)-4-(4-phenoxyphenyl)-1H-pyrazolo[3,4-c]pyridin-3-amine (65); tert-Butyl(3-(3-amino-4-(4-phenoxyphenyl)-1H-pyrazolo[3,4-c]pyridin-7-yl)benzyl)carbamate (66); 4-(4-Phenoxyphenyl)-7-(2-pyridinyl)-1H-pyrazolo[3,4-c]pyridin-3-amine (67); 4-(4-Phenoxyphenyl)-7-(2-pyrazinyl)-1H-pyrazolo[3,4-c]pyridin-3-amine (68); 4-(4-Phenoxyphenyl)-5-(4-(1-pyrrolidinylcarbonyl)phenyl)-1H-pyrazolo[3,4-c]pyridin-3-amine (69); 4,5-Bis(4-phenoxyphenyl)-1H-pyrazolo[3,4-c]pyridin-3-amine (70); 7-(4-Methoxyphenyl)-4-(4-phenoxyphenyl)-1H-pyrazolo[3,4-c]pyridin-3-amine (71); 5-(4-Methoxyphenyl)-4-(4-phenoxyphenyl)-1H-pyrazolo[3,4-c]pyridin-3-amine (72); N-(3-(3-Amino-4-(4-phenoxyphenyl)-1H-pyrazolo[3,4-c]pyridin-7-yl)benzyl)acetamide (73); 7-(3-(Aminomethyl)phenyl)-4-(4-phenoxyphenyl)-1H-pyrazolo[3,4-c]pyridin-3-amine (74);

N-(3-(3-Amino-4-(4-phenoxyphenyl)-1H-pyrazolo[3,4-c]pyridin-7-yl)benzyl)benzamide (75); N-(3-(3-Amino-4-(4-phenoxyphenyl)-1H-pyrazolo[3,4-c]pyridin-7-yl)benzyl)methanesulfonamide (76); N-(3-(3-Amino-4-(4-phenoxyphenyl)-1H-pyrazolo[3,4-c]pyridin-7-yl)benzyl)benzenesulfonamide (77); 7-Hydrazino-4-(4-phenoxyphenyl)-1H-pyrazolo[3,4-c]pyridin-3-amine (78); 4-(4-Phenoxyphenyl)-7-(4-phenyl-1H-pyrazol-1-yl)-1H-pyrazolo[3,4-c]pyridin-3-amine (79); 4-(4-Phenoxyphenyl)-7-(1H-1,2,4-triazol-1-yl)-1H-pyrazolo[3,4-c]pyridin-3-amine (80); 4-(4-Phenoxyphenyl)-7-(1H-pyrazol-1-yl)-1H-pyrazolo[3,4-c]pyridin-3-amine (81); 7-(3,4-Dichlorophenyl)-4-(4-phenoxyphenyl)-1H-pyrazolo[3,4-c]pyridin-3-amine (82); 3-(3-Amino-4-(4-phenoxyphenyl)-1H-pyrazolo[3,4-c]pyridin-7-yl)benzoic acid (83); 4-(3-Amino-4-(4-phenoxyphenyl)-1H-pyrazolo[3,4-c]pyridin-7-yl)benzoic acid (84); 7-(3-Methoxyphenyl)-4-(4-phenoxyphenyl)-1H-pyrazolo[3,4-c]pyridin-3-amine (85); 7-Dibenzo[b,d]furan-1-yl-4-(4-phenoxyphenyl)-1H-pyrazolo[3,4-c]pyridin-3-amine (86); 4-(4-Phenoxyphenyl)-7-(6-quinolinyl)-1H-pyrazolo[3,4-c]pyridin-3-amine (87); 3-(3-Amino-4-(4-phenoxyphenyl)-1H-pyrazolo[3,4-c]pyridin-7-yl)-N,N-dimethylbenzamide (88); 3-(3-Amino-4-(4-phenoxyphenyl)-1H-pyrazolo[3,4-c]pyridin-7-yl)-N-(2-furylmethyl)benzamide (89); 7-(1,3-Benzodioxol-5-yl)-4-(4-phenoxyphenyl)-1H-pyrazolo[3,4-c]pyridin-3-amine (90); 3-(3-Amino-4-(4-phenoxyphenyl)-1H-pyrazolo[3,4-c]pyridin-7-yl)phenol (91); 3-(3-Amino-4-(4-phenoxyphenyl)-1H-pyrazolo[3,4-c]pyridin-7-yl)phenol (92); (3-(3-Amino-4-(4-phenoxyphenyl)-1H-pyrazolo[3,4-c]pyridin-7-yl)phenyl)methanol (93); 7-(3-(Dimethylamino)phenyl)-4-(4-phenoxyphenyl)-1H-pyrazolo[3,4-c]pyridin-3-amine (94);

7-(1H-Indol-5-yl)-4-(4-phenoxyphenyl)-1H-pyrazolo[3,4-c]pyridin-3-amine (95); N-(4-(3-Amino-4-(4-phenoxyphenyl)-1H-pyrazolo[3,4-c]pyridin-7-yl)phenyl)methanesulfonamide (96); 4-(3-Amino-4-(4-phenoxyphenyl)-1H-pyrazolo[3,4-c]pyridin-7-yl)benzamide (97); 3-(3-Amino-4-(4-phenoxyphenyl)-1H-pyrazolo[3,4-c]pyridin-7-yl)benzamide (98); N-(4-(3-Amino-4-(4-phenoxyphenyl)-1H-pyrazolo[3,4-c]pyridin-7-yl)benzyl)acetamide (99); 4,7-Bis(4-phenoxyphenyl)-1H-pyrazolo[3,4-c]pyridin-3-amine (100); 7-(3,5-Dimethylphenyl)-4-(4-phenoxyphenyl)-1H-pyrazolo[3,4-c]pyridin-3-amine (101); 7-(3-Isobutoxyphenyl)-4-(4-phenoxyphenyl)-1H-pyrazolo[3,4-c]pyridin-3-amine (102); 3-(3-(3-Amino-4-(4-phenoxyphenyl)-1H-pyrazolo[3,4-c]pyridin-7-yl)phenyl) propanoic acid (103); 7-(3,4-Dimethoxyphenyl)-4-(4-phenoxyphenyl)-1H-pyrazolo[3,4-c]pyridin-3-amine (104); N-(4-(3-Amino-4-(4-phenoxyphenyl)-1H-pyrazolo[3,4-c]pyridin-7-yl)benzyl)methanesulfonamide (105); 3-(3-Amino-4-(4-phenoxyphenyl)-1H-pyrazolo[3,4-c]pyridin-7-yl)benzenesulfonamide (106); 7-(2-Methylphenyl)-4-(4-phenoxyphenyl)-1H-pyrazolo[3,4-c]pyridin-3-amine (107); 4-(4-Phenoxyphenyl)-7-(3-(trifluoromethyl)phenyl)-1H-pyrazolo[3,4-c]pyridin-3-amine (108); 7-(2-Naphthyl)-4-(4-phenoxyphenyl)-1H-pyrazolo[3,4-c]pyridin-3-amine (109); 7-(2,3-Dihydro-1-benzofuran-5-yl)-4-(4-phenoxyphenyl)-1H-pyrazolo[3,4-c]pyridin-3-amine (110); 7-(4-Isobutoxyphenyl)-4-(4-phenoxyphenyl)-1H-pyrazolo[3,4-c]pyridin-3-amine (111); 4-(4-Phenoxyphenyl)-7-(4-(trifluoromethoxy)phenyl)-1H-pyrazolo[3,4-c]pyridin-3-amine (112); 4-(4-Phenoxyphenyl)-7-(3-(trifluoromethoxy)phenyl)-1H-pyrazolo[3,4-c]pyridin-3-amine (113); 4-(3-Methoxyphenyl)-$N^7$-phenyl-1H-pyrazolo[3,4-c]pyridine-3,7-diamine (128); 4-(3-Methoxyphenyl)-$N^7$-(2-methylphenyl)-1H-pyrazolo[3,4-c]pyridine-3,7-diamine (129); $N^7$-(2-Chlorophenyl)-4-(3-methoxyphenyl)-1H-pyrazolo[3,4-c]pyridine-3,7-diamine (130); 3-(3-Amino-7-((2-methylphenyl)amino)-1H-pyrazolo[3,4-c]pyridin-4-yl)phenol (131); 4-(4-Methoxyphenyl)-$N^7$-(2-methylphenyl)-1H-pyrazolo[3,4-c]pyridine-3,7-diamine (132); N-((3R)-1-(3-Amino-7-((2-methylphenyl)amino)-1H-pyrazolo[3,4-c]pyridin-4-yl)-3-piperidinyl)benzamide (133); 4-(2-Methoxy-4-pyridinyl)-$N^7$-(2-methylphenyl)-1H-pyrazolo[3,4-c]pyridine-3,7-diamine (134); 4-(3-Ethoxyphenyl)-$N^7$-(2-methylphenyl)-1H-pyrazolo[3,4-c]pyridine-3,7-diamine (135); $N^7$-(2-Methylphenyl)-4-phenyl-1H-pyrazolo[3,4-c]pyridine-3,7-diamine (136); 4-(3-Isopropoxyphenyl)-$N^7$-(2-methylphenyl)-1H-pyrazolo[3,4-c]pyridine-3,7-diamine (137); 4-(1H-Indazol-5-yl)-$N^7$-(2-methylphenyl)-1H-pyrazolo[3,4-c]pyridine-3,7-diamine (138); 3-(3-Amino-7-((2-methylphenyl)amino)-1H-pyrazolo[3,4-c]pyridin-4-yl)-N-methylbenzamide (139); 4-(2-Methoxyphenyl)-$N^7$-(2-methylphenyl)-1H-pyrazolo[3,4-c]pyridine-3,7-diamine (140); 4-(3-Amino-7-((2-methylphenyl)amino)-1H-pyrazolo[3,4-c]pyridin-4-yl)-N-methylbenzamide (141); $N^7$-(2-Methylphenyl)-4-(4-phenoxyphenyl)-1H-pyrazolo[3,4-c]pyridine-3,7-diamine (142); $N^7$-(2-Methylphenyl)-4-(2-naphthyl)-1H-pyrazolo[3,4-c]pyridine-3,7-diamine (143); 4-(3-Aminophenyl)-$N^7$-(2-methylphenyl)-1H-pyrazolo[3,4-c]pyridine-3,7-diamine (144); $N^7$-(2-Methylphenyl)-4-(3-(trifluoromethoxy)phenyl)-1H-pyrazolo[3,4-c]pyridine-3,7-diamine (145); (3-(3-Amino-7-((2-methylphenyl)amino)-1H-pyrazolo[3,4-c]pyridin-4-yl)phenyl)methanol (146); $N^4$-(2-Methylphenyl)-7-(6-quinolinyl)-1H-pyrazolo[4,3-c]pyridine-3,4-diamine (147); $N^7$-(2-Methylphenyl)-4-(2-pyridinyl)-1H-pyrazolo[3,4-c]pyridine-3,7-diamine (148); $N^7$-(2-Methylphenyl)-4-(1-piperidinyl)-1H-pyrazolo[3,4-c]pyridine-3,7-diamine (149); $N^7$-(2,4-Dimethylphenyl)-4-(3-methoxyphenyl)-1H-pyrazolo[3,4-c]pyridine-3,7-diamine (150); or $N^7$-Mesityl-4-(3-methoxyphenyl)-1H-pyrazolo[3,4-c]pyridine-3,7-diamine (151).

15. The compound according to claim 2 or a pharmaceutically acceptable salt thereof, wherein said compound is: 6-(4-Methoxyphenyl)-4-(4-phenoxyphenyl)-1H-pyrazolo[4,3-c]pyridin-3-amine (152); 6-(3-Methoxyphenyl)-4-(4- phenoxyphenyl)-1H-pyrazolo[4,3-c]pyridin-3-amine (153); 6-(3-Methoxyphenyl)-4-(4-phenoxyphenyl)-1H-pyrazolo[4,3-c]pyridin-3-amine (154); 6-(2-Naphthyl)-4-(4-phenoxyphenyl)-1H-pyrazolo[4,3-c]pyridin-3-amine (155); 6-(2-Naphthyl)-4-(4-phenoxyphenyl)-1H-pyrazolo[4,3-c]pyridin-3-amine (156); 6-(1-Benzyl-1H-pyrazol-4-yl)-4-(4-phenoxyphenyl)-1H-pyrazolo[4,3-c]pyridin-3-amine (157); 4-(4-Phenoxyphenyl)-6-(4-pyridinyl)-1H-pyrazolo[4,3-c]pyridin-3-amine (158); 4-(3-Amino-4-(4-phenoxyphenyl)-1H-pyrazolo[4,3-c]pyridin-6-yl)phenol (159); 4-(4-Phenoxyphenyl)-7-phenyl-1H-pyrazolo[4,3-c]pyridin-3-amine (160); 6-Chloro-4-(4-phenoxyphenyl)-1H-pyrazolo[4,3-c]pyridin-3-amine (161); 6-Chloro-7-methyl-4-(4-phenoxyphenyl)-1H-pyrazolo[4,3-c]pyridin-3-amine (162); 6-Chloro-7-methoxy-4-(4-phenoxyphenyl)-1H-pyrazolo[4,3-c]pyridin-3-amine (163); 4-(4-Phenoxyphenyl)-1H-pyrazolo[4,3-c]pyridin-3-amine (164); 7-Methyl-4-(4-phenoxyphenyl)-1H-pyrazolo[4,3-c]pyridin-3-amine (165); 7-Methoxy-4-(4-phenoxyphenyl)-1H-pyrazolo[4,3-c]pyridin-3-amine (166); 7-Benzyl-4-(4-phenoxyphenyl)-1H-pyrazolo[4,3-c]pyridin-3-amine (167); 4-(4-Phenoxyphenyl)-1H-pyrazolo[4,3-c]quinolin-3-amine (168); (1-(3-Amino-4-(4-phenoxyphenyl)-1H-pyrazolo[4,3-c]pyridin-6-yl)-2-pyrrolidinyl)methanol (169); (1-(3-Amino-4-(4-phenoxyphenyl)-1H-pyrazolo[4,3-c]pyridin-6-yl)-3-piperidinyl)methanol (170); (1-(3-Amino-4-(4-phenoxyphenyl)-1H-pyrazolo[4,3-c]pyridin-6-yl)-4-piperidinyl)methanol (171); 6-(3-Bromophenyl)-4-(4-phenoxyphenyl)-1H-pyrazolo[4,3-c]pyridin-3-amine (172); 4-(3-Amino-4-(4-phenoxyphenyl)-1H-pyrazolo[4,3-c]pyridin-6-yl)benzonitrile (173); 6-(3-Nitrophenyl)-4-(4-phenoxyphenyl)-1H-pyrazolo[4,3-c]pyridin-3-amine (174); 4-(4-Phenoxyphenyl)-6-(3-pyridinyl)-1H-pyrazolo[4,3-c]pyridin-3-amine (175); 6-(4-(Dimethylamino)phenyl)-4-(4-phenoxyphenyl)-1H-pyrazolo[4,3-c]pyridin-3-amine (176); 4-(4-Phenoxyphenyl)-6-(2-pyridinyl)-1H-pyrazolo[4,3-c]pyridin-3-amine (177); 6-(5-Bromo-3-pyridinyl)-4-(4-phenoxyphenyl)-1H-pyrazolo[4,3-c]pyridin-3-amine (178); 4,6-Bis(4-methoxyphenyl)-1H-pyrazolo[4,3-c]pyridin-3-amine (179); 6-(3-Bromophenyl)-4-(4-methoxyphenyl)-1H-pyrazolo[4,3-c]pyridin-3-amine (180); 3-(3-Amino-4-(4-methoxyphenyl)-1H-pyrazolo[4,3-c]pyridin-6-yl)benzonitrile (181); (3-Amino-4-(4-phenoxyphenyl)-1H-pyrazolo[4,3-c]pyridin-6-yl)acetic acid (182); 2-(3-Amino-4-(4-phenoxyphenyl)-1H-pyrazolo[4,3-c]pyridin-6-yl)acetohydrazide (183); 6-(2-(4-Morpholinyl)-2-oxoethyl)-4-(4-phenoxyphenyl)-1H-pyrazolo[4,3-c]pyridin-3-amine (184); 4-(3-Amino-4-(4-phenoxyphenyl)-1H-pyrazolo[4,3-c]pyridin-6-yl)benzamide (185); 5-(3-Amino-4-(4-phenoxyphenyl)-1H-pyrazolo[4,3-c]pyridin-6-yl)-2-methoxybenzoic acid (186); Benzyl 3-(3-amino-4-(4-phenoxyphenyl)-1H-pyrazolo[4,3-c]pyridin-6-yl)-1-piperidinecarboxylate (187); Benzyl 4-(3-amino-4-(4-phenoxyphenyl)-1H-pyrazolo[4,3-c]pyridin-6-yl)-1-piperidinecarboxylate (188); 5-(3-Amino-4-(4-phenoxyphenyl)-1H-pyrazolo[4,3-c]pyridin-6-yl)nicotinonitrile (189); 5-(3-Amino-4-(4-phenoxyphenyl)-1H-pyrazolo[4,3-c]pyridin-6-yl)nicotinic acid (190); 4-(4-Phenoxyphenyl)-6-(5-(1H-tetrazol-5-yl)-3-pyridinyl)-1H-pyrazolo[4,3-c]pyridin-3-amine (191); Methyl 4-(3-amino-4-(4-phenoxyphenyl)-1H-pyrazolo[4,3-c]pyridin-6-yl)benzoate (192); 4-(3-Amino-4-(4-phenoxyphenyl)-1H-pyrazolo[4,3-c]pyridin-6-yl)benzoic acid (193); 4-(3-Amino-4-(4-phenoxyphenyl)-1H-pyrazolo[4,3-c]pyridin-6-yl)benzohydrazide (194); (4-(3-Amino-4-(4-phenoxyphenyl)-1H-pyrazolo[4,3-c]pyridin-6-yl)phenyl)methanol (195); tert-Butyl N-(4-(3-amino-4-(4-phenoxyphenyl)-1H-pyrazolo[4,3-c]pyridin-6-yl)benzoyl)glycinate (196); 6-(4-(4-Morpholinylcarbonyl)phenyl)-4-(4-phenoxyphenyl)-1H-pyrazolo[4,3-c]pyridin-3-amine (197); 4-(3-Amino-4-(4-phenoxyphenyl)-1H-pyrazolo[4,3-c]pyridin-6-yl)-N-(2-hydroxyethyl)benzamide (198); 6-(4-Aminophenyl)-4-(4-phenoxyphenyl)-1H-pyrazolo[4,3-c]pyridin-3-amine (199); 1-(4-(3-Amino-4-(4-phenoxyphenyl)-1H-pyrazolo[4,3-c]pyridin-6-yl)phenyl)-3-phenylurea (201); 1-(4-(3-Amino-4-(4-phenoxyphenyl)-1H-pyrazolo[4,3-c]pyridin-6-yl)phenyl)-3-methylurea (203); N-(4-(3-Amino-4-(4-phenoxyphenyl)-1H-pyrazolo[4,3-c]pyridin-6-yl)phenyl)hydrazinecarboxamide (204); 4-(4-Phenoxyphenyl)-6-phenyl-1H-pyrazolo[4,3-c]pyridin-3-amine (205); 6-(4-Aminophenyl)-4-(4-methoxyphenyl)-1H-pyrazolo[4,3-c]pyridin-3-amine (206); Methyl 3-(3-amino-4-(4-phenoxyphenyl)-1H-pyrazolo[4,3-c]pyridin-6-yl)benzoate (207); 3-(3-Amino-4-(4-phenoxyphenyl)-1H-pyrazolo[4,3-c]pyridin-6-yl)benzoic acid (208); 4-(4-Methoxyphenyl)-6-(3-pyridinyl)-1H-pyrazolo[4,3-c]pyridin-3-amine (209); 4-(3-Amino-6-(3-pyridinyl)-1H-pyrazolo[4,3-c]pyridin-4-yl)phenol (210); 6-(3-Aminophenyl)-4-(4-phenoxyphenyl)-1H-pyrazolo[4,3-c]pyridin-3-amine (211); 1-(3-(3-Amino-4-(4-phenoxyphenyl)-1H-pyrazolo[4,3-c]pyridin-6-yl)phenyl)-3-phenylurea (212); 3-(3-Amino-4-(4-phenoxyphenyl)-1H-pyrazolo[4,3-c]pyridin-6-yl)-N-cyclopropylbenzamide (213); 3-(3-Amino-4-(4-phenoxyphenyl)-1H-pyrazolo[4,3-c]pyridin-6-yl)-N-(methylsulfonyl)benzamide (214); 4,6-Diphenyl-1H-pyrazolo[4,3-c]pyridin-3-amine (215); 4-(3-Amino-4-(4-phenoxyphenyl)-1H-pyrazolo[4,3-c]pyridin-6-yl)-N-methylbenzamide (216); 4-(3-Amino-4-(4-phenoxyphenyl)-1H-pyrazolo[4,3-c]pyridin-6-yl)-N-1H-tetrazol-5-ylbenzamide (217); (3-(3-Amino-4-(4-phenoxyphenyl)-1H-pyrazolo[4,3-c]pyridin-6-yl)phenyl)methanol (218); N-(4-(3-Amino-4-(4-phenoxyphenyl)-1H-pyrazolo[4,3-c]pyridin-6-yl)benzoyl)glycine (219); 3-(3-Amino-4-(4-phenoxyphenyl)-1H-pyrazolo[4,3-c]pyridin-6-yl)-N-1,3,4-thiadiazol-2-ylbenzamide (220); 3-(3-Amino-4-(4-phenoxyphenyl)-1H-pyrazolo[4,3-c]pyridin-6-yl)benzonitrile (221); 4-(4-Phenoxyphenyl)-6-(3-(1H-tetrazol-5-yl)phenyl)-1H-pyrazolo[4,3-c]pyridin-3-amine (222); 4-(4-Phenoxyphenyl)-6-(4-(1H-tetrazol-5-yl)phenyl)-1H-pyrazolo[4,3-c]pyridin-3-amine (223); 3-(3-Amino-4-(4-phenoxyphenyl)-1H-pyrazolo[4,3-c]pyridin-6-yl)benzamide (224); 4-(4-Phenoxyphenyl)-7-(2-pyridinyl)-1H-pyrazolo[4,3-c]pyridin-3-amine (225); 3-(3-Amino-4-(4-phenoxyphenyl)-1H-pyrazolo[4,3-c]pyridin-7-yl)benzohydrazide (226); 3-(3-Amino-4-(4-phenoxyphenyl)-1H-pyrazolo[4,3-c]pyridin-7-yl)benzoic acid (227); 3-(3-Amino-4-(4-phenoxyphenyl)-1H-pyrazolo[4,3-c]pyridin-7-yl)-N,N-dimethylbenzamide (228); 3-(3-Amino-4-(4-phenoxyphenyl)-1H-pyrazolo[4,3-c]pyridin-7-yl)-N-benzylbenzamide (229); 74344-Morpholinylcarbonyl)phenyl)-4-(4-phenoxyphenyl)-1H-pyrazolo[4,3-c]pyridin-3-amine (230); 2-(3-(3-Amino-4-(4-phenoxyphenyl)-1H-pyrazolo[4,3-c]pyridin-6-yl)phenyl) acetohydrazide (231); (2-(3-Amino-6-(3-pyridinyl)-1H-pyrazolo[4,3-c]pyridin-4-yl)-5-methoxyphenyl)methanol (232); 4-(4-Phenoxyphenyl)-6-(3-piperidinyl)-1H-pyrazolo[4,3-c]pyridin-3-amine (233); 6-(1-Methyl-3-piperidinyl)-4-(4-phenoxyphenyl)-1H-pyrazolo[4,3-c]pyridin-3-amine (234); 6-(1-Benzoyl-3-piperidinyl)-4-(4-phenoxyphenyl)-1H-pyrazolo[4,3-c]pyridin-3-amine (235); 3-(3-Amino-4-(4-phenoxyphenyl)-1H-pyrazolo[4,3-c]pyridin-6-yl)-N-phenyl-1-piperidinecarboxamide (236); 6-(1-Acryloyl-3-piperidinyl)-4-(4-phenoxyphenyl)-1H-pyrazolo[4,3-c]pyridin-3-amine (237); Methyl(3-(3-amino-4-(4-phenoxyphenyl)-1H-pyrazolo[4,3-c]pyridin-6-yl)-1-piperidinyl)(oxo) acetate (238);

(3-(3-Amino-4-(4-phenoxyphenyl)-1H-pyrazolo[4,3-c]pyridin-6-yl)-1-piperidinyl)(oxo)acetic acid (239); 4-(4-Phenoxyphenyl)-6-(4-piperidinyl)-1H-pyrazolo[4,3-c]pyridin-3-amine (240); 6-(1-Benzoyl-4-piperidinyl)-4-(4-phenoxyphenyl)-1H-pyrazolo[4,3-c]pyridin-3-amine (241); 4-(3-Amino-4-(4-phenoxyphenyl)-1H-pyrazolo[4,3-c]pyridin-6-yl)-N-phenyl-1-piperidinecarboxamide (242); 3-(3-Amino-4-(4-phenoxyphenyl)-1H-pyrazolo[4,3-c]pyridin-6-yl)-1-pyrrolidinecarbaldehyde (243); 6-(1-Benzoyl-3-pyrrolidinyl)-4-(4-phenoxyphenyl)-1H-pyrazolo[4,3-c]pyridin-3-amine (244);

4-(3-Amino-4-(4-phenoxyphenyl)-1H-pyrazolo[4,3-c]pyridin-6-yl)-2-fluorobenzoic acid (245); (4-(3-Amino-4-(4-phenoxyphenyl)-1H-pyrazolo[4,3-c]pyridin-6-yl)-1H-pyrazol-1-yl)acetic acid (246); 5-(3-Amino-4-(4-phenoxyphenyl)-1H-pyrazolo[4,3-c]pyridin-6-yl)-2-thiophenecarboxylic acid (247); (3-((3-Amino-4-(4-phenoxyphenyl)-1H-pyrazolo[4,3-c]pyridin-6-yl)amino)-1H-pyrazol-1-yl)acetic acid (248); 2-(3-((3-Amino-4-(4-phenoxyphenyl)-1H-pyrazolo[4,3-c]pyridin-6-yl)amino)-1H-pyrazol-1-yl)-N,N-dimethylacetamide (259); 4-(3-Amino-4-(6-methoxy-2-naphthyl)-1H-pyrazolo[4,3-c]pyridin-6-yl)benzoic acid (260); 4-(3-Amino-4-dibenzo[b,d]thiophen-2-yl-1H-pyrazolo[4,3-c]pyridin-6-yl)benzoic acid (251); 4-(3-Amino-4-(4-methoxyphenyl)-1H-pyrazolo[4,3-c]pyridin-6-yl)benzoic acid (252); 4-(3-Amino-4-phenyl-1H-pyrazolo[4,3-c]pyridin-6-yl)benzoic acid (253); 4-(3-Amino-4-(4-ethoxyphenyl)-1H-pyrazolo[4,3-c]pyridin-6-yl)benzoic acid (254); 4-(3-Amino-4-(4-isopropoxyphenyl)-1H-pyrazolo[4,3-c]pyridin-6-yl)benzoic acid (255); 4-(3-Amino-4-(4-(methylsulfanyl)phenyl)-1H-pyrazolo[4,3-c]pyridin-6-yl)benzoic acid (256); 4-(3-Amino-4-(3-fluoro-4-methoxyphenyl)-1H-pyrazolo[4,3-c]pyridin-6-yl)benzoic acid (257); 4-(3-Amino-4-(2-naphthyl)-1H-pyrazolo[4,3-c]pyridin-6-yl)benzoic acid (258); 4-(3-Amino-4-(3-furyl)-1H-pyrazolo[4,3-c]pyridin-6-yl)benzoic acid (259); 4-(3-Amino-4-(3-thienyl)-1H-pyrazolo[4,3-c]pyridin-6-yl)benzoic acid (260); 4-(3-Amino-4-(1H-pyrazol-3-yl)-1H-pyrazolo[4,3-c]pyridin-6-yl)benzoic acid (261); 4-(3-Amino-4-(4-(3-fluorophenoxy)phenyl)-1H-pyrazolo[4,3-c]pyridin-6-yl)benzoic acid (262); or 4-(3-Amino-4-(4-hydroxyphenyl)-1H-pyrazolo[4,3-c]pyridin-6-yl)benzoic acid (263).

16. The compound according to claim 10 or a pharmaceutically acceptable salt thereof, wherein said compound is: 6-Chloro-4-(4-phenoxyphenyl)-1H-pyrazolo[3,4-d]pyrimidin-3-amine (114); 4-(4-Phenoxyphenyl)-6-phenyl-1H-pyrazolo[3,4-d]pyrimidin-3-amine (115); 6-(4-Ethoxyphenyl)-4-(4-phenoxyphenyl)-1H-pyrazolo[3,4-d]pyrimidin-3-amine (116); 6-(3-Methoxyphenyl)-4-(4-phenoxyphenyl)-1H-pyrazolo[3,4-d]pyrimidin-3-amine (117); 6-tert-Butyl-4-(4-phenoxyphenyl)-1H-pyrazolo[3,4-d]pyrimidin-3-amine (118); 6-tert-Butyl-4-(4-phenoxyphenyl)-1H-pyrazolo[3,4-d]pyrimidin-3-amine (119); 6-tert-Butyl-4-(4-phenoxyphenyl)-1H-pyrazolo[3,4-d]pyrimidin-3-amine (120); 6-tert-Butyl-4-(4-phenoxyphenyl)-1H-pyrazolo[3,4-d]pyrimidin-3-amine (121); 6-tert-Butyl-4-(4-phenoxyphenyl)-1H-pyrazolo[3,4-d]pyrimidin-3-amine (122); 6-tert-Butyl-4-(4-phenoxyphenyl)-1H-pyrazolo[3,4-d]pyrimidin-3-amine (123); 6-tert-Butyl-4-(4-phenoxyphenyl)-1H-pyrazolo[3,4-d]pyrimidin-3-amine (124); 6-tert-Butyl-4-(4-phenoxyphenyl)-1H-pyrazolo[3,4-d]pyrimidin-3-amine (125); 6-tert-Butyl-4-(4-phenoxyphenyl)-1H-pyrazolo[3,4-d]pyrimidin-3-amine (126); or 6-tert-Butyl-4-(4-phenoxyphenyl)-1H-pyrazolo[3,4-d]pyrimidin-3-amine (127).

* * * * *

UNITED STATES PATENT AND TRADEMARK OFFICE
CERTIFICATE OF CORRECTION

PATENT NO. : 8,846,673 B2
APPLICATION NO. : 13/388700
DATED : September 30, 2014
INVENTOR(S) : Zhonghui Lu et al.

It is certified that error appears in the above-identified patent and that said Letters Patent is hereby corrected as shown below:

In the Claims:

Claim 1, col. 228, line 23, delete "$C_{3-6}$-carbocyclyl" and insert -- $C_{3-6}$carbocyclyl --, Claim 1, col. 228, line 34, delete "$(CH_2)_rC_{3-10}$-cycloalkyl," and insert -- $(CH_2)_rC_{3-10}$cycloalkyl, --, Claim 1, col. 228, line 55, delete "$(CHR)_r$—O—$(CHR)_rR_b$," and insert -- $(CHR)_rO(CHR)_rR_b$, --, Claim 1, col. 229, line 4, delete "$(CHR)_r$—O—$(CHR)_rR_c$," and insert -- $(CHR)_rO(CHR)_rR_c$, --, Claim 1, col. 229, line 9, delete "$C_{3-6}$-carbocyclyl" and insert -- $C_{3-6}$carbocyclyl --, Claim 1, col. 229, lines 33-34, delete "$(CH_2)_r$heterocyclyl" and insert -- "$(CH_2)_r$-heterocyclyl --, Claim 1, col. 229, line 65, delete "dec-8-yl" and insert -- dec-8-yl, --, Claim 2, col. 230, line 37, delete "$(CHR)_r$—$C_{3-6}$-carbocyclyl" and insert
-- $(CHR)_r$—$C_{3-6}$carbocyclyl --, Claim 2, col. 231, line 1, delete "$(CHR)_r$—O—$(CHR)_rR_b$," and insert -- $(CHR)_rO(CHR)_rR_b$, --, Claim 2, col. 231, line 15, delete "$(CHR)_rNHC(O)R_d$" and insert -- $(CHR)_rNHC(O)R_d$, --, Claim 2, col. 231, line 22, delete "$(CH_2)_rC_{3-6}$cycloalkyl" and insert -- $(CH_2)_r$-$C_{3-6}$cycloalkyl --, Claim 2, col. 231, line 36, delete "$C_{1-4}$-haloalkyl," and insert -- $C_{1-4}$haloalkyl, --, Claim 2, col. 231, line 48, delete "$(CH_2)_rSC_{1-5}$ alkyl," and insert -- $(CH_2)_rSC_{1-5}$alkyl, --, Signed and Sealed this
Twelfth Day of May, 2015

Michelle K. Lee
*Director of the United States Patent and Trademark Office*

CERTIFICATE OF CORRECTION (continued)  
U.S. Pat. No. 8,846,673 B2

In the Claims:

Claim 2, col. 231, lines 54-55, delete "$(CH_2)_r$phenyl;" and insert -- $(CH_2)_r$-phenyl; --, Claim 3, col. 231, line 64, delete "$OR_e$," and insert -- $OR_c$, --, Claim 5, col. 232, line 26, delete "$(CH_2)_rOR$," and insert -- $(CH_2)_rOR_c$, --, Claim 6, col. 232, line 58, delete "$CHANR_aR_a$," and insert -- $(CH_2)_rNR_aR_a$, --, Claim 6, col. 233, line 23, delete "$C_{1-4}$-haloalkyl," and insert -- $C_{1-4}$haloalkyl, --, Claim 6, col. 233, line 34, delete "$(CH_2)_r$ heterocyclyl" and insert -- $(CH_2)_r$heterocyclyl --, Claim 6, col. 233, line 42, delete "$R_e$," and insert -- $R_c$, --, Claim 6, col. 233, line 43, delete "$C_{1-4}$-haloalkyl," and insert -- $C_{1-4}$haloalkyl, --, Claim 6, col. 233, line 55, delete "$(CH_2)_rC(O)NR/(C_{1-4}alkyl)$," and insert -- $(CH_2)_rC(O)NR_f(C_{1-4}alkyl)$, --, Claim 7, col. 234, line 52, delete "$CHAC_{3-6}$cycloalkyl" and insert -- $(CH_2)_rC_{3-6}$cycloalkyl --, Claim 8, col. 235, line 44, delete "$C_{1-4}$-haloalkyl," and insert -- $C_{1-4}$haloalkyl, --, Claim 8, col. 236, line 41, delete "$C_{1-4}$-haloalkyl," and insert -- $C_{1-4}$haloalkyl, --; and Claim 10, col. 236, line 49, delete "$(CHR)_rC_{3-6}$-carbocyclyl" and insert -- $(CHR)_rC_{3-6}$carbocyclyl --, therefor.